US008211444B2

(12) United States Patent
Fournillier et al.

(10) Patent No.: US 8,211,444 B2
(45) Date of Patent: Jul. 3, 2012

(54) HEPATITIS C VIRUS NON STRUCTURAL FUSION PROTEIN

(75) Inventors: Ann Fournillier, Lyon (FR); Genevieve Inchauspe, Lyon (FR); Laurence Chatel, Jozier (FR); Francois Penin, Decines (FR)

(73) Assignee: Transgene S.A. (FR)

( * ) Notice: Subject to any disclaimer, the term of this patent is extended or adjusted under 35 U.S.C. 154(b) by 33 days.

(21) Appl. No.: 12/282,146

(22) PCT Filed: Mar. 6, 2007

(86) PCT No.: PCT/EP2007/001922

§ 371 (c)(1),
(2), (4) Date: Jan. 26, 2009

(87) PCT Pub. No.: WO2007/101657

PCT Pub. Date: Sep. 13, 2007

(65) Prior Publication Data

US 2009/0186046 A1 Jul. 23, 2009

(30) Foreign Application Priority Data

Mar. 9, 2006 (EP) .................................... 06360006

(51) Int. Cl.
*A61K 39/29* (2006.01)
*C12N 7/00* (2006.01)
*N12N 5/10* (2006.01)

(52) U.S. Cl. ..................... 424/228.1; 435/325; 435/69.1

(58) Field of Classification Search ........................ None
See application file for complete search history.

(56) References Cited

U.S. PATENT DOCUMENTS

| | | | | |
|---|---|---|---|---|
| 6,428,792 | B1 | 8/2002 | Valenzuela et al. | |
| 6,630,343 | B1 * | 10/2003 | Bartenschlager | 435/320.1 |

FOREIGN PATENT DOCUMENTS

| | | |
|---|---|---|
| EP | 0 693 687 | 1/1996 |
| WO | WO 2004/046176 | 6/2004 |
| WO | WO 2004/111082 | 12/2004 |

OTHER PUBLICATIONS

Chien D.Y. et al., "Use of a Novel Hepatitis C Virus (HCV) Major-Epitope Chimeric Polypeptide for Diagnosis of HCV Infection," Journal of Clinical Microbiology, May 1995, vol. 37, No. 5, pp. 1393-1397, XP002155465.

Brinster C. et al., "Different Hepatitis C Virus Nonstructural Protein 3 (NS3)-DNA-Expressing Vaccines Induce in HLA-A2.1 Transgenic Mice Stable Cytotoxic T Lymphocytes That Target One Major Epitope," Hepatology, Dec. 2001, vol. 34, No. 6, pp. 1206-1217, Williams and Wilkins, Baltimore, Maryland, U.S., XP008028005.

Branch A.D. et al., "The Hepatitis C Virus Alternate Reading Frame (ARF) and It's Family of Novel Products: The Alternate Reading Frame Protein/F-Protein, the Double-Frameshift Protein, and Others," Seminars in Liver Disease, Feb. 2005, vol. 25, No. 1, pp. 105-117, Stuttgart, Germany, XP009062779.

Martin P. et al., "Genetic Immunization and Comprehensive Screening Approaches in HLA-A2 Transgenic Mice Lead to the Identification of Three Novel Epitopes in Hepatitis C Virus NS3 Antigen," Journal of Medical Virology, Nov. 2004, vol. 74, No. 3, pp. 397-405, Alan R. Liss, New York, New York, U.S., XP008078477.

Khudyakov Yu E. et al., "Linear B-Cell Epitopes of the NS3-NS4-NS5 Proteins of the Hepatitis C Virus as Modeled with Synthetic Peptides," Virology, Jan. 10, 1995, vol. 206, No. 1, pp. 666-672, Academic Press, Orlando, Florida, U.S., XP004786693.

* cited by examiner

*Primary Examiner* — Bao Li
(74) *Attorney, Agent, or Firm* — Buchanan Ingersoll & Rooney PC

(57) ABSTRACT

The present invention relates to an isolated fusion protein comprising at least three NS polypeptides originating from a hepatitis C virus which are configured in said fusion protein in an order which is distinct of the order in which they appear in the native configuration. The present invention also relates to a nucleic acid molecule encoding such a fusion protein and a vector comprising such a nucleic acid molecule. The present invention also provides infectious viral particles and host cells comprising such a nucleic acid molecule or such a vector. The present invention also relates to a method for recombinantly producing such a fusion protein. Finally, the present invention also provides a pharmaceutical composition comprising such a fusion protein, a nucleic acid molecule, a vector, infectious viral particles and a host cell as well as the therapeutic use thereof for treating or preventing HCV infections, HCV-associated diseases and pathologic conditions as well as a method of inducing or stimulating an immune response against HCV in a host organism.

39 Claims, 46 Drawing Sheets

Fig.1A amino acid sequence of the fusion protein NS4A-3-5B

SEQ ID NO:9

```
.        10        20        30        40        50        60
.         |         |         |         |         |         |
.                 |-> NS3
MGSVVIVGRIILSGSGSAPITAYSQQTRGLLGCIITSLTGRDKNQVDGEVQVLSTATQSF
.              linker        (antigenic domain B, NS3 protease)
NS4A interaction domain

.        70        80        90       100       110       120
.         |         |         |         |         |         |
LATCVNGVCWTVYAGAGSKTLAGPKGPITQMYTNVDQDLVGWPAPPGARSMTPCTCGSSD
.            H               (antigenic domain E, NS3 protease)

.       130       140       150       160       170       180
.         |         |         |         |         |         |
LYLVTRHADVIPVRRRGDSRGSLLSPRPVSYLKGSSGGPLLCPSGHVVGIFRAAVCTRGV

.       190       200       210       220       230       240
.         |         |         |         |         |         |
AKAVDFIPVESMETTMRSPVFTDNSSPPAVPQTFQVAHLHAPTGSGKSTKVPAAYAAQGY

.       250       260       270       280       290       300
.         |         |         |         |         |         |
KVLVLNPSVAATLGFGAYMSKAHGIEPNIRTGVRTITTGGPITYSAYGKFLADGGCSGGA
(antigenic domain A, NS3 helicase)           T

.       310       320       330       340       350       360
.         |         |         |         |         |         |
YDIIICDECHSTDWTTILGIGTVLDQAETAGARLVVLATATPPGSITVPHPNIEEVALSN

.       370       380       390       400       410       420
.         |         |         |         |         |         |
TGEIPFYGKAIPIEAIKGGRHLIFCHSKKKCDELAAKLTGLGLNAVAYYRGLDVSVIPTS

.       430       440       450       460       470       480
.         |         |         |         |         |         |
GDVVVVATDALMTGFTGDFDSVIDCNTCVTQTVDFSLDPTFTIETTTVPQDAVSRSQRRG

.       490       500       510       520       530       540
.         |         |         |         |         |         |
ATGRGRSGIYRFVTPGERPSGMFDSSVLCECYDAGCAWYELTPAETTVRLRAYLNTPGLP
R

.       550       560       570       580       590       600
.         |         |         |         |         |         |
VCQDHLEFWESVFTGLTHIDAHFLSQTKQAGDNFPYLVAYQATVCARAQAPPPSWDQMWK

.       610       620       630       640       650       660
.         |         |         |         |         |         |
.                                      NS3    <-|     |-> NS5B
CLIRLKPTLHGPTPLLYRLGAVQNEITLTHPITKFVMACMSADLEVVGSGSGSMSYTWTG
.                                                 Linker

.       670       680       690       700       710       720
.         |         |         |         |         |         |
ALITPCAAEESKLPINPLSNSLLRHHSMVYSTTSRSASLRQKKVTFDRLQVLDDHYRDVL
```

Fig.1B

```
.       730       740       750       760       770       780
.         |         |         |         |         |         |
KEMKAKASTVKARLLSIEEACKLTPPHSAKSKFGYGAKDVRSLSSRAVNHIRSVWEDLLE

.       790       800       810       820       830       840
.         |         |         |         |         |         |
DTETPIDTTIMAKNEVFCVQPEKGGRKPARLIVFPDLGVRVCEKMALYDVVSTLPQAVMG
.                              (antigenic domain D, NS5B)

.       850       860       870       880       890       900
.         |         |         |         |         |         |
PSYGFQYSPGQRVEFLVNTWKSKKCPMGFSYNTRCFDSTVTENDIRTEESIYQCCDLAPE
.                                D

.       910       920       930       940       950       960
.         |         |         |         |         |         |
ARQAIKSLTERLYIGGPLTNSKGQNCGYRRCRASGVLTTSCGNTLTCYLKATAACRAAKL

.       970       980       990      1000      1010      1020
.         |         |         |         |         |         |
QDCTMLVNGNDLVVICESAGTQEDAASLRVFTEAMTRYSAPPGDPPQPEYDLELITSCSS
.         D

.      1030      1040      1050      1060      1070      1080
.         |         |         |         |         |         |
NVSVAHDASGKRVYYLTRDPTTPLARAAWETVRHTPVNSWLGNIIMYAPTLWARMILMTH

.      1090      1100      1110      1120      1130      1140
.         |         |         |         |         |         |
FFSILLAQEQLEKALDCQIYGACYSIEPLDLPQIIERLHGLSAFSLHSYSPGEINRVASC

.      1150      1160      1170      1180      1190      1200
.         |         |         |         |         |         |
LRKLGVPPLRVWRHRARSVRAKLLSQGGRAATCGKYLFNWAVRTKLKLTPIPAASQLDLS

.      1210      1220
.         |         |
GWFVAGYNGGDIYHSLSRARPR
```

Fig. 2A amino acid sequence of the fusion protein NS4A-3-4B-5B

SEQ ID NO:10

```
.        10        20        30        40        50        60
.         |         |         |         |         |         |
.                  |-> NS3
MGSVVIVGRIILSGSGSAPITAYSQQTRGLLGCIITSLTGRDKNQVDGEVQVLSTATQSF
.             linker         (antigenic domain B, NS3 protease)
NS4A interaction domain

.        70        80        90       100       110       120
.         |         |         |         |         |         |
LATCVNGVCWTVYAGAGSKTLAGPKGPITQMYTNVDQDLVGWPAPPGARSMTPCTCGSSD
.             H                (antigenic domain E, NS3 Protease)

.       130       140       150       160       170       180
.         |         |         |         |         |         |
LYLVTRHADVIPVRRRGDSRGSLLSPRPVSYLKGSSGGPLLCPSGHVVGIFRAAVCTRGV

.       190       200       210       220       230       240
.         |         |         |         |         |         |
AKAVDFIPVESMETTMRSPVFTDNSSPPAVPQTFQVAHLHAPTGSGKSTKVPAAYAAQGY

.       250       260       270       280       290       300
.         |         |         |         |         |         |
KVLVLNPSVAATLGFGAYMSKAHGIEPNIRTGVRTITTGGPITYSAYGKFLADGGCSGGA
(antigenic domain A, NS3 helicase)            T

.       310       320       330       340       350       360
.         |         |         |         |         |         |
YDIIICDECHSTDWTTILGIGTVLDQAETAGARLVVLATATPPGSITVPHPNIEEVALSN

.       370       380       390       400       410       420
.         |         |         |         |         |         |
TGEIPFYGKAIPIEAIKGGRHLIFCHSKKKCDELAAKLTGLGLNAVAYYRGLDVSVIPTS

.       430       440       450       460       470       480
.         |         |         |         |         |         |
GDVVVVATDALMTGFTGDFDSVIDCNTCVTQTVDFSLDPTFTIETTTVPQDAVSRSQRRG

.       490       500       510       520       530       540
.         |         |         |         |         |         |
ATGRGRSGIYRFVTPGERPSGMFDSSVLCECYDAGCAWYELTPAETTVRLRAYLNTPGLP
R

.       550       560       570       580       590       600
.         |         |         |         |         |         |
VCQDHLEFWESVFTGLTHIDAHFLSQTKQAGDNFPYLVAYQATVCARAQAPPPSWDQMWK

.       610       620       630       640       650       660
.         |         |         |         |         |         |
.                                      NS3    <-|-> NS4B epitope
CLIRLKPTLHGPTPLLYRLGAVQNEITLTHPITKFVMACMSADLEVVSLMAFTASITSPL
.                                                 (antigenic

.       670       680       690       700       710       720
.         |         |         |         |         |         |
. NS4B epitope   <-|-> NS5B
TTQNTLLFNILGGWVAAQLSMSYTWTGALITPCAAEESKLPINPLSNSLLRHHSMVYSTT
. domain C, NS4B)
```

Fig.2B

```
.        730       740       750       760       770       780
.          |         |         |         |         |         |
SRSASLRQKKVTFDRLQVLDDHYRDVLKEMKAKASTVKARLLSIEEACKLTPPHSAKSKF

.        790       800       810       820       830       840
.          |         |         |         |         |         |
GYGAKDVRSLSSRAVNHIRSVWEDLLEDTETPIDTTIMAKNEVFCVQPEKGGRKPARLIV

.        850       860       870       880       890       900
.          |         |         |         |         |         |
FPDLGVRVCEKMALYDVVSTLPQAVMGPSYGFQYSPGQRVEFLVNTWKSKKCPMGFSYNT
(antigenic domain D, NS5B)                                  D

.        910       920       930       940       950       960
.          |         |         |         |         |         |
RCFDSTVTENDIRTEESIYQCCDLAPEARQAIKSLTERLYIGGPLTNSKGQNCGYRRCRA

.        970       980       990      1000      1010      1020
.          |         |         |         |         |         |
SGVLTTSCGNTLTCYLKATAACRAAKLQDCTMLVNGNDLVVICESAGTQEDAASLRVFTE
.                                    D

.       1030      1040      1050      1060      1070      1080
.          |         |         |         |         |         |
AMTRYSAPPGDPPQPEYDLELITSCSSNVSVAHDASGKRVYYLTRDPTTPLARAAWETVR

.       1090      1100      1110      1120      1130      1140
.          |         |         |         |         |         |
HTPVNSWLGNIIMYAPTLWARMILMTHFFSILLAQEQLEKALDCQIYGACYSIEPLDLPQ

.       1150      1160      1170      1180      1190      1200
.          |         |         |         |         |         |
IIERLHGLSAFSLHSYSPGEINRVASCLRKLGVPPLRVWRHRARSVRAKLLSQGGRAATC

.       1210      1220      1230      1240
.          |         |         |         |
GKYLFNWAVRTKLKLTPIPAASQLDLSGWFVAGYNGGDIYHSLSRARPR
```

Fig. 3A

4A-3-5B fusion protein_(Hs)
optimized for Homo sapiens

SEQ ID NO:21
SEQ ID NO:22
SEQ ID NO:9

```
    CGAATTGGGTACCGCCACCATGGGCAGCGTGGTGATTGTGGGCCGGATCATCCTGAGCGG
1   ---------+---------+---------+---------+---------+---------+
    GCTTAACCCATGGCGGTGGTACCCGTCGCACCACTAACACCCGGCCTAGTAGGACTCGCC
                       M__G__S__V__V__I__V__G__R__I__I__L__S__G_

    CAGCGGCAGCGCCCCCATCACCGCCTACAGCCAGCAGACCAGAGGCCTGCTGGGCTGTAT
61  ---------+---------+---------+---------+---------+---------+
    GTCGCCGTCGCGGGGGTAGTGGCGGATGTCGGTCGTCTGGTCTCCGGACGACCCGACATA
    _S__G__S__A__P__I__T__A__Y__S__Q__Q__T__R__G__L__L__G__C__I_

    CATCACCAGCCTGACCGGCAGAGACAAGAATCAGGTGGACGGCGAGGTGCAGGTGCTGTC
121 ---------+---------+---------+---------+---------+---------+
    GTAGTGGTCGGACTGGCCGTCTCTGTTCTTAGTCCACCTGCCGCTCCACGTCCACGACAG
    _I__T__S__L__T__G__R__D__K__N__Q__V__D__G__E__V__Q__V__L__S_

    CACCGCCACCCAGAGCTTCCTGGCCACCTGTGTGAATGGCGTGTGTTGGACCGTGTACGC
181 ---------+---------+---------+---------+---------+---------+
    GTGGCGGTGGGTCTCGAAGGACCGGTGGACACACTTACCGCACACAACCTGGCACATGCG
    _T__A__T__Q__S__F__L__A__T__C__V__N__G__V__C__W__T__V__Y__A_

    CGGAGCCGGCAGCAAGACCCTGGCCGGACCCAAGGGCCCCATCACCCAGATGTACACCAA
241 ---------+---------+---------+---------+---------+---------+
    GCCTCGGCCGTCGTTCTGGGACCGGCCTGGGTTCCCGGGGTAGTGGGTCTACATGTGGTT
    _G__A__G__S__K__T__L__A__G__P__K__G__P__I__T__Q__M__Y__T__N_

    CGTGGACCAGGACCTGGTGGGCTGGCCTGCCCCTCCTGGCGCCAGAAGCATGACCCCTTG
301 ---------+---------+---------+---------+---------+---------+
    GCACCTGGTCCTGGACCACCCGACCGGACGGGGAGGACCGCGGTCTTCGTACTGGGGAAC
    _V__D__Q__D__L__V__G__W__P__A__P__P__G__A__R__S__M__T__P__C_

    TACCTGTGGCAGCAGCGACCTGTACCTGGTGACCAGACACGCCGATGTGATCCCTGTGAG
361 ---------+---------+---------+---------+---------+---------+
    ATGGACACCGTCGTCGCTGGACATGGACCACTGGTCTGTGCGGCTACACTAGGGACACTC
    _T__C__G__S__S__D__L__Y__L__V__T__R__H__A__D__V__I__P__V__R_

    GAGGAGAGGCGATAGCAGAGGCAGCCTGCTGTCTCCTAGACCCGTGTCCTACCTGAAGGG
421 ---------+---------+---------+---------+---------+---------+
    CTCCTCTCCGCTATCGTCTCCGTCGGACGACAGAGGATCTGGGCACAGGATGGACTTCCC
    _R__R__G__D__S__R__G__S__L__L__S__P__R__P__V__S__Y__L__K__G_

    CAGCAGCGGCGGACCCCTGCTGTGCCCCAGCGGCCACGTGGTGGGCATCTTCAGAGCCGC
481 ---------+---------+---------+---------+---------+---------+
    GTCGTCGCCGCCTGGGGACGACACGGGGTCGCCGGTGCACCACCCGTAGAAGTCTCGGCG
    _S__S__G__G__P__L__L__C__P__S__G__H__V__V__G__I__F__R__A__A_

    CGTGTGTACCAGAGGCGTGGCCAAGGCCGTGGATTTCATCCCCGTGGAGAGCATGGAGAC
541 ---------+---------+---------+---------+---------+---------+
    GCACACATGGTCTCCGCACCGGTTCCGGCACCTAAAGTAGGGGCACCTCTCGTACCTCTG
    _V__C__T__R__G__V__A__K__A__V__D__F__I__P__V__E__S__M__E__T_
```

Fig. 3B

```
     CACCATGAGGAGCCCCGTGTTCACCGACAATAGCAGCCCCCCTGCCGTGCCTCAGACCTT
601  ---------+---------+---------+---------+---------+---------+
     GTGGTACTCCTCGGGGCACAAGTGGCTGTTATCGTCGGGGGGACGGCACGGAGTCTGGAA

     _T__M__R__S__P__V__F__T__D__N__S__S__P__P__A__V__P__Q__T__F_

     CCAGGTGGCCCACCTGCACGCCCCCACCGGCTCCGGCAAGAGCACCAAGGTGCCAGCCGC
661  ---------+---------+---------+---------+---------+---------+
     GGTCCACCGGGTGGACGTGCGGGGGTGGCCGAGGCCGTTCTCGTGGTTCCACGGTCGGCG
     _Q__V__A__H__L__H__A__P__T__G__S__G__K__S__T__K__V__P__A__A_

     CTACGCCGCCCAGGGCTACAAGGTGCTGGTGCTGAATCCCAGCGTGGCCGCCACCCTGGG
721  ---------+---------+---------+---------+---------+---------+
     GATGCGGCGGGTCCCGATGTTCCACGACCACGACTTAGGGTCGCACCGGCGGTGGGACCC
     _Y__A__A__Q__G__Y__K__V__L__V__L__N__P__S__V__A__A__T__L__G_

     CTTCGGCGCCTACATGAGCAAGGCCCACGGCATCGAGCCCAATATCCGGACCGGAGTGAG
781  ---------+---------+---------+---------+---------+---------+
     GAAGCCGCGGATGTACTCGTTCCGGGTGCCGTAGCTCGGGTTATAGGCCTGGCCTCACTC
     _F__G__A__Y__M__S__K__A__H__G__I__E__P__N__I__R__T__G__V__R_

     GACCATCACCACAGGCGGCCCTATCACCTACAGCGCCTACGGCAAGTTCCTGGCCGACGG
841  ---------+---------+---------+---------+---------+---------+
     CTGGTAGTGGTGTCCGCCGGGATAGTGGATGTCGCGGATGCCGTTCAAGGACCGGCTGCC
     _T__I__T__T__G__G__P__I__T__Y__S__A__Y__G__K__F__L__A__D__G_

     CGGCTGTAGCGGCGGAGCCTACGACATCATCATCTGTGACGAGTGCCACAGCACCGATTG
901  ---------+---------+---------+---------+---------+---------+
     GCCGACATCGCCGCCTCGGATGCTGTAGTAGTAGACACTGCTCACGGTGTCGTGGCTAAC
     _G__C__S__G__G__A__Y__D__I__I__I__C__D__E__C__H__S__T__D__W_

     GACCACCATCCTGGGCATCGGCACCGTGCTGGACCAGGCCGAGACCGCCGGAGCCAGACT
961  ---------+---------+---------+---------+---------+---------+
     CTGGTGGTAGGACCCGTAGCCGTGGCACGACCTGGTCCGGCTCTGGCGGCCTCGGTCTGA
     _T__T__I__L__G__I__G__T__V__L__D__Q__A__E__T__A__G__A__R__L_

     GGTGGTGCTGGCCACAGCCACACCCCCTGGCAGCATCACCGTGCCCCACCCCAACATCGA
1021 ---------+---------+---------+---------+---------+---------+
     CCACCACGACCGGTGTCGGTGTGGGGGACCGTCGTAGTGGCACGGGGTGGGGTTGTAGCT
     _V__V__L__A__T__A__T__P__P__G__S__I__T__V__P__H__P__N__I__E_

     GGAGGTGGCCCTGAGCAACACCGGCGAGATCCCCTTCTACGGCAAGGCCATCCCTATCGA
1081 ---------+---------+---------+---------+---------+---------+
     CCTCCACCGGGACTCGTTGTGGCCGCTCTAGGGGAAGATGCCGTTCCGGTAGGGATAGCT
     _E__V__A__L__S__N__T__G__E__I__P__F__Y__G__K__A__I__P__I__E_

     GGCCATCAAGGGCGGCAGACACCTGATCTTCTGCCACAGCAAGAAGAAGTGTGACGAGCT
1141 ---------+---------+---------+---------+---------+---------+
     CCGGTAGTTCCCGCCGTCTGTGGACTAGAAGACGGTGTCGTTCTTCTTCACACTGCTCGA
     _A__I__K__G__G__R__H__L__I__F__C__H__S__K__K__K__C__D__E__L_

     GGCCGCCAAGCTGACCGGCCTGGGCCTGAACGCCGTGGCCTACTACAGAGGCCTGGACGT
1201 ---------+---------+---------+---------+---------+---------+
     CCGGCGGTTCGACTGGCCGGACCCGGACTTGCGGCACCGGATGATGTCTCCGGACCTGCA
     _A__A__K__L__T__G__L__G__L__N__A__V__A__Y__Y__R__G__L__D__V_

     GTCCGTGATCCCTACCAGCGGCGATGTGGTGGTGGTGGCCACCGACGCCCTGATGACCGG
1261 ---------+---------+---------+---------+---------+---------+
     CAGGCACTAGGGATGGTCGCCGCTACACCACCACCACCGGTGGCTGCGGGACTACTGGCC
     _S__V__I__P__T__S__G__D__V__V__V__V__A__T__D__A__L__M__T__G_
```

Fig. 3C

CTTCACCGGCGATTTCGACAGCGTGATCGACTGTAATACCTGTGTGACCCAGACCGTGGA
1321---------+---------+---------+---------+---------+---------+
GAAGTGGCCGCTAAAGCTGTCGCACTAGCTGACATTATGGACACACTGGGTCTGGCACCT
_F__T__G__D__F__D__S__V__I__D__C__N__T__C__V__T__Q__T__V__D_

CTTCAGCCTGGACCCCACCTTCACCATCGAGACCACCACCGTGCCACAGGATGCCGTGTC
1381---------+---------+---------+---------+---------+---------+
GAAGTCGGACCTGGGGTGGAAGTGGTAGCTCTGGTGGTGGCACGGTGTCCTACGGCACAG
_F__S__L__D__P__T__F__T__I__E__T__T__T__V__P__Q__D__A__V__S_

CAGAAGCCAGAGAAGAGGCGCCACCGGCAGAGGCAGAAGCGGCATCTACAGATTCGTGAC
1441---------+---------+---------+---------+---------+---------+
GTCTTCGGTCTCTTCTCCGCGGTGGCCGTCTCCGTCTTCGCCGTAGATGTCTAAGCACTG
_R__S__Q__R__R__G__A__T__G__R__G__R__S__G__I__Y__R__F__V__T_

CCCTGGCGAGAGACCCAGCGGCATGTTCGATAGCAGCGTGCTGTGTGAGTGCTACGACGC
1501---------+---------+---------+---------+---------+---------+
GGGACCGCTCTCTGGGTCGCCGTACAAGCTATCGTCGCACGACACACTCACGATGCTGCG
_P__G__E__R__P__S__G__M__F__D__S__S__V__L__C__E__C__Y__D__A_

CGGCTGTGCCTGGTACGAGCTGACCCCAGCCGAGACCACAGTGAGGCTGAGGGCCTACCT
1561---------+---------+---------+---------+---------+---------+
GCCGACACGGACCATGCTCGACTGGGGTCGGCTCTGGTGTCACTCCGACTCCCGGATGGA
_G__C__A__W__Y__E__L__T__P__A__E__T__T__V__R__L__R__A__Y__L_

GAACACCCCTGGCCTGCCTGTGTGCCAGGATCACCTGGAGTTCTGGGAGAGCGTGTTTAC
1621---------+---------+---------+---------+---------+---------+
CTTGTGGGGACCGGACGGACACACGGTCCTAGTGGACCTCAAGACCCTCTCGCACAAATG
_N__T__P__G__L__P__V__C__Q__D__H__L__E__F__W__E__S__V__F__T_

CGGCCTGACCCACATCGATGCCCACTTTCTGAGCCAGACCAAGCAGGCCGGCGACAACTT
1681---------+---------+---------+---------+---------+---------+
GCCGGACTGGGTGTAGCTACGGGTGAAAGACTCGGTCTGGTTCGTCCGGCCGCTGTTGAA
_G__L__T__H__I__D__A__H__F__L__S__Q__T__K__Q__A__G__D__N__F_

CCCCTACCTGGTGGCCTACCAGGCCACCGTGTGTGCCAGAGCCCAGGCCCCTCCCCCCAG
1741---------+---------+---------+---------+---------+---------+
GGGGATGGACCACCGGATGGTCCGGTGGCACACACGGTCTCGGGTCCGGGGAGGGGGGTC
_P__Y__L__V__A__Y__Q__A__T__V__C__A__R__A__Q__A__P__P__P__S_

CTGGGACCAGATGTGGAAGTGCCTGATCAGGCTGAAGCCCACCCTGCACGGCCCTACCCC
1801---------+---------+---------+---------+---------+---------+
GACCCTGGTCTACACCTTCACGGACTAGTCCGACTTCGGGTGGGACGTGCCGGGATGGGG
_W__D__Q__M__W__K__C__L__I__R__L__K__P__T__L__H__G__P__T__P_

CCTGCTGTACAGACTGGGCGCCGTGCAGAATGAGATCACCCTGACCCACCCTATCACCAA
1861---------+---------+---------+---------+---------+---------+
GGACGACATGTCTGACCCGCGGCACGTCTTACTCTAGTGGGACTGGGTGGGATAGTGGTT
_L__L__Y__R__L__G__A__V__Q__N__E__I__T__L__T__H__P__I__T__K_

GTTCGTGATGGCCTGTATGAGCGCCGACCTGGAGGTGGTGGGCAGCGGCTCCGGCTCCAT
1921---------+---------+---------+---------+---------+---------+
CAAGCACTACCGGACATACTCGCGGCTGGACCTCCACCACCCGTCGCCGAGGCCGAGGTA
_F__V__M__A__C__M__S__A__D__L__E__V__V__G__S__G__S__G__S__M_

GAGCTACACCTGGACAGGCGCCCTGATCACACCCTGTGCCGCCGAGGAGAGCAAGCTGCC
1981---------+---------+---------+---------+---------+---------+
CTCGATGTGGACCTGTCCGCGGGACTAGTGTGGGACACGGCGGCTCCTCTCGTTCGACGG
_S__Y__T__W__T__G__A__L__I__T__P__C__A__A__E__E__S__K__L__P_

Fig. 3D

```
    CATCAACCCCCTGAGCAATAGCCTGCTGAGGCACCACAGCATGGTGTACAGCACCACCTC
2041---------+---------+---------+---------+---------+---------+
    GTAGTTGGGGGACTCGTTATCGGACGACTCCGTGGTGTCGTACCACATGTCGTGGTGGAG
    _I__N__P__L__S__N__S__L__L__R__H__H__S__M__V__Y__S__T__T__S_

    CAGAAGCGCCAGCCTGAGGCAGAAGAAGGTGACCTTCGACAGGCTGCAGGTGCTGGACGA
2101---------+---------+---------+---------+---------+---------+
    GTCTTCGCGGTCGGACTCCGTCTTCTTCCACTGGAAGCTGTCCGACGTCCACGACCTGCT
    _R__S__A__S__L__R__Q__K__K__V__T__F__D__R__L__Q__V__L__D__D_

    CCACTACAGGGACGTGCTGAAGGAGATGAAGGCCAAGGCCAGCACCGTGAAGGCCAGACT
2161---------+---------+---------+---------+---------+---------+
    GGTGATGTCCCTGCACGACTTCCTCTACTTCCGGTTCCGGTCGTGGCACTTCCGGTCTGA
    _H__Y__R__D__V__L__K__E__M__K__A__K__A__S__T__V__K__A__R__L_

    GCTGTCTATCGAGGAGGCCTGTAAGCTGACCCCCCCTCACAGCGCCAAGAGCAAGTTCGG
2221---------+---------+---------+---------+---------+---------+
    CGACAGATAGCTCCTCCGGACATTCGACTGGGGGGGAGTGTCGCGGTTCTCGTTCAAGCC
    _L__S__I__E__E__A__C__K__L__T__P__P__H__S__A__K__S__K__F__G_

    CTACGGCGCCAAGGATGTGAGAAGCCTGAGCAGCAGAGCCGTGAACCACATCCGGTCTGT
2281---------+---------+---------+---------+---------+---------+
    GATGCCGCGGTTCCTACACTCTTCGGACTCGTCGTCTCGGCACTTGGTGTAGGCCAGACA
    _Y__G__A__K__D__V__R__S__L__S__S__R__A__V__N__H__I__R__S__V_

    GTGGGAGGATCTGCTGGAGGATACCGAGACCCCCATCGACACCACAATCATGGCCAAGAA
2341---------+---------+---------+---------+---------+---------+
    CACCCTCCTAGACGACCTCCTATGGCTCTGGGGGTAGCTGTGGTGTTAGTACCGGTTCTT
    _W__E__D__L__L__E__D__T__E__T__P__I__D__T__T__I__M__A__K__N_

    CGAGGTGTTCTGCGTGCAGCCCGAGAAGGGCGGAAGAAAGCCCGCCAGGCTGATCGTGTT
2401---------+---------+---------+---------+---------+---------+
    GCTCCACAAGACGCACGTCGGGCTCTTCCCGCCTTCTTTCGGGCGGTCCGACTAGCACAA
    _E__V__F__C__V__Q__P__E__K__G__G__R__K__P__A__R__L__I__V__F_

    CCCTGACCTGGGAGTGAGAGTGTGTGAGAAGATGGCCCTGTACGACGTGGTGTCCACCCT
2461---------+---------+---------+---------+---------+---------+
    GGGACTGGACCCTCACTCTCACACACTCTTCTACCGGGACATGCTGCACCACAGGTGGGA
    _P__D__L__G__V__R__V__C__E__K__M__A__L__Y__D__V__V__S__T__L_

    GCCCCAGGCCGTGATGGGCCCCAGCTACGGCTTCCAGTACAGCCCTGGCCAGAGAGTGGA
2521---------+---------+---------+---------+---------+---------+
    CGGGGTCCGGCACTACCCGGGGTCGATGCCGAAGGTCATGTCGGGACCGGTCTCTCACCT
    _P__Q__A__V__M__G__P__S__Y__G__F__Q__Y__S__P__G__Q__R__V__E_

    GTTCCTGGTGAACACCTGGAAGAGCAAGAAATGCCCCATGGGCTTCAGCTACAACACCCG
2581---------+---------+---------+---------+---------+---------+
    CAAGGACCACTTGTGGACCTTCTCGTTCTTTACGGGGTACCCGAAGTCGATGTTGTGGGC
    _F__L__V__N__T__W__K__S__K__K__C__P__M__G__F__S__Y__N__T__R_

    GTGCTTCGACAGCACAGTGACCGAGAACGACATCAGGACCGAGGAGTCCATCTACCAGTG
2641---------+---------+---------+---------+---------+---------+
    CACGAAGCTGTCGTGTCACTGGCTCTTGCTGTAGTCCTGGCTCCTCAGGTAGATGGTCAC
    _C__F__D__S__T__V__T__E__N__D__I__R__T__E__E__S__I__Y__Q__C_

    CTGTGACCTGGCCCCCGAGGCCAGACAGGCCATCAAAAGCCTGACCGAGCGGCTGTACAT
2701---------+---------+---------+---------+---------+---------+
    GACACTGGACCGGGGGCTCCGGTCTGTCCGGTAGTTTTCGGACTGGCTCGCCGACATGTA
    _C__D__L__A__P__E__A__R__Q__A__I__K__S__L__T__E__R__L__Y__I_
```

Fig. 3E

```
    CGGCGGACCTCTGACCAACAGCAAGGGCCAGAACTGTGGCTACAGAAGATGTAGGGCCAG
2761---------+---------+---------+---------+---------+---------+
    GCCGCCTGGAGACTGGTTGTCGTTCCCGGTCTTGACACCGATGTCTTCTACATCCCGGTC
    _G__G__P__L__T__N__S__K__G__Q__N__C__G__Y__R__R__C__R__A__S_

    CGGCGTGCTGACCACCTCTTGTGGCAACACCCTGACCTGTTACCTGAAGGCCACCGCCGC
2821---------+---------+---------+---------+---------+---------+
    GCCGCACGACTGGTGGAGAACACCGTTGTGGGACTGGACAATGGACTTCCGGTGGCGGCG
    _G__V__L__T__T__S__C__G__N__T__L__T__C__Y__L__K__A__T__A__A_

    CTGTAGAGCCGCCAAACTGCAGGACTGTACCATGCTGGTGAACGGCAACGACCTGGTGGT

2881---------+---------+---------+---------+---------+---------+
    GACATCTCGGCGGTTTGACGTCCTGACATGGTACGACCACTTGCCGTTGCTGGACCACCA
    _C__R__A__A__K__L__Q__D__C__T__M__L__V__N__G__N__D__L__V__V_

    GATCTGTGAGAGCGCCGGCACCCAGGAGGATGCCGCCTCCCTGAGAGTGTTTACCGAGGC
2941---------+---------+---------+---------+---------+---------+
    CTAGACACTCTCGCGGCCGTGGGTCCTCCTACGGCGGAGGGACTCTCACAAATGGCTCCG
    _I__C__E__S__A__G__T__Q__E__D__A__A__S__L__R__V__F__T__E__A_

    CATGACCAGATACAGCGCCCCTCCCGGCGACCCTCCCCAGCCCGAGTACGATCTGGAGCT
3001---------+---------+---------+---------+---------+---------+
    GTACTGGTCTATGTCGCGGGGAGGGCCGCTGGGAGGGGTCGGGCTCATGCTAGACCTCGA
    _M__T__R__Y__S__A__P__P__G__D__P__P__Q__P__E__Y__D__L__E__L_

    GATCACCAGCTGCTCCAGCAATGTGGGCGTGGCTCACGACGCCAGCGGCAAGAGAGTGTA
3061---------+---------+---------+---------+---------+---------+
    CTAGTGGTCGACGAGGTCGTTACACCCGCACCGAGTGCTGCGGTCGCCGTTCTCTCACAT
    _I__T__S__C__S__S__N__V__G__V__A__H__D__A__S__G__K__R__V__Y_

    CTACCTGACCAGGGACCCCACCACCCCTCTGGCCAGAGCCGCCTGGGAGACAGTGAGACA
3121---------+---------+---------+---------+---------+---------+
    GATGGACTGGTCCCTGGGGTGGTGGGGAGACCGGTCTCGGCGGACCCTCTGTCACTCTGT
    _Y__L__T__R__D__P__T__T__P__L__A__R__A__A__W__E__T__V__R__H_

    CACCCCCGTGAACAGCTGGCTGGGCAACATCATCATGTACGCCCCTACCCTGTGGGCCAG
3181---------+---------+---------+---------+---------+---------+
    GTGGGGGCACTTGTCGACCGACCCGTTGTAGTAGTACATGCGGGGATGGGACACCCGGTC
    _T__P__V__N__S__W__L__G__N__I__I__M__Y__A__P__T__L__W__A__R_

    AATGATCCTGATGACCCACTTCTTCAGCATCCTGCTGGCCCAGGAGCAGCTGGAGAAGGC
3241---------+---------+---------+---------+---------+---------+
    TTACTAGGACTACTGGGTGAAGAAGTCGTAGGACGACCGGGTCCTCGTCGACCTCTTCCG
    _M__I__L__M__T__H__F__F__S__I__L__L__A__Q__E__Q__L__E__K__A_


    CCTGGACTGCCAGATCTACGGCGCCTGCTACAGCATCGAGCCTCTGGACCTGCCTCAGAT
3301---------+---------+---------+---------+---------+---------+
    GGACCTGACGGTCTAGATGCCGCGGACGATGTCGTAGCTCGGAGACCTGGACGGAGTCTA
    _L__D__C__Q__I__Y__G__A__C__Y__S__I__E__P__L__D__L__P__Q__I_

    CATCGAGAGACTGCACGGCCTGAGCGCCTTCAGCCTGCACAGCTACAGCCCAGGCGAGAT
3361---------+---------+---------+---------+---------+---------+
    GTAGCTCTCTGACGTGCCGGACTCGCGGAAGTCGGACGTGTCGATGTCGGGTCCGCTCTA
    _I__E__R__L__H__G__L__S__A__F__S__L__H__S__Y__S__P__G__E__I_

    CAATAGAGTGGCCAGCTGCCTGAGAAAGCTGGGCGTGCCACCTCTGAGAGTGTGGCGGCA
3421---------+---------+---------+---------+---------+---------+
    GTTATCTCACCGGTCGACGGACTCTTTCGACCCGCACGGTGGAGACTCTCACACCGCCGT
    _N__R__V__A__S__C__L__R__K__L__G__V__P__P__L__R__V__W__R__H_
```

Fig. 3F

```
     CAGAGCCAGATCTGTGAGGGCCAAGCTGCTGTCCCAGGGCGGCAGGGCCGCCACCTGTGG
3481---------+---------+---------+---------+---------+---------+
     GTCTCGGTCTAGACACTCCCGGTTCGACGACAGGGTCCCGCCGTCCCGGCGGTGGACACC
     _R__A__R__S__V__R__A__K__L__L__S__Q__G__G__R__A__A__T__C__G_

     CAAGTACCTGTTCAACTGGGCCGTGAGGACAAAGCTGAAGCTGACACCCATCCCTGCCGC
3541---------+---------+---------+---------+---------+---------+
     GTTCATGGACAAGTTGACCCGGCACTCCTGTTTCGACTTCGACTGTGGGTAGGGACGGCG
     _K__Y__L__F__N__W__A__V__R__T__K__L__K__L__T__P__I__P__A__A_

     CAGCCAGCTGGACCTGAGCGGCTGGTTCGTGGCCGGCTACAATGGCGGCGACATCTACCA
3601---------+---------+---------+---------+---------+---------+
     GTCGGTCGACCTGGACTCGCCGACCAAGCACCGGCCGATGTTACCGCCGCTGTAGATGGT
     _S__Q__L__D__L__S__G__W__F__V__A__G__Y__N__G__G__D__I__Y__H_

     CAGCCTGTCCAGGGCCAGGCCTAGATGATGAGGAGCTCCAGCTTT
3661---------+---------+---------+---------+-----
     GTCGGACAGGTCCCGGTCCGGATCTACTACTCCTCGAGGTCGAAA
     _S__L__S__R__A__R__P__R__*__*__
```

Fig. 4A

4A-3-4B-5B fusion protein (Hs) optimized for Homo sapiens

SEQ ID NO:23

SEQ ID NO:24

SEQ ID NO:10

```
              KpnI          NcoI
    GGGCGAATTGGGTACCGCCACCATGGGCAGCGTGGTGATTGTGGGCCGGATCATCCTGAG
1   ---------+---------+---------+---------+---------+---------+
    CCCGCTTAACCCATGGCGGTGGTACCCGTCGCACCACTAACACCCGGCCTAGTAGGACTC
                                M__G__S__V__V__I__V__G__R__I__I__L__S_

    CGGCAGCGGCAGCGCCCCCATCACCGCCTACAGCCAGCAGACCAGAGGCCTGCTGGGCTG
61  ---------+---------+---------+---------+---------+---------+
    GCCGTCGCCGTCGCGGGGGTAGTGGCGGATGTCGGTCGTCTGGTCTCCGGACGACCCGAC
    _G__S__G__S__A__P__I__T__A__Y__S__Q__Q__T__R__G__L__L__G__C_

    TATCATCACCAGCCTGACCGGCAGAGACAAGAATCAGGTGGACGGCGAGGTGCAGGTGCT
121 ---------+---------+---------+---------+---------+---------+
    ATAGTAGTGGTCGGACTGGCCGTCTCTGTTCTTAGTCCACCTGCCGCTCCACGTCCACGA
    _I__I__T__S__L__T__G__R__D__K__N__Q__V__D__G__E__V__Q__V__L_

    GTCCACCGCCACCCAGAGCTTCCTGGCCACCTGTGTGAATGGCGTGTGTTGGACCGTGTA
181 ---------+---------+---------+---------+---------+---------+
    CAGGTGGCGGTGGGTCTCGAAGGACCGGTGGACACACTTACCGCACACAACCTGGCACAT
    _S__T__A__T__Q__S__F__L__A__T__C__V__N__G__V__C__W__T__V__Y_

    CGCCGGAGCCGGCAGCAAGACCCTGGCCGGACCCAAGGGCCCCATCACCCAGATGTACAC
241 ---------+---------+---------+---------+---------+---------+
    GCGGCCTCGGCCGTCGTTCTGGGACCGGCCTGGGTTCCCGGGGTAGTGGGTCTACATGTG
    _A__G__A__G__S__K__T__L__A__G__P__K__G__P__I__T__Q__M__Y__T_

    CAACGTGGACCAGGACCTGGTGGGCTGGCCTGCCCCTCCTGGCGCCAGAAGCATGACCCC
301 ---------+---------+---------+---------+---------+---------+
    GTTGCACCTGGTCCTGGACCACCCGACCGGACGGGGAGGACCGCGGTCTTCGTACTGGGG
    _N__V__D__Q__D__L__V__G__W__P__A__P__P__G__A__R__S__M__T__P_

    TTGTACCTGTGGCAGCAGCGACCTGTACCTGGTGACCAGACACGCCGATGTGATCCCTGT
361 ---------+---------+---------+---------+---------+---------+
    AACATGGACACCGTCGTCGCTGGACATGGACCACTGGTCTGTGCGGCTACACTAGGGACA
    _C__T__C__G__S__S__D__L__Y__L__V__T__R__H__A__D__V__I__P__V_

    GAGGAGGAGAGGCGATAGCAGAGGCAGCCTGCTGTCTCCTAGACCCGTGTCCTACCTGAA
421 ---------+---------+---------+---------+---------+---------+
    CTCCTCCTCTCCGCTATCGTCTCCGTCGGACGACAGAGGATCTGGGCACAGGATGGACTT
    _R__R__R__G__D__S__R__G__S__L__L__S__P__R__P__V__S__Y__L__K_

    GGGCAGCAGCGGCGGACCCCTGCTGTGCCCCAGCGGCCACGTGGTGGGCATCTTCAGAGC
481 ---------+---------+---------+---------+---------+---------+
    CCCGTCGTCGCCGCCTGGGGACGACACGGGGTCGCCGGTGCACCACCCGTAGAAGTCTCG
    _G__S__S__G__G__P__L__L__C__P__S__G__H__V__V__G__I__F__R__A_

    CGCCGTGTGTACCAGAGGCGTGGCCAAGGCCGTGGATTTCATCCCCGTGGAGAGCATGGA
541 ---------+---------+---------+---------+---------+---------+
    GCGGCACACATGGTCTCCGCACCGGTTCCGGCACCTAAAGTAGGGGCACCTCTCGTACCT
    _A__V__C__T__R__G__V__A__K__A__V__D__F__I__P__V__E__S__M__E_

    GACCACCATGAGGAGCCCCGTGTTCACCGACAATAGCAGCCCCCCTGCCGTGCCTCAGAC
601 ---------+---------+---------+---------+---------+---------+
    CTGGTGGTACTCCTCGGGGCACAAGTGGCTGTTATCGTCGGGGGGACGGCACGGAGTCTG
    _T__T__M__R__S__P__V__F__T__D__N__S__S__P__P__A__V__P__Q__T_
```

Fig. 4B

```
     CTTCCAGGTGGCCCACCTGCACGCCCCCACCGGCTCCGGCAAGAGCACCAAGGTGCCAGC
661  ---------+---------+---------+---------+---------+---------+
     GAAGGTCCACCGGGTGGACGTGCGGGGGTGGCCGAGGCCGTTCTCGTGGTTCCACGGTCG
     _F__Q__V__A__H__L__H__A__P__T__G__S__G__K__S__T__K__V__P__A_

     CGCCTACGCCGCCCAGGGCTACAAGGTGCTGGTGCTGAATCCCAGCGTGGCCGCCACCCT
721  ---------+---------+---------+---------+---------+---------+
     GCGGATGCGGCGGGTCCCGATGTTCCACGACCACGACTTAGGGTCGCACCGGCGGTGGGA
     _A__Y__A__A__Q__G__Y__K__V__L__V__L__N__P__S__V__A__A__T__L_

     GGGCTTCGGCGCCTACATGAGCAAGGCCCACGGCATCGAGCCCAATATCCGGACCGGAGT
781  ---------+---------+---------+---------+---------+---------+
     CCCGAAGCCGCGGATGTACTCGTTCCGGGTGCCGTAGCTCGGGTTATAGGCCTGGCCTCA
     _G__F__G__A__Y__M__S__K__A__H__G__I__E__P__N__I__R__T__G__V_

     GAGGACCATCACCACAGGCGGCCCTATCACCTACAGCGCCTACGGCAAGTTCCTGGCCGA
841  ---------+---------+---------+---------+---------+---------+
     CTCCTGGTAGTGGTGTCCGCCGGGATAGTGGATGTCGCGGATGCCGTTCAAGGACCGGCT
     _R__T__I__T__T__G__G__P__I__T__Y__S__A__Y__G__K__F__L__A__D_

     CGGCGGCTGTAGCGGCGGAGCCTACGACATCATCATCTGTGACGAGTGCCACAGCACCGA
901  ---------+---------+---------+---------+---------+---------+
     GCCGCCGACATCGCCGCCTCGGATGCTGTAGTAGTAGACACTGCTCACGGTGTCGTGGCT
     _G__G__C__S__G__G__A__Y__D__I__I__I__C__D__E__C__H__S__T__D_

     TTGGACCACCATCCTGGGCATCGGCACCGTGCTGGACCAGGCCGAGACCGCCGGAGCCAG
961  ---------+---------+---------+---------+---------+---------+
     AACCTGGTGGTAGGACCCGTAGCCGTGGCACGACCTGGTCCGGCTCTGGCGGCCTCGGTC
     _W__T__T__I__L__G__I__G__T__V__L__D__Q__A__E__T__A__G__A__R_

     ACTGGTGGTGCTGGCCACAGCCACACCCCCTGGCAGCATCACCGTGCCCCACCCCAACAT
1021 ---------+---------+---------+---------+---------+---------+
     TGACCACCACGACCGGTGTCGGTGTGGGGGACCGTCGTAGTGGCACGGGGTGGGGTTGTA
     _L__V__V__L__A__T__A__T__P__P__G__S__I__T__V__P__H__P__N__I_

     CGAGGAGGTGGCCCTGAGCAACACCGGCGAGATCCCCTTCTACGGCAAGGCCATCCCTAT
1081 ---------+---------+---------+---------+---------+---------+
     GCTCCTCCACCGGGACTCGTTGTGGCCGCTCTAGGGGAAGATGCCGTTCCGGTAGGGATA
     _E__E__V__A__L__S__N__T__G__E__I__P__F__Y__G__K__A__I__P__I_

     CGAGGCCATCAAGGGCGGCAGACACCTGATCTTCTGCCACAGCAAGAAGAAGTGTGACGA
1141 ---------+---------+---------+---------+---------+---------+
     GCTCCGGTAGTTCCCGCCGTCTGTGGACTAGAAGACGGTGTCGTTCTTCTTCACACTGCT
     _E__A__I__K__G__G__R__H__L__I__F__C__H__S__K__K__K__C__D__E_

     GCTGGCCGCCAAGCTGACCGGCCTGGGCCTGAACGCCGTGGCCTACTACAGAGGCCTGGA
1201 ---------+---------+---------+---------+---------+---------+
     CGACCGGCGGTTCGACTGGCCGGACCCGGACTTGCGGCACCGGATGATGTCTCCGGACCT
     _L__A__A__K__L__T__G__L__G__L__N__A__V__A__Y__Y__R__G__L__D_

     CGTGTCCGTGATCCCTACCAGCGGCGATGTGGTGGTGGTGGCCACCGACGCCCTGATGAC
1261 ---------+---------+---------+---------+---------+---------+
     GCACAGGCACTAGGGATGGTCGCCGCTACACCACCACCACCGGTGGCTGCGGGACTACTG
     _V__S__V__I__P__T__S__G__D__V__V__V__V__A__T__D__A__L__M__T_

     CGGCTTCACCGGCGATTTCGACAGCGTGATCGACTGTAATACCTGTGTGACCCAGACCGT
1321 ---------+---------+---------+---------+---------+---------+
     GCCGAAGTGGCCGCTAAAGCTGTCGCACTAGCTGACATTATGGACACACTGGGTCTGGCA
     _G__F__T__G__D__F__D__S__V__I__D__C__N__T__C__V__T__Q__T__V_
```

Fig. 4C

```
     GGACTTCAGCCTGGACCCCACCTTCACCATCGAGACCACCACCGTGCCACAGGATGCCGT
1381---------+---------+---------+---------+---------+---------+
     CCTGAAGTCGGACCTGGGGTGGAAGTGGTAGCTCTGGTGGTGGCACGGTGTCCTACGGCA

     _D__F__S__L__D__P__T__F__T__I__E__T__T__T__V__P__Q__D__A__V_

     GTCCAGAAGCCAGAGAAGAGGCGCCACCGGCAGAGGCAGAAGCGGCATCTACAGATTCGT
1441---------+---------+---------+---------+---------+---------+
     CAGGTCTTCGGTCTCTTCTCCGCGGTGGCCGTCTCCGTCTTCGCCGTAGATGTCTAAGCA
     _S__R__S__Q__R__R__G__A__T__G__R__G__R__S__G__I__Y__R__F__V_

     GACCCCTGGCGAGAGACCCAGCGGCATGTTCGATAGCAGCGTGCTGTGTGAGTGCTACGA
1501---------+---------+---------+---------+---------+---------+
     CTGGGGACCGCTCTCTGGGTCGCCGTACAAGCTATCGTCGCACGACACACTCACGATGCT
     _T__P__G__E__R__P__S__G__M__F__D__S__S__V__L__C__E__C__Y__D_

     CGCCGGCTGTGCCTGGTACGAGCTGACCCCAGCCGAGACCACAGTGAGGCTGAGGGCCTA
1561---------+---------+---------+---------+---------+---------+
     GCGGCCGACACGGACCATGCTCGACTGGGGTCGGCTCTGGTGTCACTCCGACTCCCGGAT
     _A__G__C__A__W__Y__E__L__T__P__A__E__T__T__V__R__L__R__A__Y_

     CCTGAACACCCCTGGCCTGCCTGTGTGCCAGGATCACCTGGAGTTCTGGGAGAGCGTGTT
1621---------+---------+---------+---------+---------+---------+
     GGACTTGTGGGGACCGGACGGACACACGGTCCTAGTGGACCTCAAGACCCTCTCGCACAA
     _L__N__T__P__G__L__P__V__C__Q__D__H__L__E__F__W__E__S__V__F_

     TACCGGCCTGACCCACATCGATGCCCACTTTCTGAGCCAGACCAAGCAGGCCGGCGACAA
1681---------+---------+---------+---------+---------+---------+
     ATGGCCGGACTGGGTGTAGCTACGGGTGAAAGACTCGGTCTGGTTCGTCCGGCCGCTGTT
     _T__G__L__T__H__I__D__A__H__F__L__S__Q__T__K__Q__A__G__D__N_

     CTTCCCCTACCTGGTGGCCTACCAGGCCACCGTGTGTGCCAGAGCCCAGGCCCCTCCCCC
1741---------+---------+---------+---------+---------+---------+
     GAAGGGGATGGACCACCGGATGGTCCGGTGGCACACACGGTCTCGGGTCCGGGGAGGGGG
     _F__P__Y__L__V__A__Y__Q__A__T__V__C__A__R__A__Q__A__P__P__P_

     CAGCTGGGACCAGATGTGGAAGTGCCTGATCAGGCTGAAGCCCACCCTGCACGGCCCTAC
1801---------+---------+---------+---------+---------+---------+
     GTCGACCCTGGTCTACACCTTCACGGACTAGTCCGACTTCGGGTGGGACGTGCCGGGATG
     _S__W__D__Q__M__W__K__C__L__I__R__L__K__P__T__L__H__G__P__T_

     CCCCCTGCTGTACAGACTGGGCGCCGTGCAGAATGAGATCACCCTGACCCACCCTATCAC
1861---------+---------+---------+---------+---------+---------+
     GGGGGACGACATGTCTGACCCGCGGCACGTCTTACTCTAGTGGGACTGGGTGGGATAGTG
     _P__L__L__Y__R__L__G__A__V__Q__N__E__I__T__L__T__H__P__I__T_

     CAAGTTCGTGATGGCCTGTATGAGCGCCGACCTGGAGGTGGTGTCCCTGATGGCCTTCAC
1921---------+---------+---------+---------+---------+---------+
     GTTCAAGCACTACCGGACATACTCGCGGCTGGACCTCCACCACAGGGACTACCGGAAGTG
     _K__F__V__M__A__C__M__S__A__D__L__E__V__V__S__L__M__A__F__T_

     CGCCAGCATCACAAGCCCCCTGACCACCCAGAATACCCTGCTGTTCAACATCCTGGGCGG
1981---------+---------+---------+---------+---------+---------+
     GCGGTCGTAGTGTTCGGGGGACTGGTGGGTCTTATGGGACGACAAGTTGTAGGACCCGCC
     _A__S__I__T__S__P__L__T__T__Q__N__T__L__L__F__N__I__L__G__G_

     CTGGGTGGCCGCCCAGCTGTCCATGAGCTACACCTGGACAGGCGCCCTGATCACACCCTG
2041---------+---------+---------+---------+---------+---------+
     GACCCACCGGCGGGTCGACAGGTACTCGATGTGGACCTGTCCGCGGGACTAGTGTGGGAC
     _W__V__A__A__Q__L__S__M__S__Y__T__W__T__G__A__L__I__T__P__C_
```

Fig. 4D

```
    TGCCGCCGAGGAGAGCAAGCTGCCCATCAACCCCCTGAGCAATAGCCTGCTGAGGCACCA
2101---------+---------+---------+---------+---------+---------+
    ACGGCGGCTCCTCTCGTTCGACGGGTAGTTGGGGGACTCGTTATCGGACGACTCCGTGGT
    _A__A__E__E__S__K__L__P__I__N__P__L__S__N__S__L__L__R__H__H_

    CAGCATGGTGTACAGCACCACCTCCAGAAGCGCCAGCCTGAGGCAGAAGAAGGTGACCTT

2161---------+---------+---------+---------+---------+---------+
    GTCGTACCACATGTCGTGGTGGAGGTCTTCGCGGTCGGACTCCGTCTTCTTCCACTGGAA
    _S__M__V__Y__S__T__T__S__R__S__A__S__L__R__Q__K__K__V__T__F_

    CGACAGGCTGCAGGTGCTGGACGACCACTACAGGGACGTGCTGAAGGAGATGAAGGCCAA
2221---------+---------+---------+---------+---------+---------+
    GCTGTCCGACGTCCACGACCTGCTGGTGATGTCCCTGCACGACTTCCTCTACTTCCGGTT
    _D__R__L__Q__V__L__D__D__H__Y__R__D__V__L__K__E__M__K__A__K_

    GGCCAGCACCGTGAAGGCCAGACTGCTGTCTATCGAGGAGGCCTGTAAGCTGACCCCCCC
2281---------+---------+---------+---------+---------+---------+
    CCGGTCGTGGCACTTCCGGTCTGACGACAGATAGCTCCTCCGGACATTCGACTGGGGGGG
    _A__S__T__V__K__A__R__L__L__S__I__E__E__A__C__K__L__T__P__P_

    TCACAGCGCCAAGAGCAAGTTCGGCTACGGCGCCAAGGATGTGAGAAGCCTGAGCAGCAG
2341---------+---------+---------+---------+---------+---------+
    AGTGTCGCGGTTCTCGTTCAAGCCGATGCCGCGGTTCCTACACTCTTCGGACTCGTCGTC
    _H__S__A__K__S__K__F__G__Y__G__A__K__D__V__R__S__L__S__S__R_

    AGCCGTGAACCACATCCGGTCTGTGTGGGAGGATCTGCTGGAGGATACCGAGACCCCCAT
2401---------+---------+---------+---------+---------+---------+
TCGGCACTTGGTGTAGGCCAGACACACCCTCCTAGACGACCTCCTATGGCTCTGGGGGTA
    _A__V__N__H__I__R__S__V__W__E__D__L__L__E__D__T__E__T__P__I_

    CGACACCACAATCATGGCCAAGAACGAGGTGTTCTGCGTGCAGCCCGAGAAGGGCGGAAG
2461---------+---------+---------+---------+---------+---------+
    GCTGTGGTGTTAGTACCGGTTCTTGCTCCACAAGACGCACGTCGGGCTCTTCCCGCCTTC
    _D__T__T__I__M__A__K__N__E__V__F__C__V__Q__P__E__K__G__G__R_

    AAAGCCCGCCAGGCTGATCGTGTTCCCTGACCTGGGAGTGAGAGTGTGTGAGAAGATGGC
2521---------+---------+---------+---------+---------+---------+
TTTCGGGCGGTCCGACTAGCACAAGGGACTGGACCCTCACTCTCACACACTCTTCTACCG
    _K__P__A__R__L__I__V__F__P__D__L__G__V__R__V__C__E__K__M__A_

    CCTGTACGACGTGGTGTCCACCCTGCCCCAGGCCGTGATGGGCCCCAGCTACGGCTTCCA
2581---------+---------+---------+---------+---------+---------+
    GGACATGCTGCACCACAGGTGGGACGGGGTCCGGCACTACCCGGGGTCGATGCCGAAGGT
    _L__Y__D__V__V__S__T__L__P__Q__A__V__M__G__P__S__Y__G__F__Q_

    GTACAGCCCTGGCCAGAGAGTGGAGTTCCTGGTGAACACCTGGAAGAGCAAGAAATGCCC
2641---------+---------+---------+---------+---------+---------+
    CATGTCGGGACCGGTCTCTCACCTCAAGGACCACTTGTGGACCTTCTCGTTCTTTACGGG
    _Y__S__P__G__Q__R__V__E__F__L__V__N__T__W__K__S__K__K__C__P_
    CATGGGCTTCAGCTACAACACCCGGTGCTTCGACAGCACAGTGACCGAGAACGACATCAG
2701---------+---------+---------+---------+---------+---------+
    GTACCCGAAGTCGATGTTGTGGGCCACGAAGCTGTCGTGTCACTGGCTCTTGCTGTAGTC
    _M__G__F__S__Y__N__T__R__C__F__D__S__T__V__T__E__N__D__I__R_

    GACCGAGGAGTCCATCTACCAGTGCTGTGACCTGGCCCCCGAGGCCAGACAGGCCATCAA
2761---------+---------+---------+---------+---------+---------+
    CTGGCTCCTCAGGTAGATGGTCACGACACTGGACCGGGGGCTCCGGTCTGTCCGGTAGTT
    _T__E__E__S__I__Y__Q__C__C__D__L__A__P__E__A__R__Q__A__I__K_
```

Fig. 4E

```
          AAGCCTGACCGAGCGGCTGTACATCGGCGGACCTCTGACCAACAGCAAGGGCCAGAACTG
2821 ---------+---------+---------+---------+---------+---------+
          TTCGGACTGGCTCGCCGACATGTAGCCGCCTGGAGACTGGTTGTCGTTCCCGGTCTTGAC
           S  L  T  E  R  L  Y  I  G  G  P  L  T  N  S  K  G  Q  N  C

          TGGCTACAGAAGATGTAGGGCCAGCGGCGTGCTGACCACCTCTTGTGGCAACACCCTGAC
2881 ---------+---------+---------+---------+---------+---------+
          ACCGATGTCTTCTACATCCCGGTCGCCGCACGACTGGTGGAGAACACCGTTGTGGGACTG
           G  Y  R  R  C  R  A  S  G  V  L  T  T  S  C  G  N  T  L  T

          CTGTTACCTGAAGGCCACCGCCGCCTGTAGAGCCGCCAAACTGCAGGACTGTACCATGCT
2941 ---------+---------+---------+---------+---------+---------+
          GACAATGGACTTCCGGTGGCGGCGGACATCTCGGCGGTTTGACGTCCTGACATGGTACGA
           C  Y  L  K  A  T  A  A  C  R  A  A  K  L  Q  D  C  T  M  L

          GGTGAACGGCAACGACCTGGTGGTGATCTGTGAGAGCGCCGGCACCCAGGAGGATGCCGC
3001 ---------+---------+---------+---------+---------+---------+
          CCACTTGCCGTTGCTGGACCACCACTAGACACTCTCGCGGCCGTGGGTCCTCCTACGGCG
           V  N  G  N  D  L  V  V  I  C  E  S  A  G  T  Q  E  D  A  A

          CTCCCTGAGAGTGTTTACCGAGGCCATGACCAGATACAGCGCCCCTCCCGGCGACCCTCC
3061 ---------+---------+---------+---------+---------+---------+
          GAGGGACTCTCACAAATGGCTCCGGTACTGGTCTATGTCGCGGGGAGGGCCGCTGGGAGG
           S  L  R  V  F  T  E  A  M  T  R  Y  S  A  P  P  G  D  P  P

          CCAGCCCGAGTACGATCTGGAGCTGATCACCAGCTGCTCCAGCAATGTGGGCGTGGCTCA
3121 ---------+---------+---------+---------+---------+---------+
          GGTCGGGCTCATGCTAGACCTCGACTAGTGGTCGACGAGGTCGTTACACCCGCACCGAGT
           Q  P  E  Y  D  L  E  L  I  T  S  C  S  S  N  V  G  V  A  H

          CGACGCCAGCGGCAAGAGAGTGTACTACCTGACCAGGGACCCCACCACCCCTCTGGCCAG
3181 ---------+---------+---------+---------+---------+---------+
          GCTGCGGTCGCCGTTCTCTCACATGATGGACTGGTCCCTGGGGTGGTGGGGAGACCGGTC
           D  A  S  G  K  R  V  Y  Y  L  T  R  D  P  T  T  P  L  A  R

          AGCCGCCTGGGAGACAGTGAGACACACCCCCGTGAACAGCTGGCTGGGCAACATCATCAT
3241 ---------+---------+---------+---------+---------+---------+
          TCGGCGGACCCTCTGTCACTCTGTGTGGGGGCACTTGTCGACCGACCCGTTGTAGTAGTA
           A  A  W  E  T  V  R  H  T  P  V  N  S  W  L  G  N  I  I  M

          GTACGCCCCTACCCTGTGGGCCAGAATGATCCTGATGACCCACTTCTTCAGCATCCTGCT
3301 ---------+---------+---------+---------+---------+---------+
          CATGCGGGGATGGGACACCCGGTCTTACTAGGACTACTGGGTGAAGAAGTCGTAGGACGA
           Y  A  P  T  L  W  A  R  M  I  L  M  T  H  F  F  S  I  L  L

          GGCCCAGGAGCAGCTGGAGAAGGCCCTGGACTGCCAGATCTACGGCGCCTGCTACAGCAT
3361 ---------+---------+---------+---------+---------+---------+
          CCGGGTCCTCGTCGACCTCTTCCGGGACCTGACGGTCTAGATGCCGCGGACGATGTCGTA
           A  Q  E  Q  L  E  K  A  L  D  C  Q  I  Y  G  A  C  Y  S  I

          CGAGCCTCTGGACCTGCCTCAGATCATCGAGAGACTGCACGGCCTGAGCGCCTTCAGCCT
3421 ---------+---------+---------+---------+---------+---------+
          GCTCGGAGACCTGGACGGAGTCTAGTAGCTCTCTGACGTGCCGGACTCGCGGAAGTCGGA
           E  P  L  D  L  P  Q  I  I  E  R  L  H  G  L  S  A  F  S  L

          GCACAGCTACAGCCCAGGCGAGATCAATAGAGTGGCCAGCTGCCTGAGAAAGCTGGGCGT
3481 ---------+---------+---------+---------+---------+---------+
          CGTGTCGATGTCGGGTCCGCTCTAGTTATCTCACCGGTCGACGGACTCTTTCGACCCGCA
           H  S  Y  S  P  G  E  I  N  R  V  A  S  C  L  R  K  L  G  V
```

Fig. 4F

```
     GCCACCTCTGAGAGTGTGGCGGCACAGAGCCAGATCTGTGAGGGCCAAGCTGCTGTCCCA
3541---------+---------+---------+---------+---------+---------+
     CGGTGGAGACTCTCACACCGCCGTGTCTCGGTCTAGACACTCCCGGTTCGACGACAGGGT
     _P__P__L__R__V__W__R__H__R__A__R__S__V__R__A__K__L__L__S__Q_

     GGGCGGCAGGGCCGCCACCTGTGGCAAGTACCTGTTCAACTGGGCCGTGAGGACAAAGCT
3601---------+---------+---------+---------+---------+---------+
     CCCGCCGTCCCGGCGGTGGACACCGTTCATGGACAAGTTGACCCGGCACTCCTGTTTCGA
     _G__G__R__A__A__T__C__G__K__Y__L__F__N__W__A__V__R__T__K__L_

     GAAGCTGACACCCATCCCTGCCGCCAGCCAGCTGGACCTGAGCGGCTGGTTCGTGGCCGG
3661---------+---------+---------+---------+---------+---------+
     CTTCGACTGTGGGTAGGGACGGCGGTCGGTCGACCTGGACTCGCCGACCAAGCACCGGCC

     _K__L__T__P__I__P__A__A__S__Q__L__D__L__S__G__W__F__V__A__G_

     CTACAATGGCGGCGACATCTACCACAGCCTGTCCAGGGCCAGGCCTAGATGATGAGGAGC
3721---------+---------+---------+---------+---------+---------+
     GATGTTACCGCCGCTGTAGATGGTGTCGGACAGGTCCCGGTCCGGATCTACTACTCCTCG
     _Y__N__G__G__D__I__Y__H__S__L__S__R__A__R__P__R__*__*__

     TCCAGCTTTTGTTCCC
3781---------+------
     AGGTCGAAAACAAGGG
```

Fig. 5A 4A-3-5B fusion protein
Optimized for expression in: Pichia pastoris

SEQ ID NO:25
SEQ ID NO:26
SEQ ID NO:9

```
     ATGGGGTCCGTTGTTATCGTTGGTAGAATCATCTTGTCTGGTTCTGGTTCCGCTCCAATT
1    ---------+---------+---------+---------+---------+---------+
     TACCCCAGGCAACAATAGCAACCATCTTAGTAGAACAGACCAAGACCAAGGCGAGGTTAA
     M__G__S__V__V__I__V__G__R__I__I__L__S__G__S__G__S__A__P__I__

     ACTGCTTACTCCCAGCAGACTAGAGGATTGTTGGGTTGTATCATCACTTCCTTGACTGGT
61   ---------+---------+---------+---------+---------+---------+
     TGACGAATGAGGGTCGTCTGATCTCCTAACAACCCAACATAGTAGTGAAGGAACTGACCA
     T__A__Y__S__Q__Q__T__R__G__L__L__G__C__I__I__T__S__L__T__G__

     AGAGACAAGAACCAAGTTGACGGAGAGGTTCAGGTTTTGTCCACTGCTACTCAGTCTTTC
121  ---------+---------+---------+---------+---------+---------+
     TCTCTGTTCTTGGTTCAACTGCCTCTCCAAGTCCAAAACAGGTGACGATGAGTCAGAAAG
     R__D__K__N__Q__V__D__G__E__V__Q__V__L__S__T__A__T__Q__S__F__

     TTGGCTACTTGTGTTAACGGTGTTTGTTGGACTGTTTACGCTGGTGCTGGTTCTAAAACT
181  ---------+---------+---------+---------+---------+---------+
     AACCGATGAACACAATTGCCACAAACAACCTGACAAATGCGACCACGACCAAGATTTTGA
     L__A__T__C__V__N__G__V__C__W__T__V__Y__A__G__A__G__S__K__T__

     TTGGCTGGTCCAAAGGGTCCAATCACTCAGATGTACACAAACGTTGACCAGGATTTGGTT
241  ---------+---------+---------+---------+---------+---------+
     AACCGACCAGGTTTCCCAGGTTAGTGAGTCTACATGTGTTTGCAACTGGTCCTAAACCAA
     L__A__G__P__K__G__P__I__T__Q__M__Y__T__N__V__D__Q__D__L__V__

     GGTTGGCCAGCTCCACCAGGTGCTAGATCCATGACTCCATGTACTTGTGGTTCCTCCGAC
301  ---------+---------+---------+---------+---------+---------+
     CCAACCGGTCGAGGTGGTCCACGATCTAGGTACTGAGGTACATGAACACCAAGGAGGCTG
     G__W__P__A__P__P__G__A__R__S__M__T__P__C__T__C__G__S__S__D__

     TTGTACTTGGTTACTAGACACGCTGACGTTATCCCAGTTAGAAGAAGAGGAGACTCCAGA
361  ---------+---------+---------+---------+---------+---------+
     AACATGAACCAATGATCTGTGCGACTGCAATAGGGTCAATCTTCTTCTCCTCTGAGGTCT
     L__Y__L__V__T__R__H__A__D__V__I__P__V__R__R__R__G__D__S__R__

     GGATCTTTGTTGTCCCCAAGACCAGTTTCTTACTTGAAGGGATCTTCCGGTGGTCCATTG
421  ---------+---------+---------+---------+---------+---------+
     CCTAGAAACAACAGGGGTTCTGGTCAAAGAATGAACTTCCCTAGAAGGCCACCAGGTAAC
     G__S__L__L__S__P__R__P__V__S__Y__L__K__G__S__S__G__G__P__L__

     TTGTGTCCATCCGGTCACGTTGTTGGTATTTTCAGAGCTGCTGTTTGTACTAGAGGTGTT
481  ---------+---------+---------+---------+---------+---------+
     AACACAGGTAGGCCAGTGCAACAACCATAAAAGTCTCGACGACAAACATGATCTCCACAA
     L__C__P__S__G__H__V__V__G__I__F__R__A__A__V__C__T__R__G__V__

     GCTAAGGCTGTTGACTTCATCCCAGTTGAGTCCATGGAGACTACTATGAGATCCCCAGTT
541  ---------+---------+---------+---------+---------+---------+
     CGATTCCGACAACTGAAGTAGGGTCAACTCAGGTACCTCTGATGATACTCTAGGGGTCAA
     A__K__A__V__D__F__I__P__V__E__S__M__E__T__T__M__R__S__P__V__

     TTCACTGACAACTCTTCCCCACCTGCTGTTCCACAAACTTTCCAAGTTGCTCACTTGCAT
601  ---------+---------+---------+---------+---------+---------+
     AAGTGACTGTTGAGAAGGGGTGGACGACAAGGTGTTTGAAAGGTTCAACGAGTGAACGTA
     F__T__D__N__S__S__P__P__A__V__P__Q__T__F__Q__V__A__H__L__H__
```

Fig. 5B

```
     GCTCCAACTGGTTCTGGTAAGTCCACTAAGGTTCCAGCTGCTTACGCTGCTCAAGGTTAC
661  ---------+---------+---------+---------+---------+---------+
     CGAGGTTGACCAAGACCATTCAGGTGATTCCAAGGTCGACGAATGCGACGAGTTCCAATG
     A__P__T__G__S__G__K__S__T__K__V__P__A__A__Y__A__A__Q__G__Y__

     AAGGTTTTGGTTTTGAACCCATCCGTTGCTGCTACTTTGGGTTTCGGTGCTTACATGTCT
721  ---------+---------+---------+---------+---------+---------+
     TTCCAAAACCAAAACTTGGGTAGGCAACGACGATGAAACCCAAAGCCACGAATGTACAGA
     K__V__L__V__L__N__P__S__V__A__A__T__L__G__F__G__A__Y__M__S__

     AAGGCTCACGGTATTGAGCCAAACATCAGAACTGGTGTTAGAACTATCACTACTGGTGGT
781  ---------+---------+---------+---------+---------+---------+
     TTCCGAGTGCCATAACTCGGTTTGTAGTCTTGACCACAATCTTGATAGTGATGACCACCA
     K__A__H__G__I__E__P__N__I__R__T__G__V__R__T__I__T__T__G__G__

     CCTATTACTTACTCCGCTTACGGAAAGTTTTTGGCTGACGGTGGTTGTTCTGGTGGTGCT
841  ---------+---------+---------+---------+---------+---------+
     GGATAATGAATGAGGCGAATGCCTTTCAAAAACCGACTGCCACCAACAAGACCACCACGA
     P__I__T__Y__S__A__Y__G__K__F__L__A__D__G__G__C__S__G__G__A__

     TACGACATCATCATCTGTGACGAGTGTCACTCTACTGACTGGACTACTATCTTGGGTATC
901  ---------+---------+---------+---------+---------+---------+
     ATGCTGTAGTAGTAGACACTGCTCACAGTGAGATGACTGACCTGATGATAGAACCCATAG
     Y__D__I__I__I__C__D__E__C__H__S__T__D__W__T__T__I__L__G__I__

     GGTACTGTTTTGGACCAAGCTGAAACTGCTGGTGCTAGATTGGTTGTTTTGGCTACTGCT
961  ---------+---------+---------+---------+---------+---------+
     CCATGACAAAACCTGGTTCGACTTTGACGACCACGATCTAACCAACAAAACCGATGACGA
     G__T__V__L__D__Q__A__E__T__A__G__A__R__L__V__V__L__A__T__A__

     ACTCCACCAGGTTCCATTACTGTTCCACACCCAAACATCGAGGAAGTTGCTTTGTCTAAC
1021 ---------+---------+---------+---------+---------+---------+
     TGAGGTGGTCCAAGGTAATGACAAGGTGTGGGTTTGTAGCTCCTTCAACGAAACAGATTG
     T__P__P__G__S__I__T__V__P__H__P__N__I__E__E__V__A__L__S__N__

     ACTGGAGAGATCCCATTCTACGGAAAGGCTATCCCAATTGAGGCTATCAAGGGTGGTAGA
1081 ---------+---------+---------+---------+---------+---------+
     TGACCTCTCTAGGGTAAGATGCCTTTCCGATAGGGTTAACTCCGATAGTTCCCACCATCT
     T__G__E__I__P__F__Y__G__K__A__I__P__I__E__A__I__K__G__G__R__

     CACTTGATTTTCTGTCACTCCAAGAAGAAGTGTGACGAGTTGGCTGCTAAGTTGACTGGA
1141 ---------+---------+---------+---------+---------+---------+
     GTGAACTAAAAGACAGTGAGGTTCTTCTTCACACTGCTCAACCGACGATTCAACTGACCT

     TTGGGATTGAACGCTGTTGCTTACTACAGAGGATTGGACGTTTCCGTTATCCCAACTTCC
1201 ---------+---------+---------+---------+---------+---------+
     AACCCTAACTTGCGACAACGAATGATGTCTCCTAACCTGCAAAGGCAATAGGGTTGAAGG
     L__G__L__N__A__V__A__Y__Y__R__G__L__D__V__S__V__I__P__T__S__

     GGTGATGTTGTTGTTGTTGCTACTGACGCTTTGATGACTGGTTTCACTGGTGACTTCGAC
1261 ---------+---------+---------+---------+---------+---------+
     CCACTACAACAACAACAACGATGACTGCGAAACTACTGACCAAAGTGACCACTGAAGCTG
     G__D__V__V__V__V__A__T__D__A__L__M__T__G__F__T__G__D__F__D__

     TCCGTTATCGACTGTAACACTTGTGTTACTCAGACTGTTGACTTCTCCTTGGACCCAACT
1321 ---------+---------+---------+---------+---------+---------+
     AGGCAATAGCTGACATTGTGAACACAATGAGTCTGACAACTGAAGAGGAACCTGGGTTGA
     S__V__I__D__C__N__T__C__V__T__Q__T__V__D__F__S__L__D__P__T__
```

Fig. 5C

```
     TTCACTATCGAGACTACTACTGTTCCTCAAGACGCTGTTTCCAGATCCCAAAGAAGAGGT
1381---------+---------+---------+---------+---------+---------+
     AAGTGATAGCTCTGATGATGACAAGGAGTTCTGCGACAAAGGTCTAGGGTTTCTTCTCCA
     F__T__I__E__T__T__T__V__P__Q__D__A__V__S__R__S__Q__R__R__G__

     GCTACTGGTAGAGGAAGATCCGGTATCTACAGATTCGTTACTCCAGGTGAAAGACCATCT
1441---------+---------+---------+---------+---------+---------+
     CGATGACCATCTCCTTCTAGGCCATAGATGTCTAAGCAATGAGGTCCACTTTCTGGTAGA
     A__T__G__R__G__R__S__G__I__Y__R__F__V__T__P__G__E__R__P__S__

     GGAATGTTCGACTCCTCCGTTTTGTGTGAATGTTACGACGCTGGTTGTGCTTGGTACGAA
1501---------+---------+---------+---------+---------+---------+
     CCTTACAAGCTGAGGAGGCAAAACACACTTACAATGCTGCGACCAACACGAACCATGCTT
     G__M__F__D__S__S__V__L__C__E__C__Y__D__A__G__C__A__W__Y__E__

     TTGACTCCAGCTGAGACTACTGTTAGATTGAGAGCTTACTTGAACACTCCAGGATTGCCA
1561---------+---------+---------+---------+---------+---------+
     AACTGAGGTCGACTCTGATGACAATCTAACTCTCGAATGAACTTGTGAGGTCCTAACGGT
     L__T__P__A__E__T__T__V__R__L__R__A__Y__L__N__T__P__G__L__P__

     GTTTGTCAAGACCACTTGGAATTCTGGGAGTCCGTTTTCACTGGATTGACTCACATTGAC
1621---------+---------+---------+---------+---------+---------+
     CAAACAGTTCTGGTGAACCTTAAGACCCTCAGGCAAAAGTGACCTAACTGAGTGTAACTG
     V__C__Q__D__H__L__E__F__W__E__S__V__F__T__G__L__T__H__I__D__

     GCTCACTTTTTGTCCCAAACTAAGCAGGCTGGTGACAACTTTCCATACTTGGTTGCTTAC
1681---------+---------+---------+---------+---------+---------+
     CGAGTGAAAAACAGGGTTTGATTCGTCCGACCACTGTTGAAAGGTATGAACCAACGAATG
     A__H__F__L__S__Q__T__K__Q__A__G__D__N__F__P__Y__L__V__A__Y__

     CAGGCTACTGTTTGTGCTAGAGCACAAGCTCCACCACCATCTTGGGATCAGATGTGGAAG
1741---------+---------+---------+---------+---------+---------+
     GTCCGATGACAAACACGATCTCGTGTTCGAGGTGGTGGTAGAACCCTAGTCTACACCTTC
     Q__A__T__V__C__A__R__A__Q__A__P__P__P__S__W__D__Q__M__W__K__

     TGTTTGATCAGATTGAAGCCAACTTTGCACGGTCCAACTCCATTGTTGTACAGATTGGGT
1801---------+---------+---------+---------+---------+---------+
     ACAAACTAGTCTAACTTCGGTTGAAACGTGCCAGGTTGAGGTAACAACATGTCTAACCCA
     C__L__I__R__L__K__P__T__L__H__G__P__T__P__L__L__Y__R__L__G__

     GCTGTTCAGAACGAGATCACTTTGACTCACCCAATCACTAAGTTCGTTATGGCTTGCATG
1861---------+---------+---------+---------+---------+---------+
     CGACAAGTCTTGCTCTAGTGAAACTGAGTGGGTTAGTGATTCAAGCAATACCGAACGTAC
     A__V__Q__N__E__I__T__L__T__H__P__I__T__K__F__V__M__A__C__M__

     TCTGCTGACTTGGAAGTTGTTGGTTCCGGATCTGGTTCCATGTCCTACACTTGGACTGGT
1921---------+---------+---------+---------+---------+---------+
     AGACGACTGAACCTTCAACAACCAAGGCCTAGACCAAGGTACAGGATGTGAACCTGACCA
     S__A__D__L__E__V__V__G__S__G__S__G__S__M__S__Y__T__W__T__G__

     GCTTTGATCACTCCATGTGCTGCTGAAGAATCCAAGTTGCCAATCAACCCATTGTCCAAC
1981---------+---------+---------+---------+---------+---------+
     CGAAACTAGTGAGGTACACGACGACTTCTTAGGTTCAACGGTTAGTTGGGTAACAGGTTG
     A__L__I__T__P__C__A__A__E__E__S__K__L__P__I__N__P__L__S__N__

     TCTTTGTTGAGACACCACTCCATGGTTTACTCCACTACTTCCAGATCCGCTTCCTTGAGA
2041---------+---------+---------+---------+---------+---------+
     AGAAACAACTCTGTGGTGAGGTACCAAATGAGGTGATGAAGGTCTAGGCGAAGGAACTCT
     S__L__L__R__H__H__S__M__V__Y__S__T__T__S__R__S__A__S__L__R__
```

Fig. 5D

```
     CAGAAGAAGGTTACATTCGACAGATTGCAGGTTTTGGACGACCACTACAGAGATGTTTTG
2101---------+---------+---------+---------+---------+---------+
     GTCTTCTTCCAATGTAAGCTGTCTAACGTCCAAAACCTGCTGGTGATGTCTCTACAAAAC
     Q__K__K__V__T__F__D__R__L__Q__V__L__D__D__H__Y__R__D__V__L__

     AAGGAGATGAAGGCTAAGGCTTCCACTGTTAAGGCTAGATTGTTGTCCATTGAGGAGGCT
2161---------+---------+---------+---------+---------+---------+
     TTCCTCTACTTCCGATTCCGAAGGTGACAATTCCGATCTAACAACAGGTAACTCCTCCGA
     K__E__M__K__A__K__A__S__T__V__K__A__R__L__L__S__I__E__E__A__

     TGTAAGTTGACTCCACCACACTCTGCTAAGTCCAAGTTTGGTTACGGTGCTAAGGATGTT
2221---------+---------+---------+---------+---------+---------+
     ACATTCAACTGAGGTGGTGTGAGACGATTCAGGTTCAAACCAATGCCACGATTCCTACAA
     C__K__L__T__P__P__H__S__A__K__S__K__F__G__Y__G__A__K__D__V__

     AGATCCTTGTCCTCCAGAGCTGTTAACCACATCAGATCCGTTTGGGAGGATTTGTTGGAG
2281---------+---------+---------+---------+---------+---------+
     TCTAGGAACAGGAGGTCTCGACAATTGGTGTAGTCTAGGCAAACCCTCCTAAACAACCTC
     R__S__L__S__S__R__A__V__N__H__I__R__S__V__W__E__D__L__L__E__

     GACACTGAGACTCCAATCGACACTACTATCATGGCTAAGAACGAGGTTTTCTGTGTTCAA
2341---------+---------+---------+---------+---------+---------+
     CTGTGACTCTGAGGTTAGCTGTGATGATAGTACCGATTCTTGCTCCAAAAGACACAAGTT
     D__T__E__T__P__I__D__T__T__I__M__A__K__N__E__V__F__C__V__Q__

     CCAGAGAAGGGTGGAAGAAAGCCAGCTAGATTGATCGTTTTCCCAGACTTGGGTGTTAGA
2401---------+---------+---------+---------+---------+---------+
     GGTCTCTTCCCACCTTCTTTCGGTCGATCTAACTAGCAAAAGGGTCTGAACCCACAATCT
     P__E__K__G__G__R__K__P__A__R__L__I__V__F__P__D__L__G__V__R__

     GTTTGTGAGAAGATGGCTTTGTACGACGTTGTTTCCACTTTGCCACAGGCTGTTATGGGA
2461---------+---------+---------+---------+---------+---------+
     CAAACACTCTTCTACCGAAACATGCTGCAACAAAGGTGAAACGGTGTCCGACAATACCCT
     V__C__E__K__M__A__L__Y__D__V__V__S__T__L__P__Q__A__V__M__G__

     CCATCTTACGGTTTCCAATACTCCCCAGGACAAAGAGTTGAGTTCTTGGTTAACACTTGG
2521---------+---------+---------+---------+---------+---------+
     GGTAGAATGCCAAAGGTTATGAGGGGTCCTGTTTCTCAACTCAAGAACCAATTGTGAACC
     P__S__Y__G__F__Q__Y__S__P__G__Q__R__V__E__F__L__V__N__T__W__

     AAGTCCAAGAAATGTCCAATGGGATTCTCCTACAACACTAGATGTTTCGACTCCACTGTT
2581---------+---------+---------+---------+---------+---------+
     TTCAGGTTCTTTACAGGTTACCCTAAGAGGATGTTGTGATCTACAAAGCTGAGGTGACAA
     K__S__K__K__C__P__M__G__F__S__Y__N__T__R__C__F__D__S__T__V__

     ACTGAGAACGACATCAGAACAGAGGAGTCCATCTACCAGTGTTGTGACTTGGCTCCAGAA
2641---------+---------+---------+---------+---------+---------+
     TGACTCTTGCTGTAGTCTTGTCTCCTCAGGTAGATGGTCACAACACTGAACCGAGGTCTT
     T__E__N__D__I__R__T__E__E__S__I__Y__Q__C__C__D__L__A__P__E__

     GCTAGACAAGCTATCAAGTCCTTGACTGAGAGATTGTACATCGGTGGTCCTTTGACTAAC
2701---------+---------+---------+---------+---------+---------+
     CGATCTGTTCGATAGTTCAGGAACTGACTCTCTAACATGTAGCCACCAGGAAACTGATTG
     A__R__Q__A__I__K__S__L__T__E__R__L__Y__I__G__G__P__L__T__N__

     TCCAAGGGACAGAACTGTGGTTACAGAAGATGTAGAGCTTCCGGTGTTTTGACTACTTCC
2761---------+---------+---------+---------+---------+---------+
     AGGTTCCCTGTCTTGACACCAATGTCTTCTACATCTCGAAGGCCACAAAACTGATGAAGG
     S__K__G__Q__N__C__G__Y__R__R__C__R__A__S__G__V__L__T__T__S__
```

Fig. 5E

```
     TGTGGTAACACTTTGACTTGTTACTTGAAGGCTACTGCTGCTTGTAGAGCTGCTAAATTG
2821---------+---------+---------+---------+---------+---------+
     ACACCATTGTGAAACTGAACAATGAACTTCCGATGACGACGAACATCTCGACGATTTAAC
     C  G  N  T  L  T  C  Y  L  K  A  T  A  A  C  R  A  A  K  L

     CAGGACTGTACTATGTTGGTTAACGGTAACGACTTGGTTGTTATCTGTGAGTCCGCTGGT
2881---------+---------+---------+---------+---------+---------+
     GTCCTGACATGATACAACCAATTGCCATTGCTGAACCAACAATAGACACTCAGGCGACCA

     Q  D  C  T  M  L  V  N  G  N  D  L  V  V  I  C  E  S  A  G

     ACTCAAGAAGATGCTGCTTCTTTGAGAGTTTTCACAGAGGCTATGACTAGATACTCTGCT
2941---------+---------+---------+---------+---------+---------+
     TGAGTTCTTCTACGACGAAGAAACTCTCAAAAGTGTCTCCGATACTGATCTATGAGACGA
     T  Q  E  D  A  A  S  L  R  V  F  T  E  A  M  T  R  Y  S  A

     CCACCTGGTGATCCACCACAACCAGAATACGACTTGGAGTTGATCACTTCCTGTTCCTCC
3001---------+---------+---------+---------+---------+---------+
     GGTGGACCACTAGGTGGTGTTGGTCTTATGCTGAACCTCAACTAGTGAAGGACAAGGAGG
     P  P  G  D  P  P  Q  P  E  Y  D  L  E  L  I  T  S  C  S  S

     AATGTTGGTGTTGCTCACGATGCTTCCGGAAAGAGAGTTTACTACTTGACTAGAGACCCA
3061---------+---------+---------+---------+---------+---------+
     TTACAACCACAACGAGTGCTACGAAGGCCTTTCTCTCAAATGATGAACTGATCTCTGGGT
     N  V  G  V  A  H  D  A  S  G  K  R  V  Y  Y  L  T  R  D  P

     ACTACTCCATTGGCTAGAGCTGCTTGGGAAACTGTTAGACACACTCCAGTTAACTCCTGG
3121---------+---------+---------+---------+---------+---------+
     TGATGAGGTAACCGATCTCGACGAACCCTTTGACAATCTGTGTGAGGTCAATTGAGGACC
     T  T  P  L  A  R  A  A  W  E  T  V  R  H  T  P  V  N  S  W

     TTGGGTAACATCATCATGTACGCTCCAACTTTGTGGGCTAGAATGATCTTGATGACTCAC
3181---------+---------+---------+---------+---------+---------+
     AACCCATTGTAGTAGTACATGCGAGGTTGAAACACCCGATCTTACTAGAACTACTGAGTG
     L  G  N  I  I  M  Y  A  P  T  L  W  A  R  M  I  L  M  T  H

     TTCTTCTCCATCTTGTTGGCTCAAGAGCAATTGGAAAAGGCTTTGGACTGTCAGATTTAC
3241---------+---------+---------+---------+---------+---------+
     AAGAAGAGGTAGAACAACCGAGTTCTCGTTAACCTTTTCCGAAACCTGACAGTCTAAATG
     F  F  S  I  L  L  A  Q  E  Q  L  E  K  A  L  D  C  Q  I  Y

     GGTGCTTGTTACTCCATTGAGCCATTGGACTTGCCACAGATCATTGAGAGATTGCACGGT
3301---------+---------+---------+---------+---------+---------+
     CCACGAACAATGAGGTAACTCGGTAACCTGAACGGTGTCTAGTAACTCTCTAACGTGCCA
     G  A  C  Y  S  I  E  P  L  D  L  P  Q  I  I  E  R  L  H  G
     TTGTCTGCTTTCTCTTTGCACTCTTACTCCCCTGGTGAAATCAACAGAGTTGCTTCCTGT
3361---------+---------+---------+---------+---------+---------+
     AACAGACGAAAGAGAAACGTGAGAATGAGGGGACCACTTTAGTTGTCTCAACGAAGGACA
     L  S  A  F  S  L  H  S  Y  S  P  G  E  I  N  R  V  A  S  C

     TTGAGAAAGTTGGGTGTTCCACCATTGAGAGTTTGGAGACACAGAGCTAGATCCGTTAGA
3421---------+---------+---------+---------+---------+---------+
     AACTCTTTCAACCCACAAGGTGGTAACTCTCAAACCTCTGTGTCTCGATCTAGGCAATCT
     L  R  K  L  G  V  P  P  L  R  V  W  R  H  R  A  R  S  V  R

     GCTAAGTTGTTGTCCCAAGGTGGAAGAGCTGCTACTTGTGGTAAGTACTTGTTCAACTGG
3481---------+---------+---------+---------+---------+---------+
     CGATTCAACAACAGGGTTCCACCTTCTCGACGATGAACACCATTCATGAACAAGTTGACC
     A  K  L  L  S  Q  G  G  R  A  A  T  C  G  K  Y  L  F  N  W
```

Fig. 5F

```
     GCTGTTAGAACAAAGTTGAAGTTGACTCCTATTCCTGCTGCTTCCCAATTGGATTTGTCC
3541---------+---------+---------+---------+---------+---------+
     CGACAATCTTGTTTCAACTTCAACTGAGGATAAGGACGACGAAGGGTTAACCTAAACAGG
     A__V__R__T__K__L__K__L__T__P__I__P__A__A__S__Q__L__D__L__S__

     GGTTGGTTTGTTGCTGGTTACAACGGTGGTGACATCTACCACTCTTTGTCCAGAGCTAGA
3601---------+---------+---------+---------+---------+---------+
     CCAACCAAACAACGACCAATGTTGCCACCACTGTAGATGGTGAGAAACAGGTCTCGATCT
     G__W__F__V__A__G__Y__N__G__G__D__I__Y__H__S__L__S__R__A__R__

     CCAAGATAATAGACTAGTGGATCC
3661---------+---------+----

     GGTTCTATTATCTGATCACCTAGG
     P__R__*__*__
```

Fig. 6A

4A-3-4B-5B fusion protein

Optimized for expression in Pichia pastoris

SEQ ID NO:27

SEQ ID NO:28

SEQ ID NO:10

```
    ATGGGGTCCGTTGTTATCGTTGGTAGAATCATCTTGTCTGGTTCTGGTTCCGCTCCAATT
1   ---------+---------+---------+---------+---------+---------+
    TACCCCAGGCAACAATAGCAACCATCTTAGTAGAACAGACCAAGACCAAGGCGAGGTTAA
    M__G__S__V__V__I__V__G__R__I__I__L__S__G__S__G__S__A__P__I__

    ACTGCTTACTCCCAGCAGACTAGAGGATTGTTGGGTTGTATCATCACTTCCTTGACTGGT
61  ---------+---------+---------+---------+---------+---------+
    TGACGAATGAGGGTCGTCTGATCTCCTAACAACCCAACATAGTAGTGAAGGAACTGACCA
    T__A__Y__S__Q__Q__T__R__G__L__L__G__C__I__I__T__S__L__T__G__

    AGAGACAAGAACCAAGTTGACGGAGAGGTTCAGGTTTTGTCCACTGCTACTCAGTCTTTC
121 ---------+---------+---------+---------+---------+---------+
    TCTCTGTTCTTGGTTCAACTGCCTCTCCAAGTCCAAAACAGGTGACGATGAGTCAGAAAG
    R__D__K__N__Q__V__D__G__E__V__Q__V__L__S__T__A__T__Q__S__F__

    TTGGCTACTTGTGTTAACGGTGTTTGTTGGACTGTTTACGCTGGTGCTGGTTCTAAAACT
181 ---------+---------+---------+---------+---------+---------+
    AACCGATGAACACAATTGCCACAAACAACCTGACAAATGCGACCACGACCAAGATTTTGA
    L__A__T__C__V__N__G__V__C__W__T__V__Y__A__G__A__G__S__K__T__

    TTGGCTGGTCCAAAGGGTCCAATCACTCAGATGTACACAAACGTTGACCAGGATTTGGTT
241 ---------+---------+---------+---------+---------+---------+
    AACCGACCAGGTTTCCCAGGTTAGTGAGTCTACATGTGTTTGCAACTGGTCCTAAACCAA
    L__A__G__P__K__G__P__I__T__Q__M__Y__T__N__V__D__Q__D__L__V__

    GGTTGGCCAGCTCCACCAGGTGCTAGATCCATGACTCCATGTACTTGTGGTTCCTCCGAC
301 ---------+---------+---------+---------+---------+---------+
    CCAACCGGTCGAGGTGGTCCACGATCTAGGTACTGAGGTACATGAACACCAAGGAGGCTG
    G__W__P__A__P__P__G__A__R__S__M__T__P__C__T__C__G__S__S__D__

    TTGTACTTGGTTACTAGACACGCTGACGTTATCCCAGTTAGAAGAAGAGGAGACTCCAGA
361 ---------+---------+---------+---------+---------+---------+
    AACATGAACCAATGATCTGTGCGACTGCAATAGGGTCAATCTTCTTCTCCTCTGAGGTCT
    L__Y__L__V__T__R__H__A__D__V__I__P__V__R__R__R__G__D__S__R__

    GGATCTTTGTTGTCCCCAAGACCAGTTTCTTACTTGAAGGGATCTTCCGGTGGTCCATTG
421 ---------+---------+---------+---------+---------+---------+
    CCTAGAAACAACAGGGGTTCTGGTCAAAGAATGAACTTCCCTAGAAGGCCACCAGGTAAC
    G__S__L__L__S__P__R__P__V__S__Y__L__K__G__S__S__G__G__P__L__

    TTGTGTCCATCCGGTCACGTTGTTGGTATTTTCAGAGCTGCTGTTTGTACTAGAGGTGTT
481 ---------+---------+---------+---------+---------+---------+
    AACACAGGTAGGCCAGTGCAACAACCATAAAAGTCTCGACGACAAACATGATCTCCACAA
    L__C__P__S__G__H__V__V__G__I__F__R__A__A__V__C__T__R__G__V__

    GCTAAGGCTGTTGACTTCATCCCAGTTGAGTCCATGGAGACTACTATGAGATCCCCAGTT
541 ---------+---------+---------+---------+---------+---------+
    CGATTCCGACAACTGAAGTAGGGTCAACTCAGGTACCTCTGATGATACTCTAGGGGTCAA
    A__K__A__V__D__F__I__P__V__E__S__M__E__T__T__M__R__S__P__V__
```

Fig. 6B

```
    TTCACTGACAACTCTTCCCCACCTGCTGTTCCACAAACTTTCCAAGTTGCTCACTTGCAT
601 ---------+---------+---------+---------+---------+---------+
    AAGTGACTGTTGAGAAGGGGTGGACGACAAGGTGTTTGAAAGGTTCAACGAGTGAACGTA
    F__T__D__N__S__S__P__P__A__V__P__Q__T__F__Q__V__A__H__L__H__

    GCTCCAACTGGTTCTGGTAAGTCCACTAAGGTTCCAGCTGCTTACGCTGCTCAAGGTTAC
661 ---------+---------+---------+---------+---------+---------+
    CGAGGTTGACCAAGACCATTCAGGTGATTCCAAGGTCGACGAATGCGACGAGTTCCAATG
    A__P__T__G__S__G__K__S__T__K__V__P__A__A__Y__A__A__Q__G__Y__

    AAGGTTTTGGTTTTGAACCCATCCGTTGCTGCTACTTTGGGTTTCGGTGCTTACATGTCT
721 ---------+---------+---------+---------+---------+---------+
    TTCCAAAACCAAAACTTGGGTAGGCAACGACGATGAAACCCAAAGCCACGAATGTACAGA
    K__V__L__V__L__N__P__S__V__A__A__T__L__G__F__G__A__Y__M__S__

    AAGGCTCACGGTATTGAGCCAAACATCAGAACTGGTGTTAGAACTATCACTACTGGTGGT
781 ---------+---------+---------+---------+---------+---------+
    TTCCGAGTGCCATAACTCGGTTTGTAGTCTTGACCACAATCTTGATAGTGATGACCACCA
    K__A__H__G__I__E__P__N__I__R__T__G__V__R__T__I__T__T__G__G__

    CCTATTACTTACTCCGCTTACGGAAAGTTTTTGGCTGACGGTGGTTGTTCTGGTGGTGCT
841 ---------+---------+---------+---------+---------+---------+
    GGATAATGAATGAGGCGAATGCCTTTCAAAAACCGACTGCCACCAACAAGACCACCACGA
    P__I__T__Y__S__A__Y__G__K__F__L__A__D__G__G__C__S__G__G__A__

    TACGACATCATCATCTGTGACGAGTGTCACTCTACTGACTGGACTACTATCTTGGGTATC
901 ---------+---------+---------+---------+---------+---------+
    ATGCTGTAGTAGTAGACACTGCTCACAGTGAGATGACTGACCTGATGATAGAACCCATAG
    Y__D__I__I__I__C__D__E__C__H__S__T__D__W__T__T__I__L__G__I__

    GGTACTGTTTTGGACCAAGCTGAAACTGCTGGTGCTAGATTGGTTGTTTTGGCTACTGCT
961 ---------+---------+---------+---------+---------+---------+
    CCATGACAAAACCTGGTTCGACTTTGACGACCACGATCTAACCAACAAAACCGATGACGA
    G__T__V__L__D__Q__A__E__T__A__G__A__R__L__V__V__L__A__T__A__

    ACTCCACCAGGTTCCATTACTGTTCCACACCCAAACATCGAGGAAGTTGCTTTGTCTAAC
1021---------+---------+---------+---------+---------+---------+
    TGAGGTGGTCCAAGGTAATGACAAGGTGTGGGTTTGTAGCTCCTTCAACGAAACAGATTG
    T__P__P__G__S__I__T__V__P__H__P__N__I__E__E__V__A__L__S__N__

    ACTGGAGAGATCCCATTCTACGGAAAGGCTATCCCAATTGAGGCTATCAAGGGTGGTAGA
1081---------+---------+---------+---------+---------+---------+
    TGACCTCTCTAGGGTAAGATGCCTTTCCGATAGGGTTAACTCCGATAGTTCCCACCATCT
    T__G__E__I__P__F__Y__G__K__A__I__P__I__E__A__I__K__G__G__R__

    CACTTGATTTTCTGTCACTCCAAGAAGAAGTGTGACGAGTTGGCTGCTAAGTTGACTGGA
1141---------+---------+---------+---------+---------+---------+
    GTGAACTAAAAGACAGTGAGGTTCTTCTTCACACTGCTCAACCGACGATTCAACTGACCT
    H__L__I__F__C__H__S__K__K__K__C__D__E__L__A__A__K__L__T__G__

    TTGGGATTGAACGCTGTTGCTTACTACAGAGGATTGGACGTTTCCGTTATCCCAACTTCC
1201---------+---------+---------+---------+---------+---------+
    AACCCTAACTTGCGACAACGAATGATGTCTCCTAACCTGCAAAGGCAATAGGGTTGAAGG
    L__G__L__N__A__V__A__Y__Y__R__G__L__D__V__S__V__I__P__T__S__

    GGTGATGTTGTTGTTGTTGCTACTGACGCTTTGATGACTGGTTTCACTGGTGACTTCGAC
1261---------+---------+---------+---------+---------+---------+
    CCACTACAACAACAACAACGATGACTGCGAAACTACTGACCAAAGTGACCACTGAAGCTG
    G__D__V__V__V__V__A__T__D__A__L__M__T__G__F__T__G__D__F__D__
```

Fig. 6C

```
    TCCGTTATCGACTGTAACACTTGTGTTACTCAGACTGTTGACTTCTCCTTGGACCCAACT
1321---------+---------+---------+---------+---------+---------+
    AGGCAATAGCTGACATTGTGAACACAATGAGTCTGACAACTGAAGAGGAACCTGGGTTGA
    S__V__I__D__C__N__T__C__V__T__Q__T__V__D__F__S__L__D__P__T__

    TTCACTATCGAGACTACTACTGTTCCTCAAGACGCTGTTTCCAGATCCCAAAGAAGAGGT
1381---------+---------+---------+---------+---------+---------+
    AAGTGATAGCTCTGATGATGACAAGGAGTTCTGCGACAAAGGTCTAGGGTTTCTTCTCCA
    F__T__I__E__T__T__T__V__P__Q__D__A__V__S__R__S__Q__R__R__G__

    GCTACTGGTAGAGGAAGATCCGGTATCTACAGATTCGTTACTCCAGGTGAAAGACCATCT
1441---------+---------+---------+---------+---------+---------+
    CGATGACCATCTCCTTCTAGGCCATAGATGTCTAAGCAATGAGGTCCACTTTCTGGTAGA
    A__T__G__R__G__R__S__G__I__Y__R__F__V__T__P__G__E__R__P__S__

    GGAATGTTCGACTCCTCCGTTTTGTGTGAATGTTACGACGCTGGTTGTGCTTGGTACGAA
1501---------+---------+---------+---------+---------+---------+
    CCTTACAAGCTGAGGAGGCAAAACACACTTACAATGCTGCGACCAACACGAACCATGCTT
    G__M__F__D__S__S__V__L__C__E__C__Y__D__A__G__C__A__W__Y__E__

    TTGACTCCAGCTGAGACTACTGTTAGATTGAGAGCTTACTTGAACACTCCAGGATTGCCA
1561---------+---------+---------+---------+---------+---------+
    AACTGAGGTCGACTCTGATGACAATCTAACTCTCGAATGAACTTGTGAGGTCCTAACGGT
    L__T__P__A__E__T__T__V__R__L__R__A__Y__L__N__T__P__G__L__P__

    GTTTGTCAAGACCACTTGGAATTCTGGGAGTCCGTTTTCACTGGATTGACTCACATTGAC
1621---------+---------+---------+---------+---------+---------+
    CAAACAGTTCTGGTGAACCTTAAGACCCTCAGGCAAAAGTGACCTAACTGAGTGTAACTG
    V__C__Q__D__H__L__E__F__W__E__S__V__F__T__G__L__T__H__I__D__

    GCTCACTTTTTGTCCCAAACTAAGCAGGCTGGTGACAACTTTCCATACTTGGTTGCTTAC
1681---------+---------+---------+---------+---------+---------+
    CGAGTGAAAAACAGGGTTTGATTCGTCCGACCACTGTTGAAAGGTATGAACCAACGAATG
    A__H__F__L__S__Q__T__K__Q__A__G__D__N__F__P__Y__L__V__A__Y__

    CAGGCTACTGTTTGTGCTAGAGCACAAGCTCCACCACCATCTTGGGATCAGATGTGGAAG
1741---------+---------+---------+---------+---------+---------+
    GTCCGATGACAAACACGATCTCGTGTTCGAGGTGGTGGTAGAACCCTAGTCTACACCTTC
    Q__A__T__V__C__A__R__A__Q__A__P__P__P__S__W__D__Q__M__W__K__

    TGTTTGATCAGATTGAAGCCAACTTTGCACGGTCCAACTCCATTGTTGTACAGATTGGGT
1801---------+---------+---------+---------+---------+---------+
    ACAAACTAGTCTAACTTCGGTTGAAACGTGCCAGGTTGAGGTAACAACATGTCTAACCCA
    C__L__I__R__L__K__P__T__L__H__G__P__T__P__L__L__Y__R__L__G__

    GCTGTTCAGAACGAGATCACTTTGACTCACCCAATCACTAAGTTCGTTATGGCTTGCATG
1861---------+---------+---------+---------+---------+---------+
    CGACAAGTCTTGCTCTAGTGAAACTGAGTGGGTTAGTGATTCAAGCAATACCGAACGTAC
    A__V__Q__N__E__I__T__L__T__H__P__I__T__K__F__V__M__A__C__M__

    TCTGCTGACTTGGAAGTTGTTTCCTTGATGGCTTTCACTGCTTCCATTACTTCCCCATTG
1921---------+---------+---------+---------+---------+---------+
    AGACGACTGAACCTTCAACAAAGGAACTACCGAAAGTGACGAAGGTAATGAAGGGGTAAC
    S__A__D__L__E__V__V__S__L__M__A__F__T__A__S__I__T__S__P__L__

    ACTACTCAGAACACTTTGTTGTTCAACATCTTGGGAGGATGGGTTGCAGCTCAATTGTCC
1981---------+---------+---------+---------+---------+---------+
    TGATGAGTCTTGTGAAACAACAAGTTGTAGAACCCTCCTACCCAACGTCGAGTTAACAGG
    T__T__Q__N__T__L__L__F__N__I__L__G__G__W__V__A__A__Q__L__S__
```

Fig. 6D

```
     ATGTCCTACACTTGGACTGGTGCTTTGATCACTCCATGTGCTGCTGAAGAATCCAAGTTG
2041---------+---------+---------+---------+---------+---------+
     TACAGGATGTGAACCTGACCACGAAACTAGTGAGGTACACGACGACTTCTTAGGTTCAAC
     M__S__Y__T__W__T__G__A__L__I__T__P__C__A__A__E__E__S__K__L__

     CCAATCAACCCATTGTCCAACTCTTTGTTGAGACACCACTCCATGGTTTACTCCACTACT
2101---------+---------+---------+---------+---------+---------+
     GGTTAGTTGGGTAACAGGTTGAGAAACAACTCTGTGGTGAGGTACCAAATGAGGTGATGA

     P__I__N__P__L__S__N__S__L__L__R__H__H__S__M__V__Y__S__T__T__

     TCCAGATCCGCTTCCTTGAGACAGAAGAAGGTTACATTCGACAGATTGCAGGTTTTGGAC
2161---------+---------+---------+---------+---------+---------+
     AGGTCTAGGCGAAGGAACTCTGTCTTCTTCCAATGTAAGCTGTCTAACGTCCAAAACCTG
     S__R__S__A__S__L__R__Q__K__K__V__T__F__D__R__L__Q__V__L__D__

     GACCACTACAGAGATGTTTTGAAGGAGATGAAGGCTAAGGCTTCCACTGTTAAGGCTAGA
2221---------+---------+---------+---------+---------+---------+
     CTGGTGATGTCTCTACAAAACTTCCTCTACTTCCGATTCCGAAGGTGACAATTCCGATCT
     D__H__Y__R__D__V__L__K__E__M__K__A__K__A__S__T__V__K__A__R__

     TTGTTGTCCATTGAGGAGGCTTGTAAGTTGACTCCACCACACTCTGCTAAGTCCAAGTTT
2281---------+---------+---------+---------+---------+---------+
     AACAACAGGTAACTCCTCCGAACATTCAACTGAGGTGGTGTGAGACGATTCAGGTTCAAA
     L__L__S__I__E__E__A__C__K__L__T__P__P__H__S__A__K__S__K__F__

     GGTTACGGTGCTAAGGATGTTAGATCCTTGTCCTCCAGAGCTGTTAACCACATCAGGTCT
2341---------+---------+---------+---------+---------+---------+
     CCAATGCCACGATTCCTACAATCTAGGAACAGGAGGTCTCGACAATTGGTGTAGTCCAGA
     G__Y__G__A__K__D__V__R__S__L__S__S__R__A__V__N__H__I__R__S__

     GTTTGGGAGGATTTGTTGGAGGACACTGAGACTCCAATCGACACTACTATCATGGCTAAG
2401---------+---------+---------+---------+---------+---------+
     CAAACCCTCCTAAACAACCTCCTGTGACTCTGAGGTTAGCTGTGATGATAGTACCGATTC
     V__W__E__D__L__L__E__D__T__E__T__P__I__D__T__T__I__M__A__K__

     AACGAGGTTTTCTGTGTTCAACCAGAGAAGGGTGGAAGAAAGCCAGCTAGATTGATCGTT
2461---------+---------+---------+---------+---------+---------+
     TTGCTCCAAAAGACACAAGTTGGTCTCTTCCCACCTTCTTTCGGTCGATCTAACTAGCAA
     N__E__V__F__C__V__Q__P__E__K__G__G__R__K__P__A__R__L__I__V__

     TTCCCAGACTTGGGTGTTAGAGTTTGTGAGAAGATGGCTTTGTACGACGTTGTTTCCACT
2521---------+---------+---------+---------+---------+---------+
     AAGGGTCTGAACCCACAATCTCAAACACTCTTCTACCGAAACATGCTGCAACAAAGGTGA
     F__P__D__L__G__V__R__V__C__E__K__M__A__L__Y__D__V__V__S__T__

     TTGCCACAGGCTGTTATGGGACCATCTTACGGTTTCCAATACTCCCCAGGACAAAGAGTT
2581---------+---------+---------+---------+---------+---------+
     AACGGTGTCCGACAATACCCTGGTAGAATGCCAAAGGTTATGAGGGGTCCTGTTTCTCAA
     L__P__Q__A__V__M__G__P__S__Y__G__F__Q__Y__S__P__G__Q__R__V__

     GAGTTCTTGGTTAACACTTGGAAGTCCAAGAAATGTCCAATGGGATTCTCCTACAACACT
2641---------+---------+---------+---------+---------+---------+
     CTCAAGAACCAATTGTGAACCTTCAGGTTCTTTACAGGTTACCCTAAGAGGATGTTGTGA
     E__F__L__V__N__T__W__K__S__K__K__C__P__M__G__F__S__Y__N__T__

     AGATGTTTCGACTCCACTGTTACTGAGAACGACATCAGAACAGAGGAGTCCATCTACCAG
2701---------+---------+---------+---------+---------+---------+
     TCTACAAAGCTGAGGTGACAATGACTCTTGCTGTAGTCTTGTCTCCTCAGGTAGATGGTC
     R__C__F__D__S__T__V__T__E__N__D__I__R__T__E__E__S__I__Y__Q__
```

Fig. 6E

```
    TGTTGTGACTTGGCTCCAGAAGCTAGACAAGCTATCAAGTCCTTGACTGAGAGATTGTAC
2761---------+---------+---------+---------+---------+---------+
    ACAACACTGAACCGAGGTCTTCGATCTGTTCGATAGTTCAGGAACTGACTCTCTAACATG
    C__C__D__L__A__P__E__A__R__Q__A__I__K__S__L__T__E__R__L__Y__

    ATCGGTGGTCCTTTGACTAACTCCAAGGGACAGAACTGTGGTTACAGAAGATGTAGAGCT
2821---------+---------+---------+---------+---------+---------+
    TAGCCACCAGGAAACTGATTGAGGTTCCCTGTCTTGACACCAATGTCTTCTACATCTCGA
    I__G__G__P__L__T__N__S__K__G__Q__N__C__G__Y__R__R__C__R__A__

    TCCGGTGTTTTGACTACTTCCTGTGGTAACACTTTGACTTGTTACTTGAAGGCTACTGCT
2881---------+---------+---------+---------+---------+---------+
    AGGCCACAAAACTGATGAAGGACACCATTGTGAAACTGAACAATGAACTTCCGATGACGA
    S__G__V__L__T__T__S__C__G__N__T__L__T__C__Y__L__K__A__T__A__

    GCTTGTAGAGCTGCTAAATTGCAGGACTGTACTATGTTGGTTAACGGTAACGACTTGGTT
2941---------+---------+---------+---------+---------+---------+
    CGAACATCTCGACGATTTAACGTCCTGACATGATACAACCAATTGCCATTGCTGAACCAA
    A__C__R__A__A__K__L__Q__D__C__T__M__L__V__N__G__N__D__L__V__

    GTTATCTGTGAGTCCGCTGGTACTCAAGAAGATGCTGCTTCTTTGAGAGTTTTCACAGAG
3001---------+---------+---------+---------+---------+---------+
    CAATAGACACTCAGGCGACCATGAGTTCTTCTACGACGAAGAAACTCTCAAAAGTGTCTC
    V__I__C__E__S__A__G__T__Q__E__D__A__A__S__L__R__V__F__T__E__

    GCTATGACTAGATACTCTGCTCCACCTGGTGATCCACCACAACCAGAATACGACTTGGAG
3061---------+---------+---------+---------+---------+---------+
    CGATACTGATCTATGAGACGAGGTGGACCACTAGGTGGTGTTGGTCTTATGCTGAACCTC
    A__M__T__R__Y__S__A__P__P__G__D__P__P__Q__P__E__Y__D__L__E__

    TTGATCACTTCCTGTTCCTCCAATGTTGGTGTTGCTCACGATGCTTCCGGAAAGAGAGTT
3121---------+---------+---------+---------+---------+---------+
    AACTAGTGAAGGACAAGGAGGTTACAACCACAACGAGTGCTACGAAGGCCTTTCTCTCAA
    L__I__T__S__C__S__S__N__V__G__V__A__H__D__A__S__G__K__R__V__

    TACTACTTGACTAGAGACCCAACTACTCCATTGGCTAGAGCTGCTTGGGAAACTGTTAGA
3181---------+---------+---------+---------+---------+---------+
    ATGATGAACTGATCTCTGGGTTGATGAGGTAACCGATCTCGACGAACCCTTTGACAATCT
    Y__Y__L__T__R__D__P__T__T__P__L__A__R__A__A__W__E__T__V__R__

    CACACTCCAGTTAACTCCTGGTTGGGTAACATCATCATGTACGCTCCAACTTTGTGGGCT
3241---------+---------+---------+---------+---------+---------+
    GTGTGAGGTCAATTGAGGACCAACCCATTGTAGTAGTACATGCGAGGTTGAAACACCCGA
    H__T__P__V__N__S__W__L__G__N__I__I__M__Y__A__P__T__L__W__A__

    AGAATGATCTTGATGACTCACTTCTTCTCCATCTTGTTGGCTCAAGAGCAATTGGAAAAG
3301---------+---------+---------+---------+---------+---------+
    TCTTACTAGAACTACTGAGTGAAGAAGAGGTAGAACAACCGAGTTCTCGTTAACCTTTTC
    R__M__I__L__M__T__H__F__F__S__I__L__L__A__Q__E__Q__L__E__K__

    GCTTTGGACTGTCAGATTTACGGTGCTTGTTACTCCATTGAGCCATTGGACTTGCCACAG
3361---------+---------+---------+---------+---------+---------+
    CGAAACCTGACAGTCTAAATGCCACGAACAATGAGGTAACTCGGTAACCTGAACGGTGTC
    A__L__D__C__Q__I__Y__G__A__C__Y__S__I__E__P__L__D__L__P__Q__

    ATCATTGAGAGATTGCACGGTTTGTCTGCTTTCTCTTTGCACTCTTACTCCCCTGGTGAA
3421---------+---------+---------+---------+---------+---------+
    TAGTAACTCTCTAACGTGCCAAACAGACGAAAGAGAAACGTGAGAATGAGGGGACCACTT
    I__I__E__R__L__H__G__L__S__A__F__S__L__H__S__Y__S__P__G__E__
```

Fig. 6F

```
    ATCAACAGAGTTGCTTCCTGTTTGAGAAAGTTGGGTGTTCCACCATTGAGAGTTTGGAGA
3481---------+---------+---------+---------+---------+---------+
    TAGTTGTCTCAACGAAGGACAAACTCTTTCAACCCACAAGGTGGTAACTCTCAAACCTCT
    I__N__R__V__A__S__C__L__R__K__L__G__V__P__P__L__R__V__W__R__

    CACAGAGCTAGATCCGTTAGAGCTAAGTTGTTGTCCCAAGGTGGAAGAGCTGCTACTTGT
3541---------+---------+---------+---------+---------+---------+
    GTGTCTCGATCTAGGCAATCTCGATTCAACAACAGGGTTCCACCTTCTCGACGATGAACA
    H__R__A__R__S__V__R__A__K__L__L__S__Q__G__G__R__A__A__T__C__

    GGTAAGTACTTGTTCAACTGGGCTGTTAGAACAAAGTTGAAGTTGACTCCTATTCCTGCT
3601---------+---------+---------+---------+---------+---------+
    CCATTCATGAACAAGTTGACCCGACAATCTTGTTTCAACTTCAACTGAGGATAAGGACGA
    G__K__Y__L__F__N__W__A__V__R__T__K__L__K__L__T__P__I__P__A__

    GCTTCCCAATTGGATTTGTCCGGTTGGTTTGTTGCTGGTTACAACGGTGGTGACATCTAC
3661---------+---------+---------+---------+---------+---------+
    CGAAGGGTTAACCTAAACAGGCCAACCAAACAACGACCAATGTTGCCACCACTGTAGATG
    A__S__Q__L__D__L__S__G__W__F__V__A__G__Y__N__G__G__D__I__Y__

    CACTCTTTGTCCAGAGCTAGACCAAGATAATAGACTAGTGGATCC
3721---------+---------+---------+---------+-----
    GTGAGAAACAGGTCTCGATCTGGTTCTATTATCTGATCACCTAGG
    H__S__L__S__R__A__R__P__R__*__*__
```

Fig. 7A

4A-3-5B fusion protein
optimized for Escherichia coli

SEQ ID NO:29
SEQ ID NO:30
SEQ ID NO:9

```
     AGGGCGAATTGGGTACCATGGGGAGCGTTGTTATTGTTGGCCGCATTATTCTGAGCGGTA
1    ---------+---------+---------+---------+---------+---------+
     TCCCGCTTAACCCATGGTACCCCTCGCAACAATAACAACCGGCGTAATAAGACTCGCCAT
                      M__G__S__V__V__I__V__G__R__I__I__L__S__G__S

     GCGGTAGCGCCCCGATTACCGCCTATTCTCAGCAAACCCGTGGTCTGCTGGGTTGTATTA
61   ---------+---------+---------+---------+---------+---------+
     CGCCATCGCGGGGCTAATGGCGGATAAGAGTCGTTTGGGCACCAGACGACCCAACATAAT
     __G__S__A__P__I__T__A__Y__S__Q__Q__T__R__G__L__L__G__C__I__I

     TTACCAGCCTGACCGGCCGTGATAAAAATCAGGTGGATGGCGAAGTTCAGGTTCTGAGCA
121  ---------+---------+---------+---------+---------+---------+
     AATGGTCGGACTGGCCGGCACTATTTTTAGTCCACCTACCGCTTCAAGTCCAAGACTCGT
     __T__S__L__T__G__R__D__K__N__Q__V__D__G__E__V__Q__V__L__S__T

     CCGCCACCCAGAGCTTTCTGGCGACCTGTGTGAATGGTGTGTGCTGGACCGTTTATGCCG
181  ---------+---------+---------+---------+---------+---------+
     GGCGGTGGGTCTCGAAAGACCGCTGGACACACTTACCACACACGACCTGGCAAATACGGC
     __A__T__Q__S__F__L__A__T__C__V__N__G__V__C__W__T__V__Y__A__G

     GTGCCGGTAGCAAAACCCTGGCGGGTCCGAAAGGTCCGATTACCCAGATGTACACCAACG
241  ---------+---------+---------+---------+---------+---------+
     CACGGCCATCGTTTTGGGACCGCCCAGGCTTTCCAGGCTAATGGGTCTACATGTGGTTGC
     __A__G__S__K__T__L__A__G__P__K__G__P__I__T__Q__M__Y__T__N__V

     TGGATCAGGATCTGGTTGGTTGGCCGGCGCCGCCGGGTGCCCGTAGCATGACCCCGTGTA
301  ---------+---------+---------+---------+---------+---------+
     ACCTAGTCCTAGACCAACCAACCGGCCGCGGCGGCCCACGGGCATCGTACTGGGGCACAT
     __D__Q__D__L__V__G__W__P__A__P__P__G__A__R__S__M__T__P__C__T

     CCTGTGGTAGCAGCGATCTGTATCTGGTTACCCGTCATGCCGATGTTATTCCGGTTCGTC
361  ---------+---------+---------+---------+---------+---------+
     GGACACCATCGTCGCTAGACATAGACCAATGGGCAGTACGGCTACAATAAGGCCAAGCAG
     __C__G__S__S__D__L__Y__L__V__T__R__H__A__D__V__I__P__V__R__R

     GTCGTGGTGATAGCCGTGGTAGCCTGCTGTCTCCGCGTCCGGTTAGCTATCTGAAAGGTA
421  ---------+---------+---------+---------+---------+---------+
     CAGCACCACTATCGGCACCATCGGACGACAGAGGCGCAGGCCAATCGATAGACTTTCCAT
     __R__G__D__S__R__G__S__L__L__S__P__R__P__V__S__Y__L__K__G__S

     GCAGCGGTGGTCCGCTGCTGTGTCCGAGCGGTCATGTGGTGGGTATTTTTCGTGCCGCCG
481  ---------+---------+---------+---------+---------+---------+
     CGTCGCCACCAGGCGACGACACAGGCTCGCCAGTACACCACCCATAAAAAGCACGGCGGC
     __S__G__G__P__L__L__C__P__S__G__H__V__V__G__I__F__R__A__A__V

     TTTGTACCCGTGGTGTGGCGAAAGCGGTGGATTTTATCCCGGTTGAAAGCATGGAAACCA
541  ---------+---------+---------+---------+---------+---------+
     AAACATGGGCACCACACCGCTTTCGCCACCTAAAATAGGGCCAACTTTCGTACCTTTGGT
    __C__T__R__G__V__A__K__A__V__D__F__I__P__V__E__S__M__E__T__T
```

Fig. 7B

```
     CCATGCGTAGCCCGGTGTTTACCGATAATAGCAGCCCGCCGGCGGTTCCGCAGACCTTTC
601  ---------+---------+---------+---------+---------+---------+
     GGTACGCATCGGGCCACAAATGGCTATTATCGTCGGGCGGCCGCCAAGGCGTCTGGAAAG
     __M__R__S__P__V__F__T__D__N__S__S__P__P__A__V__P__Q__T__F__Q

     AGGTTGCCCATCTGCATGCGCCGACCGGTAGCGGTAAAAGCACCAAAGTTCCGGCGGCGT
661  ---------+---------+---------+---------+---------+---------+
     TCCAACGGGTAGACGTACGCGGCTGGCCATCGCCATTTTCGTGGTTTCAAGGCCGCCGCA
     __V__A__H__L__H__A__P__T__G__S__G__K__S__T__K__V__P__A__A__Y

     ATGCCGCCCAGGGTTATAAAGTGCTGGTGCTGAATCCGAGCGTGGCGGCGACCCTGGGTT
721  ---------+---------+---------+---------+---------+---------+
     TACGGCGGGTCCCAATATTTCACGACCACGACTTAGGCTCGCACCGCCGCTGGGACCCAA
     __A__A__Q__G__Y__K__V__L__V__L__N__P__S__V__A__A__T__L__G__F

     TTGGTGCCTATATGAGCAAAGCCCATGGCATTGAACCGAACATTCGTACCGGCGTTCGTA
781  ---------+---------+---------+---------+---------+---------+
     AACCACGGATATACTCGTTTCGGGTACCGTAACTTGGCTTGTAAGCATGGCCGCAAGCAT
     __G__A__Y__M__S__K__A__H__G__I__E__P__N__I__R__T__G__V__R__T

     CCATTACCACCGGTGGCCCGATTACCTATAGCGCCTACGGCAAATTTCTGGCGGATGGTG
841  ---------+---------+---------+---------+---------+---------+
     GGTAATGGTGGCCACCGGGCTAATGGATATCGCGGATGCCGTTTAAAGACCGCCTACCAC
     __I__T__T__G__G__P__I__T__Y__S__A__Y__G__K__F__L__A__D__G__G

     GCTGTAGCGGTGGCGCCTATGATATCATCATCTGTGATGAATGCCATAGCACCGATTGGA
901  ---------+---------+---------+---------+---------+---------+
     CGACATCGCCACCGCGGATACTATAGTAGTAGACACTACTTACGGTATCGTGGCTAACCT
     __C__S__G__G__A__Y__D__I__I__I__C__D__E__C__H__S__T__D__W__T

     CCACCATTCTGGGTATTGGCACCGTTCTGGATCAGGCGGAAACCGCCGGTGCCCGTCTGG
961  ---------+---------+---------+---------+---------+---------+
     GGTGGTAAGACCCATAACCGTGGCAAGACCTAGTCCGCCTTTGGCGGCCACGGGCAGACC
     __T__I__L__G__I__G__T__V__L__D__Q__A__E__T__A__G__A__R__L__V

     TTGTTCTGGCGACCGCAACGCCGCCGGGTAGCATTACCGTTCCGCATCCGAACATTGAAG
1021 ---------+---------+---------+---------+---------+---------+
     AACAAGACCGCTGGCGTTGCGGCGGCCCATCGTAATGGCAAGGCGTAGGCTTGTAACTTC
     __V__L__A__T__A__T__P__P__G__S__I__T__V__P__H__P__N__I__E__E

     AAGTGGCCCTGAGCAATACCGGCGAAATTCCGTTTTATGGCAAAGCGATTCCGATCGAAG
1081 ---------+---------+---------+---------+---------+---------+
     TTCACCGGGACTCGTTATGGCCGCTTTAAGGCAAAATACCGTTTCGCTAAGGCTAGCTTC
     __V__A__L__S__N__T__G__E__I__P__F__Y__G__K__A__I__P__I__E__A

     CGATTAAAGGCGGCCGTCATCTGATTTTTTGCCACAGCAAAAAAAAATGTGATGAACTGG
1141 ---------+---------+---------+---------+---------+---------+
     GCTAATTTCCGCCGGCAGTAGACTAAAAAACGGTGTCGTTTTTTTTTACACTACTTGACC
     __I__K__G__G__R__H__L__I__F__C__H__S__K__K__K__C__D__E__L__A

     CGGCGAAACTGACCGGTCTGGGTCTGAATGCCGTGGCGTATTATCGTGGTCTGGATGTGA
1201 ---------+---------+---------+---------+---------+---------+
     GCCGCTTTGACTGGCCAGACCCAGACTTACGGCACCGCATAATAGCACCAGACCTACACT
     __A__K__L__T__G__L__G__L__N__A__V__A__Y__Y__R__G__L__D__V__S

     GCGTTATTCCGACCAGCGGTGATGTTGTTGTGGTGGCGACCGATGCCCTGATGACCGGTT
1261 ---------+---------+---------+---------+---------+---------+
     CGCAATAAGGCTGGTCGCCACTACAACAACACCACCGCTGGCTACGGGACTACTGGCCAA
     __V__I__P__T__S__G__D__V__V__V__V__A__T__D__A__L__M__T__G__F
```

Fig. 7C

```
     TTACCGGCGATTTTGATAGCGTGATCGATTGTAACACCTGTGTGACCCAGACCGTTGATT
1321---------+---------+---------+---------+---------+---------+
     AATGGCCGCTAAAACTATCGCACTAGCTAACATTGTGGACACACTGGGTCTGGCAACTAA
     __T__G__D__F__D__S__V__I__D__C__N__T__C__V__T__Q__T__V__D__F

     TTAGCCTGGACCCGACCTTTACCATTGAAACCACCACCGTTCCGCAGGATGCCGTTAGCC
1381---------+---------+---------+---------+---------+---------+
     AATCGGACCTGGGCTGGAAATGGTAACTTTGGTGGTGGCAAGGCGTCCTACGGCAATCGG
     __S__L__D__P__T__F__T__I__E__T__T__T__V__P__Q__D__A__V__S__R

     GTAGCCAGCGTCGTGGTGCCACCGGTCGTGGTCGTAGCGGCATTTATCGTTTTGTGACGC
1441---------+---------+---------+---------+---------+---------+
     CATCGGTCGCAGCACCACGGTGGCCAGCACCAGCATCGCCGTAAATAGCAAAACACTGCG
     __S__Q__R__R__G__A__T__G__R__G__R__S__G__I__Y__R__F__V__T__P

     CGGGTGAACGTCCGAGCGGTATGTTTGATAGCAGCGTGCTGTGTGAATGTTATGATGCCG
1501---------+---------+---------+---------+---------+---------+
     GCCCACTTGCAGGCTCGCCATACAAACTATCGTCGCACGACACACTTACAATACTACGGC
     __G__E__R__P__S__G__M__F__D__S__S__V__L__C__E__C__Y__D__A__G

     GCTGTGCCTGGTATGAACTGACCCCGGCGGAAACCACCGTTCGTCTGCGCGCGTATCTGA
1561---------+---------+---------+---------+---------+---------+
     CGACACGGACCATACTTGACTGGGGCCGCCTTTGGTGGCAAGCAGACGCGCGCATAGACT
     __C__A__W__Y__E__L__T__P__A__E__T__T__V__R__L__R__A__Y__L__N

     ATACGCCGGGTCTGCCGGTTTGTCAGGATCATCTGGAATTCTGGGAAAGCGTTTTTACCG
1621---------+---------+---------+---------+---------+---------+
     TATGCGGCCCAGACGGCCAAACAGTCCTAGTAGACCTTAAGACCCTTTCGCAAAAATGGC
     __T__P__G__L__P__V__C__Q__D__H__L__E__F__W__E__S__V__F__T__G

     GCCTGACCCATATTGATGCCCATTTTCTGAGCCAGACCAAACAGGCGGGTGATAACTTTC
1681---------+---------+---------+---------+---------+---------+
     CGGACTGGGTATAACTACGGGTAAAAGACTCGGTCTGGTTTGTCCGCCCACTATTGAAAG
     __L__T__H__I__D__A__H__F__L__S__Q__T__K__Q__A__G__D__N__F__P

     CGTATCTGGTGGCGTATCAGGCGACCGTTTGTGCCCGTGCCCAGGCGCCGCCGCCGAGCT
1741---------+---------+---------+---------+---------+---------+
     GCATAGACCACCGCATAGTCCGCTGGCAAACACGGGCACGGGTCCGCGGCGGCGGCTCGA
     __Y__L__V__A__Y__Q__A__T__V__C__A__R__A__Q__A__P__P__P__S__W

     GGGATCAGATGTGGAAATGCCTGATTCGTCTGAAACCGACCCTGCATGGTCCGACCCCGC
1801---------+---------+---------+---------+---------+---------+
     CCCTAGTCTACACCTTTACGGACTAAGCAGACTTTGGCTGGGACGTACCAGGCTGGGGCG
     __D__Q__M__W__K__C__L__I__R__L__K__P__T__L__H__G__P__T__P__L

     TGCTGTATCGTCTGGGTGCCGTTCAGAACGAAATTACCCTGACCCATCCGATCACCAAAT
1861---------+---------+---------+---------+---------+---------+
     ACGACATAGCAGACCCACGGCAAGTCTTGCTTTAATGGGACTGGGTAGGCTAGTGGTTTA
     __L__Y__R__L__G__A__V__Q__N__E__I__T__L__T__H__P__I__T__K__F

     TTGTGATGGCGTGTATGAGCGCCGATCTGGAAGTTGTTGGTAGCGGTAGCGGCTCTATGA
1921---------+---------+---------+---------+---------+---------+
     AACACTACCGCACATACTCGCGGCTAGACCTTCAACAACCATCGCCATCGCCGAGATACT
     __V__M__A__C__M__S__A__D__L__E__V__V__G__S__G__S__G__S__M__S

     GCTATACCTGGACCGGTGCCCTGATTACCCCGTGTGCCGCCGAAGAAAGCAAACTGCCGA
1981---------+---------+---------+---------+---------+---------+
     CGATATGGACCTGGCCACGGGACTAATGGGGCACACGGCGGCTTCTTTCGTTTGACGGCT
     __Y__T__W__T__G__A__L__I__T__P__C__A__A__E__E__S__K__L__P__I
```

Fig. 7D

```
     TTAACCCGCTGTCTAATAGCCTGCTGCGTCATCATAGCATGGTGTATAGCACCACCAGCC
2041---------+---------+---------+---------+---------+---------+
     AATTGGGCGACAGATTATCGGACGACGCAGTAGTATCGTACCACATATCGTGGTGGTCGG
     __N__P__L__S__N__S__L__L__R__H__H__S__M__V__Y__S__T__T__S__R

     GTAGCGCCAGCCTGCGTCAGAAAAAAGTGACCTTCGATCGTCTGCAGGTGCTGGATGATC
2101---------+---------+---------+---------+---------+---------+

     CATCGCGGTCGGACGCAGTCTTTTTTCACTGGAAGCTAGCAGACGTCCACGACCTACTAG
     __S__A__S__L__R__Q__K__K__V__T__F__D__R__L__Q__V__L__D__D__H

     ATTATCGTGATGTGCTGAAAGAAATGAAAGCGAAAGCGAGCACCGTTAAAGCCCGTCTGC
2161---------+---------+---------+---------+---------+---------+
     TAATAGCACTACACGACTTTCTTTACTTTCGCTTTCGCTCGTGGCAATTTCGGGCAGACG
     __Y__R__D__V__L__K__E__M__K__A__K__A__S__T__V__K__A__R__L__L

     TGTCTATTGAAGAAGCGTGTAAACTGACCCCGCCGCATAGCGCCAAAAGCAAATTTGGCT
2221---------+---------+---------+---------+---------+---------+
     ACAGATAACTTCTTCGCACATTTGACTGGGGCGGCGTATCGCGGTTTTCGTTTAAACCGA
     __S__I__E__E__A__C__K__L__T__P__P__H__S__A__K__S__K__F__G__Y

     ATGGCGCCAAAGATGTTCGTAGCCTGAGCAGCCGTGCCGTTAATCATATTCGTAGCGTGT
2281---------+---------+---------+---------+---------+---------+
     TACCGCGGTTTCTACAAGCATCGGACTCGTCGGCACGGCAATTAGTATAAGCATCGCACA
     __G__A__K__D__V__R__S__L__S__S__R__A__V__N__H__I__R__S__V__W

     GGGAAGATCTGCTGGAAGATACCGAAACCCCGATTGATACCACCATCATGGCGAAAAACG
2341---------+---------+---------+---------+---------+---------+
     CCCTTCTAGACGACCTTCTATGGCTTTGGGGCTAACTATGGTGGTAGTACCGCTTTTTGC
     __E__D__L__L__E__D__T__E__T__P__I__D__T__T__I__M__A__K__N__E

     AAGTGTTTTGTGTTCAGCCGGAAAAAGGTGGTCGTAAACCGGCCCGTCTGATTGTTTTTC
2401---------+---------+---------+---------+---------+---------+
     TTCACAAAACACAAGTCGGCCTTTTTCCACCAGCATTTGGCCGGGCAGACTAACAAAAAG
     __V__F__C__V__Q__P__E__K__G__G__R__K__P__A__R__L__I__V__F__P

     CGGATCTGGGTGTTCGTGTGTGTGAAAAAATGGCGCTGTACGATGTTGTTAGCACCCTGC
2461---------+---------+---------+---------+---------+---------+
     GCCTAGACCCACAAGCACACACACTTTTTTACCGCGACATGCTACAACAATCGTGGGACG
     __D__L__G__V__R__V__C__E__K__M__A__L__Y__D__V__V__S__T__L__P

     CGCAGGCGGTTATGGGTCCGAGCTATGGCTTTCAGTATTCTCCGGGTCAGCGTGTTGAAT
2521---------+---------+---------+---------+---------+---------+
     GCGTCCGCCAATACCCAGGCTCGATACCGAAAGTCATAAGAGGCCCAGTCGCACAACTTA
     __Q__A__V__M__G__P__S__Y__G__F__Q__Y__S__P__G__Q__R__V__E__F

     TTCTGGTGAACACCTGGAAAAGCAAAAAATGCCCGATGGGCTTCAGCTATAACACCCGCT
2581---------+---------+---------+---------+---------+---------+
     AAGACCACTTGTGGACCTTTTCGTTTTTTACGGGCTACCCGAAGTCGATATTGTGGGCGA
     __L__V__N__T__W__K__S__K__K__C__P__M__G__F__S__Y__N__T__R__C

     GCTTTGATAGCACCGTGACCGAAAACGATATCCGTACCGAAGAAAGCATTTACCAGTGCT
2641---------+---------+---------+---------+---------+---------+
     CGAAACTATCGTGGCACTGGCTTTTGCTATAGGCATGGCTTCTTTCGTAAATGGTCACGA
     __F__D__S__T__V__T__E__N__D__I__R__T__E__E__S__I__Y__Q__C__C

     GTGATCTGGCGCCGGAAGCCCGTCAGGCGATTAAAAGCCTGACCGAACGCCTGTATATTG
2701---------+---------+---------+---------+---------+---------+
     CACTAGACCGCGGCCTTCGGGCAGTCCGCTAATTTTCGGACTGGCTTGCGGACATATAAC
     __D__L__A__P__E__A__R__Q__A__I__K__S__L__T__E__R__L__Y__I__G
```

Fig. 7E

```
     GCGGTCCGCTGACCAATAGCAAAGGCCAGAACTGTGGTTATCGTCGTTGTCGTGCCAGCG
2761---------+---------+---------+---------+---------+---------+
     CGCCAGGCGACTGGTTATCGTTTCCGGTCTTGACACCAATAGCAGCAACAGCACGGTCGC
     __G__P__L__T__N__S__K__G__Q__N__C__G__Y__R__R__C__R__A__S__G

     GTGTTCTGACCACCAGCTGTGGTAATACCCTGACCTGCTACCTGAAAGCGACCGCCGCCT
2821---------+---------+---------+---------+---------+---------+
     CACAAGACTGGTGGTCGACACCATTATGGGACTGGACGATGGACTTTCGCTGGCGGCGGA
     __V__L__T__T__S__C__G__N__T__L__T__C__Y__L__K__A__T__A__A__C

     GTCGTGCCGCCAAACTGCAGGATTGTACCATGCTGGTTAACGGCAATGATCTGGTGGTGA
2881---------+---------+---------+---------+---------+---------+
     CAGCACGGCGGTTTGACGTCCTAACATGGTACGACCAATTGCCGTTACTAGACCACCACT
     __R__A__A__K__L__Q__D__C__T__M__L__V__N__G__N__D__L__V__V__I

     TTTGTGAAAGCGCCGGCACCCAGGAAGATGCCGCCAGCCTGCGCGTTTTTACCGAAGCGA
2941---------+---------+---------+---------+---------+---------+
     AAACACTTTCGCGGCCGTGGGTCCTTCTACGGCGGTCGGACGCGCAAAAATGGCTTCGCT
     __C__E__S__A__G__T__Q__E__D__A__A__S__L__R__V__F__T__E__A__M

     TGACCCGTTATAGCGCCCCGCCGGGTGATCCGCCGCAGCCGGAATATGATCTGGAACTGA
3001---------+---------+---------+---------+---------+---------+
     ACTGGGCAATATCGCGGGGCGGCCCACTAGGCGGCGTCGGCCTTATACTAGACCTTGACT
     __T__R__Y__S__A__P__P__G__D__P__P__Q__P__E__Y__D__L__E__L__I

     TCACCAGCTGTAGCAGCAATGTTGGTGTTGCCCATGATGCCAGCGGTAAACGTGTGTATT
3061---------+---------+---------+---------+---------+---------+
     AGTGGTCGACATCGTCGTTACAACCACAACGGGTACTACGGTCGCCATTTGCACACATAA
     __T__S__C__S__S__N__V__G__V__A__H__D__A__S__G__K__R__V__Y__Y

     ACCTGACCCGTGATCCGACCACCCCGCTGGCCCGTGCCGCCTGGGAAACCGTTCGTCATA
3121---------+---------+---------+---------+---------+---------+
     TGGACTGGGCACTAGGCTGGTGGGGCGACCGGGCACGGCGGACCCTTTGGCAAGCAGTAT
     __L__T__R__D__P__T__T__P__L__A__R__A__A__W__E__T__V__R__H__T

     CCCCGGTTAATAGCTGGCTGGGCAACATTATTATGTATGCCCCGACCCTGTGGGCCCGTA
3181---------+---------+---------+---------+---------+---------+
     GGGGCCAATTATCGACCGACCCGTTGTAATAATACATACGGGGCTGGGACACCCGGGCAT
     __P__V__N__S__W__L__G__N__I__I__M__Y__A__P__T__L__W__A__R__M

     TGATTCTGATGACCCACTTCTTTAGCATTCTGCTGGCCCAGGAACAGCTGGAAAAAGCGC
3241---------+---------+---------+---------+---------+---------+
     ACTAAGACTACTGGGTGAAGAAATCGTAAGACGACCGGGTCCTTGTCGACCTTTTTCGCG
     __I__L__M__T__H__F__F__S__I__L__L__A__Q__E__Q__L__E__K__A__L

     TGGATTGCCAGATTTATGGCGCCTGCTATAGCATTGAACCGCTGGATCTGCCGCAGATTA
3301---------+---------+---------+---------+---------+---------+
     ACCTAACGGTCTAAATACCGCGGACGATATCGTAACTTGGCGACCTAGACGGCGTCTAAT
     __D__C__Q__I__Y__G__A__C__Y__S__I__E__P__L__D__L__P__Q__I__I
     TTGAACGTCTGCATGGCCTGAGCGCCTTTAGCCTGCATAGCTACTCTCCGGGTGAAATTA
3361---------+---------+---------+---------+---------+---------+
     AACTTGCAGACGTACCGGACTCGCGGAAATCGGACGTATCGATGAGAGGCCCACTTTAAT
     __E__R__L__H__G__L__S__A__F__S__L__H__S__Y__S__P__G__E__I__N

     ATCGTGTGGCGAGCTGTCTGCGTAAACTGGGTGTTCCGCCGCTGCGTGTCTGGCGTCATC
3421---------+---------+---------+---------+---------+---------+
     TAGCACACCGCTCGACAGACGCATTTGACCCACAAGGCGGCGACGCACAGACCGCAGTAG
     __R__V__A__S__C__L__R__K__L__G__V__P__P__L__R__V__W__R__H__R
```

Fig. 7F

```
     GTGCCCGTAGCGTTCGTGCCAAACTGCTGTCTCAGGGTGGCCGTGCCGCCACCTGTGGTA
3481---------+---------+---------+---------+---------+---------+
     CACGGGCATCGCAAGCACGGTTTGACGACAGAGTCCCACCGGCACGGCGGTGGACACCAT
     __A__R__S__V__R__A__K__L__L__S__Q__G__G__R__A__A__T__C__G__K

     AATACCTGTTTAACTGGGCGGTTCGTACCAAACTGAAACTGACCCCGATTCCGGCGGCGA
3541---------+---------+---------+---------+---------+---------+
     TTATGGACAAATTGACCCGCCAAGCATGGTTTGACTTTGACTGGGGCTAAGGCCGCCGCT
     __Y__L__F__N__W__A__V__R__T__K__L__K__L__T__P__I__P__A__A__S

     GCCAGCTGGATCTGAGCGGTTGGTTTGTTGCCGGTTATAACGGCGGCGATATCTATCATA
3601---------+---------+---------+---------+---------+---------+
     CGGTCGACCTAGACTCGCCAACCAAACAACGGCCAATATTGCCGCCGCTATAGATAGTAT
     __Q__L__D__L__S__G__W__F__V__A__G__Y__N__G__G__D__I__Y__H__S

     GCCTGAGCCGTGCCCGTCCGCGTTAATAAACTAGTGGATCCGGAGCTCCAGCTTTGTTCC
3661---------+---------+---------+---------+---------+---------+
     CGGACTCGGCACGGGCAGGCGCAATTATTTGATCACCTAGGCCTCGAGGTCGAAACAAGG
      __L__S__R__A__R__P__R__*__*__

     CTAG
3721----
     GATC
```

Fig. 8

4A-3-4B-5B fusion protein
optimized for Escherichia coli

SEQ ID NO:31
SEQ ID NO:32
SEQ ID NO:10

```
     GGGCGAATTGGGTACCATGGGGAGCGTTGTTATTGTTGGCCGCATTATTCTGAGCGGTAG
1    ---------+---------+---------+---------+---------+---------+
     CCCGCTTAACCCATGGTACCCCTCGCAACAATAACAACCGGCGTAATAAGACTCGCCATC
                     M__G__S__V__V__I__V__G__R__I__I__L__S__G__S_

     CGGTAGCGCCCCGATTACCGCCTATTCTCAGCAAACCCGTGGTCTGCTGGGTTGTATTAT
61   ---------+---------+---------+---------+---------+---------+
     GCCATCGCGGGGCTAATGGCGGATAAGAGTCGTTTGGGCACCAGACGACCCAACATAATA
     _G__S__A__P__I__T__A__Y__S__Q__Q__T__R__G__L__L__G__C__I__I_

     TACCAGCCTGACCGGCCGTGATAAAAATCAGGTGGATGGCGAAGTTCAGGTTCTGAGCAC
121  ---------+---------+---------+---------+---------+---------+
     ATGGTCGGACTGGCCGGCACTATTTTTAGTCCACCTACCGCTTCAAGTCCAAGACTCGTG
     _T__S__L__T__G__R__D__K__N__Q__V__D__G__E__V__Q__V__L__S__T_

     CGCCACCCAGAGCTTTCTGGCGACCTGTGTGAATGGTGTGTGCTGGACCGTTTATGCCGG
181  ---------+---------+---------+---------+---------+---------+
     GCGGTGGGTCTCGAAAGACCGCTGGACACACTTACCACACACGACCTGGCAAATACGGCC
     _A__T__Q__S__F__L__A__T__C__V__N__G__V__C__W__T__V__Y__A__G_

     TGCCGGTAGCAAAACCCTGGCGGGTCCGAAAGGTCCGATTACCCAGATGTACACCAACGT
241  ---------+---------+---------+---------+---------+---------+
     ACGGCCATCGTTTTGGGACCGCCCAGGCTTTCCAGGCTAATGGGTCTACATGTGGTTGCA
     _A__G__S__K__T__L__A__G__P__K__G__P__I__T__Q__M__Y__T__N__V_

     GGATCAGGATCTGGTTGGTTGGCCGGCGCCGCCGGGTGCCCGTAGCATGACCCCGTGTAC
301  ---------+---------+---------+---------+---------+---------+
     CCTAGTCCTAGACCAACCAACCGGCCGCGGCGGCCCACGGGCATCGTACTGGGGCACATG
     _D__Q__D__L__V__G__W__P__A__P__P__G__A__R__S__M__T__P__C__T_

     CTGTGGTAGCAGCGATCTGTATCTGGTTACCCGTCATGCCGATGTTATTCCGGTTCGTCG
361  ---------+---------+---------+---------+---------+---------+
     GACACCATCGTCGCTAGACATAGACCAATGGGCAGTACGGCTACAATAAGGCCAAGCAGC
     _C__G__S__S__D__L__Y__L__V__T__R__H__A__D__V__I__P__V__R__R_

     TCGTGGTGATAGCCGTGGTAGCCTGCTGTCTCCGCGTCCGGTTAGCTATCTGAAAGGTAG
421  ---------+---------+---------+---------+---------+---------+
     AGCACCACTATCGGCACCATCGGACGACAGAGGCGCAGGCCAATCGATAGACTTTCCATC
     _R__G__D__S__R__G__S__L__L__S__P__R__P__V__S__Y__L__K__G__S_

     CAGCGGTGGTCCGCTGCTGTGTCCGAGCGGTCATGTGGTGGGTATTTTTCGTGCCGCCGT
481  ---------+---------+---------+---------+---------+---------+
     GTCGCCACCAGGCGACGACACAGGCTCGCCAGTACACCACCCATAAAAAGCACGGCGGCA
     _S__G__G__P__L__L__C__P__S__G__H__V__V__G__I__F__R__A__A__V_

     TTGTACCCGTGGTGTGGCGAAAGCGGTGGATTTTATCCCGGTTGAAAGCATGGAAACCAC
541  ---------+---------+---------+---------+---------+---------+
     AACATGGGCACCACACCGCTTTCGCCACCTAAAATAGGGCCAACTTTCGTACCTTTGGTG
     _C__T__R__G__V__A__K__A__V__D__F__I__P__V__E__S__M__E__T__T_
```

Fig. 8B

```
    CATGCGTAGCCCGGTGTTTACCGATAATAGCAGCCCGCCGGCGGTTCCGCAGACCTTTCA
601 ---------+---------+---------+---------+---------+---------+
    GTACGCATCGGGCCACAAATGGCTATTATCGTCGGGCGGCCGCCAAGGCGTCTGGAAAGT

    _M__R__S__P__V__F__T__D__N__S__S__P__P__A__V__P__Q__T__F__Q_

    GGTTGCCCATCTGCATGCGCCGACCGGTAGCGGTAAAAGCACCAAAGTTCCGGCGGCGTA
661 ---------+---------+---------+---------+---------+---------+
    CCAACGGGTAGACGTACGCGGCTGGCCATCGCCATTTTCGTGGTTTCAAGGCCGCCGCAT
    _V__A__H__L__H__A__P__T__G__S__G__K__S__T__K__V__P__A__A__Y_

    TGCCGCCCAGGGTTATAAAGTGCTGGTGCTGAATCCGAGCGTGGCGGCGACCCTGGGTTT
721 ---------+---------+---------+---------+---------+---------+
    ACGGCGGGTCCCAATATTTCACGACCACGACTTAGGCTCGCACCGCCGCTGGGACCCAAA
    _A__A__Q__G__Y__K__V__L__V__L__N__P__S__V__A__A__T__L__G__F_

    TGGTGCCTATATGAGCAAAGCCCATGGCATTGAACCGAACATTCGTACCGGCGTTCGTAC
781 ---------+---------+---------+---------+---------+---------+
    ACCACGGATATACTCGTTTCGGGTACCGTAACTTGGCTTGTAAGCATGGCCGCAAGCATG
    _G__A__Y__M__S__K__A__H__G__I__E__P__N__I__R__T__G__V__R__T_

    CATTACCACCGGTGGCCCGATTACCTATAGCGCCTACGGCAAATTTCTGGCGGATGGTGG
841 ---------+---------+---------+---------+---------+---------+
    GTAATGGTGGCCACCGGGCTAATGGATATCGCGGATGCCGTTTAAAGACCGCCTACCACC
    _I__T__T__G__G__P__I__T__Y__S__A__Y__G__K__F__L__A__D__G__G_

    CTGTAGCGGTGGCGCCTATGATATCATCATCTGTGATGAATGCCATAGCACCGATTGGAC
901 ---------+---------+---------+---------+---------+---------+
    GACATCGCCACCGCGGATACTATAGTAGTAGACACTACTTACGGTATCGTGGCTAACCTG
    _C__S__G__G__A__Y__D__I__I__I__C__D__E__C__H__S__T__D__W__T_

    CACCATTCTGGGTATTGGCACCGTTCTGGATCAGGCGGAAACCGCCGGTGCCCGTCTGGT
961 ---------+---------+---------+---------+---------+---------+
    GTGGTAAGACCCATAACCGTGGCAAGACCTAGTCCGCCTTTGGCGGCCACGGGCAGACCA
    _T__I__L__G__I__G__T__V__L__D__Q__A__E__T__A__G__A__R__L__V_

    TGTTCTGGCGACCGCAACGCCGCCGGGTAGCATTACCGTTCCGCATCCGAACATTGAAGA
1021---------+---------+---------+---------+---------+---------+
    ACAAGACCGCTGGCGTTGCGGCGGCCCATCGTAATGGCAAGGCGTAGGCTTGTAACTTCT
    _V__L__A__T__A__T__P__P__G__S__I__T__V__P__H__P__N__I__E__E_

    AGTGGCCCTGAGCAATACCGGCGAAATTCCGTTTTATGGCAAAGCGATTCCGATCGAAGC
1081---------+---------+---------+---------+---------+---------+
    TCACCGGGACTCGTTATGGCCGCTTTAAGGCAAAATACCGTTTCGCTAAGGCTAGCTTCG
    _V__A__L__S__N__T__G__E__I__P__F__Y__G__K__A__I__P__I__E__A_

    GATTAAAGGCGGCCGTCATCTGATTTTTTGCCACAGCAAAAAAAAATGTGATGAACTGGC
1141---------+---------+---------+---------+---------+---------+
    CTAATTTCCGCCGGCAGTAGACTAAAAAACGGTGTCGTTTTTTTTTACACTACTTGACCG
    _I__K__G__G__R__H__L__I__F__C__H__S__K__K__K__C__D__E__L__A_

    GGCGAAACTGACCGGTCTGGGTCTGAATGCCGTGGCGTATTATCGTGGTCTGGATGTGAG
1201---------+---------+---------+---------+---------+---------+
    CCGCTTTGACTGGCCAGACCCAGACTTACGGCACCGCATAATAGCACCAGACCTACACTC
    _A__K__L__T__G__L__G__L__N__A__V__A__Y__Y__R__G__L__D__V__S_

    CGTTATTCCGACCAGCGGTGATGTTGTTGTGGTGGCGACCGATGCCCTGATGACCGGTTT
1261---------+---------+---------+---------+---------+---------+
    GCAATAAGGCTGGTCGCCACTACAACAACACCACCGCTGGCTACGGGACTACTGGCCAAA
    _V__I__P__T__S__G__D__V__V__V__V__A__T__D__A__L__M__T__G__F_
```

Fig. 8C

```
    TACCGGCGATTTTGATAGCGTGATCGATTGTAACACCTGTGTGACCCAGACCGTTGATTT
1321---------+---------+---------+---------+---------+---------+
    ATGGCCGCTAAAACTATCGCACTAGCTAACATTGTGGACACACTGGGTCTGGCAACTAAA
    _T__G__D__F__D__S__V__I__D__C__N__T__C__V__T__Q__T__V__D__F_

    TAGCCTGGACCCGACCTTTACCATTGAAACCACCACCGTTCCGCAGGATGCCGTTAGCCG
1381---------+---------+---------+---------+---------+---------+
    ATCGGACCTGGGCTGGAAATGGTAACTTTGGTGGTGGCAAGGCGTCCTACGGCAATCGGC
    _S__L__D__P__T__F__T__I__E__T__T__T__V__P__Q__D__A__V__S__R_

    TAGCCAGCGTCGTGGTGCCACCGGTCGTGGTCGTAGCGGCATTTATCGTTTTGTGACGCC
1441---------+---------+---------+---------+---------+---------+
    ATCGGTCGCAGCACCACGGTGGCCAGCACCAGCATCGCCGTAAATAGCAAAACACTGCGG
    _S__Q__R__R__G__A__T__G__R__G__R__S__G__I__Y__R__F__V__T__P_

    GGGTGAACGTCCGAGCGGTATGTTTGATAGCAGCGTGCTGTGTGAATGTTATGATGCCGG
1501---------+---------+---------+---------+---------+---------+
    CCCACTTGCAGGCTCGCCATACAAACTATCGTCGCACGACACACTTACAATACTACGGCC
    _G__E__R__P__S__G__M__F__D__S__S__V__L__C__E__C__Y__D__A__G_

    CTGTGCCTGGTATGAACTGACCCCGGCGGAAACCACCGTTCGTCTGCGCGCGTATCTGAA
1561---------+---------+---------+---------+---------+---------+
    GACACGGACCATACTTGACTGGGGCCGCCTTTGGTGGCAAGCAGACGCGCGCATAGACTT
    _C__A__W__Y__E__L__T__P__A__E__T__T__V__R__L__R__A__Y__L__N_

    TACGCCGGGTCTGCCGGTTTGTCAGGATCATCTGGAATTCTGGGAAAGCGTTTTTACCGG
1621---------+---------+---------+---------+---------+---------+
    ATGCGGCCCAGACGGCCAAACAGTCCTAGTAGACCTTAAGACCCTTTCGCAAAAATGGCC
    _T__P__G__L__P__V__C__Q__D__H__L__E__F__W__E__S__V__F__T__G_

    CCTGACCCATATTGATGCCCATTTTCTGAGCCAGACCAAACAGGCGGGTGATAACTTTCC
1681---------+---------+---------+---------+---------+---------+
    GGACTGGGTATAACTACGGGTAAAAGACTCGGTCTGGTTTGTCCGCCCACTATTGAAAGG
    _L__T__H__I__D__A__H__F__L__S__Q__T__K__Q__A__G__D__N__F__P_

    GTATCTGGTGGCGTATCAGGCGACCGTTTGTGCCCGTGCCCAGGCGCCGCCGCCGAGCTG
1741---------+---------+---------+---------+---------+---------+
    CATAGACCACCGCATAGTCCGCTGGCAAACACGGGCACGGGTCCGCGGCGGCGGCTCGAC
    _Y__L__V__A__Y__Q__A__T__V__C__A__R__A__Q__A__P__P__P__S__W_

    GGATCAGATGTGGAAATGCCTGATTCGTCTGAAACCGACCCTGCATGGTCCGACCCCGCT
1801---------+---------+---------+---------+---------+---------+
    CCTAGTCTACACCTTTACGGACTAAGCAGACTTTGGCTGGGACGTACCAGGCTGGGGCGA
    _D__Q__M__W__K__C__L__I__R__L__K__P__T__L__H__G__P__T__P__L_

    GCTGTATCGTCTGGGTGCCGTTCAGAACGAAATTACCCTGACCCATCCGATCACCAAATT
1861---------+---------+---------+---------+---------+---------+
    CGACATAGCAGACCCACGGCAAGTCTTGCTTTAATGGGACTGGGTAGGCTAGTGGTTTAA
    _L__Y__R__L__G__A__V__Q__N__E__I__T__L__T__H__P__I__T__K__F_

    TGTGATGGCGTGTATGAGCGCCGATCTGGAAGTTGTTAGCCTGATGGCGTTTACCGCCAG
1921---------+---------+---------+---------+---------+---------+
    ACACTACCGCACATACTCGCGGCTAGACCTTCAACAATCGGACTACCGCAAATGGCGGTC
    _V__M__A__C__M__S__A__D__L__E__V__V__S__L__M__A__F__T__A__S_

    CATTACCAGCCCGCTGACCACCCAGAATACCCTGCTGTTTAACATCCTGGGCGGTTGGGT
1981---------+---------+---------+---------+---------+---------+
    GTAATGGTCGGGCGACTGGTGGGTCTTATGGGACGACAAATTGTAGGACCCGCCAACCCA
    _I__T__S__P__L__T__T__Q__N__T__L__L__F__N__I__L__G__G__W__V_
```

Fig. 8D

```
     GGCGGCCCAGCTGTCTATGAGCTATACCTGGACCGGTGCCCTGATTACCCCGTGTGCCGC
2041---------+---------+---------+---------+---------+---------+
     CCGCCGGGTCGACAGATACTCGATATGGACCTGGCCACGGGACTAATGGGGCACACGGCG
     _A__A__Q__L__S__M__S__Y__T__W__T__G__A__L__I__T__P__C__A__A_

     CGAAGAAAGCAAACTGCCGATTAACCCGCTGTCTAATAGCCTGCTGCGTCATCATAGCAT
2101---------+---------+---------+---------+---------+---------+
     GCTTCTTTCGTTTGACGGCTAATTGGGCGACAGATTATCGGACGACGCAGTAGTATCGTA

     _E__E__S__K__L__P__I__N__P__L__S__N__S__L__L__R__H__H__S__M_

     GGTGTATAGCACCACCAGCCGTAGCGCCAGCCTGCGTCAGAAAAAAGTGACCTTCGATCG
2161---------+---------+---------+---------+---------+---------+
     CCACATATCGTGGTGGTCGGCATCGCGGTCGGACGCAGTCTTTTTTCACTGGAAGCTAGC
     _V__Y__S__T__T__S__R__S__A__S__L__R__Q__K__K__V__T__F__D__R_

     TCTGCAGGTGCTGGATGATCATTATCGTGATGTGCTGAAAGAAATGAAAGCGAAAGCGAG
2221---------+---------+---------+---------+---------+---------+
     AGACGTCCACGACCTACTAGTAATAGCACTACACGACTTTCTTTACTTTCGCTTTCGCTC
     _L__Q__V__L__D__D__H__Y__R__D__V__L__K__E__M__K__A__K__A__S_

     CACCGTTAAAGCCCGTCTGCTGTCTATTGAAGAAGCGTGTAAACTGACCCCGCCGCATAG
2281---------+---------+---------+---------+---------+---------+
     GTGGCAATTTCGGGCAGACGACAGATAACTTCTTCGCACATTTGACTGGGGCGGCGTATC
     _T__V__K__A__R__L__L__S__I__E__E__A__C__K__L__T__P__P__H__S_

     CGCCAAAAGCAAATTTGGCTATGGCGCCAAAGATGTTCGTAGCCTGAGCAGCCGTGCCGT
2341---------+---------+---------+---------+---------+---------+
     GCGGTTTTCGTTTAAACCGATACCGCGGTTTCTACAAGCATCGGACTCGTCGGCACGGCA
     _A__K__S__K__F__G__Y__G__A__K__D__V__R__S__L__S__S__R__A__V_

     TAATCATATTCGTAGCGTGTGGGAAGATCTGCTGGAAGATACCGAAACCCCGATTGATAC
2401---------+---------+---------+---------+---------+---------+
     ATTAGTATAAGCATCGCACACCCTTCTAGACGACCTTCTATGGCTTTGGGGCTAACTATG
     _N__H__I__R__S__V__W__E__D__L__L__E__D__T__E__T__P__I__D__T_

     CACCATCATGGCGAAAAACGAAGTGTTTTGTGTTCAGCCGGAAAAAGGTGGTCGTAAACC
2461---------+---------+---------+---------+---------+---------+
     GTGGTAGTACCGCTTTTTGCTTCACAAAACACAAGTCGGCCTTTTTCCACCAGCATTTGG
     _T__I__M__A__K__N__E__V__F__C__V__Q__P__E__K__G__G__R__K__P_

     GGCCCGTCTGATTGTTTTTCCGGATCTGGGTGTTCGTGTGTGTGAAAAAATGGCGCTGTA
2521---------+---------+---------+---------+---------+---------+
     CCGGGCAGACTAACAAAAAGGCCTAGACCCACAAGCACACACACTTTTTTACCGCGACAT
     _A__R__L__I__V__F__P__D__L__G__V__R__V__C__E__K__M__A__L__Y_

     CGATGTTGTTAGCACCCTGCCGCAGGCGGTTATGGGTCCGAGCTATGGCTTTCAGTATTC
2581---------+---------+---------+---------+---------+---------+
     GCTACAACAATCGTGGGACGGCGTCCGCCAATACCCAGGCTCGATACCGAAAGTCATAAG
     _D__V__V__S__T__L__P__Q__A__V__M__G__P__S__Y__G__F__Q__Y__S_

     TCCGGGTCAGCGTGTTGAATTTCTGGTGAACACCTGGAAAAGCAAAAAATGCCCGATGGG
2641---------+---------+---------+---------+---------+---------+
     AGGCCCAGTCGCACAACTTAAAGACCACTTGTGGACCTTTTCGTTTTTTACGGGCTACCC
     _P__G__Q__R__V__E__F__L__V__N__T__W__K__S__K__K__C__P__M__G_

     CTTCAGCTATAACACCCGCTGCTTTGATAGCACCGTGACCGAAAACGATATCCGTACCGA
2701---------+---------+---------+---------+---------+---------+
     GAAGTCGATATTGTGGGCGACGAAACTATCGTGGCACTGGCTTTTGCTATAGGCATGGCT
     _F__S__Y__N__T__R__C__F__D__S__T__V__T__E__N__D__I__R__T__E_
```

Fig. 8E

```
        AGAAAGCATTTACCAGTGCTGTGATCTGGCGCCGGAAGCCCGTCAGGCGATTAAAAGCCT
2761 ---------+---------+---------+---------+---------+---------+
        TCTTTCGTAAATGGTCACGACACTAGACCGCGGCCTTCGGGCAGTCCGCTAATTTTCGGA
         E  S  I  Y  Q  C  C  D  L  A  P  E  A  R  Q  A  I  K  S  L

        GACCGAACGCCTGTATATTGGCGGTCCGCTGACCAATAGCAAAGGCCAGAACTGTGGTTA
2821 ---------+---------+---------+---------+---------+---------+
        CTGGCTTGCGGACATATAACCGCCAGGCGACTGGTTATCGTTTCCGGTCTTGACACCAAT
         T  E  R  L  Y  I  G  G  P  L  T  N  S  K  G  Q  N  C  G  Y

        TCGTCGTTGTCGTGCCAGCGGTGTTCTGACCACCAGCTGTGGTAATACCCTGACCTGCTA
2881 ---------+---------+---------+---------+---------+---------+
        AGCAGCAACAGCACGGTCGCCACAAGACTGGTGGTCGACACCATTATGGGACTGGACGAT
         R  R  C  R  A  S  G  V  L  T  T  S  C  G  N  T  L  T  C  Y

        CCTGAAAGCGACCGCCGCCTGTCGTGCCGCCAAACTGCAGGATTGTACCATGCTGGTTAA
2941 ---------+---------+---------+---------+---------+---------+
        GGACTTTCGCTGGCGGCGGACAGCACGGCGGTTTGACGTCCTAACATGGTACGACCAATT
         L  K  A  T  A  A  C  R  A  A  K  L  Q  D  C  T  M  L  V  N

        CGGCAATGATCTGGTGGTGATTTGTGAAAGCGCCGGCACCCAGGAAGATGCCGCCAGCCT
3001 ---------+---------+---------+---------+---------+---------+
        GCCGTTACTAGACCACCACTAAACACTTTCGCGGCCGTGGGTCCTTCTACGGCGGTCGGA
         G  N  D  L  V  V  I  C  E  S  A  G  T  Q  E  D  A  A  S  L

        GCGCGTTTTTACCGAAGCGATGACCCGTTATAGCGCCCCGCCGGGTGATCCGCCGCAGCC
3061 ---------+---------+---------+---------+---------+---------+
        CGCGCAAAAATGGCTTCGCTACTGGGCAATATCGCGGGGCGGCCCACTAGGCGGCGTCGG
         R  V  F  T  E  A  M  T  R  Y  S  A  P  P  G  D  P  P  Q  P

        GGAATATGATCTGGAACTGATCACCAGCTGTAGCAGCAATGTTGGTGTTGCCCATGATGC
3121 ---------+---------+---------+---------+---------+---------+
        CCTTATACTAGACCTTGACTAGTGGTCGACATCGTCGTTACAACCACAACGGGTACTACG
         E  Y  D  L  E  L  I  T  S  C  S  S  N  V  G  V  A  H  D  A

        CAGCGGTAAACGTGTGTATTACCTGACCCGTGATCCGACCACCCCGCTGGCCCGTGCCGC
3181 ---------+---------+---------+---------+---------+---------+
        GTCGCCATTTGCACACATAATGGACTGGGCACTAGGCTGGTGGGGCGACCGGGCACGGCG
         S  G  K  R  V  Y  Y  L  T  R  D  P  T  T  P  L  A  R  A  A

        CTGGGAAACCGTTCGTCATACCCCGGTTAATAGCTGGCTGGGCAACATTATTATGTATGC
3241 ---------+---------+---------+---------+---------+---------+
        GACCCTTTGGCAAGCAGTATGGGGCCAATTATCGACCGACCCGTTGTAATAATACATACG
         W  E  T  V  R  H  T  P  V  N  S  W  L  G  N  I  I  M  Y  A

        CCCGACCCTGTGGGCCCGTATGATTCTGATGACCCACTTCTTTAGCATTCTGCTGGCCCA
3301 ---------+---------+---------+---------+---------+---------+
        GGGCTGGGACACCCGGGCATACTAAGACTACTGGGTGAAGAAATCGTAAGACGACCGGGT
         P  T  L  W  A  R  M  I  L  M  T  H  F  F  S  I  L  L  A  Q

        GGAACAGCTGGAAAAAGCGCTGGATTGCCAGATTTATGGCGCCTGCTATAGCATTGAACC
3361 ---------+---------+---------+---------+---------+---------+
        CCTTGTCGACCTTTTTCGCGACCTAACGGTCTAAATACCGCGGACGATATCGTAACTTGG
         E  Q  L  E  K  A  L  D  C  Q  I  Y  G  A  C  Y  S  I  E  P

        GCTGGATCTGCCGCAGATTATTGAACGTCTGCATGGCCTGAGCGCCTTTAGCCTGCATAG
3421 ---------+---------+---------+---------+---------+---------+
        CGACCTAGACGGCGTCTAATAACTTGCAGACGTACCGGACTCGCGGAAATCGGACGTATC
         L  D  L  P  Q  I  I  E  R  L  H  G  L  S  A  F  S  L  H  S
```

Fig. 8F

```
     CTACTCTCCGGGTGAAATTAATCGTGTGGCGAGCTGTCTGCGTAAACTGGGTGTTCCGCC
3481---------+---------+---------+---------+---------+---------+
     GATGAGAGGCCCACTTTAATTAGCACACCGCTCGACAGACGCATTTGACCCACAAGGCGG
     _Y__S__P__G__E__I__N__R__V__A__S__C__L__R__K__L__G__V__P__P_

     GCTGCGTGTCTGGCGTCATCGTGCCCGTAGCGTTCGTGCCAAACTGCTGTCTCAGGGTGG
3541---------+---------+---------+---------+---------+---------+
     CGACGCACAGACCGCAGTAGCACGGGCATCGCAAGCACGGTTTGACGACAGAGTCCCACC
     _L__R__V__W__R__H__R__A__R__S__V__R__A__K__L__L__S__Q__G__G_

     CCGTGCCGCCACCTGTGGTAAATACCTGTTTAACTGGGCGGTTCGTACCAAACTGAAACT
3601---------+---------+---------+---------+---------+---------+
     GGCACGGCGGTGGACACCATTTATGGACAAATTGACCCGCCAAGCATGGTTTGACTTTGA
     _R__A__A__T__C__G__K__Y__L__F__N__W__A__V__R__T__K__L__K__L_

     GACCCCGATTCCGGCGGCGAGCCAGCTGGATCTGAGCGGTTGGTTTGTTGCCGGTTATAA
3661---------+---------+---------+---------+---------+---------+
     CTGGGGCTAAGGCCGCCGCTCGGTCGACCTAGACTCGCCAACCAAACAACGGCCAATATT
     _T__P__I__P__A__A__S__Q__L__D__L__S__G__W__F__V__A__G__Y__N_

     CGGCGGCGATATCTATCATAGCCTGAGCCGTGCCCGTCCGCGTTAATAAACTAGTGGATC
3721---------+---------+---------+---------+---------+---------+
     GCCGCCGCTATAGATAGTATCGGACTCGGCACGGGCAGGCGCAATTATTTGATCACCTAG
     _G__G__D__I__Y__H__S__L__S__R__A__R__P__R__*__*__

     CGGAGCTCCAGCTTTTGTTCCC
3781---------+---------+--
     GCCTCGAGGTCGAAAACAAGGG
```

HEPATITIS C VIRUS NON STRUCTURAL FUSION PROTEIN

HCV belongs to the Flaviviridae family and is a major cause of acute hepatitis and chronic liver diseases. The HCV viral infection is associated with a high rate (54-86%) of chronicity that, in 5 to 24% of cases, can evolve to cirrhosis and subsequently to hepatocellular carcinoma over a 20- to 30-year period (McHutchinson, 2004, *The American Journal of Managed Care* 10, S21-29). Currently, in Europe and United States, 20-30% of liver transplantations and 15-33% of liver cancers are attributable to HCV infection. The World Health Organization estimated in 1999 that about 170 million people are chronically infected by HCV worldwide and 3 to 4 millions persons are newly infected each year.

HCV is an enveloped virus with a positive, single-stranded ribonucleic acid (RNA) genome of approximately 9,600 nucleotides which organization is common to all HCV strains and isolates. Translation of the HCV genome in the 0 phase generates a large polyprotein of 3010 to 3030 amino acids according to the genotype that is proteolytically cleaved by viral and cellular proteases to produce 10 viral proteins. The amino-terminal one-third of the polyprotein encodes the virion structural proteins: the Core (C) protein, and envelope glycoproteins E1 and E2. After the structural region comes a small integral membrane protein, p7, which seems to function as an ion channel. The remainder of the genome encodes the nonstructural (NS) proteins NS2, NS3, NS4A, NS4B, NS5A and NS5B, which mediate the intracellular processes of the virus life cycle (Penin, 2004, Hepatology 39, 5-19). HCV also encodes small proteins, called F (frame shift) or ARFP (alternative reading frame protein), that can be produced by ribosomal frame shifting or internal initiation into an alternative +1 reading frame within the core gene (see Branch et al., 2005, Semin. Liver Dis. 25:105-117; and WO2004/069864). The polyprotein encoding sequences are flanked at both extremities by two highly conserved untranslated regions (UTR), 5'UTR and 3'UTR respectively. An internal ribosome entry site, located in 5'UTR allows ribosome fixation for translation initiation whereas the 3'UTR is thought to play an important role in initiating viral replication.

The current standard therapy for chronically infected HCV patients is a combination of pegylated Interferon alpha (PEG-IFN-$\alpha$) and ribavirin (Fried et al., 2002, N. Engl. J. Med. 347, 975-982). However, this therapy is costly, associated with significant side effects leading to premature ending of treatment in 10% of cases and is inadequate for a significant number of patients (e.g. those with decompensated liver cirrhosis, autoimmune diseases, history of depression and pregnancy). More importantly, only 50% of the treated patients are responders (Falck-Ytter, et al., 2002, Ann. Intern. Med. 136, 288-292) and the response rate is still lower for genotype 1 infected patients (27%-35%).

Overall, a number of experimental evidence is accumulating to emphasize the critical role played by T-cell immunity in the control of HCV infection, particularly $CD4^+$ and $CD8^+$ T-cell mediated responses directed to the non-structural (NS) proteins (e.g. Francavilla et al., 2004, Eur. J. Immunol. 34, 427-37; Grakoui et al., 2003, Science 302, 659-662; Shoukry et al., 2003, J. Exp. Med. 197, 1645-1655; Thimme et al., 2001, J. Exp. Med. 194, 1395-1406; Lechner et al., 2000, J. Exp. Med. 191, 1499-1512; Gerlach, 1999, Gastroenterology 117, 933-941; Folgori et al., 2006, Nat. Med. 12, 190-197). Indeed, vigorous HCV-specific T cell responses are typically observed in patients who recover spontaneously from acute, self-limited hepatitis C whereas T cell responses are weak and narrowly focused in persistently infected patients. On the other hand, the role played by the neutralizing antibodies (B cell-mediated immunity) is much less clear (Logvinoff, 2004, Proc. Natl. Acad. Sci. USA 101, 10149-54).

Since the discovery of the HCV virus over 15 years ago, there is as yet no vaccine against HCV due to the difficulty of achieving efficient growth of the virus in cell culture and the lack of readily available laboratory models of viral infection. However, a number of vaccine candidates have now emerged (Barth and Baumert, 2004, Novel vaccine strategies, p. 214-227, In State of the Art of Hepatology: Molecular and Cell Biology eds Kluwer Academic Publishers; Inchauspe and Feinstone, 2003, Clin. Liver Dis. 7, 243-259), which are based for example on HCV-derived peptides (Cerny et al., 1995, J. Clin. Invest. 95, 521-30), recombinantly-produced HCV antigens, DNA and virus-based vaccines (Brinster et al., 2001, Hepatology 34, 1206-1217; Forms et al., 2000, Hepatology 32, 618-625) and HCV virus-like particles (Baumert et al., 1999, Gastroenterology 117, 1397-1407; Jeong et al., 2004, J. Virol. 78, 6995-7003). Several candidates are currently evaluated in preclinical models and the first wave is entering clinical trials. The most advanced vaccines currently in phase II use adjuvanted E1 envelope proteins (Innogenetics) and adjuvanted CD4+ and CD8+ T cell epitopes (Intercell).

An approach which has been actively explored during this last decade, resides in the use of polyproteins associating various antigenic domains as immunogens. A vast majority of the prior art polyproteins results from the fusion to one another of antigenic polypeptides, fragments or epitopes originating from various NS HCV proteins in order to form a single and hopefully immunogenic polypeptide. For example, WO01/30812 and WO03/031588 disclose the fusion of HCV polypeptides from NS3 through NS5B to form a single polypeptide encompassing the major NS proteins. WO03/097677 describes the fusion of antigenic fragments of 30 to 70 amino acids originating from NS3, NS4B and NS5B polypeptides. WO2004/046176 discloses a polyprotein comprising Core, NS3, NS4B and NS5B. WO2004/111082 describes adenovirus and MVA vectors for co-expressing NS3, NS4 and NS5B where NS3 and NS4 are expressed as a fusion protein and NS5B is expressed independently.

It has to be noted that the configuration of the prior art polyproteins is as in the native context, the various components appearing in the order in which they naturally occur in the native HCV precursor. In particular, NS3 is followed by NS4 which is followed by NS5. However, the “native” configuration is not optimal in terms of expression and immunogenicity of the resulting polyproteins.

One may expect that HCV will continue to be a serious global health threat for many years due to the chronic and persistent nature of the infection, its high prevalence and the significant morbidity of the associated diseases. Thus, there is an important need to develop more immunogenic polypeptides, expressing vectors, methods for preparation thereof, and uses thereof, for improving prevention and treatment of HCV infections or HCV-associated diseases or disorders.

The present invention relates to fusion proteins involving non-structural (NS) polypeptides arranged in a non-native configuration. Specific fragments of the HCV NS polypeptides (e.g. NS3, NS4A, NS5B and optionally NS4B) were selected and specifically configured in order to optimise the immunogenicity and/or recombinant production process of the resulting fusion proteins. As compared to native NS polypeptides, the novel HCV fusion proteins provided by the present invention or their encoding nucleotide sequences may permit an improvement of an anti-HCV immune response and/or an improvement of the overall cytotoxic response upon introduction in a host organism and/or an improvement of the production of clinical lots. Thus, the invention represents a significant advance in current treatment and prevention of HCV infections or HCV-associated diseases or disorders. In particular, it may be used to reinforce existing therapies or provide an alternative treatment to chronically infected patients, especially to those who are non-responders to conventional therapy.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

Accordingly, in a first aspect, the present invention provides an isolated fusion protein comprising at least three NS polypeptides which originate from a hepatitis C virus (HCV) wherein said NS polypeptides are configured in said fusion protein in an order which is distinct of the order in which they appear in the native configuration.

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

The terms "amino acids" and "residues" are synonyms and encompass natural amino acids as well as amino acid analogs (e.g. non-natural, synthetic and modified amino acids, including D or L, optical isomers).

The terms "polypeptide", "peptide" and "protein" are used herein interchangeably to refer to polymers of amino acid residues which comprise ten or more amino acids bonded via peptide bonds. The polymer can be linear, branched or cyclic and may comprise naturally occurring and/or amino acid analogs and it may be interrupted by non-amino acids. As a general indication, if the amino acid polymer is long (e.g. more than 50 amino acid residues), it is preferably referred to as a polypeptide or a protein.

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) molecules (e.g., mRNA, antisense RNA) or mixed polyribo-polydeoxyribinucleotides. They encompass single or double-stranded, linear or circular, natural or synthetic polynucleotides. Moreover, a polynucleotide may comprise non-naturally occurring nucleotides, such as methylated nucleotides and nucleotide analogs (see U.S. Pat. No. 5,525,711, U.S. Pat. No. 4,711,955 or EPA 302 175 as examples of modifications) and may be interrupted by non-nucleotide components. If present, modifications to the nucleotide may be imparted before or after polymerization.

As used herein, when used to define products, compositions and methods, the term "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps. For example, a polypeptide "consists of" an amino acid sequence when the polypeptide does not contain any amino acids but the recited amino acid sequence. A polypeptide "consists essentially of" an amino acid sequence when such an amino acid sequence is present together with only a few additional amino acid residues, typically from about 1 to about 50 or so additional residues. A polypeptide "comprises" an amino acid sequence when the amino acid sequence is at least part of the final amino acid sequence of the polypeptide. Such a polypeptide can have a few up to several hundred additional amino acids residues. Such additional amino acid residues may play a role in polypeptide trafficking, facilitate polypeptide production or purification; prolong half-life, among other things. The same can be applied for nucleotide sequences.

As used herein, the term "isolated" refers to a protein, polypeptide, peptide or a nucleic acid that is purified or removed from its natural environment. The term "purified" refers to a protein, polypeptide, peptide or a nucleic acid that is separated from at least one other component(s) with which it is naturally associated.

"HCV" means "hepatitis C virus". Extensive phylogenetic analyses have led to the classification of HCV isolates into 6 major genotypes (1 to 6) containing different subtypes (a, b, c, etc. . . . ) (Simmons et al., 2005, Hepatology 42, 962-973). Exemplary HCV isolates of genotype 1a include without limitation, HCV-1 (Choo et al., 1991, Proc. Natl. Acad. Sci. USA 88, 2451-2455), -Jl (Okamoto et al., 1992, Nucleic Acids Res. 20, 6410-6410) and –H (Inchauspé et al., 1991, Proc. Natl. Acad. Sci. 88, 10292-10296). Exemplary HCV isolates of genotype 1b include without limitation, HCV-JA (Kato et al., 1990, Proc. Natl. Acad., Sci. 87, 9524-9528) and BK (Takamizawa et al., 1991, J. Virol. 65, 1105-1113). Exemplary HCV isolates of genotype 1c include without limitation, HCV-G9 (Okamoto et al., 1994, J. Gen. Virol. 45, 629-635). Exemplary HCV isolates of genotype 2a include without limitation, HCV-J6 (Okamoto et al., 1991, J. Gen. Virol. 72, 2697-2704). Exemplary HCV isolates of genotype 2b include without limitation, HCV-J8 (Okamoto et al., 1992, Virology 188, 331-341). Exemplary HCV isolates of genotype 2c include without limitation, HCV-BEBE1 (Nako et al., 1996, J. Gen. Virol. 141, 701-704). Exemplary HCV isolates of genotype 3a include without limitation, HCV-NZL1 (Sakamoto et al., 1994, J. Gen. Virol. 75, 1761-1768). Exemplary HCV isolates of genotype 3b include without limitation, HCV-Tr (Chayama et al., 1994, J. Gen. Virol. 75, 3623-3628). Exemplary HCV isolates of genotype 4a include without limitation, HCV-ED43 (Chamberlain et al., 1997, J. Gen. Virol. 78, 1341-1347). Exemplary HCV isolates of genotype 5a include without limitation, HCV-EUH1480 (Chamberlain et al., 1997, Biochem. Biophys. Res. Commum. 236, 44-49). Exemplary HCV isolates of genotype 6a include without limitation, HCV-EUHK2 (Adams et al., 1997, Biochem. Biophys. Res. Commun. 234, 393-396).

The term "fusion" or "fusion protein" as used herein refers to the combination with one another of at least three NS polypeptides (or fragment(s) or variant(s) thereof) in one polypeptide chain. Preferably, the fusion between the various NS polypeptides is performed by genetic means, i.e. by fusing in frame the nucleotide sequences encoding each of the NS polypeptides. By "fused in frame", it is meant that the expression of the fused coding sequences results in a single protein without any translational terminator between each of the NS polypeptides.

The fusion between each of the NS polypeptides can be direct or through a linker. As used herein, "direct" refers to a fusion between two NS polypeptides without any additional amino acid residues in between (e.g. the codons encoding a NS polypeptide are contiguous to the codons encoding the following NS polypeptide). Alternatively, one may use a linker peptide at the junction of at least two NS polypeptides. The presence of a linker may facilitate correct formation, folding and/or functioning of the fusion protein. The present invention is not limited by the form, size or number of linker sequences employed and multiple copies of a linker sequence may be inserted at the junction between two NS polypeptides. Suitable linkers in accordance with the invention are 3 to 30 amino acids long and composed of repeats of amino acid residues such as glycine, serine, threonine, asparagine, alanine and/or proline (see for example Wiederrecht et al., 1988, Cell 54, 841; Aumailly et al., 1990 FEBS Lett. 262, 82; and Dekker et al., 1993, Nature 362, 852). Representative examples of suitable linkers include a Ser-Gly-Ser (SEQ ID NO:33) linker to connect the N-terminus NS polypeptide to the second NS polypeptide and a Gly-Ser-Gly-Ser-Gly (SEQ ID NO:34) linker to connect the second NS polypeptide to the third NS polypeptide. Alternatively, one may also use HCV-derived sequences to connect one to another two NS polypeptides (e.g. the C-terminal portion of a native NS4A polypeptide extending from approximately position 1691 to approximately position 1711 numbered relative to the full length HCV-1 polyprotein).

"At least three" means a number which is three or greater than three, with a special preference for three or four.

As used herein the term "NS polypeptide" refers to an art-recognized non structural protein, preferably selected among the group consisting of NS2, NS3, NS4A, NS4B and NS5B polypeptides. It is nonetheless preferred that the fusion protein contains no NS5A polypeptide. In the context of the invention the NS polypeptides included in the fusion protein of the invention may originate independently from any HCV strain or isolate identified at present time, such as those described above in connection with the term "HCV". The term "originate" means be isolated, cloned, derived or related. Thus, in accordance with the present invention, each of the NS polypeptides included in the fusion protein may originate from a native NS polypeptide or from a modified NS polypeptide, as further defined below.

A "native" NS polypeptide refers to a NS protein, polypeptide or peptide that can be found or isolated from a source in nature, as distinct from being artificially modified or altered by man in the laboratory. Thus the term "native NS polypeptide" would include naturally-occurring NS polypeptides and fragments thereof. Such sources in nature include biological samples (e.g. blood, plasma or sera from HCV-infected patients or that have been infected in the past by an HCV), cultured cells, as well as recombinant materials (e.g. HCV virus or genome, genomic or cDNA libraries, plasmids containing fragments of HCV genome, recombinant pre-processed precursor or mature processed NS polypeptide and the like). The nucleotide and amino acid sequences of a number of native NS polypeptides/genes have been described in the literature and are available in specialized data banks. Representative examples of native NS polypeptides are set forth at SEQ ID NO: 1-4 (SEQ ID NO: 1-4 provide the amino acid sequences of the native NS3, NS4A, NS4B and NS5B polypeptides of the genotype 1b HCV JA strain). However, native NS polypeptides are not limited to these exemplary sequences. Indeed the amino acid sequences can vary between different HCV genotypes, subtypes and isolates and this natural scope of genetic variation is included within the scope of the invention.

One or more of the NS polypeptides included in the fusion protein of the invention can independently from each other include one or more amino acid modification(s) from the exemplary sequences or other native NS polypeptides. Modification(s) can be generated by way of mutation and/or addition of chemical moieties (e.g. alkylation, acetylation, amidation, phosphorylation and the like) or labeling moieties. Mutation(s) include deletion, substitution or addition of one or more amino acid residue(s) or any combination of these possibilities. When several modifications are contemplated, they can concern consecutive residues and/or non consecutive residues. Modification(s) can be made in a number of ways known to those skilled in the art. For example the nucleotide sequence encoding the NS polypeptide can be modified using routine recombinant techniques, such as enzymatic cutting followed by modification and ligation of defined fragment, site-directed mutagenesis (e.g. using the Sculptor™ in vitro mutagenesis system of Amersham, Les Ullis, France), PCR mutagenesis or DNA shuffling.

A preferred modified NS polypeptide retains a high degree of amino acid sequence identity with the corresponding native NS polypeptide, e.g. at least 75% of identical amino acid residues over the full length amino acid sequence or a shorter fragment thereof (e.g. of at least 10, 15, 20, 25, 30, 40, 50, 100 amino acids in length). More specifically, in the context of the invention, the modified NS polypeptide in use in the invention share a degree of identity with the corresponding native NS polypeptide which is greater than 75%, advantageously greater than 80%, desirably greater than 85%, preferably greater than 90%, more preferably greater than 95%, still more preferably greater than 97%. The percent identity between the two polypeptides is a function of the number of identical positions shared by the sequences, taking into account the number of gaps which need to be introduced for optimal alignment and the length of each gap. Various computer programs and mathematical algorithms are available in the art to determine percentage identities between amino acid sequences such as for example the Blast program (e.g. Altschul et al., 1997, Nucleic Acids Res. 25, 3389-3402; Altschul et al., 2005, FEBS J. 272, 5101-5109) available at NCBI.

For example, any or all of the NS polypeptides included in the fusion protein of the invention can be modified so as to be representative of a specific genotype or subtype, and thus comprise an amino acid sequence corresponding to a consensus or a near-consensus sequence which is typically determined after sequence alignment of various NS of a particular genotype or subtype. Any or all of the NS polypeptides can also be modified to provide a NS polypeptide with modified functional properties, such as a reduced enzymatic function, and/or a reduced ability to be anchored in a cell membrane and/or a reduced ability to be post-translationally processed, as described below. Amino acids that are critical for such functional properties may be identified by routine methods, such as by structural and functional analysis. One of skill in the art can readily determine the type of modification(s) that is able to reduce or disrupt a given enzymatic activity. For example, one may proceed by site-directed mutagenesis or PCR techniques in order to delete or substitute one or more amino acid(s) within an active region of the enzymatic activity (e.g. in the catalytic site) such that the native enzymatic activity is significantly reduced or abolished. The reduction or lack of a biological activity can be easily determined in appropriate assays according to the enzymatic activity to be tested using methods known to those of skill in the art. Membrane anchorage domains are usually predicted on the basis of their hydrophobic nature.

In accordance with the present invention, the at least three NS polypeptides included in the fusion protein of the invention are configured in an order which is distinct of the order in which they appear in the native configuration. The native configuration is known in the art (see the overview given in the introduction section of the present application) and the order in which the NS polypeptides appear is as found in a HCV polyprotein precursor, i.e. from the N to the C-terminus NS2-NS3-NS4A-NS4B-NS5A-NS5B. According to the native configuration:

A NS2 polypeptide always precedes a NS3 polypeptide or a NS4A polypeptide or a NS4B polypeptide or a NS5A polypeptide or a NS5B polypeptide; and A NS3 polypeptide always precedes a NS4A polypeptide or a NS4B polypeptide or a NS5A polypeptide or a NS5B polypeptide; and A NS4A polypeptide always precedes a NS4B polypeptide or a NS5A polypeptide or a NS5B polypeptide; and A NS4B polypeptide always precedes a NS5A polypeptide or a NS5B polypeptide; and A NS5A polypeptide always precedes a NS5B polypeptide.

In the fusion protein of the invention, the configuration is not native in the sense that at least one of the NS polypeptides appears in an order which is distinct from that of the native configuration. Thus, if the fusion protein comprises a NS3 polypeptide, a NS4A polypeptide and a NS5B polypeptide, the native configuration would be NS3-NS4A-NS5B with NS3 at the N-terminus and NS5B at the C-terminus. In contrast, a non-native configuration can be NS5B-NS3-NS4A, NS5B-NS4A-NS3, NS4A-NS3-NS5B, NS4A-NS5B-NS3 or NS3-NS5B-NS4A.

In particular, the fusion protein of the invention comprises at least one of the followings:

A NS4A polypeptide fused directly or through a linker to the N-terminus of a NS3 polypeptide;

A NS3 polypeptide fused directly or through a linker to the N-terminus of a NS5B polypeptide;

A NS4B polypeptide fused directly or through a linker to the N-terminus of a NS5B polypeptide;

A NS4A polypeptide fused directly or through a linker to the N-terminus of a NS3 polypeptide which is fused directly or through a linker to the N-terminus of a NS4B polypeptide; and/or A NS3 polypeptide fused directly or through a linker to the N-terminus of a NS4B polypeptide which is fused directly or through a linker to the N-terminus of a NS5B polypeptide.

In such specific portions of the fusion protein of the invention, each of the NS polypeptides can be independently native or modified. For example, the NS4A polypeptide included in the NS4A-NS3 portion can be native whereas the NS3 polypeptide comprises at least one of the modifications described below.

In one embodiment, all the NS polypeptides included in the fusion protein of the invention originate from the same HCV strain or isolate. Alternatively, at least two of the NS polypeptides originate from different HCV strains or isolates in order to provide protection against a broader range of HCV genotypes. It could be also interesting to adapt the fusion protein to the specific geographic region where it will be used by including at least one NS polypeptide from a HCV isolate that is endemic in this region (e.g. genotypes 1a, 1b, 2 and 3 are the most prevalent in North America, Europe and Asia; genotype 4 is predominant in North and Central Africa; genotype 5 has so far been mostly identified in South Africa and genotype 6 isolates have been found primarily in Vietnam and Hong Kong). For example, if the fusion protein comprises a NS3 polypeptide, a NS4A polypeptide and a NS5B polypeptide, the NS3 polypeptide can originate from a first strain of HCV, and the NS4A and NS5B polypeptides from a second strain of HCV. Alternatively, the NS4A polypeptide can originate from a first strain of HCV, and the NS3 and NS5B polypeptides from a second strain of HCV. Alternatively, the NS5B polypeptide can originate from a first strain of HCV, and the NS3 and NS4A polypeptides from a second strain of HCV. Alternatively, NS3, NS4A and NS5B polypeptides each originate from different HCV strains. When the fusion protein of the invention also comprises a NS4B polypeptide, it can originate from the same HCV strain or from a different HCV strain than the other polypeptides.

Preferred embodiments of the invention are directed to a fusion which comprises, or essentially consists of, or consists of a NS4A polypeptide, a NS3 polypeptide, and a NS5B polypeptide with NS4A at the N-terminus and NS5B at the C-terminus (NS4A-3-5B fusion). Optionally, the fusion may also include a NS4B polypeptide (or fragment(s) or variant(s) thereof) to further improve the immunogenic activity of the resulting fusion protein. The NS4B polypeptide is preferably included between the NS3 and the NS5B polypeptides. Therefore, the present invention also pertains to a fusion protein which comprises, or essentially consists of, or consists of a NS4A polypeptide, a NS3 polypeptide, a NS4B polypeptide and a NS5B polypeptide with NS4A at the N-terminus and NS5B at the Cry terminus (NS4A-3-4B-5B fusion). Apart from the NS3, NS4A, NS5B and the optional NS4B polypeptides, it is nonetheless preferred that the fusion protein of the invention contains no other HCV polypeptides, and especially no core and as discussed above in connection with the NS polypeptides no NS5A polypeptide.

More specifically, the term "NS3 polypeptide" refers to a native NS3 protein, polypeptide or peptide obtained from any HCV strain or to a modified NS3 protein, polypeptide or peptide as defined above. The NS3 polypeptide in use in the invention has a length of at least 200 amino acids, advantageously at least 300 amino acids, preferably at least 400 amino acids, more preferably at least 500 amino acids and even more preferably at least 600 amino acids. For purpose of illustration, the native HCV-1 NS3 protein is 631 amino acids long and is located approximately from positions 1027 to 1657 in the polyprotein precursor. A native NS3 polypeptide comprises two distinct active domains, a serine protease domain in the N-terminus and a helicase domain in the C-terminus. NS3 protease is responsible for processing the HCV polyprotein precursor at NS3/NS4A, NS4A/NS4B, NS4B/NS5A and NS5A/NS5B junctions, and requires NS4A as a cofactor for proteolytic activity (Tomei et al., 1993, J. Virol. 67, 4017-4026) and for proper folding (Yao et al., 1999, Structure (London) 7 pp 1353). A motif consisting of an aspartic or glutamic acid at position 6 and a cysteine or threonine at position 1 upstream from the cleavage site and a serine or alanine at position 1 downstream the cleavage site is specifically recognized by the HCV NS3 protease. The NS3 helicase is thought to be important for unwinding the double-stranded RNA intermediate during viral replication (Tai et al., 1996, J. Virol. 70, 8477-8484).

By a "NS4A polypeptide", it is meant a native NS4A protein, polypeptide or peptide from any HCV strain or a modified NS4A protein, polypeptide or peptide as defined above. The NS4A polypeptide in use in the invention has a length of at least 10 amino acids, advantageously at least 11 amino acids, preferably at least 12 amino acids, more preferably at least 13 amino acids. By a "NS4B polypeptide", it is meant a native NS4B protein, polypeptide or peptide from any HCV strain or a modified NS4B protein, polypeptide or peptide as defined above. The NS4B polypeptide in use in the invention has a length of at least 20 amino acids, advantageously at least 25 amino acids, preferably at least 30 amino acids, more preferably at least 31 amino acids and even more preferably at least 32 amino acids. For purpose of illustration, the native HCV-1 NS4 (A-B) protein is 315 amino acids long and is located approximately from positions 1658 to 1972 in the polyprotein precursor. The NS4A polypeptide (positions 1658 to 1711) is a co-factor of NS3 protease but is also required for NS3 stability and localization in the endoplasmic reticulum (ER) membrane (Failla et al., 1994, J. Virol. 68, 3753-3760). The NS4B polypeptide (positions 1712 to 1972) is an integral membrane protein which function is yet unknown. Predicted algorithms suggest the presence of four to six trans-membrane segments. Its expression however induces the formation of a seemingly ER-derived membranous web (Egger et al., 2002, J. Virol. 76, 5974-5984).

By a "NS5B polypeptide", it is meant a native NS5B protein, polypeptide or peptide from any HCV strain or a modified NS5B protein, polypeptide or peptide as defined above. The NS5B polypeptide in use in the invention has a length of at least 200 amino acids, advantageously at least 300 amino acids, preferably at least 400 amino acids, more preferably at least 500 amino acids and even more preferably at least 550 amino acids. For purpose of illustration, the native HCV-1 NS5B protein is 591 amino acids long and is located approximately from positions 2421 to 3011 in the polyprotein precursor. The native NS5B protein acts as a RNA-dependent RNA polymerase, which presumably permits the synthesis of a negative stranded RNA intermediate and positive-stranded progeny copies (Lohman et al., 1997, J. Virol. 71, 8416-8428). It is found associated to the endoplasmic reticulum membrane by its 21 C-terminus amino acid sequence (Schmidt-Mende et al., 2001, J. Biol. Chem. 276, 44052-44063).

For sake of clarity, the amino acid stretches referred herein in connection with NS3, NS4A, NS4B and NS5B polypeptides are given with respect to their positions in HCV-1 polyprotein precursor (as described by Choo et al., 1991, Proc. Natl. Acad. Sci. USA 88, 2451-2455 or in GenBank under accession number M62321). However, as discussed above, the present invention also encompasses NS polypeptides of other HCV strains and isolates, as well as modified NS polypeptides. Therefore, unless the context clearly dictates otherwise, when it is referred herein to a NS polypeptide or a peptide thereof by reference to HCV-1 polyprotein precursor, this means the NS polypeptide or the peptide thereof of HCV-1, a NS polypeptide or the peptide thereof of any other HCV strain or isolate or a modified NS polypeptide or peptide thereof. A preferred embodiment of the present invention is directed to a fusion protein comprising the NS3, NS4A, NS5B and the optional NS4B polypeptides originating from the genotype 1b HCV JA strain (Kato et al., 1990, Proc. Natl. Acad., Sci. 87, 9524-9528).

In one embodiment, the NS3 polypeptide included in the fusion protein of the present invention is modified as compared to the corresponding native NS3 polypeptide so as to exhibit a significantly reduced protease activity, and thus be unable to mediate the cleavage of the fusion protein into individual polypeptides. The protease activity has been located in the N-terminal portion of the NS3 polypeptide, from about position 1027 to about position 1207 numbered relative to the full-length HCV-1 polyprotein (from about position 1 to about position 181 of the native HCV-JA NS3 polypeptide shown SEQ ID NO: 1). More specifically, the NS3 protease activity has been attributed to the catalytic triad residues His (H) at position 1083, Asp (D) at position 1107 and Ser (S) at position 1165 (respectively positions 57, 81 and 139 of SEQ ID NO: 1). Representative examples of suitable protease-deficient NS3 polypeptides are described in Bartenshlager et al., 1993, J. Virol. 67, 3835-3844 and Tomei et al., 1993, J. Virol. 67, 4017-4026. Preferably, as the catalytic Asp and Ser residues lie within a predicted antigenic domain, the NS3 polypeptide in use in the present invention comprises the substitution of the His residue in position 1083 (corresponding to position 57 of SEQ ID NO: 1) or of the amino acid residue located in an equivalent position of a native NS3 polypeptide of another HCV serotype, to any amino acid residue other than His, with a special preference for a substitution to an Ala residue (H1083A). The disruption of the protease activity can be determined using assays well known in the art (Takeshita et al., 1997, Anal. Biochem. 247, 242-246; Kakiuchi et al., 1997 J. Biochem 122, 749-755; Sali et al., 1998, Biochemistry 37, 3392-3401; Kakiuchi et al., 1999, J. Virol. Meth. 80, 77-84).

Alternatively or in combination, the NS3 polypeptide included in the fusion protein of the invention is modified as compared to the corresponding native NS3 polypeptide so as to exhibit a significantly reduced helicase activity. Four residues have been involved in the NS3-associated helicase activity, respectively Thr in position 1295, Thr in position 1437, Arg in position 1490 and Arg in position 1493 numbered relative to the full length HCV-1 polyprotein (which corresponds to Thr residues in positions 269 and 411 and Arg residues at positions 464 and 467 of the native HCV-JA NS3 polypeptide shown in SEQ ID NO: 1). Representative examples of suitable helicase-deficient NS3 polypeptides are described in Kim et al. (1997, J. Virol. 71, 9400) and Lin and Kim (1999, J. Virol. 73, 8798-8807). Preferably, the NS3 polypeptide in use in the present invention comprises the substitution of the Arg residue in position 1490 (corresponding to position 464 of SEQ ID NO: 1) or of the amino acid residue located in an equivalent position of a native NS3 polypeptide of another HCV serotype to any amino acid residue other than Arg and the substitution of the Thr residue in position 1295 (corresponding to position 269 of SEQ ID NO: 1) or of the amino acid residue located in an equivalent position of a native NS3 polypeptide of another HCV serotype to any amino acid residue other than Thr, with a special preference for a substitution to an Ala residue in both cases (T1295A and R1490A). The disruption of the helicase activity can be determined using assays well known in the art, e.g. by evaluating the unwinding activity.

Most preferably, the NS3 polypeptide in use in the present invention is mutated to reduce or disrupt both the protease and the helicase activities of the native NS3 polypeptide and comprise the modifications discussed above in connection with these enzymatic functions, with a special preference for mutations H1083A, T1295A and R1490A.

Alternatively or in combination with the modifications proposed above in connection with the NS3 polypeptide, the NS5B polypeptide included in the fusion protein of the invention is modified as compared to the corresponding native NS5B polypeptide so as to exhibit a significantly reduced RNA-dependent RNA polymerase activity. Two Asp residues have been involved in this enzymatic function, respectively in positions 2640 and 2738 numbered relative to the hill length HCV-1 polyprotein (which corresponds to Asp residues in positions 220 and 318 of the native HCV-JA NS5B polypeptide shown in SEQ ID NO: 4). Representative examples of suitable polymerase-deficient NS5B polypeptides are described in Lohmann et al. (1997, J. Virol. 71, 8416-8428). Preferably, the NS5B polypeptide in use in the present invention comprises at least the substitution of the Asp residue in position 2640 (corresponding to position 220 of SEQ ID NO: 4) or of the amino acid residue located in an equivalent position of a native NS5B polypeptide of another HCV serotype to any amino acid residue other than Asp and/or the substitution of the Asp residue in position 2738 (corresponding to position 318 of SEQ ID NO: 4) or of the amino acid residue located in an equivalent position of a native NS5B polypeptide of another HCV serotype to any amino acid residue other than Asp, with a special preference for a substitution to an Asn residue in both cases. The disruption of the RNA polymerase activity can be determined using assays well known in the art, e.g. conventional replicase assays based on incorporation of radioactive nucleotide substrate into a nascent RNA product (see for example Behrens et al., 1996, EMBO J. 15, 12-22; Ferrari et al., 1999, J. Virol. 73, 1649-1654).

In another embodiment, the NS polypeptides included in the fusion protein of the invention may further comprise additional modifications as compared to the corresponding native NS polypeptides. Suitable modifications are those which are beneficial to the processing, stability and solubility of the resulting fusion protein, e.g. those aimed to inactivate potential cleavage sites, membrane anchorage and/or glycosylation as described below.

Advantageously, the fusion protein of the invention does not comprise one or more of the NS3-recognized cleavage site(s) normally present in the native HCV polyprotein precursor at the NS3/NS4A, NS4A/NS4B, NS4B/NS5A and NS5A/NS5B junctions, in order to avoid the processing into individual NS polypeptides. Although the preferred NS3 polypeptide in use in the present invention exhibits a significantly reduced protease activity, inactivation of the NS3-recognized cleavage sites introduces a further degree of security. The consensus sequence of cleavage site is Asp/Glu-X4-Cys/Thr-Ser/Ala, wherein X is any amino acid residue. The cleavage by the native NS3 polypeptide was shown to occur after the Cys/Thr residue. Preferably, the NS3 polypeptide in use in the invention does not comprise the Thr or Cys residue normally present at the C-terminus of a native NS3 polypeptide (position 1657 numbered relative to the HCV-1 polyprotein which corresponds to position 361 of SEQ ID NO: 1 or an equivalent position of a native NS3 polypeptide of another HCV serotype). Alternatively or in combination, the NS4A polypeptide does not comprise the Cys residue normally present at the C-terminus of a native NS4A polypeptide (position 1711 numbered relative to the HCV-1 polyprotein which corresponds to position 54 of SEQ ID NO: 2 or an equivalent position of a native NS4A polypeptide of another HCV serotype). Alternatively or in combination, the optional NS413 polypeptide does not comprise the Cys residue normally present at the C-terminus of a native NS4B polypeptide (position 1972 numbered relative to the HCV-1 polyprotein which corresponds to position 261 of SEQ ID NO: 3 or an equivalent position of a native NS4B polypeptide of another HCV serotype).

In still another embodiment, the fusion protein of the invention may be further modified so as to delete one or more hydrophobic domain(s) which are normally involved in membrane anchorage of the native NS4A, NS4B and/or NS5B polypeptides. Six membrane-anchorage hydrophobic domains have been identified in the native NS4B polypeptide whereas one is present in the N-terminus portion of the native NS4A polypeptide and one in the C-terminal portion of the NS5B native polypeptide. Their at least partial deletion may permit to improve the solubility of the fusion protein and thus facilitate its production by recombinant means. This may also permit to limit the overall cytotoxicity of the fusion protein as compared upon administration of the individual HCV polypeptides in a given host organism.

In this respect, the NS4A polypeptide is advantageously modified by deletion or substitution of one or more hydrophobic amino acid residues normally present within the N-terminal portion of the native NS4A polypeptide. A preferred NS4A polypeptide is deleted of up to 20 first amino acids at the N-terminus (e.g. preferred deletion from approximately position 1658 to approximately position 1677 numbered relative to the full length HCV-1 polyprotein which corresponds to deletion from approximately position 1 to approximately position 20 of the native HCV-JA NS4A polypeptide shown in SEQ ID NO: 2) while nevertheless retaining the portion of the native NS4A polypeptide extending from approximately position 1678 to approximately position 1690 numbered relative to the full length HCV-1 polyprotein (from approximately position 21 to approximately position 33 of the native HCV-JA NS4A polypeptide shown in SEQ ID NO: 2). It may or may not retain the C-terminal portion of the native NS4A polypeptide, e.g. the portion extending from approximately position 1691 to approximately position 1711 numbered relative to the full length HCV-1 polyprotein (which corresponds to from approximately position 34 to approximately position 54 of the native HCV-JA NS4A polypeptide shown in SEQ ID NO: 2). Most preferably, the NS4A polypeptide included in the fusion protein of the invention consists of the portion of a native NS4A polypeptide extending from position 1678 to position 1690 numbered relative to the full length HCV-1 polyprotein, (which corresponds to the NS4A portion extending from position 21 to position 33 of the native HCV-JA NS4A polypeptide shown SEQ ID NO: 2).

Alternatively or in combination, a preferred NS5B polypeptide is deleted of 10 to 30 amino acid residues normally present at the C-terminus of a native NS5B polypeptide, with a special preference for deletion of the last 21 C-terminus amino acid residues (e.g. from position 2991 to position 3011 numbered relative to the HCV-1 polyprotein which corresponds from position 571 to position 591 of SEQ ID NO: 4).

Alternatively or in combination, a preferred optional NS4B polypeptide is deleted of at least one of the six membrane-anchorage hydrophobic domains. More preferably, the optional NS4B polypeptide is truncated by one or more amino acids at both the N- and C-terminus of the corresponding native NS4B polypeptide so as to essentially retain the internal antigenic domain. Preferably, the optional NS4B polypeptide in use in the invention comprises or alternatively essentially consists of the amino acid stretch extending from approximately position 1789 to approximately position 1820 numbered relative to the full length HCV-1 polyprotein (which corresponds to approximately position 78 to approximately position 109 of the native HCV-J NS4B polypeptide shown in SEQ ID NO: 3).

In still another embodiment, the fusion protein of the invention is further modified so as to suppress potential N-glycosylation upon expression in a given host cell. In this regard, a consensus glycosylation site Asn-Val-Ser-Val has been identified in the native NS5B polypeptide from position 2789 to position 2792 numbered relative to the full length HCV-1 polyprotein (position 369 to position 372 of the native HCV-JA NS5B protein shown in SEQ ID NO: 4). An exemplary mutation in this regard consists in the substitution of the Ser residue in position 2791 numbered relative to the full length HCV-1 polyprotein (position 371 of SEQ ID NO: 4) by a residue different of a Ser residue, such as a Gly residue.

Desirably, the fusion protein of the invention is immunogenic, in the sense that it is capable of inducing or stimulating an antigen-specific immune response, whether humoral or cellular or both-upon introduction in a host organism. The present invention also encompasses fusion proteins that have been engineered so as to enhance immunogenicity (e.g. by disulfide bond oxidation). Desirably, the folding of the various NS polypeptides included in the fusion protein of the invention is as the folding of the native NS polypeptides. In the context of the invention, it is preferred that the fusion protein retains one or more antigenic domains recognized by a T cell receptor. A number of HCV antigenic domains that can be suitably retained in the fusion protein are described in the literature (see, e.g., Chien et al., 1992, Proc. Natl. Acad. Sci. USA 89, 10011-10015; Chien et al., 1993, J. Gastroent. Hepatol. 8, S33-39 and WO03/097677).

Preferably, the NS3 polypeptide included in the fusion protein of the invention retains the portions of the native NS3 polypeptide extending from approximately position 1038 to approximately position 1082, from approximately position 1096 to approximately position 1181 and from approximately position 1244 to approximately position 1274 numbered relative to the full length HCV-1 polyprotein (e.g. from approximately position 12 to approximately position 56, from approximately position 70 to approximately position 155, and/or from approximately position 218 to approximately position 248 of the native HCV-JA NS3 polypeptide disclosed in SEQ ID NO: 1). Preferably, the NS5B polypeptide included in the fusion protein of the invention retains the portion of the native NS5B polypeptide extending from approximately position 2573 to approximately position 2601 numbered relative to the full length HCV-1 polyprotein (e.g. from approximately position 155 to approximately position 182 of the native HCV-J NS5B polypeptide disclosed in SEQ ID NO: 4). When the fusion protein of the invention comprises a NS4B polypeptide, it preferably retains the portion of the native NS4B polypeptide from approximately position 1789 to approximately position 1820 numbered relative to the full length HCV-1 polyprotein (e.g. from approximately position 78 to approximately position 109 of the native HCV-J NS4B polypeptide disclosed in SEQ ID NO: 3).

The immunogenic activity of the fusion protein of the invention can be evaluated by a number of techniques which are routine in the art, such as those described hereinafter in connection with the method of the invention or illustrated in Examples. In the context of the invention, it is preferred that the immunogenic activity of the fusion protein be greater in extend and/or in nature than the usual immunogenic activity provided by a native NS polypeptide. For example, upon introduction of the fusion protein in a host organism, the immune response may be of a greater strength, of a broader nature (e.g. involving more immune cells such as CD4+ and CD8+ cells) or its scope may be different (e.g. directed to a non-dominant cryptic epitope) than upon introduction of a native NS polypeptide. This would provide an enhanced therapeutic effect, thus allowing reducing dosing regimens and improving (quality of life.

A preferred NS3 polypeptide originates from the native HCV-JA NS3 protein shown in SEQ ID NO: 1 which is modified at least in such a manner that:

- it retains the portion extending from position 12 to position 56, from position 70 to position 155, and from position 218 to position 248;
- it comprises the substitution of the His residue in position 57 by an amino acid residue different of a His, such as an Ala residue;
- it comprises the substitution of the Thr residue in position 269 by an amino acid residue different of a Thr, such as an Ala residue; and
- it comprises the substitution of the Arg residue in position 464 by an amino acid residue different of an Arg, such as an Ala residue; and
- it does not comprise the Thr, residue in position 631.

Even more preferably, the NS3 polypeptide in use in the invention comprises, essentially consists of or alternatively consists of the amino acid sequence shown in SEQ ID NO: 5.

A preferred NS4A polypeptide originates from the native HCV-JA NS4A protein shown in SEQ ID NO: 2 which is modified at least in such a manner that:

- it contains the portion of SEQ ID NO: 2 from position 21 to position 33;
- it does not contain the portion of SEQ ID NO: 2 from position 1 to position 20;

Even more preferably, the NS4A polypeptide has an amino acid sequence which consists essentially of the portion of SEQ ID NO: 2 from position 21 to position 33 preceded by an initiator Met residue. Most preferably, the NS4A polypeptide consists essentially of the amino acid sequence shown in SEQ ID NO: 6 preceded by an initiator Met residue.

A preferred optional NS4B polypeptide originates from the native HCV-JA NS4B protein shown in SEQ ID NO: 3 which is modified at least in such a manner that:

- it comprises the portion extending from the Ser residue in position 78 to the Leu residue in position 109;
- it does not comprise the Cys residue in position 261.

Even more preferably, the optional NS4B polypeptide consists essentially or alternatively consists of the amino acid sequence as shown in SEQ ID NO: 7.

A preferred NS5B polypeptide originates from the native HCV-JA NS5B protein shown in SEQ ID NO: 4 which is modified at least in such a manner that:

- it comprises the portion extending from the Arg residue in position 154 to the Leu residue in position 182;
- it comprises the substitution of the Asp residue in position 220 by an amino acid residue different of an Asp, such as an Asn residue;
- it comprises the substitution of the Asp residue in position 318 by an amino acid residue different of an Asp, such as an Asn residue; and
- it does not comprise the portion extending from the Trp residue in position 571 to the Arg residue in position 591.

Even more preferably, the NS5B polypeptide comprises, consists essentially of or alternatively consists of the amino acid sequence as shown in SEQ ID NO: 8.

Most preferred fusion proteins of the invention comprise, or alternatively consist essentially of, or alternatively consist of an amino acid sequence which is homologous or identical to the amino acid sequence recited in SEQ ID NO: 9 or 10. The sequence recited in SEQ ID NO: 9 (FIG. 1) corresponds to the fusion of the preferred NS4A, NS3 and NS5B polypeptides described above, with a N-terminal initiator Met in position 1, the NS4A polypeptide extending from amino acid residue 2 to amino acid residue 14, the linker peptide extending from amino acid residue 15 to amino acid residue 17, the NS3 polypeptide extending from amino acid residue 18 to amino acid residue 647, the linker extending from amino acid residue 648 to amino acid residue 652 and the NS5B polypeptide extending from amino acid residue 653 to amino acid residue 1222. The sequence recited in SEQ ID NO: 10 (FIG.

2) corresponds to the fusion of the most preferred NS4A, NS3, NS4B and NS5B polypeptides described above, with a N-terminal initiator Met in position 1, the NS4A polypeptide extending from amino acid residue 2 to amino acid residue 14, the linker peptide extending from amino acid residue 15 to amino acid residue 17, the NS3 polypeptide extending from amino acid residue 18 to amino acid residue 647, the NS4B polypeptide extending from amino acid residue 648 to amino acid residue 679 and the NS5B polypeptide extending from amino acid residue 680 to amino acid residue 1249.

Further included in the scope of the present invention are novel peptide fragments of the fusion proteins of the invention, and especially of those recited in SEQ ID NO: 9 or SEQ ID NO: 10. As used herein, a fragment comprises at least 10, 15, 20, 50 or more contiguous amino acid residues from the fusion proteins disclosed herein. Such fragments can be chosen based on their ability to perform a function, e.g. to bind a substrate or to act as an immunogen. Suitable peptide fragments are typically those comprising a domain or motif of the fusion protein containing novel immunogenic structures. Predicted immunogenic domains are readily identifiable by computer programs well known and readily available to those of skill in the art. Peptide fragments of the invention can be synthesized using known protein synthesis methods.

The fusion protein of the present invention and peptide fragments thereof can be produced by any suitable method, for example, by standard direct peptide synthesizing techniques (e.g. Bodanszky, 1984 in Principles of peptide synthesis, Springer-Verlag) and by recombinant DNA technology as described below in connection with the vectors of the invention.

Thus, the present invention also provides an isolated nucleic acid molecule encoding the fusion protein of the invention, with a special preference for nucleic acid molecules which encode a fusion protein comprising or alternatively consisting essentially of, or alternatively consisting of an amino acid sequence as shown in SEQ ID NO: 9 or SEQ ID NO: 10 or an amino acid sequence homologous to SEQ ID NO: 9 or SEQ ID NO: 10.

Desirably the nucleic acid molecules of the invention are optimized for providing high level expression in a particular host cell, e.g. mammalian, yeast (e.g. *Saccharomyces cerevisiae, Saccharomyces pombe* or *Pichia pastoris*) or prokaryotic (e.g. *E. coli*) host cells. It has been indeed observed that, when more than one codon is available to code for a given amino acid, the codon usage patterns of organisms are highly non-random (see for example Wada et al., 1992, Nucleic Acids Res. 20, 2111-2118) and the utilisation of codons may be markedly different between different hosts (see for example Nakamura et al., 1996, Nucleic Acids Res. 24, 214-215). As the NS-encoding nucleotide sequences used in the invention are of viral origin (HCV), they may have an inappropriate codon usage pattern for efficient expression in host cells such as bacterial or lower eukaryotic cells.

Typically, codon optimisation is performed by replacing one or more "native" (e.g. HCV) codon corresponding to a codon infrequently used in this particular host cell by one or more codon encoding the same amino acid which is more frequently used. This can be achieved by conventional mutagenesis or by chemical synthetic techniques (e.g. resulting in a synthetic nucleic acid molecule). It is not necessary to replace all native codons corresponding to infrequently used (codons since increased expression can be achieved even with partial replacement. Moreover, some deviations from strict adherence to optimised codon usage may be made to accommodate the introduction of restriction site(s) into the resulting nucleic acid molecule.

Further to optimization of the codon usage, expression in the host cell can further be improved through additional modifications of the nucleotide sequence. For example, the nucleic acid molecule of the invention can be modified so as to prevent clustering of rare, non-optimal codons being present in concentrated areas and/or to suppress or modify at least partially negative sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; RNA secondary structures; and/or internal cryptic regulatory elements such as internal TATA-boxes, chi-sites, ribosome entry sites, and/or splicing donor/acceptor sites.

The optimized nucleic acid molecule of the invention is preferably capable of expressing the fusion protein of the invention in a given host cell at a higher level, i.e. at least 110%, advantageously at least 150% and preferably at least 200%, as compared to the level expressed by a nucleic acid molecule involving the corresponding native HCV genes under identical conditions (e.g. same cell type, same culture conditions, same expression vector, etc.). Expression levels can be evaluated by conventional techniques such as Western blotting using an antibody specific for one of the HCV polypeptides included in the fusion protein of the invention.

According to a preferred embodiment, the present invention provides nucleic acid molecules which comprise, or alternatively consist essentially of, or alternatively consist of a nucleotide sequence which is homologous or even more preferably identical to any of the nucleotide sequences shown in SEQ ID NO: 11-16. The nucleic acid molecule of SEQ ID NO: 11 encodes a NS4A-3-5B fusion protein which nucleotide sequence has been optimised for expression in mammalian (e.g. human) cells. The nucleic acid molecule of SEQ ID NO: 12 encodes a NS4A-3-4B-5B fusion which nucleotide sequence has been optimised for expression in mammalian (e.g. human cells). The nucleic acid molecule of SEQ ID NO: 13 encodes a NS4A-3-5B fusion which nucleotide sequence has been optimised for expression in yeast (e.g. *P. pastoris*). The nucleic acid molecule of SEQ ID NO: 14 encodes a NS4A-3-4B-5B fusion which nucleotide sequence has been optimised for expression in yeast (e.g. *P. pastoris*. The nucleic acid molecule of SEQ ID NO: 15 encodes a NS4A-3-5B fusion which nucleotide sequence has been optimised for expression in prokaryote (e.g. *E. coli*). The nucleic acid molecule of SEQ ID NO: 16 encodes a NS4A-3-4B-5B fusion which nucleotide sequence has been optimised for expression in prokaryote (e.g. *E. coli*). Of course, the sequences may be equipped with 5' and 3' non coding sequences providing if needed an initiator Met at 5' end, one or more STOP codons at the 3' end and suitable restriction sites at both extremities to facilitate clonage steps. Exemplary nucleic acid molecules are also provided in FIGS. 3-8.

The present invention also pertains to nucleic acid molecules which are capable of hybridizing under stringent conditions to the nucleic acid molecules as defined above. Stringent hybridization conditions are known to those skilled in the art. Typically, hybridization is performed in 6 times sodium chloride/sodium citrate (SSC) at about 45° C., and is followed by one or more washes in 0.2 times SSC, 0.1% SDS at 50-65° C. Preferably, such hybridizing nucleic acids share a degree of sequence identity with the above-defined nucleic acid molecules greater than 70% over the full length nucleotide sequence or a shorter fragment thereof (e.g. of at least 30, 45, 50, 60, 80, 100, 150, 200 nucleotides in length). More preferably, the degree of identity between them is greater than 70%, advantageously greater than 80%, desirably greater than 85%, preferably greater than 90%, more preferably greater than 95%, still more preferably greater than 97%.

Representative examples of such hybridizing nucleic acid molecules include without limitation, nucleic acid molecules which are complementary to at least about 20, 30, 40, 50, 100, or 150 contiguous nucleotides included in any of SEQ ID NOs: 11-16 (e.g. antisense nucleic acid molecules). Variations of the exemplary sequences, such as degenerate codons, or polymorphism between different isolates/strains of HCV or variations resulting from techniques such as DNA shuffling are also encompassed by the present invention.

Another embodiment of the invention pertains to fragments of the nucleic acid molecule of the invention, e.g. restriction endonuclease and PCR-generated fragments. Such fragments can be used as probes, primers or fragments encoding an immunogenic portion of the fusion protein.

The nucleic acid molecule of the present invention can be generated using sequence data accessible in the art and the sequence information provided herein. The DNA sequence coding for each of the HCV polypeptides included in the fusion protein of the present invention can be isolated directly from HCV-containing cells, cDNA and genomic libraries, viral genomes or any prior art vector known to include it, by conventional molecular biology or PCR techniques, and, if needed, can further be modified by routine mutagenesis techniques, (e.g. to optimize expression in a particular host cell, to comply with a genotype or subtype-specific sequence, as described above). Fusing the sequences encoding each of the HCV polypeptides may be accomplished for example, by ligation in-frame either directly or through a sequence encoding a peptide linker. Alternatively, the nucleic acid molecule of the invention can also be generated by chemical synthesis in automatised process (e.g. assembled from overlapping synthetic oligonucleotides as described for example in Edge, 1981, Nature 292, 756; Nambair et al., 1984, Science 223, 1299; Jay et al., 1984, J. Biol. Chem. 259, 6311).

Also provided by the present invention is a vector comprising one or more copies of the nucleic acid molecule(s) of the invention. For example, it may be advantageous to include in the same vector nucleic acid molecules encoding fusion proteins originating from different genotypes or subtypes.

The term "vector" as used herein refers to both expression and non-expression vectors and includes viral as well as non viral vectors, including extrachromosomal vectors (e.g. multicopy plasmids) and integrating vectors designed for being incorporated into the host chromosome(s). Particularly important in the context of the invention are vectors for use in gene therapy (i.e. which are capable of delivering the nucleic acid molecule to a host organism) as well as expression vectors for use in various expression systems.

A variety of host-vector systems may be used to express the fusion protein of the invention, including prokaryotic organisms such as bacteria (e.g. *E. coli* or *Bacillus subtilis*) transformed with bacteriophage, plasmid or cosmid vectors containing the fusion-encoding nucleic acid molecule; yeast (e.g. *Saccharomyces cerevisiae, Saccharomyces pombe, Pichia pastoris*) transformed with yeast expression vectors containing the fusion-encoding nucleic acid molecule; insect cell systems (e.g. Sf 9 cells) infected with virus expression vectors (e.g. baculovirus) containing the fusion-encoding nucleic acid molecule; plant cell systems infected with virus expression vectors (e.g. cauliflower mosaic virus CaMV; tobacco mosaic virus TMV) or transformed with plasmid expression vectors (e.g. Ti plasmid) containing the fusion-encoding nucleic acid molecule; or mammalian cell systems (e.g. cultured cells) transfected or infected with plasmid or virus expression vectors containing the fusion-encoding nucleic acid molecule.

Suitable vectors for use in prokaryotic systems include without limitation pBR322 (Gibco BRL), pUC (Gibco BRL), pbluescript (Stratagene), p Poly (Lathe et al., 1987, Gene 57, 193-201), pTrc (Amann et al., 1988, Gene 69, 301-315); pET lid (Studier et al., 1990, Gene Expression Technology: Methods in Enzymology 185, 60-89); pIN (Inouye et al., 1985, Nucleic Acids Res. 13, 3101-3109; Van Heeke et al., 1989, J. Biol. Chem. 264, 5503-5509); and pGEX vectors where the nucleic acid molecule of the invention can be expressed in fusion with glutathione S-transferase (GST). The plasmid pGEX-2T (Amersham Biosciences Product code: 27-4801-01, Genbank accession No. U13850) is particularly suitable in the content of the invention.

Suitable vectors for expression in yeast (e.g. *S. cerevisiae*) include, but are not limited to pYepSec1 (Baldari et al., 1987, EMBO J. 6, 229-234), pMFa (Kujan et al., 1982, Cell 30, 933-943), pJRY88 (Schultz et al., 1987, Gene 54, 113-123), pYES2 (Invitrogen Corporation, San Diego, Calif.) and pTEF-MF (Dualsystems Biotech Product code: P03303).

The vectors suited for expression in mammalian host cells can be of viral or non viral (e.g. plasmid DNA) origin. Suitable plasmid vectors include, without limitation, pREP4, pCEP4 (Invitrogene), pCI (Promega), pCDM8 (Seed, 1987, Nature 329, 840) and pMT2PC (Kaufman et al., 1987, EMBO J. 6, 187-195), pVAX and pgWiz (Gene Therapy System Inc; Himoudi et al., 2002, J. Virol. 76, 12735-12746).

Moreover, the host vector systems used in the context of the present invention may also comprise one or more additional element(s) enabling maintenance, propagation or expression of the nucleic acid molecule of the present invention in the host cell. Such additional elements include without limitation marker gene(s) in order to facilitate identification and isolation of the recombinant host cells (e.g. by complementation of a cell auxotrophy or by antibiotic resistance), stabilising elements (e.g. cer sequence as described in Summers and Sherrat, 1984, Cell 36, 1097-1103 and DAP system as described in U.S. Pat. No. 5,198,343), and integrative elements (e.g. LTR viral sequences and transposons).

Suitable marker genes for expression in prokaryotic host cells include tetracycline and ampicillin-resistance genes. Also, resistance genes can be used for expression in mammalian host cells such as dihydrofolate reductase (dhfr) which confers resistance to methotrexate (Wigler et al., 1980, Proc. Natl. Acad. Sci. USA 77, 3567; O'Hare et al., 1981, Proc. Natl. Acad. Sci. USA 78, 1527); gpt which confers resistance to mycophenolic acid (Mulligan and Berg, 1981, Proc. Natl. Acad. Sci. USA 78, 2072); neo which confers resistance to the aminoglycoside G-418 (Colberre-Garapin et al., 1981, J. Mol. Biol. 150, 1); zeo which confers resistance to zeomycin, kana which confers resistance to kanamycin and hygro, which confers resistance to hygromycin (Santerre et al., 1984, Gene 30, 147). URA3 and LEU2 genes can be used for expression in yeast systems, which provide for complementation of ura3 or leu2 yeast mutants. In particular, the URA3 gene from which its promoter has been deleted may advantageously be used.

A member of viral-based expression systems can also be utilized in the context of the invention derived from a variety of different viruses (e.g. retrovirus, adenovirus, AAV, poxvirus, herpes virus, measle virus, foamy virus and the like). As used herein, the term "viral vector" encompasses vector DNA as well as viral particles generated thereof. Viral vectors can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells).

Such vectors include for example adenoviral vectors which have a number of well-documented advantages for gene transfer or for recombinant production (for a review, see "Adenoviral vectors for gene therapy", 2002, Ed D. Curiel and J. Douglas, Academic Press). The adenoviral vectors for use in accordance with the present invention can be derived from a variety of human or animal sources. Any serotype can be employed from the adenovirus serotypes 1 through 51, with a special preference for human adenoviruses 2 (Ad2), 5 (Ad5), 6 (Ad6), 11 (Ad11), 24 (Ad24) and 35 (Ad35). The cited adenovirus are available from the American Type Culture Collection (ATCC, Rockville, Md.), and have been the subject of numerous publications describing their sequence, organization and methods of producing, allowing the artisan to apply them (see for example U.S. Pat. No. 6,133,028; U.S. Pat. No. 6,110,735; WO 02/40665; WO 00/50573; EP 1016711; Vogels et al., 2003, J. Virol. 77, 8263-8271).

In one embodiment, the adenoviral vector of the present invention is replication-competent. Examples of such replication-competent adenoviral vectors are well known in the art and readily available to those skill in the art (see, for example, Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727). Suitable replication-competent adenoviral vectors for use in the invention can be engineered from a wild-type adenovirus genome by deletion in the E1A CR2 domain to abrogate binding to the Rb (see for example WO00/24408) and/or by replacement of the native E1 and/or E4 promoters with tissue, tumor or cell status-specific promoters (see for example U.S. Pat. No. 5,998,205, WO99/25860, U.S. Pat. No. 5,698,443, WO00/46355, WO00/15820 and WO01/36650).

In another embodiment, the adenoviral vector of the invention is replication-defective (see for example WO94/28152; Lusky et al., 1998, J. Virol 72, 2022-2032). Preferred replication-defective adenoviral vectors are E1-defective (see for example U.S. Pat. No. 6,136,594 and U.S. Pat. No. 6,013,638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity can further be improved by deleting additional position(s) of the adenoviral genome (all or part of the non essential E3 region or of other essential E2, E4 regions).

The nucleic acid molecule of the present invention can be inserted in any location of the adenoviral genome. Preferably, it is inserted in replacement of the E1 region. It may be positioned in sense or antisense orientation relative to the natural transcriptional direction of the region in question.

Other suitable viral vectors are derived from poxviruses (see for example Cox et al. in "Viruses in Human Gene Therapy" Ed J. M. Hos, Carolina Academic Press). In the context of the present invention, a poxviral vector may be obtained from any member of the poxviridae, in particular canarypox, fowlpox and vaccinia virus, the latter being preferred. Suitable vaccinia viruses include without limitation the Copenhagen strain (Goebel et al., 1990, Virol. 179, 247-266 and 517-563; Johnson et al., 1993, Virol. 196, 381-401), the Wyeth strain and the modified Ankara (MVA) strain (Antoine et al., 1998, Virol. 244, 365-396). The general conditions for constructing recombinant poxvirus are well known in the art (see for example EP 206 920; Mayr et al., 1975, Infection 3, 6-14; Sutter and Moss, 1992, Proc. Natl. Acad. Sci. USA 89, 10847-10851; U.S. Pat. No. 6,440,422). The nucleic acid molecule of the present invention is preferably inserted within the poxviral genome in a non-essential locus. Thymidine kinase gene is particularly appropriate for insertion in Copenhagen vaccinia vectors (Hruby et al., 1983, Proc. Natl. Acad. Sci. USA 80, 3411-3415; Weir et al., 1983, J. Virol. 46, 530-537) and deletion II or III for insertion in MVA vector (Meyer et al., 1991, J. Gen. Virol. 72, 1031-1038; Sutter et al., 1994, Vaccine 12, 1032-1040).

According to a preferred embodiment, the vectors of the invention comprise the nucleic acid molecule of the invention in a form suitable for its expression in a host cell or organism, which means that the nucleic acid molecule is placed under the control of one or more regulatory sequences, appropriate to the vector and/or the host cell. As used herein, the term "regulatory sequence" refers to any sequence that allows, contributes or modulates the expression of a nucleic acid molecule in a given host cell, including replication, duplication, transcription, splicing, translation, stability and/or transport of the nucleic acid or one of its derivative (i.e. mRNA) into the host cell. It will be appreciated by those skilled in the art that the choice of the regulatory sequences can depend on such factors as the host cell, the level of expression desired, etc.

The promoter is of special importance and suitable promoters useful in the context of the present invention include constitutive promoters which direct expression of the nucleic acid molecule in many types of host cell and those which direct expression of the nucleotide sequence only in certain host cells (e.g., liver-specific regulatory sequences) or in response to specific events or exogenous factors (e.g. by temperature, nutrient additive, hormone or other ligand).

Promoters suitable for expression in *E. Coli* host cell include, but are not limited to, the bacteriophage lambda pL promoter, the lac, TRP and IPTG-inducible pTAC promoters. Promoters suitable for expression in yeast include the TEF (Mumberg et al., 1995, Gene 156, 119-122), PGK (Hitzeman et al., 1983, Science 219, 620-625), MF alpha (Inokuchi et al., 1987, Mol. Cell. Biol. 7, 3185-3193), CYC-1 (Guarente et al, 1981, Proc. Natl. Acad. Sci. USA 78, 2199), GAL-1, GAL4, GAL10, PHO5, glyceraldehyde-3-phosphate dehydrogenase (GAP or GAPDH), and alcohol dehydrogenase (ADH) (Denis et al., 1983, J. Biol. Chem. 25, 1165) promoters. For expression in poxviral vectors, one may use the vaccinia 7.5K, H5R, TK, p28, p11 or K1L promoter, the synthetic promoters described in Chakrabarti et al. (1997, Biotechniques 23, 1094-1097), Hammond et al. (1997, J. Virological Methods 66, 135-138) and Kumar and Boyle (1990, Virology 179, 151-158) as well as early/late chimeric promoters. Promoters suitable for constitutive expression in mammalian cells include the cytomegalovirus (CMV) immediate early promoter (Boshart et al., 1985, Cell 41, 521-530), the adenovirus major late promoter, the phosphoglycero kinase (PGK) promoter (Adra et al., 1987, Gene 60, 65-74), and the thymidine kinase (TK) promoter of herpes simplex virus (HSV)-1. Inducible eukaryotic promoters regulated by exogenously supplied compounds, include without limitation, the zinc-inducible metallothionein (MT) promoter (Mc Ivor et al., 1987, Mol. Cell Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441) and the rapamycin-inducible promoter (Magari et al., 1997, J. Clin. Invest. 100, 2865-2872).

Tissue-specific promoters may also be used, especially those permitting to target the HCV-infected cells where therapeutic benefit is desired. Suitable promoters include liver-specific promoters such as those of HMG-CoA reductase (Luskey, 1987, Mol. Cell. Biol. 7, 1881-1893); sterol regulatory element 1 (SRE-1; Smith et al., 1990, J. Biol. Chem. 265, 2306-2310); albumin (Pinkert et al., 1987, Genes Dev. 1, 268-277); phosphoenol pyruvate carboxy kinase (PEPCK) (Eisenberger et al., 1992, Mol. Cell Biol. 12, 1396-1403); human C-reactive protein (CRP) (Li et al., 1990, J. Biol. Chem. 265, 4136-4142); human glucokinase (Tanizawa et al., 1992, Mol. Endocrinology 6, 1070-1081); cholesterol 7-alpha hydroylase (CYP-7) (Lee et al., 1994, J. Biol. Chem. 269, 14681-14689); alpha-1 antitrypsin (Ciliberto et al., 1985, Cell 41, 531-540); insulin-like growth factor binding protein (IGFBP-1) (Babajko et al., 1993, Biochem Biophys. Res. Comm. 196, 480-486); human transferrin (Mendelzon et al., 1990, Nucleic Acids Res. 18, 5717-5721); collagen type I (Houglum et al., 1994, J. Clin. Invest. 94, 808-814) and FIX (U.S. Pat. No. 5,814,716) genes.

Additional promoters suitable for use in this invention can be obtained from genes that are preferentially expressed in proliferative tumor cells, such as the promoters of the alpha-foetoprotein gene overexpressed in liver cancers (Kanai et al., 1997, Cancer Res. 57, 461-465), the telomerase reverse transcriptase (TERT) (WO99/27113, WO 02/053760 and Horikawa et al., 1999, Cancer Res. 59, 826), and hypoxia-responsive element (HRE).

Those skilled in the art will appreciate that the regulatory elements controlling the expression of the nucleic acid molecule of the invention may further comprise additional elements for proper initiation, regulation and/or termination of transcription (e.g. polyA transcription termination sequences), in RNA transport (e.g. nuclear localization signal sequences), processing (e.g. splicing signals), and stability (e.g. introns and non-coding 5' and 3' sequences), translation (e.g. peptide signal, propeptide, tripartite leader sequences, ribosome binding sites, Shine-Dalgamo sequences, etc.) into the host cell or organism and purification steps (e.g. a tag).

For example, a signal peptide, eventually in combination with a pro peptide, may be used for facilitating secretion of the fusion protein in the culture medium. The signal peptide is typically inserted at the N-terminus of the fusion protein immediately after the Met initiator, and, if needed, the pro peptide is inserted downstream the signal peptide. The choice of signal and/or pro peptides is wide and is accessible to persons skilled in the art. Examples of signal/pro peptides appropriate for the present invention include, but are not limited to, the signal peptide sequences of the mating factor (MF) alpha (Kurjan and Herskowitz, 1982, Cell 30, 933-934 and U.S. Pat. No. 5,879,926); invertase (WO84/01153); PHO5 (DK 3614/83); YAP3 (yeast aspartic protease 3; WO95/02059); and BAR1 (WO87/02670). During entry into the ER, the signal peptide is cleaved off the precursor polypeptide at a processing site. The processing site can comprise any peptide sequence that is recognized by a host cell proteolytic enzyme. Examples of preferred processing sites include, but are not limited to, any combination of the two basic residues Lys and Arg (with a special preference for Lys-Arg) which are cleaved by the endopeptidase encoded by the KEX2 gene of *Saccharomyces cerevisiae* (see Fuller et al., 1986, Microbiology, 273-278) or the equivalent protease of other yeast species (see Julius et al., 1983, Cell 32, 839-852).

A peptide tag (e.g. a short peptide sequence able to be recognized by available antisera) may be used for facilitating purification of the recombinant fusion protein from the host cell or culture supernatant. Preferably, the tag is inserted at the C-terminus of the fusion protein. Exemplary tags include without limitation His tag (e.g. composed of 6 or more histidine residues), peptide sequence from glutathione-S-transferase (GST) from *S. mansoni*, maltose binding protein (MPB) from *E. Coli*, human alkaline phosphatase, the FLAG octapeptide, and e-tag (U.S. Pat. No. 6,686,152).

A preferred embodiment of the invention is directed to a shuttle plasmid for expression in yeast comprising the nucleic acid molecule of the invention (e.g. the nucleotide sequence of SEQ ID NO: 13 and 14) placed under the control of the TEF promoter and an appropriate transcriptional terminator sequence (e.g. cytochrome eye terminator) which further comprises origins of replication for *E. coli* and yeast host cells (e.g. ORI and 2μ respectively), selection markers suitable for expression in *E. coli* (e.g. ampicillin resistance gene) and yeast (e.g. auxotrophy URA3 and leu2-3).

Another preferred embodiment of the invention is directed to a pGEX plasmid suitable for expression in *E. coli* comprising the nucleic acid molecule of the invention (e.g. the nucleotide sequence of SEQ ID NO: 15 and 16) placed under the control of the IPTG-inducible pTAC promoter and an appropriate transcriptional terminator sequence which further comprises a suitable origin of replication for *E. coli* (e.g. OR1), and a suitable selection marker (e.g. ampicillin resistance gene).

Still another preferred embodiment of the invention is directed to a replication-defective adenoviral vector for expression in mammalian cells comprising the nucleic acid molecule of the invention (e.g. the nucleotide sequence of SEQ ID NO: 11 and 12) placed under appropriate regulatory elements. Preferably the replication defective adenoviral vector is an Ad5 genome E1 and E3 deleted, with E1 deletion extending from approximately nucleotide 459 to approximately nucleotide 3511 and E3 deletion from approximately nucleotide 28592 to approximately nucleotide 30470. A preferred adenoviral vector comprises Ad5 sequences from approximately nucleotide 1 to approximately nucleotide 458, the expression cassette containing, from 5' to 3', the CMV immediate-early enhancer/promoter, a chimeric human β-globin/IgG intron (as found in pCI vector available in Promega), the sequence encoding either of the two polyprotein forms (SEQ ID NO: 11 or 12) and the SV40 late polyadenylation signal followed by Ad5 sequence from approximately nucleotide 3512 to approximately nucleotides 28592 and from approximately nucleotide 30470 to approximately nucleotide 35935.

If needed, the vector of the invention can further comprise one or more transgene(s), e.g. a gene of interest to be expressed together with the nucleic acid molecule of the invention in a host cell or organism. Desirably, the expression of the transgene has a therapeutic or protective activity to an HCV-associated disease or condition. Suitable transgene include without limitation cytokine encoding genes (e.g. IL-2, IL-7, IL-15, IL-18, IL-21, IFNg), toxin-encoding genes (e.g. ricin, diphtheria toxin, cholera toxin), suicide genes, and especially the genes encoding TK HSV-1 (Caruso et al., 1993, Proc. Natl. Acad. Sci. USA 90, 7024-7028) which is to be used in combination with acyclovir or ganciclovir prodrug, cytosine deaminase (CDase), uracil phosphoribosyl transferase (UPRTase) which are to be used in combination with the prodrug 5-fluorocytosine (5-FC). The FCU-1 gene product (described in WO 99/54481) is particularly useful in this context. If a transgene is used, it is placed under the control of appropriate regulatory elements and can be inserted in any location of the vector of the invention or in an independent vector which is used in combination with the vector of the invention.

Inserting the nucleic acid molecule of the invention into a vector backbone can be performed by routine molecular biology, e.g. as described in Sambrook et al. (2001, Molecular Cloning-A Laboratory Manual, Cold Spring Harbor Laboratory). Insertion into an adenoviral vector or a poxviral vector can be performed through homologous recombination as described respectively in Chartier et al. (1996, J. Virol. 70, 4805-4810) and Paul et al. (2002, Cancer gene Ther. 9, 470-477).

The present invention also encompasses vectors (e.g. plasmid DNA) complexed to lipids or polymers to form particulate structures such as liposomes, lipoplexes or nanoparticles. Such technologies are available in the art (see for example Arangoa et al., 2003, Gene Ther. 10: 5-14; Eliaz et al., 2002, Gene Ther. 9, 1230-1237 and Betageri et al., 1993, "Liposome drug delivery systems", Technomic Publishing Company, Inc)

In another embodiment, the present invention provides infectious viral particles comprising the above-(described nucleic acid molecules or vectors of the present invention.

Typically, such viral particles are produced by a process comprising the steps of:

(a) introducing the viral vector of the invention into a suitable cell line, (b) culturing said cell line under suitable conditions so as to allow the production of said infectious viral particle, (c) recovering the produced infectious viral particle from the culture of said cell line, and (d) optionally purifying said recovered infectious viral particle.

When the viral vector is defective, the infectious particles are usually produced in a complementation cell line or via the use of a helper virus, which supplies in trans the non functional viral genes. For example, suitable cell lines for complementing E1-deleted adenoviral vectors include the 293 cells (Graham et al., 1997, J. Gen. Virol. 36, 59-72) as well as the PER-C6 cells (Fallaux et al., 1998, Human Gene Ther. 9, 1909-1917). Cells appropriate for propagating poxvirus vectors are avian cells, and most preferably primary chicken embryo fibroblasts (CEF) prepared from chicken embryos obtained from fertilized eggs.

The infectious viral particles may be recovered from the culture supernatant or from the cells after lysis. They can be further purified according to standard techniques (chromatography, ultracentrifugation in a cesium chloride gradient as described for example in WO96/27677, WO98/00524, WO98/22588, WO98/26048, WO00/40702, EP1016700 and WO00/50573).

The present invention also encompasses vectors or viral particles that have been modified to allow preferential targeting to a particular target cell (see for example Wickam et al., 1997, J. Virol. 71, 8221-8229; Arnberg et al., 1997, Virol. 227, 239-244; Michael et al., 1995, Gene Therapy 2, 660-668; WO94/10323; WO02/96939 and EP 1 146 125). A characteristic feature of targeted vectors and viral particles of the invention is the presence at their surface of a ligand capable of recognizing and binding to a cellular and surface-exposed component such as a cell-specific marker (e.g. an HCV-infected cell), a tissue-specific marker (e.g. a liver-specific marker), as well as a viral (e.g. HCV) antigen. Examples of suitable ligands include antibodies or fragments thereof directed to an HCV antigenic domain. Cell targeting can be carried out by genetically inserting the ligand into a polypeptide present on the surface of the virus (e.g. adenoviral fiber, penton, pIX or vaccinia p14 gene product).

The invention also relates to host cells which comprise the nucleic acid molecules, vectors or infectious viral particles of the invention described herein. In the context of the present invention, the term "host cell" should be understood broadly without any limitation concerning particular organization in tissue, organ, or isolated cells. Such cells may be of a unique type of cells or a group of different types of cells and encompass cultured cell lines, primary cells and proliferative cells.

In the context of the invention, host cells include prokaryotic cells, lower eukaryotic cells such as yeast, and other eukaryotic cells such as insect cells, plant and mammalian (e.g. human or non-human) cells. Preferred *E. coli* host cells include without limitation *E. coli* BL21 (available at Amersham Biosciences). Preferred yeast host cells include without limitation *S. cerevisiae, S. pombe, Pichia pastoris*, with a special preference for KEX-2 expressing yeast cells such as TGY47.1 (or its isogenic $Leu^+$ convertant TGY73.4) strain described in EP 607 080 and those described in U.S. Pat. No. 5,879,926, U.S. Pat. No. 5,162,208 and U.S. Pat. No. 6,103,515. Preferred mammalian host cells include without limitation BHK (baby hamster kidney), CV-1 (African monkey kidney cell line), COS (e.g., COS-7) cells, chinese hamster ovary (CHO) cells, mouse NIH/3T3 cells, HeLa cells and Vero cells. Host cells also encompass complementing cells capable of complementing at least one defective function of a replication-defective vector of the invention (e.g. adenoviral vector) such as 293 and PERC.6 cells.

According to a specific embodiment of the invention, the host cell can be further encapsulated. Cell encapsulation technology has been previously described (Tresco et al., 1992, ASAIO J. 38, 17-23; Aebischer et al., 1996, Human Gene Ther. 7, 851-860).

Still a further aspect of the present invention is a method for recombinantly producing the fusion protein, employing the vectors, infectious viral particles and/or host cells of the invention. The method for producing the fusion protein comprises (a) introducing a vector or an infectious viral particle of the invention into a suitable host cell to produce a transfected or infected host cell, (b) culturing in-vitro said transfected or infected host cell under conditions suitable for growth of the host cell, (c) recovering the fusion protein from the cell culture, and (d) optionally, purifying the recovered fusion protein.

It is expected that those skilled in the art are knowledgeable in the numerous expression systems available for producing the fusion proteins of the invention in appropriate host cells and of the methods for introducing a vector or an infectious viral particle into a host cell. Such methods include, but are not limited to, microinjection (Capechi et al., 1980, Cell 22, 479-488), $CaPO_4$-mediated transfection (Chen and Okayama, 1987, Mol. Cell. Biol. 7, 2745-2752), DEAE-dextran-mediated transfection, electroporation (Chu et al., 1987, Nucleic Acid Res. 15, 1311-1326), lipofection/liposome fusion (Felgner et al., 1987, Proc. Natl. Acad. Sci. USA 84, 7413-7417), particle bombardment (Yang et al., 1990, Proc. Natl. Acad. Sci. USA 87, 9568-9572), gene guns, transduction, viral infection as well as direct administration into a host organism via various means.

The vectors of the invention can be used in association with transfection reagents in order to facilitate introduction of the vector in the host cell, such as polycationic polymers (e.g. chitosan, polymethacrylate, PEI, etc) and cationic lipids (e.g.DC-Chol/DOPE, transfectam lipofectin now available from Promega). Moreover, as discussed above, recombinant DNA technologies can be used to improve expression of the nucleic acid molecule in the host cell, e.g. by using high-copy number vectors, substituting or modifying one or more transcriptional regulatory sequences (e.g. promoter, enhancer and the like), optimising the codon usage of the fusion-encoding nucleic acid molecule to the host cell, and suppressing negative sequences that may destabilize the transcript.

Host cells of the present invention can be cultured in conventional fermentation bioreactors, flasks, and petri plates. Culturing can be carried out at a temperature, pH and oxygen content appropriate for a given host cell. No attempts to describe in detail the various methods known for the production of proteins in prokaryote and eukaryote cells will be made here. Production of the fusion protein can be periplasmic, intracellular or secreted outside the host cell (e.g. in the culture medium).

Where the fusion protein is not secreted outside the producing host cell or where it is not secreted completely, it can be recovered by standard lysis procedures, including freeze thaw, sonication, mechanical disruption, use of lysing agents and the like. If secreted, it can be recovered directly from the culture medium.

The fusion protein can then be purified by well-known purification methods including ammonium sulfate precipitation, acid extraction, gel electrophoresis, filtration and chromatographic methods (e.g. reverse phase, size exclusion, ion exchange, affinity, phosphocellulose, hydrophobic-interaction, hydroxylapatite, or high performance liquid chromatography). The conditions and technology used to purify a particular fusion protein of the invention will depend on factors such as net charge, molecular weight, hydrophobicity, hydrophilicity and will be apparent to those having skill in the art. Moreover, the level of purification will depend on the intended use. It is also understood that depending upon the producing host cell, the fusion proteins can have various glycosylation patterns, or may be non-glycosylated (e.g. when produced in bacteria).

In another aspect, this invention provides a composition comprising the fusion protein, the nucleic acid molecule, the vector, the infectious viral particle, the host cell of the invention (also referred herein to "active agent") or any combination thereof (e.g. combination of fusion proteins or vectors/viral particles encoding fusion proteins of different genotypes or subtypes). Preferably, the composition is a pharmaceutical composition which comprises further to a therapeutically effective amount of the active agent(s), a pharmaceutically acceptable vehicle. As used herein a "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition. For example, a therapeutically effective amount for inducing an immune response could be that amount necessary to cause activation of the immune system (e.g. resulting in the development of an anti-HCV response).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the invention comprises a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams & Wilkins). The composition of the invention is suitably buffered in order to be appropriate for human use at a physiological or slightly basic pH (e.g. between about pH 7 to about pH 9). Suitable buffers include without limitation phosphate buffer (e.g. PBS), bicarbonate buffer and/or Tris buffer.

The composition can also contain other pharmaceutically acceptable excipients for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. liver). Suitable excipients include amino acids.

The pharmaceutically acceptable vehicles included in the composition of the invention must also permit to preserve its stability under the conditions of manufacture and long-term storage (i.e. at least one month) at freezing (e.g. −70° C., −20° C.), refrigerated (e.g. 4° C.) or ambient temperatures. In this respect, formulations which are particularly adapted to the composition of the invention include:

1M saccharose, 150 mM NaCl, 1 mM $MgCl_2$, 54 mg/l Tween 80, 10 mM Tris pH 8.5 (especially when the active agent is an adenoviral vector), and 10 mg/ml mannitol, 1 mg/ml HSA, 20 mM Tris, pH 7.2, and 150 mM NaCl physiological saline In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72, 4931-4939; WO 98/56415), imidazo-quinoline compounds such as Imiquimod (Suader, 2000, J. Am Acad Dermatol. 43, S6-S11) and related compound S-27609 (Smorlesi, 2005, Gene Ther. 12, 1324-1332), cytosine phosphate guanosine oligodeoxynucleotides such as CpG (Chu et al., 1997, J. Exp. Med. 186: 1623; Tritel et al., 2003, J. Immunol. 171: 2358-2547) and catatonic peptides such as IC-31 (Kritsch et al., 2005, J. Chromatogr Anal. Technol Biomed Life Sci 822, 263-270).

The composition of the present invention may be administered by a variety of modes of administration, including systemic, topical and localized administration. Injection can be performed by any means, for example by subcutaneous, intradermal, intramuscular, intravenous, intraperitoneal, intratumoral, intravascular, intraarterial injection or by direct injection into an artery (e.g. by hepatic artery infusion) or a vein feeding liver (e.g. injection into the portal vein). Injections can be made with conventional syringes and needles, or any other appropriate devices available in the art. Alternatively the composition of the present invention may be administered via a mucosal route, such as the oral/alimentary, nasal, intratracheal, intrapulmonary, intravaginal or intra-rectal route. Administration in the respiratory tract can be performed through nebulisation or aerosolization of droplet, spray, or dry powdered compositions using a pressured container (e.g. with a suitable propellant such as dichlorodifluoromethane, propane, nitrogen and the like), or in a non-pressurized dispenser. Topical administration can also be performed using transdermal means (e.g. patch and the like). In the context of the invention, intramuscular and subcutaneous administrations constitute the preferred routes.

The composition of the invention can be in various forms, e.g. solid, liquid or frozen. Solid (e.g. dry powdered or lyophilized) compositions can be obtained by a process involving vacuum drying and freeze-drying. For mucosal administration, the compositions can be formulated as gastroresistant capsules and granules for oral administration, suppositories for rectal or vaginal administration, eventually in combination with absorption enhancers useful to increase the pore size of the mucosal membranes. Such absorption enhancers are typically substances having structural similarities to the phospholipid domains of the mucosal membranes such as sodium deoxycholate, sodium glycocholate, dimethyl-beta-cyclodextrin, lauroyl-l-lysophosphatidylcholine).

The appropriate dosage can be adapted as a function of various parameters, in particular the mode of administration; the composition employed; the age, health, and weight of the host organism; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances. For general guidance, suitable dosage for a virus-comprising composition (e.g. adenovirus particles) varies from about $10^5$ to $10^{13}$ in (infectious units), desirably from about $10^7$ and $10^{12}$ iu. A composition based on vector plasmids may be administered in (loses of between 10 μg and 20 mg, advantageously between 100 μg and 2 mg. A protein composition may be administered in one or more doses of between 10 ng and 20 mg, with a special preference for a dosage from about 0.1 μg to about 2 mg of the therapeutic protein per kg body weight. The administration may take place in a single dose or a dose repeated one or several times after a certain time interval.

The pharmaceutical composition of the invention may be employed in methods for treating a variety of diseases and pathologic conditions, especially those associated with an HCV infection. As used herein, the term "treatment" or "treating" encompasses prophylaxis and/or therapy. It is especially useful for treating HCV persistent infection and liver cancer in HCV-infected patients. The term "cancer" encompasses any cancerous conditions including diffuse or localized tumors, metastasis, cancerous polyps as well as preneoplastic lesions (e.g. cirrhosis). Preferably, upon introduction into a host organism according to the modalities described herein, the composition of the invention provides a therapeutic benefit to the treated host. The term "host organism" is intended to encompass any animal, particularly mammal, such as any murine, rat, bovine, porcine, canine, feline, equine, monkey or human subject, for example a human infected with HCV. The therapeutic benefit can be evidenced by a number of ways, for instance a decrease of HCV viremia detected in blood, plasma or sera of an infected individual as compared to before treatment, and/or by the detection of an anti-HCV immune response (e.g. production of anti-HCV antibodies and/or T cell-mediated immunity) or by the delay of the symptoms associated with an HCV infection (e.g. delay in the development of liver cirrhosis or cancer), or by a decrease of liver inflammation/steatosis/fibrosis conditions typically associated with HCV infection or by an improved response of the individual to conventional therapies.

Accordingly, the present invention also encompasses the use of the fusion protein, nucleic acid molecule, vector, infectious viral particle, host cell or composition of the invention for the preparation of a drug intended for treating or preventing HCV infections, HCV-associated diseases and pathologic conditions, according to the modalities described above.

The present invention also provides a method for the treatment or prevention of a human or animal organism, comprising administering to said organism a therapeutically effective amount of the fusion protein, the nucleic acid molecule, the vector, the infectious viral particle, the host cell or the composition of the invention.

If desired, the method of the invention can be carried out in conjunction with one or more conventional therapeutic modalities (e.g. radiation, chemotherapy and/or surgery). The use of multiple therapeutic approaches provides the patient with a broader based intervention. In one embodiment, the method of the invention can be preceded or followed by a surgical intervention. In another embodiment, it can be preceded or followed by radiotherapy (e.g. gamma radiation). Those skilled in the art can readily formulate appropriate radiation therapy protocols and parameters which can be used (see for example Perez and Brady, 1992, Principles and Practice of Radiation Oncology, 2nd Ed. JB Lippincott Co; using appropriate adaptations and modifications as will be readily apparent to those skilled in the field).

In still another embodiment, the method or use of the invention is associated to chemotherapy with one or more HCV drugs which are conventionally used for treating or preventing HCV infections, HCV-associated diseases and pathologic conditions. Representative examples of HCV drugs include without limitation protease inhibitors (e.g. serine protease inhibitors such as VX950 of Vertex), polymerase inhibitors, helicase inhibitors, antifibrotics, nucleoside analogs, TLR agonists, N-glycosylation inhibitors, siRNA, antisense oligonucleotides, anti-HCV antibodies, immune modulators, therapeutic vaccines and antitumor agents usually used in the treatment of HCV-associated hepatocarcinomas (e.g. adriamycin or a mixture of adriamycin lipiodol and spougel usually administered by chimioembolisation in the hepatic artery). For example, therapeutic vaccines include recombinant antigens, VLPs, vectors or synthetic peptides based on or encoding HCV structural proteins (Core, envelope E1 and/or E2) which are particularly suited to trigger an anti-HCV humoral response. Such HCV drugs can be provided in a single dose or, alternatively, in multiple doses according to standard protocols, dosages and regimens over several hours, days and/or weeks. Their administration may precede, be concomitant, or subsequent to the administration of the composition of the invention. A particularly suitable combination includes treatment with pegylated IFN-α2a (e.g. at a dose of 10 μg/week) and/or ribavirin (e.g. at 800 to 1200 mg/day) for 24 to 48 weeks, before, in parallel or subsequently to the method of the invention.

In another embodiment, the method or use of the invention is carried out according to a prime boost therapeutic modality which comprises sequential administration of one or more primer composition(s) and one or more booster composition(s). Typically, the priming and the boosting compositions use different vehicles which comprise or encode at least an antigenic domain in common. The priming composition is initially administered to the host organism and the boosting composition is subsequently administered to the same host organism after a period varying from one day to twelve months. The method of the invention may comprise one to ten sequential administrations of the priming composition followed by one to ten sequential administrations of the boosting composition. Desirably, injection intervals are a matter of one week to six months. Moreover, the priming and boosting compositions can be administered at the same site or at alternative sites by the same route or by different routes of administration. For example, compositions based on polypeptide can be administered by a mucosal route whereas compositions based on vectors are preferably injected, e.g. subcutaneous injection for a MVA vector, intramuscular injection for a DNA plasmid and for an adenoviral vector.

In the context of the invention, a composition of the invention is used to either prime or boost or both prime and boost an anti-HCV immune response. Preferred priming compositions of the invention are preferably those comprising a fusion-encoding adenoviral vector/virus and a fusion encoding plasmid DNA. Fusion-encoding MVA vectors/virus are preferably used for boosting. On the other hand, recombinantly-produced fusion protein can be used independently for priming or boosting. For example, one may prime with a recombinantly-produced fusion protein having the amino acid sequence shown in SEQ ID NO: 9 or SEQ ID NO: 10 and boost with an adenoviral vector encoding such a fusion protein. As another example, one may prime with a DNA plasmid encoding a fusion protein having the amino acid sequence shown in SEQ ID NO: 9 or SEQ ID NO: 10 and boost with MVA virus particles encoding such a fusion protein.

It is also possible to use the composition of the invention in combination with any of the prior art material encoding or comprising an antigenic domain in common with the composition of the invention (e.g. an antigenic domain of NS3, NS4B and/or NS5B polypeptide). The source of such material is wide and includes without limitation peptides, proteins, viral vector from a variety of viruses, plasmid DNA, proteinaceous particles such as virus-like particles (Bursts et al., 1994, Mol. Biol. Techno. 1, 137-145), cellular materials such as irradiated cells, virus particles, etc. For example, particularly appropriate vectors useful in this context are the adenoviral and MVA vectors described in WO2004/111082 which encode NS3, NS4 and NS5B. As another example, the peptides described in WO03/097677 comprising antigenic domains of NS3, NS4B and NS5B are also useful in the context of the invention. For illustrative purposes, one may prime with the adenovirus particles of WO2004/111082 and subsequently boost with the recombinantly-produced fusion protein of SEQ ID NO: 9 or SEQ ID NO: 10 or with the MVA vector/virus encoding the fusion protein of SEQ ID NO: 9 or SEQ ID NO: 10 as defined above. As another example, one may prime with a DNA plasmid encoding the fusion protein of SEQ ID NO: 9 or SEQ ID NO: 10, and boost with the MVA vector of WO2004/111082.

However other prime boost combinations are also possible in the context of the invention.

The present invention also provides a method of inducing or stimulating an immune response against HCV in a host organism comprising administering to said organism the fusion protein, nucleic acid molecule, vector, infectious viral particle, host cell or composition of the invention so as to induce or stimulate said immune response. The immune response can be a specific and/or a nonspecific, a humoral and/or a cell-mediated response. The immune response is preferably a T cell response directed to an HCV antigen.

The ability of the method of the invention to induce or stimulate an anti-HCV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4d- and CD8+ T-cells (e.g. quantification of IL-10 or IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The ability to stimulate a humoral response may be determined by antibody binding and/or competition in binding (see for example Harlow, 1989, Antibodies, Cold Spring Harbor Press). The method of the invention can also be further validated in animal models challenged with an appropriate infectious or tumor-inducing agent (e.g. a vaccinia virus expressing NS genes) to determine neutralization of the infectious or tumor-inducing agent and eventually partial resistance to the associated symptoms, reflecting an induction or an enhancement of an anti-HCV immune response. Testing and validation of the compositions of the invention are also illustrated in the appended Example section.

The invention also provides antibodies that selectively bind to the fusion protein of the present invention or peptide fragments thereof. As used herein, an antibody selectively binds a target peptide when it binds the target peptide and does not significantly bind to unrelated proteins. In certain cases, it would be understood that antibody binding to the peptide is still selective despite some degree of cross-reactivity. It is nonetheless preferred that the antibody of the invention does not bind with high affinity or high selectivity to individual native NS polypeptides and to fusions of NS polypeptides configured in a native configuration.

As used herein, an antibody is defined in terms consistent with that recognized within the art. The antibodies of the present invention include polyclonal antibodies and monoclonal antibodies, as well as fragments of such antibodies, including, but not limited to, Fab or F(ab').sub.2, and Fv fragments. Antibodies of the present invention can be produced using conventional techniques in the art, e.g. following administering to an animal an effective amount of a fusion protein of the present invention and/or a peptide fragment thereof. Antibodies are preferably prepared from regions or discrete fragments of the fusion protein of the invention comprising unique sequences, such as the ones overlapping the fusion site between the NS4A and the NS3 polypeptides and the NS3 and NS5B polypeptides.

Antibodies of the present invention have a variety of potential uses that are within the scope of the present invention. For example, such antibodies can be used (a) as reagents in assays to detect a fusion protein of the present invention, (b) as reagents in assays to detect the presence of a HCV virus in a biological sample, and/or (c) as tools to recover the recombinantly-produced fusion protein of the present invention from a mixture of proteins and other contaminants (e.g. by permitting purification by affinity chromatography or immunoprecipitation from cultured host cells).

The present invention also relates to a method for the detection and/or quantification an HCV virus or an anti-HCV antibody in a biological sample (e.g. plasma, serum, tissue) taken from an individual susceptible to be infected by said HCV virus using the fusion protein, nucleic acid molecule, vector, infectious viral particle, host cell, composition or antibody of the invention.

In one embodiment, the method is more particularly suited for the detection and/or quantification an HCV virus in a biological sample and comprises at least the steps of bringing said biological sample into contact with at least one of the antibodies of the invention under conditions allowing the formation of a complex between the virus and the antibody and detecting and/or quantifying the formation of said complex by any appropriate means.

In another embodiment, the method is more particularly suited for the detection and/or quantification an anti-HCV antibody in a biological sample and comprises at least the steps of bringing said biological sample into contact with at least one of the fusion protein, nucleic acid molecule, vector, infectious viral particle, host cell, composition of the invention under conditions allowing the formation of a complex between the anti-HCV antibody and the fusion protein, nucleic acid molecule, vector, infectious viral particle, host cell, composition of the invention and detecting and/or quantifying the formation of said complex by any appropriate means.

A person skilled in the art will easily determine the quantity of antibody, fusion protein, nucleic acid molecule, vector, infectious viral particle, host cell, composition to be used in the methods of the invention. The means of detection and/or quantification of the virus are routine and well known to a person skilled in the art. By way of illustration, one may mention blots, ELISA, so-called sandwich techniques, competition techniques, and PCR techniques, in particular so called "real-time" techniques. The use of an antibody, fusion protein, nucleic acid molecule, vector, infectious viral particle, host cell, or composition of the present invention as reagent can be facilitated by coupling (i.e., physically linking) to a detectable substance. Examples of detectable substances include various enzymes (e.g. horseradish peroxidase, alkaline phosphatase, beta-galactosidase or acetylcholinesterase), prosthetic groups (e.g. streptavidin/biotin, or avidin/biotin), fluorescent materials (e.g. umbelliferone, fluorescein, or fluorescein derivatives), luminescent materials, bioluminescent materials (e.g. luciferase, luciferin, or acquorin), and radioactive materials (e.g. $^{125}I$, $^{131}I$, $^{35}S$ or $^{3}H$).

Finally, the invention relates to the use of the fusion protein, nucleic acid molecule, vector, infectious viral particle, host cell, composition, or antibody of the invention for the in vitro diagnosis of an HCV infection in a biological sample.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF FIGURES

FIG. 1 illustrates the amino acid sequence of a NS4A-3-5B fusion protein (SEQ ID NO:9). Added or modified amino acid residues are underlined whereas replaced native residues are shown below the sequence.

FIG. 2 illustrates the amino acid sequence of a NS4A-3-4B-5B fusion protein (SEQ ID NO:10). Added or modified amino acid residues are underlined whereas replaced native residues are shown below the sequence.

FIG. 3 illustrates the nucleotide sequence encoding the NS4A-3-5B fusion protein (and its complement (SEQ ID NOs. 21 and 22) and the corresponding amino acid sequence (SEQ ID NO:9)) optimized for expression in mammalian cells.

FIG. 4 illustrates the nucleotide sequence encoding the NS4A-3-4B-5B fusion protein (and its complement (SEQ ID NOs. 23 and 24) and the corresponding amino acid sequence (SEQ ID NO:10)) optimized for expression in mammalian cells.

FIG. 5 illustrates the nucleotide sequence encoding the NS4A-3-5B fusion protein (and its complement (SEQ ID NOs. 25 and 26) and the corresponding amino acid sequence (SEQ ID NO:9)) optimized for expression in yeast cells.

FIG. 6 illustrates the nucleotide sequence encoding the NS4A-3-4B-5B fusion protein (and its complement (SEQ ID NOs. 27 and 28) and the corresponding amino acid sequence (SEQ ID NO:10)) optimized for expression in yeast cells.

FIG. 7 illustrates the nucleotide sequence encoding the NS4A-3-5B fusion protein (and its complement (SEQ ID NOs. 29 and 30) and the corresponding amino acid sequence (SEQ ID NO:9)) optimized for expression in prokaryotic cells.

FIG. 8 illustrates the nucleotide sequence encoding the NS4A-3-4B-5B fusion protein (and its complement (SEQ ID NOs. 31 and 32) and the corresponding amino acid sequence (SEQ ID NO:10)) optimized for expression in prokaryotic cells.

Figure 11:
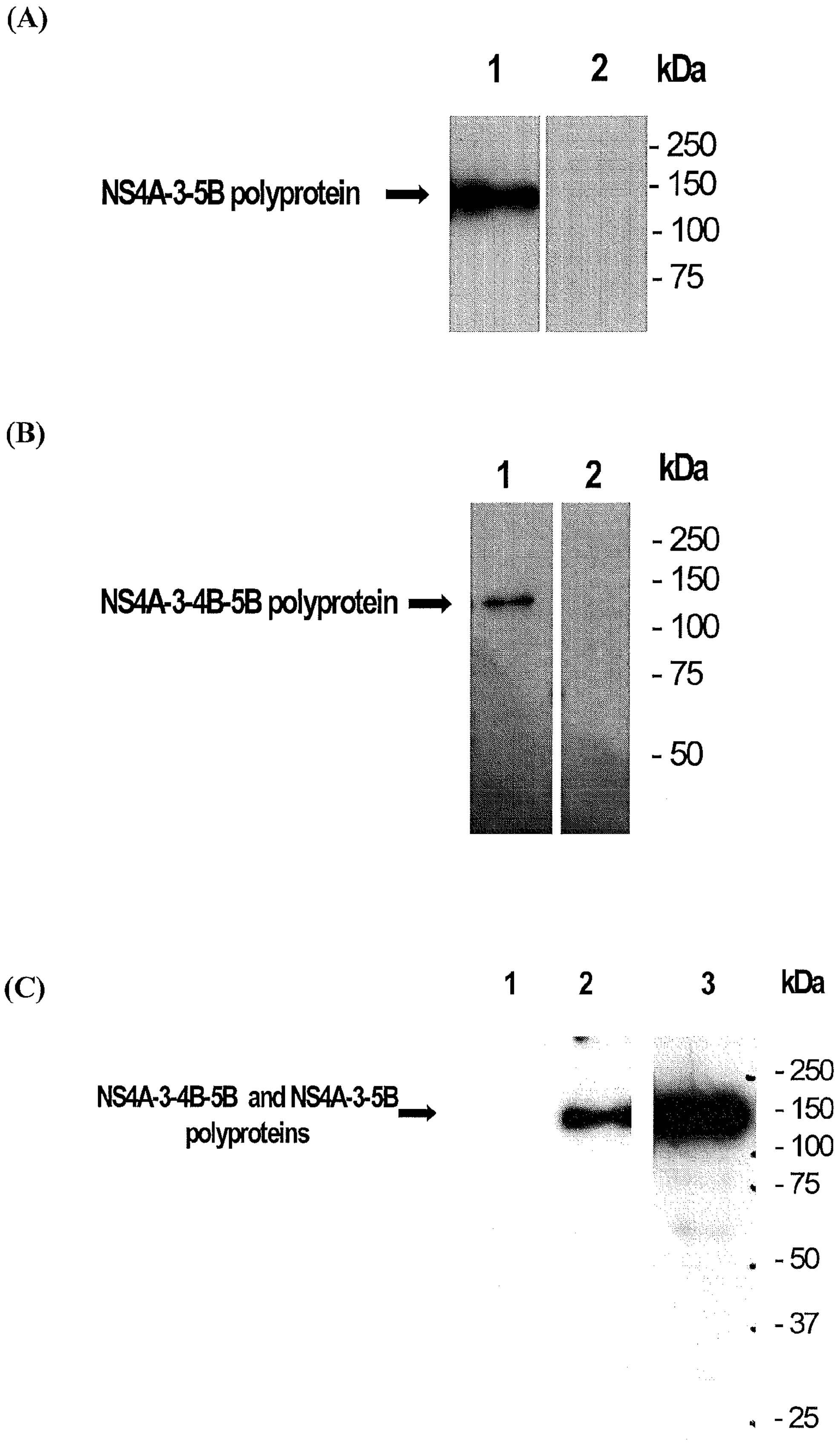

FIG. 11 illustrates the in vitro expression by Western blot following transfection of Huh-7 cells with gWiz NS4A-3-5B (A lane 1 and C lane 3), gWiz NS4A-3-4B-5B (B lane 1 and C lane 2) and gWiz (A lane 2, B lane 2 and C lane 1) plasmids. Transfected Huh-7 cells were lysed at 48 h after transfection and fusion proteins were detected by Western blot analysis using mouse monoclonal anti-NS3 (A and B) or mouse monoclonal anti-NS5B (C) antibodies.

Figure 12:
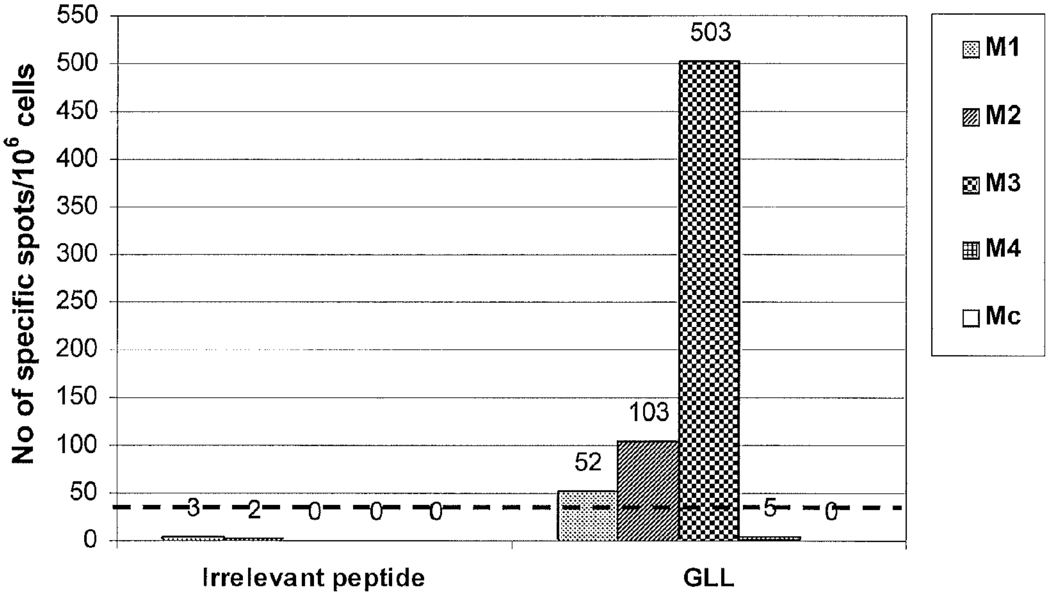

FIG. 12 illustrates the evaluation of $CD8^{+}$ T cell responses specific of NS3 by IFNγ EISPOT assay following intramuscular injection of gWiz NS4A-3-5B Hs. Splenocytes of individual mouse were cultured in the presence of NS3 specific peptide GLL or an irrelevant peptide for 40 h. Results are shown as the mean value of the number of spots detected for $10^{6}$ splenocytes obtained for triplicate wells. M1, M2, M3 and M4 represent 4 mice immunized with the gWiz NS4A-3-5B Hs. Mc is a control mouse.

Figure 13:
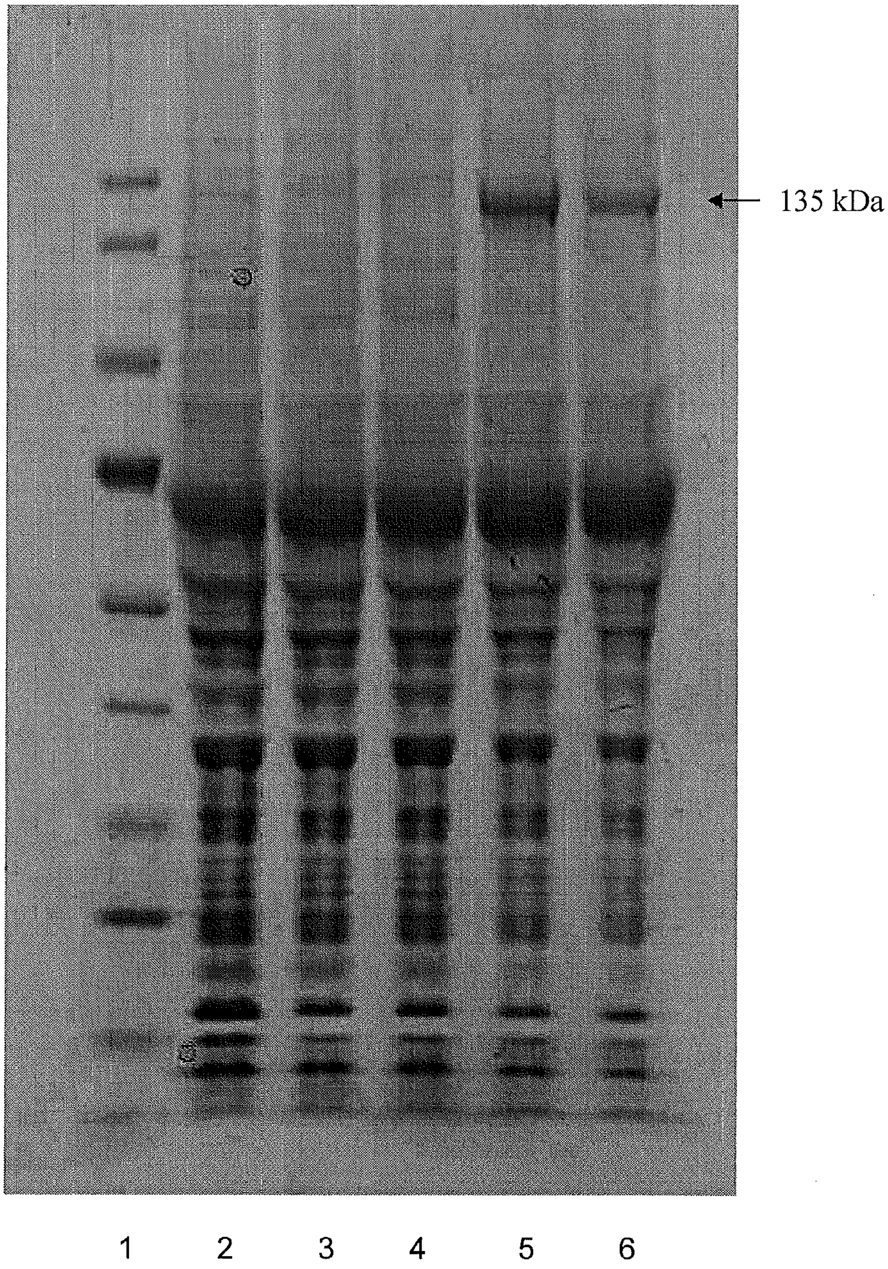

FIG. 13 illustrates expression of the fusion proteins from adenovirus-infected cells. A549 cells ($1.5\times10^{6}$ cells) were infected at a MOI of 10 with different adenoviruses, respectively the fusion-expressing adenoviruses AdTG17476 and AdTG17477, as well as an empty adenovirus and an irrelevant recombinant adenovirus as negative controls. Cells were cultured for 48 h with 10% serum before being lysed with Laemmli buffer. Protein samples (1/20 volume) were loaded on a SDS PAGE electrophoresis gel. The proteins were detected by Coomnassie Blue. Lane 1: molecular weight markers; Lane 2: non-infected A549 cells; Lane 3: A 549 cells infected with empty adenovirus; Lane 4: A 549 cells infected with an irrelevant adenovirus; Lane 5: A 549 cells infected with AdTG17476; and Lane 6: A 549 cells infected with AdTG17477.

Figure 14:
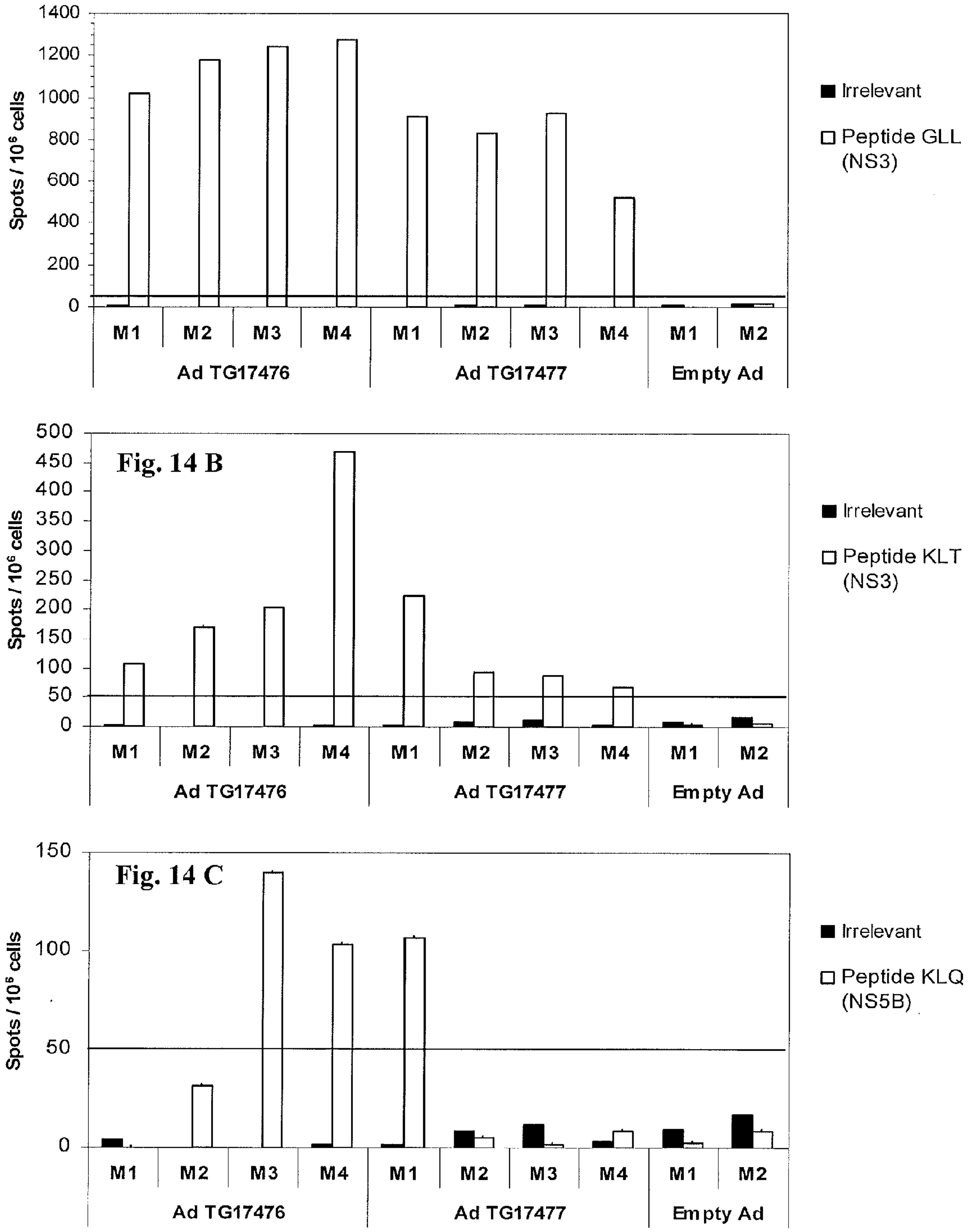

FIG. 14 illustrates IFNγ Elispot responses induced with Ad HCV fusion proteins in HLA-A2.1 transgenic mice. AdTG17476, AdTG17477 or Empty Ad were injected intramuscularly in the tibialis anterior muscle 1 time at a dose of $10^9$ IU/mouse. Cellular immune responses were investigated 2 weeks after injection by IFNγ ELISPOT for each animal group (including 4 mice for test groups and 2 mice for control group). Responses of individual mice (M1 to 4) against NS3-specific HLA-A2 restricted epitopes GLL (FIG. 14A) and KLT (FIG. 14B) and NS5B-specific HLA-A2 restricted epitope KLQ (FIG. 14C) are presented. The irrelevant peptide DLM is used as negative control. An ELISPOT response is considered as positive if the number of spots for $10^6$ splenocytes is greater than 50 (cut-off line).

The following examples serve to illustrate the present invention.

EXAMPLES

Materials and Methods

The constructs described below are prepared according to the general techniques of genetic engineering and of molecular cloning, as detailed in Sambrook et al. (2001, Molecular Cloning; A Laboratory Manual, Cold Spring Harbor Laboratory Press, Cold Spring Harbor N.Y.) or according to the manufacturer's recommendations when a commercial kit is used. The PCR amplification techniques are known to those skilled in the art (see for example PCR Protocols—A guide to Methods and applications, 1990; Ed Innis, Gelfand, Sninsky and White, Academic Press Inc). The human Huh-7 hepatoma cell line was used to evaluate the correct expression of the fusion proteins from the constructs described in the examples which follow. The culturing conditions are conventional in the art. For illustrative purposes, the cells are grown at 37° C. in 5% $CO_2$ atmosphere in complete DMEM medium containing Dulbecco's modified Eagles medium supplemented with 10% Fetal Calf Serum, 2 mM L-Glutamine and 100 IU/ml penicillin/streptomycins (Sigma). Cells are transfected using the Lipofectamine Plus reagent (Invitrogen) and according to the manufacturer instructions. Murine monoclonal antibodies directed to NS3 and NS5B can be purchased commercially or can be prepared according to techniques conventional in the art.

Plasmids Constructions

Figure 9:
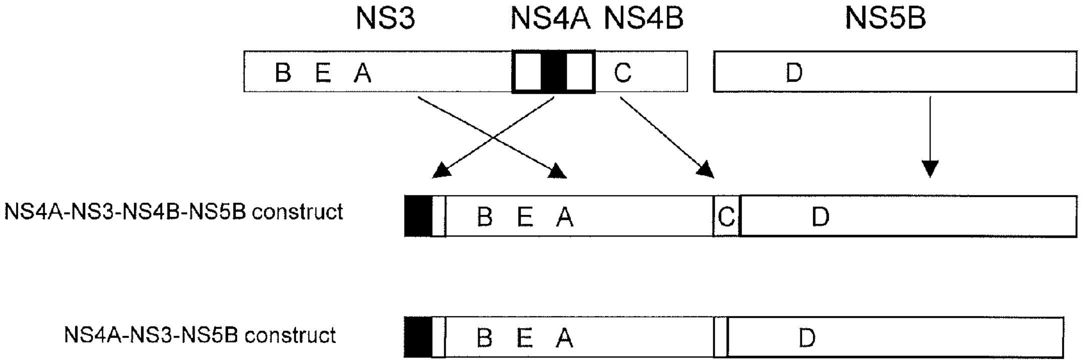
FIG. 9 illustrates the schematic design of the fission proteins NS4A-3-5B and NS4A-3-4B-5B illustrated in the following Examples. A, B, C, D and E represent antigenic domains which can be predicted in NS3, NS4B and NS5B polypeptides (see WO03/097677).

Overlapping oligonucleotides were used to generate synthetic genes (GeneART, Regensburg, Germany) encoding respectively NS4A-NS3-NS5B (3666 nucleotides) and NS4A-NS3-NS4B-NS5B (3747 nucleotides) fusions proteins. The design of the fusions is illustrated in FIG. 9. The nucleotide sequences were optimized for high expression in *homo sapiens* (SEQ ID NO: 11 and 12 and FIGS. 3 and 4), *Pichia* (SEQ ID NO: 13 and 14 and FIGS. 5 and 6) and *E. coli* (SEQ ID NO: 15 and 16 and FIGS. 7 and 8). The amino acid sequence of the resulting fusions is illustrated in SEQ ID NO: 9 for NS4A-NS3-NS5B and in SEQ ID NO: 10 for NS4A-NS3-NS4B-NS5B. Each of the synthetic nucleotide sequences was cloned into the SacI and KpnI restriction sites of the pPCR-Script plasmid (Stratagene).

Figure 10:
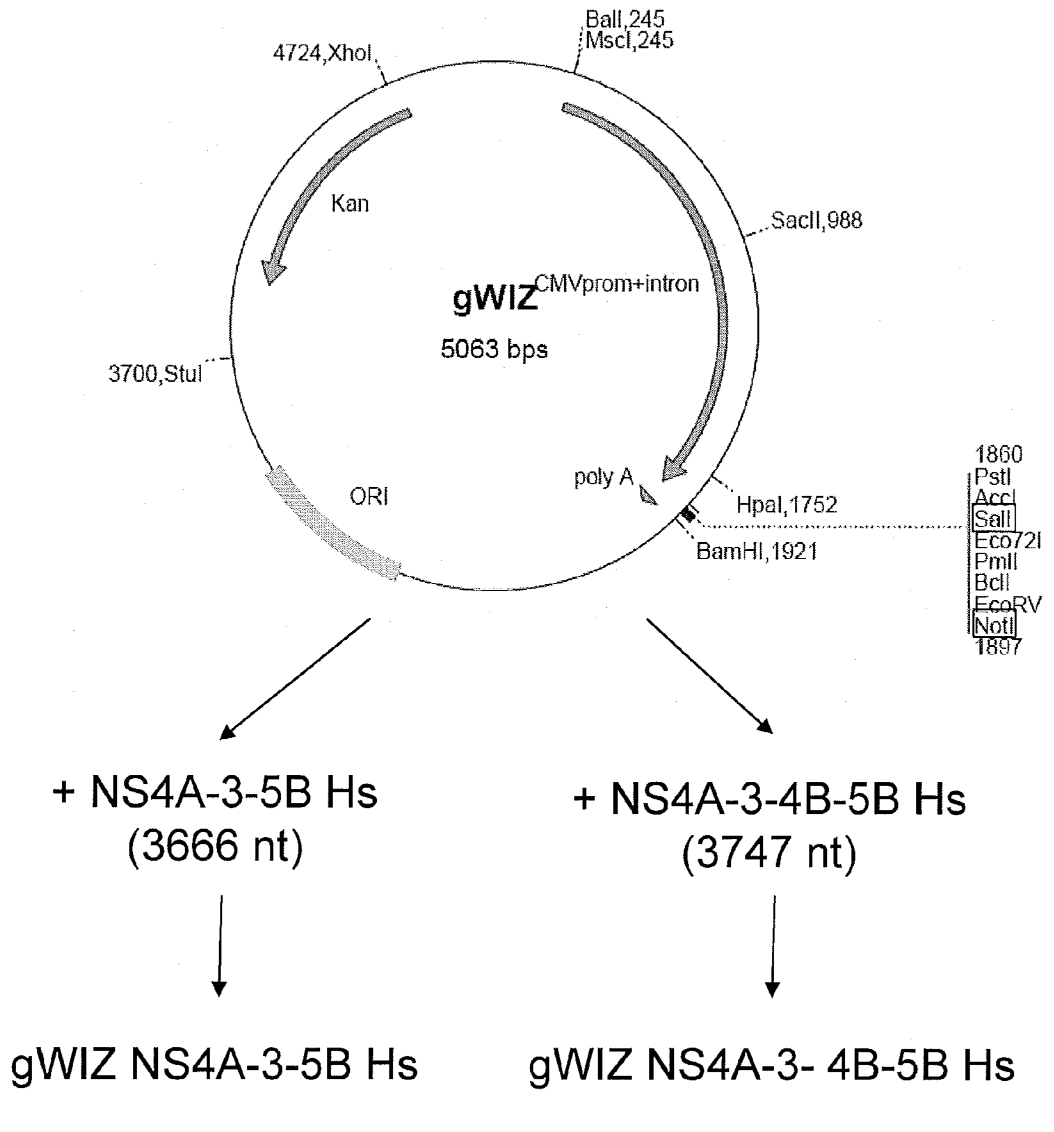
FIG. 10 illustrates the schematic construction of gWiz NS4A-3-5B Hs and the gWiz NS4A-3-4B-5B Hs expression vectors.

For transient expression in mammalian cells, the fusion-encoding synthetic genes optimized for expression in *homo sapiens* (SEQ ID NO: 11-12 and FIGS. 3 and 4) were inserted into the SacI and NotI restriction sites of gWiz expression vector (Gene Therapy Systems) under the transcriptional control of the cytomegalovirus promoter, to generate gWiz NS4A-3-5B Hs and the gWiz NS4A-3-4B-5B Hs vectors (FIG. 10). The sequence was then modified to improve Kozak consensus sequence (underlined) using the oligonucleotide shown in SEQ ID NO: 17 (5'-ATG TAC GTC GAC <u>CACC ATG G</u>GC AGC GTG GTG ATT GTG GGC CGG ATC 3') and to create stop codons (bold) using the oligonucleotide shown in SEQ ID NO: 18 (5'-CAT GTA GC GGC CGC TCA TCA TCT AGG CCT GGC CCT GGA CAG-3'). All plasmids were verified by sequencing.

In Vitro Expression Studies

Western Blot Analysis

One day before transfection, Huh-7 ($5\times10^5$ per well) were plated into 6-well plate. Cells were transfected with gWiz NS4A-3-5B Hs, gWiz NS4A-3-4B-5B Hs vector or gWiz plasmid as negative control. At 48 h post-transfection, cells were lysed in 501 nM Tris-HCl, 150 mM NaCl, 0.1% SDS, 1% NP40 and 0.5% Na-deoxycholate. Lysates samples were heated at 95° C. for 5 mil and proteins were separated by electrophoresis on SDS-8% polyacrylamide. Immunoblotting was performed using murine monoclonal antibodies specific of NS3 (e.g. 8G4C3, bioMérieux) or NS5B (e.g. 11F6C8, bioMérieux) as primary antibody followed by a goat anti-mouse IgG-Peroxydase antibody (Sigma) as secondary antibody. Signals were revealed using the commercial ECL kit (Amersham Biosciences).

Immunofluorescence Analysis

One day before transfection, glass coverslips were placed into 6-well plate and treated with 0.2% Gelatin for 10 min then $5\times10^5$ Huh-7 cells were plated into each well. Cell monolayers were transfected with gWiz NS4A-3-5B Hs, gWiz NS4A-3-4B-5B Hs vector or gWiz plasmid as negative control. At 48 h post-transfection, coverslips were washed twice in PBS and cells were fixed for 10 min with 4% PFA then washed and permeabilized with 0.1% Triton X-100 in PBS for 10 min. Coverslips were washed and treated with a murine monoclonal antibodies specific of NS3 (e.g. 8D8E1, bioMérieux) or NS5B (e.g. 5B-12B7 provided by D. Moradpour) as primary antibody for 1 h at room temperature. After washing, TRITC anti-mouse IgG (Dako) was added for 30 min. After washing, coverslips were mounted in 80% glycerol. Lames were observed with Carl Zeiss Axioplan microscope and images were taken with AxioCam Color digital camera.

In Vivo Expression Studies

HLA-A2.1 transgenic mice produced as described by Pascolo et al. (1997, J. of Experimental Medicine 185, 2043-2051) were bred. These mice have the 1-2 $D^b$ and murine $\beta_2$-microglobulin genes knocked-out and express a transgenic mono chain histocompatibility class I molecule in which the C-terminus of the human β2m is covalently linked to the N-terminus of a chimeric heavy chain (HLA-A2.1 α1-α2, H-2 $D^b$ α3 transmembrane and intracytoplasmic domains).

Immunization Protocols

HLA-A2 transgenic mice received a pre-treatment with 10 μM cardiotoxin (Latoxan) five days before plasmids injection. gWiz NS4A-3-5B, gWIZNS4A-3-4B-5B and gWiz (negative control) plasmids were injected intramuscularly in 2 times at 2 weeks-intervals at a dose of 100 μg (in 100 μl 1×PBS). HLA-A2 restricted $CD8^+$-T cell responses were investigated 2 weeks after the $2^{nd}$ immunization such as described in Himoudi et al. (2002, J. Virol. 76, 12735-46).

Monitoring of the Immune Response by ELISPOT Assays

Splenocytes ($2\times10^5$) were cultured in triplicate wells for 40 h in Multiscreen plates (Millipore) coated with anti-mouse IFNγ monoclonal antibody (Pharmingen; 10 μg/ml) in complete αMEM culture medium (Invitrogen) in presence of 10 units/ml of recombinant IL-2 (PeproTech Inc, England) alone as negative control, or 5 μg/ml T of Concavalin A as positive control or with 10 μM of peptide (DLM irrelevant peptide, GLL peptide located in the NS3 protein described in Martin et al., 2004, J. Med. Virol. 74, 397-405 and Himoudi et al., 2002, J. Virol. 76, 12735-46). IFNγ-producing cells were quantified by cytokine-specific enzyme linked immunospot assay (ELISPOT) as previously described (Himoudi et al., 2002, J. Virol. 76, 12735-46). The number of spots (representing individual IFNγ-producing cells) in negative control wells was subtracted from the number in test wells containing peptides. Results are shown as the mean value obtained for triplicate wells.

Example 1

In Vitro Expression of the NS4A-3-5B and NS4A-3-4B-5B Polyproteins

The sequences encoding the fusion proteins NS4A-3-5B and NS4A-3-4B-5B were constructed as outlined in FIG. 9. The sequences were optimized for expression in three different hosts (GeneART, Regensburg, Germany), human (Hs) *Pichia pastoris* (Pp) and *E. coli* (Ec) respectively, as listed below:

- NS4A-3-5B Hs optimized for expression in *homo sapiens* (SEQ ID NO: 11 and FIG. 3)
- NS4A-3-5B Pp optimized for expression in *Pichia* (SEQ ID NO: 13 and FIG. 5)
- NS4A-3-5B Ec optimized for expression in *E. coli* (SEQ ID NO: 15 and FIG. 7)
- NS4A-3-4B-5B Hs optimized for expression in *homo sapiens* (SEQ ID NO: 12 and FIG. 4)
- NS4A-3-4B 5B Pp optimized for expression in *Pichia* (SEQ ID NO: 14 and FIG. 6)
- NS4A-3-4B-5B Ec optimized for expression in *E. coli* (SEQ ID NO: 16 and FIG. 8)

The sequences optimized for expression in *homo sapiens* encoding the NS4A-NS3-NS4B-NS5B and NS4A-NS3-NS5B fusions were cloned in the gWiz expression vector (GeneTherapy Systems) Linder the transcriptional control of the cytomegalovirus promoter (FIG. 10). Expression of the NS fusion proteins was evaluated by Western blot and immunofluorescence in Huh-7 cells transfected with gWiz NS4A-3-5B Hs, gWiz NS4A-3-4B-5B Hs vectors or gWiz plasmid as negative control.

As shown in FIG. 11, Western Blot analysis revealed a unique band having the expected molecular weight of about 135 kDa for each individual fusion (FIG. 11A lane 1, and FIG. 11C lane 3 for the short NS4A-3-5B fusion and FIG. 11B lane 1, and FIG. 11C lane 2 for the long NS4A-3-4B-5B fusion) following detection with anti-NS3 (FIGS. 11A and 7B) or anti-NS5B (FIG. 11C) specific antibodies. As expected, no proteins were detected in samples obtained from Huh-7 cells transfected with gWiz plasmid (FIG. 11A lane 2, FIG. 11B lane 2 and FIG. 11C lane 1). These results confirm that the short fusion NS4A-NS3-NS5B and the long fusion additionally incorporating NS4B are expressed in Huh-7 cells.

Immunofluorescence analysis confirmed expression of the two fusion proteins in Huh-7 transfected cells. Interestingly, both fusion proteins showed a cytoplasmic localisation suggesting a proper processing as a result of the deletion of the majority of the hydrophobic membrane anchorage domains. Cells transfected with gWiz plasmid did not display any signal.

Example 2

In Vivo Evaluation of gWIZ NS4A-3-5B Hs and NS4A-3-4B-5B Hs Immunogenicity

To evaluate the capacity of plasmids gWiz NS4A-3-5B Hs and NS4A-3-4B-5B Hs to induce $CD8^+$-T cell responses in HLA-A2 transgenic mice, an immunogenicity study was performed following HLA-A2 transgenic mice as described in Material and Methods. HLA-TO A2 restricted $CD8^+$-T cell responses were investigated by IFNγ ELISPOT assay 2 weeks after the $2^{nd}$ immunization. As illustrated in FIG. 12, the pgWiz NS4A-3-5B was able to induce IFNγ-producing T cells specific of the HLA-A2 restricted well known and immunodominant GLL peptide (NS3 protein, Martin et al., 2004, J. Med. Virol. 74, 397-405) suggesting a correct presentation of this epitope.

It is also possible to use preclinical murine challenge assays in order to evaluate the fusion proteins for protective immunity. As mice are not able to be directly infected by HCV viruses, these assays employ either recombinant vaccinia viruses (WR strain) or *Listeria* expressing the HCV NS antigens. After injection of vaccinia virus or *Listeria*, mice develop an infection that peaks 2 to 6 days post injection resulting in virus or bacteria detected in either the ovaries (vaccinia model) or livers (*Listeria* model) of injected mice. Preclinical evaluation involves the vaccination of mice with the candidate vaccine (administration of the recombinant fusion protein or of adenovirus particles expressing the fusion protein), controls (e.g. administration of fusion of NS polypeptides in native configuration) and negative constructs (e.g. non-HCV antigens or empty adenovirus). The animals are subsequently challenged with a recombinant vaccinia virus expressing all of the HCV NS antigens (NS2 to NS5) or *Listeria* expressing one of the NS antigens included in the vaccine candidate. If the vaccine successfully primes specific T cells, challenged mice with develop immune response to the vaccinia or the *Listeria* vector and to the NS antigen(s). The protective activity of the candidate vaccine will result in decreased vaccinia or *Listeria* titers as measured in the ovaries or livers of the vaccinated mice as compared with vaccinia or *Listeria* titers measured in the ovaries or livers of the non-vaccinated mice.

Example 3

Expression of the NS4A-3-5B and NS4A-3-4B-5B Fusion Protein in Mammalian Cells The fusion-encoding synthetic genes optimized for expression in *homo sapiens* (SEQ ID NO: 11-12), corresponding to NS4A-NS3-NS5B (3666 nucleotides) and NS4A-NS3-NS4B-NS5B (3747 nucleotides), were amplified by PCR from the corresponding pPCR-Script plasmids, using the following primers OTG18033 (GGGGGGCTAGCGCCACCATGGGCAGCGTGGTGATTG; SEQ ID NO: 19) and OTG18036 (GGGGGGGTACCCTCATCATCTAGGCCTGGCCCTG; SEQ ID NO: 20). Both fragments were inserted into the NheI and KpnI restriction sites of an adenoviral shuttle plasmid containing a CMV-driven expression cassette sulfonamide by adenoviral sequences (adenoviral nucleotides 1-458 and nucleotides 3328-5788 respectively) to allow generation of the vector genome by homologous recombination (Chartier et al., 1996, J. Virol. 70, 4805-4810). The resulting adenoviral vectors are E3 (nucleotides 28592-30470) and E1 (nucleotides 459-3511) deleted, with the E1 region replaced by the expression cassette containing, from 5' to 3', the CMV intermediate-early enhancer/promoter, a chimeric human β-globin/IgG intron (as found in pCI vector available in Promega), the sequence encoding either of the two polyprotein forms and the SV40 late polyadenylation signal. The resulting adenoviral vectors were named pTG17476 (NS4A-3-4B-5B) and pTG17477 (NS4A-3-5B). The recombinant adenoviruses, AdTGT7476 and AdTG17477, were generated by transfecting the PacI linearized viral genomes into a conventional E1 complementation cell line. Virus propagation, purification and titration were made as described previously (Erbs, 2000, Cancer Res. 60, 3813-3822).

Expression of the fusion proteins was evaluated in adenovirus infected cells by SDS PAGE electrophoresis. A549 cells ($1.5\times10^6$ cells) (ATCC CCL-185) were infected at a MOI of 10 or 100 with the fusion-expressing adenoviruses AdTG17476 and AdTG17477, as well as an empty adenovirus and an irrelevant recombinant adenovirus as negative controls. Cells were cultured for 48 h with 10% serum before being lysed with Laemmli buffer. Protein samples (1/20 volume) were loaded on a SDS PAGE electrophoresis gel and the proteins were stained by Coomassie Blue. As illustrated in FIG. 13, a unique band having the expected molecular weight of approximately 135 kDa was clearly observed in cells infected with AdTG17476 and AdTG17477 (Lanes 5 and 6), reflecting high expression levels in cells infected with the fusion-encoding adenovirus vectors. On the other hand, this band is lacking in the samples collected from the cells infected with the negative controls (Lanes 3 and 4) as well as in non infected A549 cells (Lane 2).

Expression levels were analysed by Western Blot in the A549 cells infected with the viral constructs at MOI of 10 for 48 hours. The cell pellets were collected and probed with an anti-NS3 murine monoclonal antibody (e.g. 1B6, bioMerieux) and an anti-NS4 rabbit polyclonal antibody (e.g. RB, bioMerieux). A major band having the expected molecular weight was revealed in the samples collected from cells infected with AdTG17476 and AdTG17477 following detection with the anti-NS3 or anti-NS4 specific antibodies, confirming the high expression levels detected following Coomassie Blue staining.

Example 4

Immunogenicity of Adenoviruses Expressing the HCV Polyproteins in HLA A2 Transgenic Mice Animal Model HLA-A2.1 transgenic mice were produced as described by Pascolo et al. (1997, J Ex Med). These mice have the H-$2D^b$ and murine $\beta_2$-microglobulin genes knocked-out and express a transgenic monochain histocompatibility class I molecule in which the C-terminus of the human β2m is covalently linked to the N-terminus of a chimeric heavy chain (HLA-A2.1 α1-α2, H-$2D^b$ α3 transmembrane and intracytoplasmic domains).

Immunization Protocol

Three groups of mice were included in the protocol, respectively four mice injected with AdTG17476 (Ad NS4A-3-4B-5B), four mice injected with AdTG17477 (Ad NS4A-3-5B) and two control mice injected with an empty Ad (Ad1514). Adenoviruses were injected intra-muscularly in the tibialis anterior muscle 1 time at a dose of $10^9$ IU in 100 μl of 1×PBS. Cellular immune responses were investigated 2 weeks after injection.

Monitoring of the Immune Response

ELISPOT Assays

Splenocytes from mice of each group were collected and red blood cells were lysed. $2.10^5$ cells were cultured in triplicate wells for 40 h in Multiscreen plates (Millipore) coated with anti-mouse IFNγ monoclonal antibody (Pharmingen; 10 μg/ml) in complete αMEM culture medium (GIBCO BRL) in presence of 10 units/ml of recombinant murine IL-2 (Pepro-Tech Inc, England), alone as negative control, or with 10 μM of peptide (DLM irrelevant peptide, GLL and KLT peptides located in the NS3 protein, KLQ peptide located in NS5B protein (Martin et al., 2004, J Med Virol. 74, 397-405) and (Himoudi et al., 2002, J Virol., 76, 12735-12746), or 5 μg/ml of Concavalin A as positive control. IFNγ-producing T cells were quantified by cytokine-specific enzyme linked immunospot assay (ELISPOT) as previously described (Himoudi et al., J Virol 2002). The number of spots (representing individual IFNγ-producing T cell) in negative control wells was subtracted from the number in test wells containing peptides. Results are shown as the mean value obtained for triplicate wells.

Results

HLA-A2 restricted T cell responses were investigated by IFNγ ELISPOT assay 2 weeks after adenovirus immunization. As shown in FIG. 14, both AdTG17476 and AdTG17477 were able to induce, in all vaccinated animals, high frequencies of IFNγ-producing T cells specific of the HLA-A2 restricted GLL epitope (FIG. 14A; median value: 1210 and 868 spots, respectively) with a statistically significant higher efficiency for AdTG17476 (Mann-Whitney test: P=0,0209). Both viruses induced also IFNγ-producing T cells specific of the subdominant KLT epitope (FIG. 14B) with lower frequencies (median value: 187 and 90 spots). In addition, 2:4 mice vaccinated with AdTG17476 and 1:4 mice vaccinated with AdTG17477 developed responses targeting the KLQ epitope of the NS5B protein (FIG. 14C).

This demonstrates that fusion proteins in accordance with the invention can be produced at high levels in eukaryotic systems and that the resulting proteins are immunogenic in conventional model animals.

The invention claimed is:

1. An isolated fusion protein comprising at least three non-structural (NS) polypeptides of hepatitis C virus (HCV), wherein said NS polypeptides are configured in said fusion protein in an order which is distinct from the order in which they appear in the native configuration, wherein NS4A polypeptide is located at the N-terminus.

2. The isolated fusion protein according to claim 1, wherein the fusion between each of the NS polypeptides is direct or through a linker.

3. The isolated fusion protein according to claim 1, wherein all the NS polypeptides originate from the same HCV strain or isolate.

4. The isolated fusion protein according to claim 1, wherein at least two of the NS polypeptides originate from different HCV strains or isolates.

5. The isolated fusion protein according to claim 1, comprising a NS4A polypeptide, a NS3 polypeptide, and a NS5B polypeptide, with NS5B at the C-terminus of said fusion protein.

6. The isolated fusion protein according to claim 1, comprising a NS4A polypeptide, a NS3 polypeptide, a NS4B polypeptide and a NS5B polypeptide with NS5B at the C-terminus of said fusion protein.

7. The isolated fusion protein according to claim 5 or 6, wherein the NS3 polypeptide is modified as compared to a native NS3 polypeptide, so as to exhibit a significantly reduced protease activity.

8. The isolated fusion protein according to claim 5 or 6, wherein the NS3 polypeptide is modified as compared to a native NS3 polypeptide so as to exhibit a significantly reduced helicase activity.

9. The isolated fusion protein according to claim 5 or 6, wherein the NS5B polypeptide is modified as compared to a native NS5B polypeptide so as to exhibit a significantly reduced RNA-dependent RNA polymerase activity.

10. The isolated fusion protein according to claim 5 or 6, wherein said fusion protein does not comprise one or more of the NS3-recognized cleavage site(s) normally present in a native HCV polyprotein precursor at the NS3/NS4A, NS4A/NS4B, NS4B/NS5A and NS5A/NS5B junctions.

11. The isolated fusion protein according to claim 5 or 6, wherein the NS4A, NS4B and/or NS5B polypeptides are modified so as to delete one or more hydrophobic domain(s) which are normally involved in membrane anchorage of the native NS4A, NS4B and/or NS5B polypeptides.

12. The isolated fusion protein according to claim 5 or 6, wherein the NS3 polypeptide originates from the native NS3 protein shown in SEQ ID NO: 1 which is modified at least in such a manner that:

it retains the portion extending from position 12 to position 56, from position 70 to position 155, and from position 218 to position 248;

it comprises the substitution of the His residue in position 57 by an Ala residue;

it comprises the substitution of the Thr residue in position 269 by an Ala residue; and it comprises the substitution of the Arg residue in position 464 by an Ala residue; and it does not comprise the Thr residue in position 631.

13. The isolated fusion protein according to claim 12, wherein the NS3 polypeptide comprises the amino acid sequence shown in SEQ ID NO: 5.

14. The isolated fusion protein according to claim 1, wherein the NS4A polypeptide originates from the native NS4A protein shown in SEQ ID NO: 2 which is modified at least in such a manner that:

it contains the portion of SEQ ID NO: 2 from position 21 to position 33;

it does not contain the portion of SEQ ID NO: 2 from position 1 to position 20.

15. The isolated fusion protein according to claim 14, wherein the NS4A polypeptide consists essentially of the amino acid sequence shown in SEQ ID NO: 6 preceded by an initiator Met residue.

16. The isolated fusion protein according to claim 5 or 6, wherein the NS4B polypeptide originates from the native NS4B protein shown in SEQ ID NO: 3 which is modified at least in such a manner that:

it comprises the portion extending from the Ser residue in position 78 to the Leu residue in position 109;

it does not comprise the Cys residue in position 261.

17. The isolated fusion protein according to claim 16, wherein the optional NS4B polypeptide consists essentially of the amino acid sequence as shown in SEQ ID NO: 7.

18. The isolated fusion protein according to claim 5 or 6, wherein the NS5B polypeptide originates from the native NS5B protein shown in SEQ ID NO: 4 which is modified at least in such a manner that:

it comprises the portion extending from the Arg residue in position 155 to the Leu residue in position 182;

it comprises the substitution of the Asp residue in position 220 by an Asn residue;

it comprises the substitution of the Asp residue in position 318 by an Asn residue;

it does not comprise the portion extending from the Trp residue in position 571 to the Arg residue in position 591.

19. The isolated fusion protein according to claim 18, wherein the NS5B polypeptide comprises the amino acid sequence as shown in SEQ ID NO: 8.

20. The isolated fusion protein according to claim 12, wherein said fusion protein comprises the amino acid sequence shown in SEQ ID NO: 9 or 10.

21. An isolated nucleic acid molecule encoding the fusion protein according to claim 1.

22. The isolated nucleic acid molecule according to claim 21, comprising a nucleotide sequence optimized for expression in a mammalian host cell.

23. The isolated nucleic acid molecule according to claim 22, comprising the nucleotide sequences shown in SEQ ID NO: 11 or SEQ ID NO: 12.

24. The isolated nucleic acid molecule according to claim 21, having a nucleotide sequence optimized for expression in a yeast host cell.

25. The isolated nucleic acid molecule according to claim 24, wherein the yeast host cell is selected among the group consisting of *Saccharomyces cerevisiae, Saccharomyces pombe* and *Pichia pastoris*.

26. The isolated nucleic acid molecule according to claim 25, comprising the nucleotide sequences shown in SEQ ID NO: 13 or SEQ ID NO: 14.

27. The isolated nucleic acid molecule according to claim 21, having a nucleotide sequence optimized for expression in a prokaryotic host cell.

28. The isolated nucleic acid molecule according to claim 27, comprising the nucleotide sequences shown in SEQ ID NO: 15 or SEQ ID NO: 16.

29. A vector comprising one or more copies of the nucleic acid molecule according to claim 21.

30. An isolated infectious viral particle comprising the nucleic acid molecule of claim 21.

31. An isolated infectious viral particle comprising the vector of claim 29.

32. An isolated host cell comprising the nucleic acid molecule of claim 21.

33. An isolated host cell comprising the vector of claim 29.

34. An isolated host cell comprising the infectious viral particle of claim 30.

35. A method for recombinantly producing a fusion protein comprising at least three non-structural (NS) polypeptides of hepatitis C virus (HCV), wherein said NS polypeptides are configured in said fusion protein in an order which is distinct from the order in which they appear in the native configuration, wherein NS4A polypeptide is located at the N-terminus, which comprises:

(a) introducing a vector or an infectious viral particle comprising one or more copies of a nucleic acid molecule, coding for said fusion protein, into a host cell to produce a transfected or infected host cell comprising said vector or said infectious viral particle, (b) culturing in-vitro said transfected or infected host cell under a condition suitable for growth of the host cell, (c) recovering the fusion protein from the host cell culture, and (d) optionally, purifying the recovered fusion protein.

36. A composition comprising at least one element chosen among:

an isolated fusion protein comprising at least three non-structural (NS) polypeptides of hepatitis C virus (HCV), wherein said NS polypeptides are configured in said fusion protein in an order which is distinct from the order in which they appear in the native configuration, wherein NS4A polypeptide is located at the N-terminus, an isolated nucleic acid molecule coding for said fusion protein, an isolated vector comprising one or more copies of said nucleic acid molecule, an isolated infectious viral particle comprising said nucleic acid molecule, and an isolated host cell comprising said vector, or comprising said isolated infectious viral particle, or any combination thereof.

37. A method of inducing or stimulating an immune response against HCV in a host organism comprising administering to said organism a therapeutically effective amount of one element chosen among:

a fusion protein comprising at least three non-structural (NS) polypeptides of hepatitis C virus (HCV), wherein said NS polypeptides are configured in said fusion protein in an order which is distinct from the order in which they appear in the native configuration, wherein NS4A polypeptide is located at the N-terminus, a nucleic acid molecule coding for said fusion protein, a vector comprising one or more copies of said nucleic acid molecule, an isolated infectious viral particle comprising said nucleic acid molecule, or comprising said vector, a host cell comprising said vector, or comprising said isolated infectious viral particle, and a composition comprising at least one of the following elements:

said fusion protein, said nucleic acid molecule, said vector, said isolated infectious viral particles, and said host cell, or any combination thereof, so as to induce or stimulate said immune response.

38. A method of inducing or stimulating an immune response against HCV in a host organism comprising administering to said organism a therapeutically effective amount of a composition, said composition comprising at least one of the following elements:

a fusion protein comprising at least three non-structural (NS) polypeptides of hepatitis C virus (HCV), wherein said NS polypeptides are configured in said fusion protein in an order which is distinct from the order in which they appear in the native configuration, wherein NS4A polypeptide is located at the N-terminus, a nucleic acid molecule coding for said fusion protein, a vector comprising one or more copies of said nucleic acid molecule, an isolated infectious viral particle comprising said nucleic acid molecule, or comprising said vector, and a isolated host cell comprising said vector, or comprising said isolated infectious viral particle, or any combination thereof, said composition being used to either prime or boost or both prime and boost an anti-HCV immune response.

39. The method of claim 37, said method being associated to chemotherapy with one or more HCV drugs.

* * * * *

UNITED STATES PATENT AND TRADEMARK OFFICE

CERTIFICATE OF CORRECTION

PATENT NO. : 8,211,444 B2
APPLICATION NO. : 12/282146
DATED : July 3, 2012
INVENTOR(S) : Anne Fournillier et al.

It is certified that error appears in the above-identified patent and that said Letters Patent is hereby corrected as shown below:

On the cover page, first column, Inventors should read:

(75) INVENTORS

Anne Fournillier, Lyon (FR); Genevieve Inchauspe, Lyon (FR); Laurence Chatel, Jozier (FR); Francois Penin, Decines (FR)

Signed and Sealed this
Sixth Day of November, 2012

David J. Kappos
*Director of the United States Patent and Trademark Office*

SEQUENCE LISTING

```
<160> NUMBER OF SEQ ID NOS: 34

<210> SEQ ID NO 1
<211> LENGTH: 631
<212> TYPE: PRT
<213> ORGANISM: Hepatitis C virus

<400> SEQUENCE: 1

Ala Pro Ile Thr Ala Tyr Ser Gln Gln Thr Arg Gly Leu Leu Gly Cys
```

-continued

```
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Pro Ala Pro Pro Gly Ala Arg Ser Met Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Val Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Glu Pro Asn Ile Arg Thr Gly Val
                245                 250                 255

Arg Thr Ile Thr Thr Gly Gly Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Trp Thr Thr Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Ile Thr Val Pro His Pro Asn Ile
                325                 330                 335

Glu Glu Val Ala Leu Ser Asn Thr Gly Glu Ile Pro Phe Tyr Gly Lys
            340                 345                 350

Ala Ile Pro Ile Glu Ala Ile Lys Gly Gly Arg His Leu Ile Phe Cys
        355                 360                 365

His Ser Lys Lys Lys Cys Asp Glu Leu Ala Ala Lys Leu Thr Gly Leu
    370                 375                 380

Gly Leu Asn Ala Val Ala Tyr Tyr Arg Gly Leu Asp Val Ser Val Ile
385                 390                 395                 400

Pro Thr Ser Gly Asp Val Val Val Val Ala Thr Asp Ala Leu Met Thr
                405                 410                 415

Gly Phe Thr Gly Asp Phe Asp Ser Val Ile Asp Cys Asn Thr Cys Val
            420                 425                 430
```

```
Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
    450                 455                 460

Thr Gly Arg Gly Arg Ser Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Thr Val Arg
            500                 505                 510

Leu Arg Ala Tyr Leu Asn Thr Pro Gly Leu Pro Val Cys Gln Asp His
        515                 520                 525

Leu Glu Phe Trp Glu Ser Val Phe Thr Gly Leu Thr His Ile Asp Ala
    530                 535                 540

His Phe Leu Ser Gln Thr Lys Gln Ala Gly Asp Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Ile Thr Leu Thr His Pro Ile Thr Lys Phe Val Met Ala Cys Met Ser
    610                 615                 620

Ala Asp Leu Glu Val Val Thr
625                 630


<210> SEQ ID NO 2
<211> LENGTH: 54
<212> TYPE: PRT
<213> ORGANISM: Hepatitis C virus

<400> SEQUENCE: 2

Ser Thr Trp Val Leu Val Gly Gly Val Leu Ala Ala Leu Ala Ala Tyr
1               5                   10                  15

Cys Leu Thr Thr Gly Ser Val Val Ile Val Gly Arg Ile Ile Leu Ser
            20                  25                  30

Gly Arg Pro Ala Val Val Pro Asp Arg Glu Val Leu Tyr Arg Glu Phe
        35                  40                  45

Asp Glu Met Glu Glu Cys
    50


<210> SEQ ID NO 3
<211> LENGTH: 261
<212> TYPE: PRT
<213> ORGANISM: Hepatitis C virus

<400> SEQUENCE: 3

Ala Ser His Leu Pro Tyr Ile Glu Gln Gly Met Gln Leu Ala Glu Gln
1               5                   10                  15

Phe Lys Gln Lys Ala Leu Gly Leu Leu Gln Thr Ala Thr Lys Gln Ala
            20                  25                  30

Glu Ala Ala Ala Pro Val Val Glu Ser Arg Trp Arg Ala Leu Glu Ala
        35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
```

```
65                  70                  75                  80

Ala Phe Thr Ala Ser Ile Thr Ser Pro Leu Thr Thr Gln Asn Thr Leu
                85                  90                  95

Leu Phe Asn Ile Leu Gly Gly Trp Val Ala Ala Gln Leu Ala Pro Pro
            100                 105                 110

Ser Ala Ala Ser Ala Phe Val Gly Ala Gly Ile Ala Gly Ala Ala Ile
        115                 120                 125

Gly Ser Ile Gly Leu Gly Lys Val Leu Val Asp Ile Leu Ala Gly Tyr
    130                 135                 140

Gly Ala Gly Val Ala Gly Ala Leu Val Ala Phe Lys Val Met Ser Gly
145                 150                 155                 160

Glu Ala Pro Ser Ala Glu Asp Leu Val Asn Leu Leu Pro Ala Ile Leu
                165                 170                 175

Ser Pro Gly Ala Leu Val Val Gly Ile Val Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
            260


<210> SEQ ID NO 4
<211> LENGTH: 591
<212> TYPE: PRT
<213> ORGANISM: Hepatitis C virus

<400> SEQUENCE: 4

Ser Met Ser Tyr Thr Trp Thr Gly Ala Leu Ile Thr Pro Cys Ala Ala
1               5                   10                  15

Glu Glu Ser Lys Leu Pro Ile Asn Pro Leu Ser Asn Ser Leu Leu Arg
            20                  25                  30

His His Ser Met Val Tyr Ser Thr Thr Ser Arg Ser Ala Ser Leu Arg
        35                  40                  45

Gln Lys Lys Val Thr Phe Asp Arg Leu Gln Val Leu Asp Asp His Tyr
    50                  55                  60

Arg Asp Val Leu Lys Glu Met Lys Ala Lys Ala Ser Thr Val Lys Ala
65                  70                  75                  80

Arg Leu Leu Ser Ile Glu Glu Ala Cys Lys Leu Thr Pro Pro His Ser
                85                  90                  95

Ala Lys Ser Lys Phe Gly Tyr Gly Ala Lys Asp Val Arg Ser Leu Ser
            100                 105                 110

Ser Arg Ala Val Asn His Ile Arg Ser Val Trp Glu Asp Leu Leu Glu
        115                 120                 125

Asp Thr Glu Thr Pro Ile Asp Thr Thr Ile Met Ala Lys Asn Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Ala Val Met Gly Pro Ser Tyr Gly
```

-continued

```
            180                 185                 190

Phe Gln Tyr Ser Pro Gly Gln Arg Val Glu Phe Leu Val Asn Thr Trp
        195                 200                 205

Lys Ser Lys Lys Cys Pro Met Gly Phe Ser Tyr Asp Thr Arg Cys Phe
    210                 215                 220

Asp Ser Thr Val Thr Glu Asn Asp Ile Arg Thr Glu Glu Ser Ile Tyr
225                 230                 235                 240

Gln Cys Cys Asp Leu Ala Pro Glu Ala Arg Gln Ala Ile Lys Ser Leu
                245                 250                 255

Thr Glu Arg Leu Tyr Ile Gly Gly Pro Leu Thr Asn Ser Lys Gly Gln
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Leu Lys Ala Thr Ala Ala Cys Arg
    290                 295                 300

Ala Ala Lys Leu Gln Asp Cys Thr Met Leu Val Asn Gly Asp Asp Leu
305                 310                 315                 320

Val Val Ile Cys Glu Ser Ala Gly Thr Gln Glu Asp Ala Ala Ser Leu
                325                 330                 335

Arg Val Phe Thr Glu Ala Met Thr Arg Tyr Ser Ala Pro Pro Gly Asp
            340                 345                 350

Pro Pro Gln Pro Glu Tyr Asp Leu Glu Leu Ile Thr Ser Cys Ser Ser
        355                 360                 365

Asn Val Ser Val Ala His Asp Ala Ser Gly Lys Arg Val Tyr Tyr Leu
    370                 375                 380

Thr Arg Asp Pro Thr Thr Pro Leu Ala Arg Ala Ala Trp Glu Thr Val
385                 390                 395                 400

Arg His Thr Pro Val Asn Ser Trp Leu Gly Asn Ile Ile Met Tyr Ala
                405                 410                 415

Pro Thr Leu Trp Ala Arg Met Ile Leu Met Thr His Phe Phe Ser Ile
            420                 425                 430

Leu Leu Ala Gln Glu Gln Leu Glu Lys Ala Leu Asp Cys Gln Ile Tyr
        435                 440                 445

Gly Ala Cys Tyr Ser Ile Glu Pro Leu Asp Leu Pro Gln Ile Ile Glu
    450                 455                 460

Arg Leu His Gly Leu Ser Ala Phe Ser Leu His Ser Tyr Ser Pro Gly
465                 470                 475                 480

Glu Ile Asn Arg Val Ala Ser Cys Leu Arg Lys Leu Gly Val Pro Pro
                485                 490                 495

Leu Arg Val Trp Arg His Arg Ala Arg Ser Val Arg Ala Lys Leu Leu
            500                 505                 510

Ser Gln Gly Gly Arg Ala Ala Thr Cys Gly Lys Tyr Leu Phe Asn Trp
        515                 520                 525

Ala Val Arg Thr Lys Leu Lys Leu Thr Pro Ile Pro Ala Ala Ser Gln
    530                 535                 540

Leu Asp Leu Ser Gly Trp Phe Val Ala Gly Tyr Asn Gly Gly Asp Ile
545                 550                 555                 560

Tyr His Ser Leu Ser Arg Ala Arg Pro Arg Trp Phe Met Leu Cys Leu
                565                 570                 575

Leu Leu Leu Ser Val Gly Val Gly Ile Tyr Leu Leu Pro Asn Arg
            580                 585                 590
```

<210> SEQ ID NO 5
<211> LENGTH: 630

-continued

<212> TYPE: PRT
<213> ORGANISM: artificial sequence
<220> FEATURE:
<223> OTHER INFORMATION: NS3 moiety derived from HCV-JA NS3
polypeptide with protease and helicase activities inactivated

<400> SEQUENCE: 5

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Val
        35                  40                  45

Asn Gly Val Cys Trp Thr Val Tyr Ala Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Pro Ala Pro Pro Gly Ala Arg Ser Met Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Val Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Glu Pro Asn Ile Arg Thr Gly Val
                245                 250                 255

Arg Thr Ile Thr Thr Gly Gly Pro Ile Thr Tyr Ser Ala Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Trp Thr Thr Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Ile Thr Val Pro His Pro Asn Ile
                325                 330                 335

Glu Glu Val Ala Leu Ser Asn Thr Gly Glu Ile Pro Phe Tyr Gly Lys
            340                 345                 350

Ala Ile Pro Ile Glu Ala Ile Lys Gly Gly Arg His Leu Ile Phe Cys
        355                 360                 365

His Ser Lys Lys Lys Cys Asp Glu Leu Ala Ala Lys Leu Thr Gly Leu
    370                 375                 380
```

-continued

Gly Leu Asn Ala Val Ala Tyr Tyr Arg Gly Leu Asp Val Ser Val Ile
385 390 395 400

Pro Thr Ser Gly Asp Val Val Val Val Ala Thr Asp Ala Leu Met Thr
405 410 415

Gly Phe Thr Gly Asp Phe Asp Ser Val Ile Asp Cys Asn Thr Cys Val
420 425 430

Thr Gln Thr Val Asp Phe Ser Leu Asp Pro Thr Phe Thr Ile Glu Thr
435 440 445

Thr Thr Val Pro Gln Asp Ala Val Ser Arg Ser Gln Arg Arg Gly Ala
450 455 460

Thr Gly Arg Gly Arg Ser Gly Ile Tyr Arg Phe Val Thr Pro Gly Glu
465 470 475 480

Arg Pro Ser Gly Met Phe Asp Ser Ser Val Leu Cys Glu Cys Tyr Asp
485 490 495

Ala Gly Cys Ala Trp Tyr Glu Leu Thr Pro Ala Glu Thr Thr Val Arg
500 505 510

Leu Arg Ala Tyr Leu Asn Thr Pro Gly Leu Pro Val Cys Gln Asp His
515 520 525

Leu Glu Phe Trp Glu Ser Val Phe Thr Gly Leu Thr His Ile Asp Ala
530 535 540

His Phe Leu Ser Gln Thr Lys Gln Ala Gly Asp Asn Phe Pro Tyr Leu
545 550 555 560

Val Ala Tyr Gln Ala Thr Val Cys Ala Arg Ala Gln Ala Pro Pro Pro
565 570 575

Ser Trp Asp Gln Met Trp Lys Cys Leu Ile Arg Leu Lys Pro Thr Leu
580 585 590

His Gly Pro Thr Pro Leu Leu Tyr Arg Leu Gly Ala Val Gln Asn Glu
595 600 605

Ile Thr Leu Thr His Pro Ile Thr Lys Phe Val Met Ala Cys Met Ser
610 615 620

Ala Asp Leu Glu Val Val
625 630

<210> SEQ ID NO 6
<211> LENGTH: 13
<212> TYPE: PRT
<213> ORGANISM: artificial sequence
<220> FEATURE:
<223> OTHER INFORMATION: NS4A moiety derived from HCV JA NS4A polypeptide by N and C-terminal truncation

<400> SEQUENCE: 6

Gly Ser Val Val Ile Val Gly Arg Ile Ile Leu Ser Gly
1 5 10

<210> SEQ ID NO 7
<211> LENGTH: 32
<212> TYPE: PRT
<213> ORGANISM: artificial sequence
<220> FEATURE:
<223> OTHER INFORMATION: NS4B moiety derived from HCV JA NS4B polypeptide by N and C truncation

<400> SEQUENCE: 7

Ser Leu Met Ala Phe Thr Ala Ser Ile Thr Ser Pro Leu Thr Thr Gln
1 5 10 15

Asn Thr Leu Leu Phe Asn Ile Leu Gly Gly Trp Val Ala Ala Gln Leu
20 25 30

-continued

<210> SEQ ID NO 8
<211> LENGTH: 570
<212> TYPE: PRT
<213> ORGANISM: artificial sequence
<220> FEATURE:
<223> OTHER INFORMATION: NS5B moiety derived from HCV JA NS5B polypeptide with polymerase activity inactivated and C terminus truncation

<400> SEQUENCE: 8

```
Ser Met Ser Tyr Thr Trp Thr Gly Ala Leu Ile Thr Pro Cys Ala Ala
1               5                   10                  15

Glu Glu Ser Lys Leu Pro Ile Asn Pro Leu Ser Asn Ser Leu Leu Arg
            20                  25                  30

His His Ser Met Val Tyr Ser Thr Thr Ser Arg Ser Ala Ser Leu Arg
        35                  40                  45

Gln Lys Lys Val Thr Phe Asp Arg Leu Gln Val Leu Asp Asp His Tyr
    50                  55                  60

Arg Asp Val Leu Lys Glu Met Lys Ala Lys Ala Ser Thr Val Lys Ala
65                  70                  75                  80

Arg Leu Leu Ser Ile Glu Glu Ala Cys Lys Leu Thr Pro Pro His Ser
                85                  90                  95

Ala Lys Ser Lys Phe Gly Tyr Gly Ala Lys Asp Val Arg Ser Leu Ser
            100                 105                 110

Ser Arg Ala Val Asn His Ile Arg Ser Val Trp Glu Asp Leu Leu Glu
        115                 120                 125

Asp Thr Glu Thr Pro Ile Asp Thr Thr Ile Met Ala Lys Asn Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Ala Val Met Gly Pro Ser Tyr Gly
            180                 185                 190

Phe Gln Tyr Ser Pro Gly Gln Arg Val Glu Phe Leu Val Asn Thr Trp
        195                 200                 205

Lys Ser Lys Lys Cys Pro Met Gly Phe Ser Tyr Asn Thr Arg Cys Phe
    210                 215                 220

Asp Ser Thr Val Thr Glu Asn Asp Ile Arg Thr Glu Glu Ser Ile Tyr
225                 230                 235                 240

Gln Cys Cys Asp Leu Ala Pro Glu Ala Arg Gln Ala Ile Lys Ser Leu
                245                 250                 255

Thr Glu Arg Leu Tyr Ile Gly Gly Pro Leu Thr Asn Ser Lys Gly Gln
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Leu Lys Ala Thr Ala Ala Cys Arg
    290                 295                 300

Ala Ala Lys Leu Gln Asp Cys Thr Met Leu Val Asn Gly Asn Asp Leu
305                 310                 315                 320

Val Val Ile Cys Glu Ser Ala Gly Thr Gln Glu Asp Ala Ala Ser Leu
                325                 330                 335

Arg Val Phe Thr Glu Ala Met Thr Arg Tyr Ser Ala Pro Pro Gly Asp
            340                 345                 350

Pro Pro Gln Pro Glu Tyr Asp Leu Glu Leu Ile Thr Ser Cys Ser Ser
        355                 360                 365
```

```
Asn Val Ser Val Ala His Asp Ala Ser Gly Lys Arg Val Tyr Tyr Leu
    370                 375                 380

Thr Arg Asp Pro Thr Thr Pro Leu Ala Arg Ala Ala Trp Glu Thr Val
385                 390                 395                 400

Arg His Thr Pro Val Asn Ser Trp Leu Gly Asn Ile Ile Met Tyr Ala
                405                 410                 415

Pro Thr Leu Trp Ala Arg Met Ile Leu Met Thr His Phe Phe Ser Ile
            420                 425                 430

Leu Leu Ala Gln Glu Gln Leu Glu Lys Ala Leu Asp Cys Gln Ile Tyr
        435                 440                 445

Gly Ala Cys Tyr Ser Ile Glu Pro Leu Asp Leu Pro Gln Ile Ile Glu
    450                 455                 460

Arg Leu His Gly Leu Ser Ala Phe Ser Leu His Ser Tyr Ser Pro Gly
465                 470                 475                 480

Glu Ile Asn Arg Val Ala Ser Cys Leu Arg Lys Leu Gly Val Pro Pro
                485                 490                 495

Leu Arg Val Trp Arg His Arg Ala Arg Ser Val Arg Ala Lys Leu Leu
            500                 505                 510

Ser Gln Gly Gly Arg Ala Ala Thr Cys Gly Lys Tyr Leu Phe Asn Trp
        515                 520                 525

Ala Val Arg Thr Lys Leu Lys Leu Thr Pro Ile Pro Ala Ala Ser Gln
    530                 535                 540

Leu Asp Leu Ser Gly Trp Phe Val Ala Gly Tyr Asn Gly Gly Asp Ile
545                 550                 555                 560

Tyr His Ser Leu Ser Arg Ala Arg Pro Arg
                565                 570
```

```
<210> SEQ ID NO 9
<211> LENGTH: 1222
<212> TYPE: PRT
<213> ORGANISM: artificial sequence
<220> FEATURE:
<223> OTHER INFORMATION: fusion of NS4A, NS3 and NS5B HCV JA moieties

<400> SEQUENCE: 9

Met Gly Ser Val Val Ile Val Gly Arg Ile Ile Leu Ser Gly Ser Gly
1               5                   10                  15

Ser Ala Pro Ile Thr Ala Tyr Ser Gln Gln Thr Arg Gly Leu Leu Gly
            20                  25                  30

Cys Ile Ile Thr Ser Leu Thr Gly Arg Asp Lys Asn Gln Val Asp Gly
        35                  40                  45

Glu Val Gln Val Leu Ser Thr Ala Thr Gln Ser Phe Leu Ala Thr Cys
    50                  55                  60

Val Asn Gly Val Cys Trp Thr Val Tyr Ala Gly Ala Gly Ser Lys Thr
65                  70                  75                  80

Leu Ala Gly Pro Lys Gly Pro Ile Thr Gln Met Tyr Thr Asn Val Asp
                85                  90                  95

Gln Asp Leu Val Gly Trp Pro Ala Pro Pro Gly Ala Arg Ser Met Thr
            100                 105                 110

Pro Cys Thr Cys Gly Ser Ser Asp Leu Tyr Leu Val Thr Arg His Ala
        115                 120                 125

Asp Val Ile Pro Val Arg Arg Arg Gly Asp Ser Arg Gly Ser Leu Leu
    130                 135                 140

Ser Pro Arg Pro Val Ser Tyr Leu Lys Gly Ser Ser Gly Gly Pro Leu
145                 150                 155                 160

Leu Cys Pro Ser Gly His Val Val Gly Ile Phe Arg Ala Ala Val Cys
```

-continued

```
                165                 170                 175

Thr Arg Gly Val Ala Lys Ala Val Asp Phe Ile Pro Val Glu Ser Met
            180                 185                 190

Glu Thr Thr Met Arg Ser Pro Val Phe Thr Asp Asn Ser Ser Pro Pro
        195                 200                 205

Ala Val Pro Gln Thr Phe Gln Val Ala His Leu His Ala Pro Thr Gly
    210                 215                 220

Ser Gly Lys Ser Thr Lys Val Pro Ala Ala Tyr Ala Ala Gln Gly Tyr
225                 230                 235                 240

Lys Val Leu Val Leu Asn Pro Ser Val Ala Ala Thr Leu Gly Phe Gly
                245                 250                 255

Ala Tyr Met Ser Lys Ala His Gly Ile Glu Pro Asn Ile Arg Thr Gly
            260                 265                 270

Val Arg Thr Ile Thr Thr Gly Gly Pro Ile Thr Tyr Ser Ala Tyr Gly
        275                 280                 285

Lys Phe Leu Ala Asp Gly Gly Cys Ser Gly Gly Ala Tyr Asp Ile Ile
    290                 295                 300

Ile Cys Asp Glu Cys His Ser Thr Asp Trp Thr Thr Ile Leu Gly Ile
305                 310                 315                 320

Gly Thr Val Leu Asp Gln Ala Glu Thr Ala Gly Ala Arg Leu Val Val
                325                 330                 335

Leu Ala Thr Ala Thr Pro Pro Gly Ser Ile Thr Val Pro His Pro Asn
            340                 345                 350

Ile Glu Glu Val Ala Leu Ser Asn Thr Gly Glu Ile Pro Phe Tyr Gly
        355                 360                 365

Lys Ala Ile Pro Ile Glu Ala Ile Lys Gly Gly Arg His Leu Ile Phe
    370                 375                 380

Cys His Ser Lys Lys Lys Cys Asp Glu Leu Ala Ala Lys Leu Thr Gly
385                 390                 395                 400

Leu Gly Leu Asn Ala Val Ala Tyr Tyr Arg Gly Leu Asp Val Ser Val
                405                 410                 415

Ile Pro Thr Ser Gly Asp Val Val Val Val Ala Thr Asp Ala Leu Met
            420                 425                 430

Thr Gly Phe Thr Gly Asp Phe Asp Ser Val Ile Asp Cys Asn Thr Cys
        435                 440                 445

Val Thr Gln Thr Val Asp Phe Ser Leu Asp Pro Thr Phe Thr Ile Glu
    450                 455                 460

Thr Thr Thr Val Pro Gln Asp Ala Val Ser Arg Ser Gln Arg Arg Gly
465                 470                 475                 480

Ala Thr Gly Arg Gly Arg Ser Gly Ile Tyr Arg Phe Val Thr Pro Gly
                485                 490                 495

Glu Arg Pro Ser Gly Met Phe Asp Ser Ser Val Leu Cys Glu Cys Tyr
            500                 505                 510

Asp Ala Gly Cys Ala Trp Tyr Glu Leu Thr Pro Ala Glu Thr Thr Val
        515                 520                 525

Arg Leu Arg Ala Tyr Leu Asn Thr Pro Gly Leu Pro Val Cys Gln Asp
    530                 535                 540

His Leu Glu Phe Trp Glu Ser Val Phe Thr Gly Leu Thr His Ile Asp
545                 550                 555                 560

Ala His Phe Leu Ser Gln Thr Lys Gln Ala Gly Asp Asn Phe Pro Tyr
                565                 570                 575

Leu Val Ala Tyr Gln Ala Thr Val Cys Ala Arg Ala Gln Ala Pro Pro
            580                 585                 590
```

```
Pro Ser Trp Asp Gln Met Trp Lys Cys Leu Ile Arg Leu Lys Pro Thr
        595                 600                 605

Leu His Gly Pro Thr Pro Leu Leu Tyr Arg Leu Gly Ala Val Gln Asn
    610                 615                 620

Glu Ile Thr Leu Thr His Pro Ile Thr Lys Phe Val Met Ala Cys Met
625                 630                 635                 640

Ser Ala Asp Leu Glu Val Val Gly Ser Gly Ser Gly Ser Met Ser Tyr
                645                 650                 655

Thr Trp Thr Gly Ala Leu Ile Thr Pro Cys Ala Ala Glu Glu Ser Lys
            660                 665                 670

Leu Pro Ile Asn Pro Leu Ser Asn Ser Leu Leu Arg His His Ser Met
        675                 680                 685

Val Tyr Ser Thr Thr Ser Arg Ser Ala Ser Leu Arg Gln Lys Lys Val
    690                 695                 700

Thr Phe Asp Arg Leu Gln Val Leu Asp Asp His Tyr Arg Asp Val Leu
705                 710                 715                 720

Lys Glu Met Lys Ala Lys Ala Ser Thr Val Lys Ala Arg Leu Leu Ser
                725                 730                 735

Ile Glu Glu Ala Cys Lys Leu Thr Pro Pro His Ser Ala Lys Ser Lys
            740                 745                 750

Phe Gly Tyr Gly Ala Lys Asp Val Arg Ser Leu Ser Ser Arg Ala Val
        755                 760                 765

Asn His Ile Arg Ser Val Trp Glu Asp Leu Leu Glu Asp Thr Glu Thr
    770                 775                 780

Pro Ile Asp Thr Thr Ile Met Ala Lys Asn Glu Val Phe Cys Val Gln
785                 790                 795                 800

Pro Glu Lys Gly Gly Arg Lys Pro Ala Arg Leu Ile Val Phe Pro Asp
                805                 810                 815

Leu Gly Val Arg Val Cys Glu Lys Met Ala Leu Tyr Asp Val Val Ser
            820                 825                 830

Thr Leu Pro Gln Ala Val Met Gly Pro Ser Tyr Gly Phe Gln Tyr Ser
        835                 840                 845

Pro Gly Gln Arg Val Glu Phe Leu Val Asn Thr Trp Lys Ser Lys Lys
    850                 855                 860

Cys Pro Met Gly Phe Ser Tyr Asn Thr Arg Cys Phe Asp Ser Thr Val
865                 870                 875                 880

Thr Glu Asn Asp Ile Arg Thr Glu Glu Ser Ile Tyr Gln Cys Cys Asp
                885                 890                 895

Leu Ala Pro Glu Ala Arg Gln Ala Ile Lys Ser Leu Thr Glu Arg Leu
            900                 905                 910

Tyr Ile Gly Gly Pro Leu Thr Asn Ser Lys Gly Gln Asn Cys Gly Tyr
        915                 920                 925

Arg Arg Cys Arg Ala Ser Gly Val Leu Thr Thr Ser Cys Gly Asn Thr
    930                 935                 940

Leu Thr Cys Tyr Leu Lys Ala Thr Ala Ala Cys Arg Ala Ala Lys Leu
945                 950                 955                 960

Gln Asp Cys Thr Met Leu Val Asn Gly Asn Asp Leu Val Val Ile Cys
                965                 970                 975

Glu Ser Ala Gly Thr Gln Glu Asp Ala Ala Ser Leu Arg Val Phe Thr
            980                 985                 990

Glu Ala Met Thr Arg Tyr Ser Ala  Pro Pro Gly Asp Pro  Pro Gln Pro
        995                 1000                1005

Glu Tyr  Asp Leu Glu Leu Ile  Thr Ser Cys Ser Ser  Asn Val Ser
    1010                 1015                 1020
```

Val Ala His Asp Ala Ser Gly Lys Arg Val Tyr Tyr Leu Thr Arg
1025 1030 1035

Asp Pro Thr Thr Pro Leu Ala Arg Ala Ala Trp Glu Thr Val Arg
1040 1045 1050

His Thr Pro Val Asn Ser Trp Leu Gly Asn Ile Ile Met Tyr Ala
1055 1060 1065

Pro Thr Leu Trp Ala Arg Met Ile Leu Met Thr His Phe Phe Ser
1070 1075 1080

Ile Leu Leu Ala Gln Glu Gln Leu Glu Lys Ala Leu Asp Cys Gln
1085 1090 1095

Ile Tyr Gly Ala Cys Tyr Ser Ile Glu Pro Leu Asp Leu Pro Gln
1100 1105 1110

Ile Ile Glu Arg Leu His Gly Leu Ser Ala Phe Ser Leu His Ser
1115 1120 1125

Tyr Ser Pro Gly Glu Ile Asn Arg Val Ala Ser Cys Leu Arg Lys
1130 1135 1140

Leu Gly Val Pro Pro Leu Arg Val Trp Arg His Arg Ala Arg Ser
1145 1150 1155

Val Arg Ala Lys Leu Leu Ser Gln Gly Gly Arg Ala Ala Thr Cys
1160 1165 1170

Gly Lys Tyr Leu Phe Asn Trp Ala Val Arg Thr Lys Leu Lys Leu
1175 1180 1185

Thr Pro Ile Pro Ala Ala Ser Gln Leu Asp Leu Ser Gly Trp Phe
1190 1195 1200

Val Ala Gly Tyr Asn Gly Gly Asp Ile Tyr His Ser Leu Ser Arg
1205 1210 1215

Ala Arg Pro Arg
1220

<210> SEQ ID NO 10
<211> LENGTH: 1249
<212> TYPE: PRT
<213> ORGANISM: artificial sequence
<220> FEATURE:
<223> OTHER INFORMATION: fusion of the NS4A, NS3, NS4B and NS5B HCV JA moieties

<400> SEQUENCE: 10

Met Gly Ser Val Val Ile Val Gly Arg Ile Ile Leu Ser Gly Ser Gly
1 5 10 15

Ser Ala Pro Ile Thr Ala Tyr Ser Gln Gln Thr Arg Gly Leu Leu Gly
20 25 30

Cys Ile Ile Thr Ser Leu Thr Gly Arg Asp Lys Asn Gln Val Asp Gly
35 40 45

Glu Val Gln Val Leu Ser Thr Ala Thr Gln Ser Phe Leu Ala Thr Cys
50 55 60

Val Asn Gly Val Cys Trp Thr Val Tyr Ala Gly Ala Gly Ser Lys Thr
65 70 75 80

Leu Ala Gly Pro Lys Gly Pro Ile Thr Gln Met Tyr Thr Asn Val Asp
85 90 95

Gln Asp Leu Val Gly Trp Pro Ala Pro Pro Gly Ala Arg Ser Met Thr
100 105 110

Pro Cys Thr Cys Gly Ser Ser Asp Leu Tyr Leu Val Thr Arg His Ala
115 120 125

Asp Val Ile Pro Val Arg Arg Arg Gly Asp Ser Arg Gly Ser Leu Leu
130 135 140

-continued

```
Ser Pro Arg Pro Val Ser Tyr Leu Lys Gly Ser Ser Gly Gly Pro Leu
145                 150                 155                 160

Leu Cys Pro Ser Gly His Val Val Gly Ile Phe Arg Ala Ala Val Cys
                165                 170                 175

Thr Arg Gly Val Ala Lys Ala Val Asp Phe Ile Pro Val Glu Ser Met
            180                 185                 190

Glu Thr Thr Met Arg Ser Pro Val Phe Thr Asp Asn Ser Ser Pro Pro
        195                 200                 205

Ala Val Pro Gln Thr Phe Gln Val Ala His Leu His Ala Pro Thr Gly
    210                 215                 220

Ser Gly Lys Ser Thr Lys Val Pro Ala Ala Tyr Ala Ala Gln Gly Tyr
225                 230                 235                 240

Lys Val Leu Val Leu Asn Pro Ser Val Ala Ala Thr Leu Gly Phe Gly
                245                 250                 255

Ala Tyr Met Ser Lys Ala His Gly Ile Glu Pro Asn Ile Arg Thr Gly
            260                 265                 270

Val Arg Thr Ile Thr Thr Gly Gly Pro Ile Thr Tyr Ser Ala Tyr Gly
        275                 280                 285

Lys Phe Leu Ala Asp Gly Gly Cys Ser Gly Gly Ala Tyr Asp Ile Ile
    290                 295                 300

Ile Cys Asp Glu Cys His Ser Thr Asp Trp Thr Thr Ile Leu Gly Ile
305                 310                 315                 320

Gly Thr Val Leu Asp Gln Ala Glu Thr Ala Gly Ala Arg Leu Val Val
                325                 330                 335

Leu Ala Thr Ala Thr Pro Pro Gly Ser Ile Thr Val Pro His Pro Asn
            340                 345                 350

Ile Glu Glu Val Ala Leu Ser Asn Thr Gly Glu Ile Pro Phe Tyr Gly
        355                 360                 365

Lys Ala Ile Pro Ile Glu Ala Ile Lys Gly Gly Arg His Leu Ile Phe
    370                 375                 380

Cys His Ser Lys Lys Lys Cys Asp Glu Leu Ala Ala Lys Leu Thr Gly
385                 390                 395                 400

Leu Gly Leu Asn Ala Val Ala Tyr Tyr Arg Gly Leu Asp Val Ser Val
                405                 410                 415

Ile Pro Thr Ser Gly Asp Val Val Val Val Ala Thr Asp Ala Leu Met
            420                 425                 430

Thr Gly Phe Thr Gly Asp Phe Asp Ser Val Ile Asp Cys Asn Thr Cys
        435                 440                 445

Val Thr Gln Thr Val Asp Phe Ser Leu Asp Pro Thr Phe Thr Ile Glu
    450                 455                 460

Thr Thr Thr Val Pro Gln Asp Ala Val Ser Arg Ser Gln Arg Arg Gly
465                 470                 475                 480

Ala Thr Gly Arg Gly Arg Ser Gly Ile Tyr Arg Phe Val Thr Pro Gly
                485                 490                 495

Glu Arg Pro Ser Gly Met Phe Asp Ser Ser Val Leu Cys Glu Cys Tyr
            500                 505                 510

Asp Ala Gly Cys Ala Trp Tyr Glu Leu Thr Pro Ala Glu Thr Thr Val
        515                 520                 525

Arg Leu Arg Ala Tyr Leu Asn Thr Pro Gly Leu Pro Val Cys Gln Asp
    530                 535                 540

His Leu Glu Phe Trp Glu Ser Val Phe Thr Gly Leu Thr His Ile Asp
545                 550                 555                 560

Ala His Phe Leu Ser Gln Thr Lys Gln Ala Gly Asp Asn Phe Pro Tyr
```

-continued

```
                565                 570                 575

Leu Val Ala Tyr Gln Ala Thr Val Cys Ala Arg Ala Gln Ala Pro Pro
            580                 585                 590

Pro Ser Trp Asp Gln Met Trp Lys Cys Leu Ile Arg Leu Lys Pro Thr
        595                 600                 605

Leu His Gly Pro Thr Pro Leu Leu Tyr Arg Leu Gly Ala Val Gln Asn
    610                 615                 620

Glu Ile Thr Leu Thr His Pro Ile Thr Lys Phe Val Met Ala Cys Met
625                 630                 635                 640

Ser Ala Asp Leu Glu Val Val Ser Leu Met Ala Phe Thr Ala Ser Ile
                645                 650                 655

Thr Ser Pro Leu Thr Thr Gln Asn Thr Leu Leu Phe Asn Ile Leu Gly
            660                 665                 670

Gly Trp Val Ala Ala Gln Leu Ser Met Ser Tyr Thr Trp Thr Gly Ala
        675                 680                 685

Leu Ile Thr Pro Cys Ala Ala Glu Glu Ser Lys Leu Pro Ile Asn Pro
    690                 695                 700

Leu Ser Asn Ser Leu Leu Arg His His Ser Met Val Tyr Ser Thr Thr
705                 710                 715                 720

Ser Arg Ser Ala Ser Leu Arg Gln Lys Lys Val Thr Phe Asp Arg Leu
                725                 730                 735

Gln Val Leu Asp Asp His Tyr Arg Asp Val Leu Lys Glu Met Lys Ala
            740                 745                 750

Lys Ala Ser Thr Val Lys Ala Arg Leu Leu Ser Ile Glu Glu Ala Cys
        755                 760                 765

Lys Leu Thr Pro Pro His Ser Ala Lys Ser Lys Phe Gly Tyr Gly Ala
    770                 775                 780

Lys Asp Val Arg Ser Leu Ser Ser Arg Ala Val Asn His Ile Arg Ser
785                 790                 795                 800

Val Trp Glu Asp Leu Leu Glu Asp Thr Glu Thr Pro Ile Asp Thr Thr
                805                 810                 815

Ile Met Ala Lys Asn Glu Val Phe Cys Val Gln Pro Glu Lys Gly Gly
            820                 825                 830

Arg Lys Pro Ala Arg Leu Ile Val Phe Pro Asp Leu Gly Val Arg Val
        835                 840                 845

Cys Glu Lys Met Ala Leu Tyr Asp Val Val Ser Thr Leu Pro Gln Ala
    850                 855                 860

Val Met Gly Pro Ser Tyr Gly Phe Gln Tyr Ser Pro Gly Gln Arg Val
865                 870                 875                 880

Glu Phe Leu Val Asn Thr Trp Lys Ser Lys Lys Cys Pro Met Gly Phe
                885                 890                 895

Ser Tyr Asn Thr Arg Cys Phe Asp Ser Thr Val Thr Glu Asn Asp Ile
            900                 905                 910

Arg Thr Glu Glu Ser Ile Tyr Gln Cys Cys Asp Leu Ala Pro Glu Ala
        915                 920                 925

Arg Gln Ala Ile Lys Ser Leu Thr Glu Arg Leu Tyr Ile Gly Gly Pro
    930                 935                 940

Leu Thr Asn Ser Lys Gly Gln Asn Cys Gly Tyr Arg Arg Cys Arg Ala
945                 950                 955                 960

Ser Gly Val Leu Thr Thr Ser Cys Gly Asn Thr Leu Thr Cys Tyr Leu
                965                 970                 975

Lys Ala Thr Ala Ala Cys Arg Ala Ala Lys Leu Gln Asp Cys Thr Met
            980                 985                 990
```

```
Leu Val Asn Gly Asn Asp Leu Val  Val Ile Cys Glu Ser  Ala Gly Thr
        995                 1000                 1005

Gln Glu  Asp Ala Ala Ser Leu  Arg Val Phe Thr Glu  Ala Met Thr
    1010                 1015                 1020

Arg Tyr  Ser Ala Pro Pro Gly  Asp Pro Pro Gln Pro  Glu Tyr Asp
    1025                 1030                 1035

Leu Glu  Leu Ile Thr Ser Cys  Ser Ser Asn Val Ser  Val Ala His
    1040                 1045                 1050

Asp Ala  Ser Gly Lys Arg Val  Tyr Tyr Leu Thr Arg  Asp Pro Thr
    1055                 1060                 1065

Thr Pro  Leu Ala Arg Ala Ala  Trp Glu Thr Val Arg  His Thr Pro
    1070                 1075                 1080

Val Asn  Ser Trp Leu Gly Asn  Ile Ile Met Tyr Ala  Pro Thr Leu
    1085                 1090                 1095

Trp Ala  Arg Met Ile Leu Met  Thr His Phe Phe Ser  Ile Leu Leu
    1100                 1105                 1110

Ala Gln  Glu Gln Leu Glu Lys  Ala Leu Asp Cys Gln  Ile Tyr Gly
    1115                 1120                 1125

Ala Cys  Tyr Ser Ile Glu Pro  Leu Asp Leu Pro Gln  Ile Ile Glu
    1130                 1135                 1140

Arg Leu  His Gly Leu Ser Ala  Phe Ser Leu His Ser  Tyr Ser Pro
    1145                 1150                 1155

Gly Glu  Ile Asn Arg Val Ala  Ser Cys Leu Arg Lys  Leu Gly Val
    1160                 1165                 1170

Pro Pro  Leu Arg Val Trp Arg  His Arg Ala Arg Ser  Val Arg Ala
    1175                 1180                 1185

Lys Leu  Leu Ser Gln Gly Gly  Arg Ala Ala Thr Cys  Gly Lys Tyr
    1190                 1195                 1200

Leu Phe  Asn Trp Ala Val Arg  Thr Lys Leu Lys Leu  Thr Pro Ile
    1205                 1210                 1215

Pro Ala  Ala Ser Gln Leu Asp  Leu Ser Gly Trp Phe  Val Ala Gly
    1220                 1225                 1230

Tyr Asn  Gly Gly Asp Ile Tyr  His Ser Leu Ser Arg  Ala Arg Pro
    1235                 1240                 1245

Arg


<210> SEQ ID NO 11
<211> LENGTH: 3666
<212> TYPE: DNA
<213> ORGANISM: artificial sequence
<220> FEATURE:
<223> OTHER INFORMATION: nucleotide sequence encoding HCV JA NS4A-3-5B
      fusion optimised for expression in mammalian cells

<400> SEQUENCE: 11

atgggcagcg tggtgattgt gggccggatc atcctgagcg gcagcggcag cgcccccatc      60

accgcctaca gccagcagac cagaggcctg ctgggctgta tcatcaccag cctgaccggc     120

agagacaaga atcaggtgga cggcgaggtg caggtgctgt ccaccgccac ccagagcttc     180

ctggccacct gtgtgaatgg cgtgtgttgg accgtgtacg ccggagccgg cagcaagacc     240

ctggccggac ccaagggccc catcacccag atgtacacca acgtggacca ggacctggtg     300

ggctggcctg cccctcctgg cgccagaagc atgacccctt gtacctgtgg cagcagcgac     360

ctgtacctgg tgaccagaca cgccgatgtg atccctgtga ggaggagagg cgatagcaga     420

ggcagcctgc tgtctcctag acccgtgtcc tacctgaagg gcagcagcgg cggacccctg     480
```

-continued

```
ctgtgcccca gcggccacgt ggtgggcatc ttcagagccg ccgtgtgtac cagaggcgtg    540
gccaaggccg tggatttcat ccccgtggag agcatggaga ccaccatgag gagccccgtg    600
ttcaccgaca atagcagccc ccctgccgtg cctcagacct tccaggtggc ccacctgcac    660
gcccccaccg gctccggcaa gagcaccaag gtgccagccg cctacgccgc ccagggctac    720
aaggtgctgg tgctgaatcc cagcgtggcc gccaccctgg gcttcggcgc ctacatgagc    780
aaggcccacg gcatcgagcc caatatccgg accggagtga ggaccatcac cacaggcggc    840
cctatcacct acagcgccta cggcaagttc ctggccgacg gcggctgtag cggcggagcc    900
tacgacatca tcatctgtga cgagtgccac agcaccgatt ggaccaccat cctgggcatc    960
ggcaccgtgc tggaccaggc cgagaccgcc ggagccagac tggtggtgct ggccacagcc   1020
acacccccctg gcagcatcac cgtgccccac cccaacatcg aggaggtggc cctgagcaac   1080
accggcgaga tcccccttcta cggcaaggcc atccctatcg aggccatcaa gggcggcaga   1140
cacctgatct tctgccacag caagaagaag tgtgacgagc tggccgccaa gctgaccggc   1200
ctgggcctga acgccgtggc ctactacaga ggcctggacg tgtccgtgat ccctaccagc   1260
ggcgatgtgg tggtggtggc caccgacgcc ctgatgaccg gcttcaccgg cgatttcgac   1320
agcgtgatcg actgtaatac ctgtgtgacc cagaccgtgg acttcagcct ggaccccacc   1380
ttcaccatcg agaccaccac cgtgccacag gatgccgtgt ccagaagcca gagaagaggc   1440
gccaccggca gaggcagaag cggcatctac agattcgtga cccctggcga gagacccagc   1500
ggcatgttcg atagcagcgt gctgtgtgag tgctacgacg ccggctgtgc ctggtacgag   1560
ctgaccccag ccgagaccac agtgaggctg agggcctacc tgaacacccc tggcctgcct   1620
gtgtgccagg atcacctgga gttctgggag agcgtgttta ccggcctgac ccacatcgat   1680
gcccactttc tgagccagac caagcaggcc ggcgacaact tcccctacct ggtggcctac   1740
caggccaccg tgtgtgccag agcccaggcc cctcccccca gctgggacca gatgtggaag   1800
tgcctgatca ggctgaagcc caccctgcac ggccctaccc ccctgctgta cagactgggc   1860
gccgtgcaga atgagatcac cctgacccac cctatcacca agttcgtgat ggcctgtatg   1920
agcgccgacc tggaggtggt gggcagcggc tccggctcca tgagctacac ctggacaggc   1980
gccctgatca caccctgtgc cgccgaggag agcaagctgc ccatcaaccc cctgagcaat   2040
agcctgctga ggcaccacag catggtgtac agcaccacct ccagaagcgc cagcctgagg   2100
cagaagaagg tgaccttcga caggctgcag gtgctggacg accactacag ggacgtgctg   2160
aaggagatga aggccaaggc cagcaccgtg aaggccagac tgctgtctat cgaggaggcc   2220
tgtaagctga cccccccctca cagcgccaag agcaagttcg gctacggcgc caaggatgtg   2280
agaagcctga gcagcagagc cgtgaaccac atccggtctg tgtgggagga tctgctggag   2340
gataccgaga cccccatcga caccacaatc atggccaaga acgaggtgtt ctgcgtgcag   2400
cccgagaagg gcggaagaaa gcccgccagg ctgatcgtgt tccctgacct gggagtgaga   2460
gtgtgtgaga agatggccct gtacgacgtg gtgtccaccc tgccccaggc cgtgatgggc   2520
cccagctacg gcttccagta cagccctggc cagagagtgg agttcctggt gaacacctgg   2580
aagagcaaga aatgccccat gggcttcagc tacaacaccc ggtgcttcga cagcacagtg   2640
accgagaacg acatcaggac cgaggagtcc atctaccagt gctgtgacct ggcccccgag   2700
gccagacagg ccatcaaaag cctgaccgag cggctgtaca tcggcggacc tctgaccaac   2760
agcaagggcc agaactgtgg ctacagaaga tgtagggcca gcggcgtgct gaccacctct   2820
tgtggcaaca ccctgacctg ttacctgaag gccaccgccg cctgtagagc cgccaaactg   2880
```

-continued caggactgta ccatgctggt gaacggcaac gacctggtgg tgatctgtga gagcgccggc 2940
acccaggagg atgccgcctc cctgagagtg tttaccgagg ccatgaccag atacagcgcc 3000
cctcccggcg accctcccca gcccgagtac gatctggagc tgatcaccag ctgctccagc 3060
aatgtgggcg tggctcacga cgccagcggc aagagagtgt actacctgac cagggacccc 3120
accacccctc tggccagagc cgcctgggag acagtgagac acacccccgt gaacagctgg 3180
ctgggcaaca tcatcatgta cgcccctacc ctgtgggcca gaatgatcct gatgacccac 3240
ttcttcagca tcctgctggc ccaggagcag ctggagaagg ccctggactg ccagatctac 3300
ggcgcctgct acagcatcga gcctctggac ctgcctcaga tcatcgagag actgcacggc 3360
ctgagcgcct tcagcctgca cagctacagc ccaggcgaga tcaatagagt ggccagctgc 3420
ctgagaaagc tgggcgtgcc acctctgaga gtgtggcggc acagagccag atctgtgagg 3480
gccaagctgc tgtcccaggg cggcagggcc gccacctgtg gcaagtacct gttcaactgg 3540
gccgtgagga caaagctgaa gctgacaccc atccctgccg ccagccagct ggacctgagc 3600
ggctggttcg tggccggcta caatggcggc gacatctacc acagcctgtc cagggccagg 3660
cctaga 3666

<210> SEQ ID NO 12
<211> LENGTH: 3747
<212> TYPE: DNA
<213> ORGANISM: artificial sequence
<220> FEATURE:
<223> OTHER INFORMATION: nucleotide sequence of the HCV JA NS4A-3-4B-5B
      fusion optimised for expression in mammalian

<400> SEQUENCE: 12
atgggcagcg tggtgattgt gggccggatc atcctgagcg gcagcggcag cgcccccatc 60
accgcctaca gccagcagac cagaggcctg ctgggctgta tcatcaccag cctgaccggc 120
agagacaaga atcaggtgga cggcgaggtg caggtgctgt ccaccgccac ccagagcttc 180
ctggccacct gtgtgaatgg cgtgtgttgg accgtgtacg ccggagccgg cagcaagacc 240
ctggccggac ccaagggccc catcacccag atgtacacca acgtggacca ggacctggtg 300
ggctggcctg cccctcctgg cgccagaagc atgacccctt gtacctgtgg cagcagcgac 360
ctgtacctgg tgaccagaca cgccgatgtg atccctgtga ggaggagagg cgatagcaga 420
ggcagcctgc tgtctcctag acccgtgtcc tacctgaagg gcagcagcgg cggacccctg 480
ctgtgcccca gcggccacgt ggtgggcatc ttcagagccg ccgtgtgtac cagaggcgtg 540
gccaaggccg tggatttcat ccccgtggag agcatggaga ccaccatgag gagccccgtg 600
ttcaccgaca atagcagccc ccctgccgtg cctcagacct tccaggtggc ccacctgcac 660
gcccccaccg gctccggcaa gagcaccaag gtgccagccg cctacgccgc ccagggctac 720
aaggtgctgg tgctgaatcc cagcgtggcc gccaccctgg gcttcggcgc ctacatgagc 780
aaggcccacg gcatcgagcc caatatccgg accggagtga ggaccatcac cacaggcggc 840
cctatcacct acagcgccta cggcaagttc ctggccgacg gcggctgtag cggcggagcc 900
tacgacatca tcatctgtga cgagtgccac agcaccgatt ggaccaccat cctgggcatc 960
ggcaccgtgc tggaccaggc cgagaccgcc ggagccagac tggtggtgct ggccacagcc 1020 acacccccctg gcagcatcac cgtgccccac cccaacatcg aggaggtggc cctgagcaac 1080
accggcgaga tccccttcta cggcaaggcc atccctatcg aggccatcaa gggcggcaga 1140
cacctgatct tctgccacag caagaagaag tgtgacgagc tggccgccaa gctgaccggc 1200
ctgggcctga acgccgtggc ctactacaga ggcctggacg tgtccgtgat ccctaccagc 1260

-continued

```
ggcgatgtgg tggtggtggc caccgacgcc ctgatgaccg gcttcaccgg cgatttcgac   1320
agcgtgatcg actgtaatac ctgtgtgacc cagaccgtgg acttcagcct ggaccccacc   1380
ttcaccatcg agaccaccac cgtgccacag gatgccgtgt ccagaagcca gagaagaggc   1440
gccaccggca gaggcagaag cggcatctac agattcgtga cccctggcga gagacccagc   1500
ggcatgttcg atagcagcgt gctgtgtgag tgctacgacg ccggctgtgc ctggtacgag   1560
ctgaccccag ccgagaccac agtgaggctg agggcctacc tgaacacccc tggcctgcct   1620
gtgtgccagg atcacctgga gttctgggag agcgtgttta ccggcctgac ccacatcgat   1680
gcccactttc tgagccagac caagcaggcc ggcgacaact tcccctacct ggtggcctac   1740
caggccaccg tgtgtgccag agcccaggcc cctcccccca gctgggacca gatgtggaag   1800
tgcctgatca ggctgaagcc caccctgcac ggccctaccc ccctgctgta cagactgggc   1860
gccgtgcaga atgagatcac cctgacccac cctatcacca agttcgtgat ggcctgtatg   1920
agcgccgacc tggaggtggt gtccctgatg gccttcaccg ccagcatcac aagccccctg   1980
accacccaga ataccctgct gttcaacatc ctgggcggct gggtggccgc ccagctgtcc   2040
atgagctaca cctggacagg cgccctgatc acaccctgtg ccgccgagga gagcaagctg   2100
cccatcaacc ccctgagcaa tagcctgctg aggcaccaca gcatggtgta cagcaccacc   2160
tccagaagcg ccagcctgag gcagaagaag gtgaccttcg acaggctgca ggtgctggac   2220
gaccactaca gggacgtgct gaaggagatg aaggccaagg ccagcaccgt gaaggccaga   2280
ctgctgtcta tcgaggaggc ctgtaagctg acccccccctc acagcgccaa gagcaagttc   2340
ggctacggcg ccaaggatgt gagaagcctg agcagcagag ccgtgaacca catccggtct   2400
gtgtgggagg atctgctgga ggataccgag acccccatcg acaccacaat catggccaag   2460
aacgaggtgt tctgcgtgca gcccgagaag ggcggaagaa agcccgccag gctgatcgtg   2520
ttccctgacc tgggagtgag agtgtgtgag aagatggccc tgtacgacgt ggtgtccacc   2580
ctgccccagg ccgtgatggg ccccagctac ggcttccagt acagccctgg ccagagagtg   2640
gagttcctgg tgaacacctg gaagagcaag aaatgcccca tgggcttcag ctacaacacc   2700
cggtgcttcg acagcacagt gaccgagaac gacatcagga ccgaggagtc catctaccag   2760
tgctgtgacc tggcccccga ggccagacag gccatcaaaa gcctgaccga gcggctgtac   2820
atcggcggac ctctgaccaa cagcaagggc cagaactgtg gctacagaag atgtagggcc   2880
agcggcgtgc tgaccacctc ttgtggcaac accctgacct gttacctgaa ggccaccgcc   2940
gcctgtagag ccgccaaact gcaggactgt accatgctgg tgaacggcaa cgacctggtg   3000
gtgatctgtg agagcgccgg cacccaggag gatgccgcct ccctgagagt gtttaccgag   3060
gccatgacca gatacagcgc ccctcccggc gaccctcccc agcccgagta cgatctggag   3120
ctgatcacca gctgctccag caatgtgggc gtggctcacg acgccagcgg caagagagtg   3180
tactacctga ccagggaccc caccacccct ctggccagag ccgcctggga gacagtgaga   3240
cacacccccg tgaacagctg gctgggcaac atcatcatgt acgcccctac cctgtgggcc   3300
agaatgatcc tgatgaccca cttcttcagc atcctgctgg cccaggagca gctggagaag   3360
gccctggact gccagatcta cggcgcctgc tacagcatcg agcctctgga cctgcctcag   3420
atcatcgaga gactgcacgg cctgagcgcc ttcagcctgc acagctacag cccaggcgag   3480
atcaatagag tggccagctg cctgagaaag ctgggcgtgc cacctctgag agtgtggcgg   3540
cacagagcca gatctgtgag ggccaagctg ctgtcccagg gcggcagggc cgccacctgt   3600
ggcaagtacc tgttcaactg ggccgtgagg acaaagctga agctgacacc catccctgcc   3660
```

gccagccagc tggacctgag cggctggttc gtggccggct acaatggcgg cgacatctac 3720
cacagcctgt ccagggccag gcctaga 3747

<210> SEQ ID NO 13
<211> LENGTH: 3666
<212> TYPE: DNA
<213> ORGANISM: artificial sequence
<220> FEATURE:
<223> OTHER INFORMATION: nucleotide sequence encoding the HCV JA NS4A-3-5B fusion optimised for expression in Pichia

<400> SEQUENCE: 13
atggggtccg ttgttatcgt tggtagaatc atcttgtctg gttctggttc cgctccaatt 60
actgcttact cccagcagac tagaggattg ttgggttgta tcatcacttc cttgactggt 120
agagacaaga accaagttga cggagaggtt caggttttgt ccactgctac tcagtctttc 180
ttggctactt gtgttaacgg tgtttgttgg actgtttacg ctggtgctgg ttctaaaact 240
ttggctggtc caaagggtcc aatcactcag atgtacacaa acgttgacca ggatttggtt 300
ggttggccag ctccaccagg tgctagatcc atgactccat gtacttgtgg ttcctccgac 360
ttgtacttgg ttactagaca cgctgacgtt atcccagtta gaagaagagg agactccaga 420
ggatctttgt tgtccccaag accagtttct tacttgaagg gatcttccgg tggtccattg 480
ttgtgtccat ccggtcacgt tgttggtatt ttcagagctg ctgtttgtac tagaggtgtt 540
gctaaggctg ttgacttcat cccagttgag tccatggaga ctactatgag atccccagtt 600
ttcactgaca actcttcccc acctgctgtt ccacaaactt tccaagttgc tcacttgcat 660
gctccaactg gttctggtaa gtccactaag gttccagctg cttacgctgc tcaaggttac 720
aaggttttgg ttttgaaccc atccgttgct gctactttgg gtttcggtgc ttacatgtct 780
aaggctcacg gtattgagcc aaacatcaga actggtgtta gaactatcac tactggtggt 840
cctattactt actccgctta cggaaagttt ttggctgacg gtggttgttc tggtggtgct 900
tacgacatca tcatctgtga cgagtgtcac tctactgact ggactactat cttgggtatc 960
ggtactgttt tggaccaagc tgaaactgct ggtgctagat tggttgtttt ggctactgct 1020
actccaccag gttccattac tgttccacac ccaaacatcg aggaagttgc tttgtctaac 1080
actggagaga tcccattcta cggaaaggct atcccaattg aggctatcaa gggtggtaga 1140
cacttgattt tctgtcactc caagaagaag tgtgacgagt tggctgctaa gttgactgga 1200
ttgggattga acgctgttgc ttactacaga ggattggacg tttccgttat cccaacttcc 1260
ggtgatgttg ttgttgttgc tactgacgct ttgatgactg gtttcactgg tgacttcgac 1320
tccgttatcg actgtaacac ttgtgttact cagactgttg acttctcctt ggacccaact 1380
ttcactatcg agactactac tgttcctcaa gacgctgttt ccagatccca aagaagaggt 1440
gctactggta gaggaagatc cggtatctac agattcgtta ctccaggtga aagaccatct 1500
ggaatgttcg actcctccgt tttgtgtgaa tgttacgacg ctggttgtgc ttggtacgaa 1560
ttgactccag ctgagactac tgttagattg agagcttact tgaacactcc aggattgcca 1620
gtttgtcaag accacttgga attctgggag tccgttttca ctggattgac tcacattgac 1680
gctcactttt tgtcccaaac taagcaggct ggtgacaact ttccatactt ggttgcttac 1740
caggctactg tttgtgctag agcacaagct ccaccaccat cttgggatca gatgtggaag 1800
tgtttgatca gattgaagcc aactttgcac ggtccaactc cattgttgta cagattgggt 1860
gctgttcaga acgagatcac tttgactcac ccaatcacta agttcgttat ggcttgcatg 1920

```
tctgctgact tggaagttgt tggttccgga tctggttcca tgtcctacac ttggactggt   1980

gctttgatca ctccatgtgc tgctgaagaa tccaagttgc caatcaaccc attgtccaac   2040

tctttgttga gacaccactc catggtttac tccactactt ccagatccgc ttccttgaga   2100

cagaagaagg ttacattcga cagattgcag gttttggacg accactacag agatgttttg   2160

aaggagatga aggctaaggc ttccactgtt aaggctagat tgttgtccat tgaggaggct   2220

tgtaagttga ctccaccaca ctctgctaag tccaagtttg gttacggtgc taaggatgtt   2280

agatccttgt cctccagagc tgttaaccac atcagatccg tttgggagga tttgttggag   2340

gacactgaga ctccaatcga cactactatc atggctaaga acgaggtttt ctgtgttcaa   2400

ccagagaagg gtggaagaaa gccagctaga ttgatcgttt tcccagactt gggtgttaga   2460

gtttgtgaga agatggcttt gtacgacgtt gtttccactt tgccacaggc tgttatggga   2520

ccatcttacg gtttccaata ctccccagga caaagagttg agttcttggt taacacttgg   2580

aagtccaaga aatgtccaat gggattctcc tacaacacta gatgtttcga ctccactgtt   2640

actgagaacg acatcagaac agaggagtcc atctaccagt gttgtgactt ggctccagaa   2700

gctagacaag ctatcaagtc cttgactgag agattgtaca tcggtggtcc tttgactaac   2760

tccaagggac agaactgtgg ttacagaaga tgtagagctt ccggtgtttt gactacttcc   2820

tgtggtaaca ctttgacttg ttacttgaag gctactgctg cttgtagagc tgctaaattg   2880

caggactgta ctatgttggt taacggtaac gacttggttg ttatctgtga gtccgctggt   2940

actcaagaag atgctgcttc tttgagagtt ttcacagagg ctatgactag atactctgct   3000

ccacctggtg atccaccaca accagaatac gacttggagt tgatcacttc ctgttcctcc   3060

aatgttggtg ttgctcacga tgcttccgga aagagagttt actacttgac tagagaccca   3120

actactccat tggctagagc tgcttgggaa actgttagac acactccagt taactcctgg   3180

ttgggtaaca tcatcatgta cgctccaact ttgtgggcta gaatgatctt gatgactcac   3240

ttcttctcca tcttgttggc tcaagagcaa ttggaaaagg ctttggactg tcagatttac   3300

ggtgcttgtt actccattga gccattggac ttgccacaga tcattgagag attgcacggt   3360

ttgtctgctt tctctttgca ctcttactcc cctggtgaaa tcaacagagt tgcttcctgt   3420

ttgagaaagt tgggtgttcc accattgaga gtttggagac acagagctag atccgttaga   3480

gctaagttgt tgtcccaagg tggaagagct gctacttgtg gtaagtactt gttcaactgg   3540

gctgttagaa caaagttgaa gttgactcct attcctgctg cttcccaatt ggatttgtcc   3600

ggttggtttg ttgctggtta caacggtggt gacatctacc actctttgtc cagagctaga   3660

ccaaga                                                              3666
```

<210> SEQ ID NO 14
<211> LENGTH: 3747
<212> TYPE: DNA
<213> ORGANISM: artificial sequence
<220> FEATURE:
<223> OTHER INFORMATION: nucleotide sequence encoding the HCV JA
      NS4A-3-4B-5B fusion optmised for expression in Pichia

<400> SEQUENCE: 14

```
atggggtccg ttgttatcgt tggtagaatc atcttgtctg gttctggttc cgctccaatt     60

actgcttact cccagcagac tagaggattg ttgggttgta tcatcacttc cttgactggt    120

agagacaaga accaagttga cggagaggtt caggttttgt ccactgctac tcagtctttc    180

ttggctactt gtgttaacgg tgtttgttgg actgtttacg ctggtgctgg ttctaaaact    240

ttggctggtc caaagggtcc aatcactcag atgtacacaa acgttgacca ggatttggtt    300
```

```
ggttggccag ctccaccagg tgctagatcc atgactccat gtacttgtgg ttcctccgac    360
ttgtacttgg ttactagaca cgctgacgtt atcccagtta gaagaagagg agactccaga    420
ggatctttgt tgtccccaag accagtttct tacttgaagg gatcttccgg tggtccattg    480
ttgtgtccat ccggtcacgt tgttggtatt ttcagagctg ctgtttgtac tagaggtgtt    540
gctaaggctg ttgacttcat cccagttgag tccatggaga ctactatgag atccccagtt    600
ttcactgaca actcttcccc acctgctgtt ccacaaactt tccaagttgc tcacttgcat    660
gctccaactg gttctggtaa gtccactaag gttccagctg cttacgctgc tcaaggttac    720
aaggttttgg ttttgaaccc atccgttgct gctactttgg gtttcggtgc ttacatgtct    780
aaggctcacg gtattgagcc aaacatcaga actggtgtta gaactatcac tactggtggt    840
cctattactt actccgctta cggaaagttt ttggctgacg gtggttgttc tggtggtgct    900
tacgacatca tcatctgtga cgagtgtcac tctactgact ggactactat cttgggtatc    960
ggtactgttt tggaccaagc tgaaactgct ggtgctagat tggttgtttt ggctactgct   1020
actccaccag gttccattac tgttccacac ccaaacatcg aggaagttgc tttgtctaac   1080
actggagaga tcccattcta cggaaaggct atcccaattg aggctatcaa gggtggtaga   1140
cacttgattt tctgtcactc caagaagaag tgtgacgagt tggctgctaa gttgactgga   1200
ttgggattga acgctgttgc ttactacaga ggattggacg tttccgttat cccaacttcc   1260
ggtgatgttg ttgttgttgc tactgacgct ttgatgactg gtttcactgg tgacttcgac   1320
tccgttatcg actgtaacac ttgtgttact cagactgttg acttctcctt ggacccaact   1380
ttcactatcg agactactac tgttcctcaa gacgctgttt ccagatccca aagaagaggt   1440
gctactggta gaggaagatc cggtatctac agattcgtta ctccaggtga aagaccatct   1500
ggaatgttcg actcctccgt tttgtgtgaa tgttacgacg ctggttgtgc ttggtacgaa   1560
ttgactccag ctgagactac tgttagattg agagcttact tgaacactcc aggattgcca   1620
gtttgtcaag accacttgga attctgggag tccgttttca ctggattgac tcacattgac   1680
gctcactttt tgtcccaaac taagcaggct ggtgacaact ttccatactt ggttgcttac   1740
caggctactg tttgtgctag agcacaagct ccaccaccat cttgggatca gatgtggaag   1800
tgtttgatca gattgaagcc aactttgcac ggtccaactc cattgttgta cagattgggt   1860
gctgttcaga acgagatcac tttgactcac ccaatcacta agttcgttat ggcttgcatg   1920
tctgctgact tggaagttgt ttccttgatg gctttcactg cttccattac ttccccattg   1980
actactcaga acactttgtt gttcaacatc ttgggaggat gggttgcagc tcaattgtcc   2040
atgtcctaca cttggactgg tgctttgatc actccatgtg ctgctgaaga atccaagttg   2100
ccaatcaacc cattgtccaa ctctttgttg agacaccact ccatggttta ctccactact   2160
tccagatccg cttccttgag acagaagaag gttacattcg acagattgca ggttttggac   2220
gaccactaca gagatgtttt gaaggagatg aaggctaagg cttccactgt taaggctaga   2280
ttgttgtcca ttgaggaggc ttgtaagttg actccaccac actctgctaa gtccaagttt   2340
ggttacggtg ctaaggatgt tagatccttg tcctccagag ctgttaacca catcaggtct   2400
gtttgggagg atttgttgga ggacactgag actccaatcg acactactat catggctaag   2460
aacgaggttt tctgtgttca accagagaag ggtggaagaa agccagctag attgatcgtt   2520
ttcccagact tgggtgttag agtttgtgag aagatggctt tgtacgacgt tgtttccact   2580
ttgccacagg ctgttatggg accatcttac ggtttccaat actccccagg acaaagagtt   2640
gagttcttgg ttaacacttg gaagtccaag aaatgtccaa tgggattctc ctacaacact   2700
```

```
agatgtttcg actccactgt tactgagaac gacatcagaa cagaggagtc catctaccag   2760

tgttgtgact tggctccaga agctagacaa gctatcaagt ccttgactga gagattgtac   2820

atcggtggtc ctttgactaa ctccaaggga cagaactgtg gttacagaag atgtagagct   2880

tccggtgttt tgactacttc ctgtggtaac actttgactt gttacttgaa ggctactgct   2940

gcttgtagag ctgctaaatt gcaggactgt actatgttgg ttaacggtaa cgacttggtt   3000

gttatctgtg agtccgctgg tactcaagaa gatgctgctt ctttgagagt tttcacagag   3060

gctatgacta gatactctgc tccacctggt gatccaccac aaccagaata cgacttggag   3120

ttgatcactt cctgttcctc caatgttggt gttgctcacg atgcttccgg aaagagagtt   3180

tactacttga ctagagaccc aactactcca ttggctagag ctgcttggga aactgttaga   3240

cacactccag ttaactcctg gttgggtaac atcatcatgt acgctccaac tttgtgggct   3300

agaatgatct tgatgactca cttcttctcc atcttgttgg ctcaagagca attggaaaag   3360

gctttggact gtcagattta cggtgcttgt tactccattg agccattgga cttgccacag   3420

atcattgaga gattgcacgg tttgtctgct ttctctttgc actcttactc ccctggtgaa   3480

atcaacagag ttgcttcctg tttgagaaag ttgggtgttc caccattgag agtttggaga   3540

cacagagcta gatccgttag agctaagttg ttgtcccaag gtggaagagc tgctacttgt   3600

ggtaagtact tgttcaactg ggctgttaga acaaagttga agttgactcc tattcctgct   3660

gcttcccaat tggatttgtc cggttggttt gttgctggtt acaacggtgg tgacatctac   3720

cactctttgt ccagagctag accaaga                                      3747
```

<210> SEQ ID NO 15
<211> LENGTH: 3666
<212> TYPE: DNA
<213> ORGANISM: artificial sequence
<220> FEATURE:
<223> OTHER INFORMATION: nucleotide sequence encoding the NS4A-3-5B fusion optimized for expression in E. coli

<400> SEQUENCE: 15

```
atggggagcg ttgttattgt tggccgcatt attctgagcg gtagcggtag cgccccgatt     60

accgcctatt ctcagcaaac ccgtggtctg ctgggttgta ttattaccag cctgaccggc    120

cgtgataaaa atcaggtgga tggcgaagtt caggttctga gcaccgccac ccagagcttt    180

ctggcgacct gtgtgaatgg tgtgtgctgg accgtttatg ccggtgccgg tagcaaaacc    240

ctggcgggtc cgaaaggtcc gattacccag atgtacacca acgtggatca ggatctggtt    300

ggttggccgg cgccgccggg tgcccgtagc atgaccccgt gtacctgtgg tagcagcgat    360

ctgtatctgg ttacccgtca tgccgatgtt attccggttc gtcgtcgtgg tgatagccgt    420

ggtagcctgc tgtctccgcg tccggttagc tatctgaaag gtagcagcgg tggtccgctg    480

ctgtgtccga gcggtcatgt ggtgggtatt tttcgtgccg ccgtttgtac ccgtggtgtg    540

gcgaaagcgg tggattttat cccggttgaa agcatggaaa ccaccatgcg tagcccggtg    600

tttaccgata atagcagccc gccggcggtt ccgcagacct ttcaggttgc ccatctgcat    660

gcgccgaccg gtagcggtaa aagcaccaaa gttccggcgg cgtatgccgc ccagggttat    720

aaagtgctgg tgctgaatcc gagcgtggcg gcgaccctgg gttttggtgc ctatatgagc    780

aaagcccatg gcattgaacc gaacattcgt accggcgttc gtaccattac caccggtggc    840

ccgattacct atagcgccta cggcaaattt ctggcggatg gtggctgtag cggtggcgcc    900

tatgatatca tcatctgtga tgaatgccat agcaccgatt ggaccaccat tctgggtatt    960
```

```
ggcaccgttc tggatcaggc ggaaaccgcc ggtgcccgtc tggttgttct ggcgaccgca   1020
acgccgccgg gtagcattac cgttccgcat ccgaacattg aagaagtggc cctgagcaat   1080
accggcgaaa ttccgtttta tggcaaagcg attccgatcg aagcgattaa aggcggccgt   1140
catctgattt tttgccacag caaaaaaaaa tgtgatgaac tggcggcgaa actgaccggt   1200
ctgggtctga atgccgtggc gtattatcgt ggtctggatg tgagcgttat tccgaccagc   1260
ggtgatgttg ttgtggtggc gaccgatgcc ctgatgaccg gttttaccgg cgattttgat   1320
agcgtgatcg attgtaacac ctgtgtgacc cagaccgttg attttagcct ggacccgacc   1380
tttaccattg aaaccaccac cgttccgcag gatgccgtta gccgtagcca gcgtcgtggt   1440
gccaccggtc gtggtcgtag cggcatttat cgttttgtga cgccgggtga acgtccgagc   1500
ggtatgtttg atagcagcgt gctgtgtgaa tgttatgatg ccggctgtgc ctggtatgaa   1560
ctgaccccgg cggaaaccac cgttcgtctg cgcgcgtatc tgaatacgcc gggtctgccg   1620
gtttgtcagg atcatctgga attctgggaa agcgttttta ccggcctgac ccatattgat   1680
gcccatttc tgagccagac caaacaggcg ggtgataact ttccgtatct ggtggcgtat   1740
caggcgaccg tttgtgcccg tgcccaggcg ccgccgccga gctgggatca gatgtggaaa   1800
tgcctgattc gtctgaaacc gaccctgcat ggtccgaccc cgctgctgta tcgtctgggt   1860
gccgttcaga acgaaattac cctgacccat ccgatcacca aatttgtgat ggcgtgtatg   1920
agcgccgatc tggaagttgt tggtagcggt agcggctcta tgagctatac ctggaccggt   1980
gccctgatta ccccgtgtgc cgccgaagaa agcaaactgc cgattaaccc gctgtctaat   2040
agcctgctgc gtcatcatag catggtgtat agcaccacca gccgtagcgc cagcctgcgt   2100
cagaaaaaag tgaccttcga tcgtctgcag gtgctggatg atcattatcg tgatgtgctg   2160
aaagaaatga aagcgaaagc gagcaccgtt aaagcccgtc tgctgtctat tgaagaagcg   2220
tgtaaactga ccccgccgca tagcgccaaa agcaaatttg gctatggcgc caaagatgtt   2280
cgtagcctga gcagccgtgc cgttaatcat attcgtagcg tgtgggaaga tctgctggaa   2340
gataccgaaa ccccgattga taccaccatc atggcgaaaa acgaagtgtt ttgtgttcag   2400
ccggaaaaag gtggtcgtaa accggcccgt ctgattgttt ttccggatct gggtgttcgt   2460
gtgtgtgaaa aaatggcgct gtacgatgtt gttagcaccc tgccgcaggc ggttatgggt   2520
ccgagctatg gctttcagta ttctccgggt cagcgtgttg aatttctggt gaacacctgg   2580
aaaagcaaaa aatgcccgat gggcttcagc tataacaccc gctgctttga tagcaccgtg   2640
accgaaaacg atatccgtac cgaagaaagc atttaccagt gctgtgatct ggcgccggaa   2700
gcccgtcagg cgattaaaag cctgaccgaa cgcctgtata ttggcggtcc gctgaccaat   2760
agcaaaggcc agaactgtgg ttatcgtcgt tgtcgtgcca gcggtgttct gaccaccagc   2820
tgtggtaata ccctgacctg ctacctgaaa gcgaccgccg cctgtcgtgc cgccaaactg   2880
caggattgta ccatgctggt taacggcaat gatctggtgg tgatttgtga aagcgccggc   2940
acccaggaag atgccgccag cctgcgcgtt tttaccgaag cgatgacccg ttatagcgcc   3000
ccgccgggtg atccgccgca gccggaatat gatctggaac tgatcaccag ctgtagcagc   3060
aatgttggtg ttgcccatga tgccagcggt aaacgtgtgt attacctgac ccgtgatccg   3120
accaccccgc tggcccgtgc cgcctgggaa accgttcgtc ataccccggt taatagctgg   3180
ctgggcaaca ttattatgta tgccccgacc ctgtgggccc gtatgattct gatgacccac   3240
ttctttagca ttctgctggc ccaggaacag ctggaaaaag cgctggattg ccagatttat   3300
ggcgcctgct atagcattga accgctggat ctgccgcaga ttattgaacg tctgcatggc   3360
```

-continued

```
ctgagcgcct ttagcctgca tagctactct ccgggtgaaa ttaatcgtgt ggcgagctgt   3420

ctgcgtaaac tgggtgttcc gccgctgcgt gtctggcgtc atcgtgcccg tagcgttcgt   3480

gccaaactgc tgtctcaggg tggccgtgcc gccacctgtg gtaaatacct gtttaactgg   3540

gcggttcgta ccaaactgaa actgaccccg attccggcgg cgagccagct ggatctgagc   3600

ggttggtttg ttgccggtta taacggcggc gatatctatc atagcctgag ccgtgcccgt   3660

ccgcgt                                                              3666
```

```
<210> SEQ ID NO 16
<211> LENGTH: 3747
<212> TYPE: DNA
<213> ORGANISM: artificial sequence
<220> FEATURE:
<223> OTHER INFORMATION: nucleotide sequence encoding the NS4A-3-4B-5B
      fusion optimized for expression in E. coli

<400> SEQUENCE: 16

atggggagcg ttgttattgt tggccgcatt attctgagcg gtagcggtag cgccccgatt     60

accgcctatt ctcagcaaac ccgtggtctg ctgggttgta ttattaccag cctgaccggc    120

cgtgataaaa atcaggtgga tggcgaagtt caggttctga gcaccgccac ccagagcttt    180

ctggcgacct gtgtgaatgg tgtgtgctgg accgtttatg ccggtgccgg tagcaaaacc    240

ctggcgggtc cgaaaggtcc gattacccag atgtacacca acgtggatca ggatctggtt    300

ggttggccgg cgccgccggg tgcccgtagc atgaccccgt gtacctgtgg tagcagcgat    360

ctgtatctgg ttacccgtca tgccgatgtt attccggttc gtcgtcgtgg tgatagccgt    420

ggtagcctgc tgtctccgcg tccggttagc tatctgaaag gtagcagcgg tggtccgctg    480

ctgtgtccga gcggtcatgt ggtgggtatt tttcgtgccg ccgtttgtac ccgtggtgtg    540

gcgaaagcgg tggattttat cccggttgaa agcatggaaa ccaccatgcg tagcccggtg    600

tttaccgata atagcagccc gccggcggtt ccgcagacct ttcaggttgc ccatctgcat    660

gcgccgaccg gtagcggtaa aagcaccaaa gttccggcgg cgtatgccgc ccagggttat    720

aaagtgctgg tgctgaatcc gagcgtggcg gcgaccctgg gttttggtgc ctatatgagc    780

aaagcccatg gcattgaacc gaacattcgt accggcgttc gtaccattac caccggtggc    840

ccgattacct atagcgccta cggcaaattt ctggcggatg gtggctgtag cggtggcgcc    900

tatgatatca tcatctgtga tgaatgccat agcaccgatt ggaccaccat tctgggtatt    960

ggcaccgttc tggatcaggc ggaaaccgcc ggtgcccgtc tggttgttct ggcgaccgca   1020

acgccgccgg gtagcattac cgttccgcat ccgaacattg aagaagtggc cctgagcaat   1080

accggcgaaa ttccgtttta tggcaaagcg attccgatcg aagcgattaa aggcggccgt   1140

catctgattt tttgccacag caaaaaaaaa tgtgatgaac tggcggcgaa actgaccggt   1200

ctgggtctga atgccgtggc gtattatcgt ggtctggatg tgagcgttat tccgaccagc   1260

ggtgatgttg ttgtggtggc gaccgatgcc ctgatgaccg gttttaccgg cgattttgat   1320

agcgtgatcg attgtaacac ctgtgtgacc cagaccgttg attttagcct ggacccgacc   1380

tttaccattg aaaccaccac cgttccgcag gatgccgtta gccgtagcca gcgtcgtggt   1440

gccaccggtc gtggtcgtag cggcatttat cgttttgtga cgccgggtga acgtccgagc   1500

ggtatgtttg atagcagcgt gctgtgtgaa tgttatgatg ccggctgtgc ctggtatgaa   1560

ctgaccccgg cggaaaccac cgttcgtctg cgcgcgtatc tgaatacgcc gggtctgccg   1620

gtttgtcagg atcatctgga attctgggaa agcgttttta ccggcctgac ccatattgat   1680

gcccattttc tgagccagac caaacaggcg ggtgataact ttccgtatct ggtggcgtat   1740
```

```
caggcgaccg tttgtgcccg tgcccaggcg ccgccgccga gctgggatca gatgtggaaa   1800
tgcctgattc gtctgaaacc gaccctgcat ggtccgaccc cgctgctgta tcgtctgggt   1860
gccgttcaga acgaaattac cctgacccat ccgatcacca aatttgtgat ggcgtgtatg   1920
agcgccgatc tggaagttgt tagcctgatg gcgtttaccg ccagcattac cagcccgctg   1980
accacccaga ataccctgct gtttaacatc ctgggcggtt gggtggcggc ccagctgtct   2040
atgagctata cctggaccgg tgccctgatt accccgtgtg ccgccgaaga aagcaaactg   2100
ccgattaacc cgctgtctaa tagcctgctg cgtcatcata gcatggtgta tagcaccacc   2160
agccgtagcg ccagcctgcg tcagaaaaaa gtgaccttcg atcgtctgca ggtgctggat   2220
gatcattatc gtgatgtgct gaaagaaatg aaagcgaaag cgagcaccgt taaagcccgt   2280
ctgctgtcta ttgaagaagc gtgtaaactg accccgccgc atagcgccaa aagcaaattt   2340
ggctatggcg ccaaagatgt tcgtagcctg agcagccgtg ccgttaatca tattcgtagc   2400
gtgtgggaag atctgctgga agataccgaa accccgattg ataccaccat catggcgaaa   2460
aacgaagtgt tttgtgttca gccggaaaaa ggtggtcgta aaccggcccg tctgattgtt   2520
tttccggatc tgggtgttcg tgtgtgtgaa aaaatggcgc tgtacgatgt tgttagcacc   2580
ctgccgcagg cggttatggg tccgagctat ggctttcagt attctccggg tcagcgtgtt   2640
gaatttctgg tgaacacctg gaaaagcaaa aaatgcccga tgggcttcag ctataacacc   2700
cgctgctttg atagcaccgt gaccgaaaac gatatccgta ccgaagaaag catttaccag   2760
tgctgtgatc tggcgccgga agcccgtcag gcgattaaaa gcctgaccga acgcctgtat   2820
attggcggtc cgctgaccaa tagcaaaggc cagaactgtg gttatcgtcg ttgtcgtgcc   2880
agcggtgttc tgaccaccag ctgtggtaat accctgacct gctacctgaa agcgaccgcc   2940
gcctgtcgtg ccgccaaact gcaggattgt accatgctgg ttaacggcaa tgatctggtg   3000
gtgatttgtg aaagcgccgg cacccaggaa gatgccgcca gcctgcgcgt tttaccgaa   3060
gcgatgaccc gttatagcgc cccgccgggt gatccgccgc agccggaata tgatctggaa   3120
ctgatcacca gctgtagcag caatgttggt gttgcccatg atgccagcgg taaacgtgtg   3180
tattacctga cccgtgatcc gaccaccccg ctggcccgtg ccgcctggga aaccgttcgt   3240
cataccccgg ttaatagctg gctgggcaac attattatgt atgccccgac cctgtgggcc   3300
cgtatgattc tgatgaccca cttctttagc attctgctgg cccaggaaca gctggaaaaa   3360
gcgctggatt gccagattta tggcgcctgc tatagcattg aaccgctgga tctgccgcag   3420
attattgaac gtctgcatgg cctgagcgcc tttagcctgc atagctactc tccgggtgaa   3480
attaatcgtg tggcgagctg tctgcgtaaa ctgggtgttc cgccgctgcg tgtctggcgt   3540
catcgtgccc gtagcgttcg tgccaaactg ctgtctcagg gtggccgtgc cgccacctgt   3600
ggtaaatacc tgtttaactg ggcggttcgt accaaactga aactgacccc gattccggcg   3660
gcgagccagc tggatctgag cggttggttt gttgccggtt ataacggcgg cgatatctat   3720
catagcctga gccgtgcccg tccgcgt                                       3747
```

<210> SEQ ID NO 17
<211> LENGTH: 46
<212> TYPE: DNA
<213> ORGANISM: artificial sequence
<220> FEATURE:
<223> OTHER INFORMATION: oligonucleotide for improving kozak consensus

<400> SEQUENCE: 17

```
atgtacgtcg accaccatgg gcagcgtggt gattgtgggc cggatc                    46
```

<210> SEQ ID NO 18
<211> LENGTH: 41
<212> TYPE: DNA
<213> ORGANISM: artificial sequence
<220> FEATURE:
<223> OTHER INFORMATION: oligonucleotide to create stop codons

<400> SEQUENCE: 18
catgtagcgg ccgctcatca tctaggcctg gccctggaca g                  41

<210> SEQ ID NO 19
<211> LENGTH: 36
<212> TYPE: DNA
<213> ORGANISM: artificial sequence
<220> FEATURE:
<223> OTHER INFORMATION: primer

<400> SEQUENCE: 19 gggggggctag cgccaccatg ggcagcgtgg tgattg                       36

<210> SEQ ID NO 20
<211> LENGTH: 34
<212> TYPE: DNA
<213> ORGANISM: artificial sequence
<220> FEATURE:
<223> OTHER INFORMATION: PCR primer

<400> SEQUENCE: 20
gggggggtac cctcatcatc taggcctggc cctg                          34

<210> SEQ ID NO 21
<211> LENGTH: 3705
<212> TYPE: DNA
<213> ORGANISM: artificial sequence
<220> FEATURE:
<223> OTHER INFORMATION: optimised sequence of NS4A-NS3-NS5B in homo
      sapiens <400> SEQUENCE: 21
cgaattgggt accgccacca tgggcagcgt ggtgattgtg ggccggatca tcctgagcgg 60
cagcggcagc gcccccatca ccgcctacag ccagcagacc agaggcctgc tgggctgtat 120
catcaccagc ctgaccggca gagacaagaa tcaggtggac ggcgaggtgc aggtgctgtc 180
caccgccacc cagagcttcc tggccacctg tgtgaatggc gtgtgttgga ccgtgtacgc 240
cggagccggc agcaagaccc tggccggacc caagggcccc atcacccaga tgtacaccaa 300
cgtggaccag gacctggtgg gctggcctgc ccctcctggc gccagaagca tgaccccttg 360
tacctgtggc agcagcgacc tgtacctggt gaccagacac gccgatgtga tccctgtgag 420
gaggagaggc gatagcagag gcagcctgct gtctcctaga cccgtgtcct acctgaaggg 480
cagcagcggc ggacccctgc tgtgccccag cggccacgtg gtgggcatct tcagagccgc 540
cgtgtgtacc agaggcgtgg ccaaggccgt ggatttcatc cccgtggaga gcatggagac 600
caccatgagg agccccgtgt tcaccgacaa tagcagcccc cctgccgtgc ctcagacctt 660
ccaggtggcc cacctgcacg cccccaccgg ctccggcaag agcaccaagg tgccagccgc 720
ctacgccgcc cagggctaca aggtgctggt gctgaatccc agcgtggccg ccaccctggg 780
cttcggcgcc tacatgagca aggcccacgg catcgagccc aatatccgga ccggagtgag 840
gaccatcacc acaggcggcc ctatcaccta cagcgcctac ggcaagttcc tggccgacgg 900
cggctgtagc ggcggagcct acgacatcat catctgtgac gagtgccaca gcaccgattg 960

```
gaccaccatc ctgggcatcg gcaccgtgct ggaccaggcc gagaccgccg gagccagact   1020
ggtggtgctg gccacagcca cacccccctgg cagcatcacc gtgccccacc ccaacatcga   1080
ggaggtggcc ctgagcaaca ccggcgagat ccccttctac ggcaaggcca tccctatcga   1140
ggccatcaag ggcggcagac acctgatctt ctgccacagc aagaagaagt gtgacgagct   1200
ggccgccaag ctgaccggcc tgggcctgaa cgccgtggcc tactacagag gcctggacgt   1260
gtccgtgatc cctaccagcg gcgatgtggt ggtggtggcc accgacgccc tgatgaccgg   1320
cttcaccggc gatttcgaca gcgtgatcga ctgtaatacc tgtgtgaccc agaccgtgga   1380
cttcagcctg gaccccacct tcaccatcga gaccaccacc gtgccacagg atgccgtgtc   1440
cagaagccag agaagaggcg ccaccggcag aggcagaagc ggcatctaca gattcgtgac   1500
ccctggcgag agacccagcg gcatgttcga tagcagcgtg ctgtgtgagt gctacgacgc   1560
cggctgtgcc tggtacgagc tgaccccagc cgagaccaca gtgaggctga gggcctacct   1620
gaacacccct ggcctgcctg tgtgccagga tcacctggag ttctgggaga gcgtgtttac   1680
cggcctgacc cacatcgatg cccactttct gagccagacc aagcaggccg gcgacaactt   1740
cccctacctg gtggcctacc aggccaccgt gtgtgccaga gcccaggccc ctcccccccag   1800
ctgggaccag atgtggaagt gcctgatcag gctgaagccc accctgcacg gccctacccc   1860
cctgctgtac agactgggcg ccgtgcagaa tgagatcacc ctgacccacc ctatcaccaa   1920
gttcgtgatg gcctgtatga gcgccgacct ggaggtggtg ggcagcggct ccggctccat   1980
gagctacacc tggacaggcg ccctgatcac accctgtgcc gccgaggaga gcaagctgcc   2040
catcaacccc ctgagcaata gcctgctgag gcaccacagc atggtgtaca gcaccacctc   2100
cagaagcgcc agcctgaggc agaagaaggt gaccttcgac aggctgcagg tgctggacga   2160
ccactacagg gacgtgctga aggagatgaa ggccaaggcc agcaccgtga aggccagact   2220
gctgtctatc gaggaggcct gtaagctgac ccccccctcac agcgccaaga gcaagttcgg   2280
ctacggcgcc aaggatgtga gaagcctgag cagcagagcc gtgaaccaca tccggtctgt   2340
gtgggaggat ctgctggagg ataccgagac cccccatcgac accacaatca tggccaagaa   2400
cgaggtgttc tgcgtgcagc ccgagaaggg cggaagaaag cccgccaggc tgatcgtgtt   2460
ccctgacctg ggagtgagag tgtgtgagaa gatggccctg tacgacgtgg tgtccaccct   2520
gccccaggcc gtgatgggcc ccagctacgg cttccagtac agccctggcc agagagtgga   2580
gttcctggtg aacacctgga agagcaagaa atgccccatg ggcttcagct acaacacccg   2640
gtgcttcgac agcacagtga ccgagaacga catcaggacc gaggagtcca tctaccagtg   2700
ctgtgacctg gccccccgagg ccagacaggc catcaaaagc ctgaccgagc ggctgtacat   2760
cggcggacct ctgaccaaca gcaagggcca gaactgtggc tacagaagat gtagggccag   2820
cggcgtgctg accacctctt gtggcaacac cctgacctgt tacctgaagg ccaccgccgc   2880
ctgtagagcc gccaaactgc aggactgtac catgctggtg aacggcaacg acctggtggt   2940
gatctgtgag agcgccggca cccaggagga tgccgcctcc ctgagagtgt ttaccgaggc   3000
catgaccaga tacagcgccc ctcccggcga ccctccccag cccgagtacg atctggagct   3060
gatcaccagc tgctccagca atgtgggcgt ggctcacgac gccagcggca agagagtgta   3120
ctacctgacc agggacccca ccacccctct ggccagagcc gcctgggaga cagtgagaca   3180
cacccccgtg aacagctggc tgggcaacat catcatgtac gcccctaccc tgtgggccag   3240
aatgatcctg atgacccact tcttcagcat cctgctggcc caggagcagc tggagaaggc   3300
cctggactgc cagatctacg gcgcctgcta cagcatcgag cctctggacc tgcctcagat   3360
```

```
catcgagaga ctgcacggcc tgagcgcctt cagcctgcac agctacagcc caggcgagat   3420

caatagagtg gccagctgcc tgagaaagct gggcgtgcca cctctgagag tgtggcggca   3480

cagagccaga tctgtgaggg ccaagctgct gtcccagggc ggcagggccg ccacctgtgg   3540

caagtacctg ttcaactggg ccgtgaggac aaagctgaag ctgacaccca tccctgccgc   3600

cagccagctg gacctgagcg gctggttcgt ggccggctac aatggcggcg acatctacca   3660

cagcctgtcc agggccaggc ctagatgatg aggagctcca gcttt                   3705
```

<210> SEQ ID NO 22
<211> LENGTH: 3705
<212> TYPE: DNA
<213> ORGANISM: artificial sequence
<220> FEATURE:
<223> OTHER INFORMATION: complementary strand of SEQ ID NO:21

<400> SEQUENCE: 22

```
gcttaaccca tggcggtggt acccgtcgca ccactaacac ccggcctagt aggactcgcc     60

gtcgccgtcg cgggggtagt ggcggatgtc ggtcgtctgg tctccggacg acccgacata    120

gtagtggtcg gactggccgt ctctgttctt agtccacctg ccgctccacg tccacgacag    180

gtggcggtgg gtctcgaagg accggtggac acacttaccg cacacaacct ggcacatgcg    240

gcctcggccg tcgttctggg accggcctgg gttcccgggg tagtgggtct acatgtggtt    300

gcacctggtc ctggaccacc cgaccggacg gggaggaccg cggtcttcgt actggggaac    360

atggacaccg tcgtcgctgg acatggacca ctggtctgtg cggctacact agggacactc    420

ctcctctccg ctatcgtctc cgtcggacga cagaggatct gggcacagga tggacttccc    480

gtcgtcgccg cctggggacg acacggggtc gccggtgcac cacccgtaga agtctcggcg    540

gcacacatgg tctccgcacc ggttccggca cctaaagtag gggcacctct cgtacctctg    600

gtggtactcc tcggggcaca agtggctgtt atcgtcgggg ggacggcacg gagtctggaa    660

ggtccaccgg gtggacgtgc gggggtggcc gaggccgttc tcgtggttcc acggtcggcg    720

gatgcggcgg gtcccgatgt tccacgacca cgacttaggg tcgcaccggc ggtgggaccc    780

gaagccgcgg atgtactcgt tccgggtgcc gtagctcggg ttataggcct ggcctcactc    840

ctggtagtgg tgtccgccgg gatagtggat gtcgcggatg ccgttcaagg accggctgcc    900

gccgacatcg ccgcctcgga tgctgtagta gtagacactg ctcacggtgt cgtggctaac    960

ctggtggtag gacccgtagc cgtggcacga cctggtccgg ctctggcggc ctcggtctga   1020

ccaccacgac cggtgtcggt gtgggggacc gtcgtagtgg cacggggtgg ggttgtagct   1080

cctccaccgg gactcgttgt ggccgctcta ggggaagatg ccgttccggt agggatagct   1140

ccggtagttc ccgccgtctg tggactagaa gacggtgtcg ttcttcttca cactgctcga   1200

ccggcggttc gactggccgg acccggactt gcggcaccgg atgatgtctc cggacctgca   1260

caggcactag ggatggtcgc cgctacacca ccaccaccgg tggctgcggg actactggcc   1320

gaagtggccg ctaaagctgt cgcactagct gacattatgg acacactggg tctggcacct   1380

gaagtcggac ctggggtgga agtggtagct ctggtggtgg cacggtgtcc tacggcacag   1440

gtcttcggtc tcttctccgc ggtggccgtc tccgtcttcg ccgtagatgt ctaagcactg   1500

gggaccgctc tctgggtcgc cgtacaagct atcgtcgcac gacacactca cgatgctgcg   1560

gccgacacgg accatgctcg actggggtcg gctctggtgt cactccgact cccggatgga   1620

cttgtgggga ccggacggac acacggtcct agtggacctc aagaccctct cgcacaaatg   1680

gccggactgg gtgtagctac gggtgaaaga ctcggtctgg ttcgtccggc cgctgttgaa   1740
```

```
ggggatggac caccggatgg tccggtggca cacacggtct cgggtccggg gagggggGtc   1800
gaccctggtc tacaccttca cggactagtc cgacttcggg tgggacgtgc cgggatgggg   1860
ggacgacatg tctgacccgc ggcacgtctt actctagtgg gactgggtgg gatagtggtt   1920
caagcactac cggacatact cgcggctgga cctccaccac ccgtcgccga ggccgaggta   1980
ctcgatgtgg acctgtccgc gggactagtg tgggacacgg cggctcctct cgttcgacgg   2040
gtagttgggg gactcgttat cggacgactc cgtggtgtcg taccacatgt cgtggtggag   2100
gtcttcgcgg tcggactccg tcttcttcca ctggaagctg tccgacgtcc acgacctgct   2160
ggtgatgtcc ctgcacgact tcctctactt ccggttccgg tcgtggcact tccggtctga   2220
cgacagatag ctcctccgga cattcgactg ggggggagtg tcgcggttct cgttcaagcc   2280
gatgccgcgg ttcctacact cttcggactc gtcgtctcgg cacttggtgt aggccagaca   2340
caccctccta gacgacctcc tatggctctg gggGtagctg tggtgttagt accggttctt   2400
gctccacaag acgcacgtcg ggctcttccc gccttctttc gggcggtccg actagcacaa   2460
gggactggac cctcactctc acacactctt ctaccgggac atgctgcacc acaggtggga   2520
cggggtccgg cactacccgg ggtcgatgcc gaaggtcatg tcgggaccgg tctctcacct   2580
caaggaccac ttgtggacct tctcgttctt tacggggtac ccgaagtcga tgttgtgggc   2640
cacgaagctg tcgtgtcact ggctcttgct gtagtcctgg ctcctcaggt agatggtcac   2700
gacactggac cgggggctcc ggtctgtccg gtagttttcg gactggctcg ccgacatgta   2760
gccgcctgga gactggttgt cgttcccggt cttgacaccg atgtcttcta catcccggtc   2820
gccgcacgac tggtggagaa caccgttgtg ggactggaca atggacttcc ggtggcggcg   2880
gacatctcgg cggtttgacg tcctgacatg gtacgaccac ttgccgttgc tggaccacca   2940
ctagacactc tcgcggccgt gggtcctcct acggcggagg gactctcaca aatggctccg   3000
gtactggtct atgtcgcggg gagggccgct gggaggggtc gggctcatgc tagacctcga   3060
ctagtggtcg acgaggtcgt tacacccgca ccgagtgctg cggtcgccgt tctctcacat   3120
gatggactgg tccctggggt ggtggggaga ccggtctcgg cggaccctct gtcactctgt   3180
gtgggggcac ttgtcgaccg acccgttgta gtagtacatg cggggatggg acacccggtc   3240
ttactaggac tactgggtga agaagtcgta ggacgaccgg gtcctcgtcg acctcttccg   3300
ggacctgacg gtctagatgc cgcggacgat gtcgtagctc ggagacctgg acggagtcta   3360
gtagctctct gacgtgccgg actcgcggaa gtcggacgtg tcgatgtcgg gtccgctcta   3420
gttatctcac cggtcgacgg actctttcga cccgcacggt ggagactctc acaccgccgt   3480
gtctcggtct agacactccc ggttcgacga cagggtcccg ccgtcccggc ggtggacacc   3540
gttcatggac aagttgaccc ggcactcctg tttcgacttc gactgtgggt agggacggcg   3600
gtcggtcgac ctggactcgc cgaccaagca ccggccgatg ttaccgccgc tgtagatggt   3660
gtcggacagg tcccggtccg gatctactac tcctcgaggt cgaaa                   3705
```

<210> SEQ ID NO 23
<211> LENGTH: 3796
<212> TYPE: DNA
<213> ORGANISM: artificial sequence
<220> FEATURE:
<223> OTHER INFORMATION: optimised sequence of NS4A-NS3-NS4B-NS5B in homo sapiens

<400> SEQUENCE: 23

```
gggcgaattg ggtaccgcca ccatgggcag cgtggtgatt gtgggccgga tcatcctgag     60
cggcagcggc agcgccccca tcaccgccta cagccagcag accagaggcc tgctgggctg    120
```

-continued

```
tatcatcacc agcctgaccg gcagagacaa gaatcaggtg gacggcgagg tgcaggtgct    180
gtccaccgcc acccagagct tcctggccac ctgtgtgaat ggcgtgtgtt ggaccgtgta    240
cgccggagcc ggcagcaaga ccctggccgg acccaagggc cccatcaccc agatgtacac    300
caacgtggac caggacctgg tgggctggcc tgcccctcct ggcgccagaa gcatgacccc    360
ttgtacctgt ggcagcagcg acctgtacct ggtgaccaga cacgccgatg tgatccctgt    420
gaggaggaga ggcgatagca gaggcagcct gctgtctcct agacccgtgt cctacctgaa    480
gggcagcagc ggcggacccc tgctgtgccc cagcggccac gtggtgggca tcttcagagc    540
cgccgtgtgt accagaggcg tggccaaggc cgtggatttc atccccgtgg agagcatgga    600
gaccaccatg aggagccccg tgttcaccga caatagcagc ccccctgccg tgcctcagac    660
cttccaggtg gcccacctgc acgcccccac cggctccggc aagagcacca aggtgccagc    720
cgcctacgcc gcccagggct acaaggtgct ggtgctgaat cccagcgtgg ccgccaccct    780
gggcttcggc gcctacatga gcaaggccca cggcatcgag cccaatatcc ggaccggagt    840
gaggaccatc accacaggcg gccctatcac ctacagcgcc tacggcaagt tcctggccga    900
cggcggctgt agcggcggag cctacgacat catcatctgt gacgagtgcc acagcaccga    960
ttggaccacc atcctgggca tcggcaccgt gctggaccag gccgagaccg ccggagccag   1020
actggtggtg ctggccacag ccacaccccc tggcagcatc accgtgcccc accccaacat   1080
cgaggaggtg gccctgagca acaccggcga gatccccttc tacggcaagg ccatccctat   1140
cgaggccatc aagggcggca gacacctgat cttctgccac agcaagaaga agtgtgacga   1200
gctggccgcc aagctgaccg gcctgggcct gaacgccgtg gcctactaca gaggcctgga   1260
cgtgtccgtg atccctacca gcggcgatgt ggtggtggtg gccaccgacg ccctgatgac   1320
cggcttcacc ggcgatttcg acagcgtgat cgactgtaat acctgtgtga cccagaccgt   1380
ggacttcagc ctggacccca ccttcaccat cgagaccacc accgtgccac aggatgccgt   1440
gtccagaagc cagagaagag gcgccaccgg cagaggcaga agcggcatct acagattcgt   1500
gacccctggc gagagaccca gcggcatgtt cgatagcagc gtgctgtgtg agtgctacga   1560
cgccggctgt gcctggtacg agctgacccc agccgagacc acagtgaggc tgagggccta   1620
cctgaacacc cctggcctgc ctgtgtgcca ggatcacctg gagttctggg agagcgtgtt   1680
taccggcctg acccacatcg atgcccactt tctgagccag accaagcagg ccggcgacaa   1740
cttcccctac ctggtggcct accaggccac cgtgtgtgcc agagcccagg cccctccccc   1800
cagctgggac cagatgtgga agtgcctgat caggctgaag cccaccctgc acggccctac   1860
ccccctgctg tacagactgg gcgccgtgca gaatgagatc accctgaccc accctatcac   1920
caagttcgtg atggcctgta tgagcgccga cctggaggtg gtgtccctga tggccttcac   1980
cgccagcatc acaagccccc tgaccaccca gaataccctg ctgttcaaca tcctgggcgg   2040
ctgggtggcc gcccagctgt ccatgagcta cacctggaca ggcgccctga tcacaccctg   2100
tgccgccgag gagagcaagc tgcccatcaa ccccctgagc aatagcctgc tgaggcacca   2160
cagcatggtg tacagcacca cctccagaag cgccagcctg aggcagaaga aggtgacctt   2220
cgacaggctg caggtgctgg acgaccacta cagggacgtg ctgaaggaga tgaaggccaa   2280
ggccagcacc gtgaaggcca gactgctgtc tatcgaggag gcctgtaagc tgaccccccc   2340
tcacagcgcc aagagcaagt tcggctacgg cgccaaggat gtgagaagcc tgagcagcag   2400
agccgtgaac cacatccggt ctgtgtggga ggatctgctg gaggataccg agacccccat   2460
cgacaccaca atcatggcca agaacgaggt gttctgcgtg cagcccgaga agggcggaag   2520
```

```
aaagcccgcc aggctgatcg tgttccctga cctgggagtg agagtgtgtg agaagatggc   2580
cctgtacgac gtggtgtcca ccctgcccca ggccgtgatg ggccccagct acggcttcca   2640
gtacagccct ggccagagag tggagttcct ggtgaacacc tggaagagca agaaatgccc   2700
catgggcttc agctacaaca cccggtgctt cgacagcaca gtgaccgaga acgacatcag   2760
gaccgaggag tccatctacc agtgctgtga cctggccccc gaggccagac aggccatcaa   2820
aagcctgacc gagcggctgt acatcggcgg acctctgacc aacagcaagg gccagaactg   2880
tggctacaga agatgtaggg ccagcggcgt gctgaccacc tcttgtggca acaccctgac   2940
ctgttacctg aaggccaccg ccgcctgtag agccgccaaa ctgcaggact gtaccatgct   3000
ggtgaacggc aacgacctgg tggtgatctg tgagagcgcc ggcacccagg aggatgccgc   3060
ctccctgaga gtgtttaccg aggccatgac cagatacagc gcccctcccg gcgaccctcc   3120
ccagcccgag tacgatctgg agctgatcac cagctgctcc agcaatgtgg gcgtggctca   3180
cgacgccagc ggcaagagag tgtactacct gaccagggac cccaccaccc ctctggccag   3240
agccgcctgg gagacagtga gacacacccc cgtgaacagc tggctgggca acatcatcat   3300
gtacgcccct accctgtggg ccagaatgat cctgatgacc cacttcttca gcatcctgct   3360
ggcccaggag cagctggaga aggccctgga ctgccagatc tacggcgcct gctacagcat   3420
cgagcctctg gacctgcctc agatcatcga gagactgcac ggcctgagcg ccttcagcct   3480
gcacagctac agcccaggcg agatcaatag agtggccagc tgcctgagaa agctgggcgt   3540
gccacctctg agagtgtggc ggcacagagc cagatctgtg agggccaagc tgctgtccca   3600
gggcggcagg gccgccacct gtggcaagta cctgttcaac tggggccgtga ggacaaagct   3660
gaagctgaca cccatccctg ccgccagcca gctggacctg agcggctggt tcgtggccgg   3720
ctacaatggc ggcgacatct accacagcct gtccagggcc aggcctagat gatgaggagc   3780
tccagctttt gttccc                                                   3796
```

<210> SEQ ID NO 24
<211> LENGTH: 3796
<212> TYPE: DNA
<213> ORGANISM: artificial sequence
<220> FEATURE:
<223> OTHER INFORMATION: complementary strain of SEQ ID NO23

<400> SEQUENCE: 24

```
cccgcttaac ccatggcggt ggtacccgtc gcaccactaa cacccggcct agtaggactc     60
gccgtcgccg tcgcgggggt agtggcggat gtcggtcgtc tggtctccgg acgacccgac    120
atagtagtgg tcggactggc cgtctctgtt cttagtccac ctgccgctcc acgtccacga    180
caggtggcgg tgggtctcga aggaccggtg gacacactta ccgcacacaa cctggcacat    240
gcggcctcgg ccgtcgttct gggaccggcc tgggttcccg gggtagtggg tctacatgtg    300
gttgcacctg gtcctggacc acccgaccgg acggggagga ccgcggtctt cgtactgggg    360
aacatggaca ccgtcgtcgc tggacatgga ccactggtct gtgcggctac actagggaca    420
ctcctcctct ccgctatcgt ctccgtcgga cgacagagga tctgggcaca ggatggactt    480
cccgtcgtcg ccgcctgggg acgacacggg gtcgccggtg caccacccgt agaagtctcg    540
gcggcacaca tggtctccgc accggttccg gcacctaaag taggggcacc tctcgtacct    600
ctggtggtac tcctcggggc acaagtggct gttatcgtcg gggggacggc acggagtctg    660
gaaggtccac cgggtggacg tgcgggggtg gccgaggccg ttctcgtggt tccacggtcg    720
gcggatgcgg cgggtcccga tgttccacga ccacgactta gggtcgcacc ggcggtggga    780
```

-continued

```
cccgaagccg cggatgtact cgttccgggt gccgtagctc gggttatagg cctggcctca    840
ctcctggtag tggtgtccgc cgggatagtg gatgtcgcgg atgccgttca aggaccggct    900
gccgccgaca tcgccgcctc ggatgctgta gtagtagaca ctgctcacgg tgtcgtggct    960
aacctggtgg taggacccgt agccgtggca cgacctggtc cggctctggc ggcctcggtc   1020
tgaccaccac gaccggtgtc ggtgtggggg accgtcgtag tggcacgggg tggggttgta   1080
gctcctccac cgggactcgt tgtggccgct ctaggggaag atgccgttcc ggtagggata   1140
gctccggtag ttcccgccgt ctgtggacta gaagacggtg tcgttcttct tcacactgct   1200
cgaccggcgg ttcgactggc cggacccgga cttgcggcac cggatgatgt ctccggacct   1260
gcacaggcac tagggatggt cgccgctaca ccaccaccac cggtggctgc gggactactg   1320
gccgaagtgg ccgctaaagc tgtcgcacta gctgacatta tggacacact gggtctggca   1380
cctgaagtcg gacctggggt ggaagtggta gctctggtgg tggcacggtg tcctacggca   1440
caggtcttcg gtctcttctc cgcggtggcc gtctccgtct tcgccgtaga tgtctaagca   1500
ctggggaccg ctctctgggt cgccgtacaa gctatcgtcg cacgacacac tcacgatgct   1560
gcggccgaca cggaccatgc tcgactgggg tcggctctgg tgtcactccg actcccggat   1620
ggacttgtgg ggaccggacg gacacacggt cctagtggac ctcaagaccc tctcgcacaa   1680
atggccggac tgggtgtagc tacgggtgaa agactcggtc tggttcgtcc ggccgctgtt   1740
gaaggggatg gaccaccgga tggtccggtg gcacacacgg tctcgggtcc ggggaggggg   1800
gtcgaccctg gtctacacct tcacggacta gtccgacttc gggtgggacg tgccgggatg   1860
gggggacgac atgtctgacc cgcggcacgt cttactctag tgggactggg tgggatagtg   1920
gttcaagcac taccggacat actcgcggct ggacctccac cacagggact accggaagtg   1980
gcggtcgtag tgttcggggg actggtgggt cttatgggac gacaagttgt aggacccgcc   2040
gacccaccgg cgggtcgaca ggtactcgat gtggacctgt ccgcgggact agtgtgggac   2100
acggcggctc ctctcgttcg acgggtagtt gggggactcg ttatcggacg actccgtggt   2160
gtcgtaccac atgtcgtggt ggaggtcttc gcggtcggac tccgtcttct tccactggaa   2220
gctgtccgac gtccacgacc tgctggtgat gtccctgcac gacttcctct acttccggtt   2280
ccggtcgtgg cacttccggt ctgacgacag atagctcctc cggacattcg actggggggg   2340
agtgtcgcgg ttctcgttca agccgatgcc gcggttccta cactcttcgg actcgtcgtc   2400
tcggcacttg gtgtaggcca gacacaccct cctagacgac ctcctatggc tctgggggta   2460
gctgtggtgt tagtaccggt tcttgctcca caagacgcac gtcgggctct tcccgccttc   2520
tttcgggcgg tccgactagc acaagggact ggaccctcac tctcacacac tcttctaccg   2580
ggacatgctg caccacaggt gggacggggt ccggcactac ccggggtcga tgccgaaggt   2640
catgtcggga ccggtctctc acctcaagga ccacttgtgg accttctcgt tctttacggg   2700
gtacccgaag tcgatgttgt gggccacgaa gctgtcgtgt cactggctct tgctgtagtc   2760
ctggctcctc aggtagatgg tcacgacact ggaccggggg ctccggtctg tccggtagtt   2820
ttcggactgg ctcgccgaca tgtagccgcc tggagactgg ttgtcgttcc cggtcttgac   2880
accgatgtct tctacatccc ggtcgccgca cgactggtgg agaacaccgt tgtgggactg   2940
gacaatggac ttccggtggc ggcggacatc tcggcggttt gacgtcctga catggtacga   3000
ccacttgccg ttgctggacc accactagac actctcgcgg ccgtgggtcc tcctacggcg   3060
gagggactct cacaaatggc tccggtactg gtctatgtcg cggggagggc cgctgggagg   3120
ggtcgggctc atgctagacc tcgactagtg gtcgacgagg tcgttacacc cgcaccgagt   3180
```

```
gctgcggtcg ccgttctctc acatgatgga ctggtccctg gggtggtggg gagaccggtc   3240
tcggcggacc ctctgtcact ctgtgtgggg gcacttgtcg accgacccgt tgtagtagta   3300
catgcgggga tgggacaccc ggtcttacta ggactactgg gtgaagaagt cgtaggacga   3360
ccgggtcctc gtcgacctct tccgggacct gacggtctag atgccgcgga cgatgtcgta   3420
gctcggagac ctggacggag tctagtagct ctctgacgtg ccggactcgc ggaagtcgga   3480
cgtgtcgatg tcgggtccgc tctagttatc tcaccggtcg acggactctt tcgacccgca   3540
cggtggagac tctcacaccg ccgtgtctcg gtctagacac tcccggttcg acgacagggt   3600
cccgccgtcc cggcggtgga caccgttcat ggacaagttg acccggcact cctgtttcga   3660
cttcgactgt gggtagggac ggcggtcggt cgacctggac tcgccgacca agcaccggcc   3720
gatgttaccg ccgctgtaga tggtgtcgga caggtcccgg tccggatcta ctactcctcg   3780
aggtcgaaaa caaggg                                                  3796
```

```
<210> SEQ ID NO 25
<211> LENGTH: 3684
<212> TYPE: DNA
<213> ORGANISM: artificial sequence
<220> FEATURE:
<223> OTHER INFORMATION: optimised sequence of NS4A-NS3-NS5B in Pichia

<400> SEQUENCE: 25

atggggtccg ttgttatcgt tggtagaatc atcttgtctg gttctggttc cgctccaatt     60
actgcttact cccagcagac tagaggattg ttgggttgta tcatcacttc cttgactggt    120
agagacaaga accaagttga cggagaggtt caggttttgt ccactgctac tcagtctttc    180
ttggctactt gtgttaacgg tgtttgttgg actgtttacg ctggtgctgg ttctaaaact    240
ttggctggtc caaagggtcc aatcactcag atgtacacaa acgttgacca ggatttggtt    300
ggttggccag ctccaccagg tgctagatcc atgactccat gtacttgtgg ttcctccgac    360
ttgtacttgg ttactagaca cgctgacgtt atcccagtta gaagaagagg agactccaga    420
ggatctttgt tgtccccaag accagtttct tacttgaagg gatcttccgg tggtccattg    480
ttgtgtccat ccggtcacgt tgttggtatt ttcagagctg ctgtttgtac tagaggtgtt    540
gctaaggctg ttgacttcat cccagttgag tccatggaga ctactatgag atccccagtt    600
ttcactgaca actcttcccc acctgctgtt ccacaaactt tccaagttgc tcacttgcat    660
gctccaactg gttctggtaa gtccactaag gttccagctg cttacgctgc tcaaggttac    720
aaggttttgg ttttgaaccc atccgttgct gctactttgg gtttcggtgc ttacatgtct    780
aaggctcacg gtattgagcc aaacatcaga actggtgtta gaactatcac tactggtggt    840
cctattactt actccgctta cggaaagttt ttggctgacg gtggttgttc tggtggtgct    900
tacgacatca tcatctgtga cgagtgtcac tctactgact ggactactat cttgggtatc    960
ggtactgttt tggaccaagc tgaaactgct ggtgctagat tggttgtttt ggctactgct   1020
actccaccag gttccattac tgttccacac ccaaacatcg aggaagttgc tttgtctaac   1080
actggagaga tcccattcta cggaaaggct atcccaattg aggctatcaa gggtggtaga   1140
cacttgattt tctgtcactc caagaagaag tgtgacgagt tggctgctaa gttgactgga   1200
ttgggattga acgctgttgc ttactacaga ggattggacg tttccgttat cccaacttcc   1260
ggtgatgttg ttgttgttgc tactgacgct ttgatgactg gtttcactgg tgacttcgac   1320
tccgttatcg actgtaacac ttgtgttact cagactgttg acttctcctt ggacccaact   1380
ttcactatcg agactactac tgttcctcaa gacgctgttt ccagatccca aagaagaggt   1440
```

```
gctactggta gaggaagatc cggtatctac agattcgtta ctccaggtga aagaccatct   1500
ggaatgttcg actcctccgt tttgtgtgaa tgttacgacg ctggttgtgc ttggtacgaa   1560
ttgactccag ctgagactac tgttagattg agagcttact tgaacactcc aggattgcca   1620
gtttgtcaag accacttgga attctgggag tccgttttca ctggattgac tcacattgac   1680
gctcactttt tgtcccaaac taagcaggct ggtgacaact ttccatactt ggttgcttac   1740
caggctactg tttgtgctag agcacaagct ccaccaccat cttgggatca gatgtggaag   1800
tgtttgatca gattgaagcc aactttgcac ggtccaactc cattgttgta cagattgggt   1860
gctgttcaga acgagatcac tttgactcac ccaatcacta agttcgttat ggcttgcatg   1920
tctgctgact tggaagttgt tggttccgga tctggttcca tgtcctacac ttggactggt   1980
gctttgatca ctccatgtgc tgctgaagaa tccaagttgc caatcaaccc attgtccaac   2040
tctttgttga gacaccactc catggtttac tccactactt ccagatccgc ttccttgaga   2100
cagaagaagg ttacattcga cagattgcag gttttggacg accactacag agatgttttg   2160
aaggagatga aggctaaggc ttccactgtt aaggctagat tgttgtccat tgaggaggct   2220
tgtaagttga ctccaccaca ctctgctaag tccaagtttg gttacggtgc taaggatgtt   2280
agatccttgt cctccagagc tgttaaccac atcagatccg tttgggagga tttgttggag   2340
gacactgaga ctccaatcga cactactatc atggctaaga acgaggtttt ctgtgttcaa   2400
ccagagaagg gtggaagaaa gccagctaga ttgatcgttt tcccagactt gggtgttaga   2460
gtttgtgaga agatggcttt gtacgacgtt gtttccactt tgccacaggc tgttatggga   2520
ccatcttacg gtttccaata ctccccagga caaagagttg agttcttggt taacacttgg   2580
aagtccaaga aatgtccaat gggattctcc tacaacacta gatgtttcga ctccactgtt   2640
actgagaacg acatcagaac agaggagtcc atctaccagt gttgtgactt ggctccagaa   2700
gctagacaag ctatcaagtc cttgactgag agattgtaca tcggtggtcc tttgactaac   2760
tccaagggac agaactgtgg ttacagaaga tgtagagctt ccggtgtttt gactacttcc   2820
tgtggtaaca ctttgacttg ttacttgaag gctactgctg cttgtagagc tgctaaattg   2880
caggactgta ctatgttggt taacggtaac gacttggttg ttatctgtga gtccgctggt   2940
actcaagaag atgctgcttc tttgagagtt ttcacagagg ctatgactag atactctgct   3000
ccacctggtg atccaccaca accagaatac gacttggagt tgatcacttc ctgttcctcc   3060
aatgttggtg ttgctcacga tgcttccgga aagagagttt actacttgac tagagaccca   3120
actactccat tggctagagc tgcttgggaa actgttagac acactccagt taactcctgg   3180
ttgggtaaca tcatcatgta cgctccaact ttgtgggcta gaatgatctt gatgactcac   3240
ttcttctcca tcttgttggc tcaagagcaa ttggaaaagg ctttggactg tcagatttac   3300
ggtgcttgtt actccattga gccattggac ttgccacaga tcattgagag attgcacggt   3360
ttgtctgctt tctctttgca ctcttactcc cctggtgaaa tcaacagagt tgcttcctgt   3420
ttgagaaagt tgggtgttcc accattgaga gtttggagac acagagctag atccgttaga   3480
gctaagttgt tgtcccaagg tggaagagct gctacttgtg gtaagtactt gttcaactgg   3540
gctgttagaa caaagttgaa gttgactcct attcctgctg cttcccaatt ggatttgtcc   3600
ggttggtttg ttgctggtta caacggtggt gacatctacc actctttgtc cagagctaga   3660
ccaagataat agactagtgg atcc                                          3684
```

<210> SEQ ID NO 26
<211> LENGTH: 3684

<212> TYPE: DNA
<213> ORGANISM: artificial sequence
<220> FEATURE:
<223> OTHER INFORMATION: complementary strain of SEQ ID NO25

<400> SEQUENCE: 26

```
taccccaggc aacaatagca accatcttag tagaacagac caagaccaag gcgaggttaa     60

tgacgaatga gggtcgtctg atctcctaac aacccaacat agtagtgaag gaactgacca    120

tctctgttct tggttcaact gcctctccaa gtccaaaaca ggtgacgatg agtcagaaag    180

aaccgatgaa cacaattgcc acaaacaacc tgacaaatgc gaccacgacc aagattttga    240

aaccgaccag gtttcccagg ttagtgagtc tacatgtgtt tgcaactggt cctaaaccaa    300

ccaaccggtc gaggtggtcc acgatctagg tactgaggta catgaacacc aaggaggctg    360

aacatgaacc aatgatctgt gcgactgcaa tagggtcaat cttcttctcc tctgaggtct    420

cctagaaaca acaggggttc tggtcaaaga atgaacttcc ctagaaggcc accaggtaac    480

aacacaggta ggccagtgca acaaccataa aagtctcgac gacaaacatg atctccacaa    540

cgattccgac aactgaagta gggtcaactc aggtacctct gatgatactc taggggtcaa    600

aagtgactgt tgagaagggg tggacgacaa ggtgtttgaa aggttcaacg agtgaacgta    660

cgaggttgac caagaccatt caggtgattc caaggtcgac gaatgcgacg agttccaatg    720

ttccaaaacc aaaacttggg taggcaacga cgatgaaacc caaagccacg aatgtacaga    780

ttccgagtgc cataactcgg tttgtagtct tgaccacaat cttgatagtg atgaccacca    840

ggataatgaa tgaggcgaat gcctttcaaa aaccgactgc caccaacaag accaccacga    900

atgctgtagt agtagacact gctcacagtg agatgactga cctgatgata gaacccatag    960

ccatgacaaa acctggttcg actttgacga ccacgatcta accaacaaaa ccgatgacga   1020

tgaggtggtc caaggtaatg acaaggtgtg ggtttgtagc tccttcaacg aaacagattg   1080

tgacctctct agggtaagat gcctttccga tagggttaac tccgatagtt cccaccatct   1140

gtgaactaaa agacagtgag gttcttcttc acactgctca accgacgatt caactgacct   1200

aaccctaact tgcgacaacg aatgatgtct cctaacctgc aaaggcaata gggttgaagg   1260

ccactacaac aacaacaacg atgactgcga aactactgac caaagtgacc actgaagctg   1320

aggcaatagc tgacattgtg aacacaatga gtctgacaac tgaagaggaa cctgggttga   1380

aagtgatagc tctgatgatg acaaggagtt ctgcgacaaa ggtctagggt ttcttctcca   1440

cgatgaccat ctccttctag gccatagatg tctaagcaat gaggtccact ttctggtaga   1500

ccttacaagc tgaggaggca aaacacactt acaatgctgc gaccaacacg aaccatgctt   1560

aactgaggtc gactctgatg acaatctaac tctcgaatga acttgtgagg tcctaacggt   1620

caaacagttc tggtgaacct taagaccctc aggcaaaagt gacctaactg agtgtaactg   1680

cgagtgaaaa acagggtttg attcgtccga ccactgttga aaggtatgaa ccaacgaatg   1740

gtccgatgac aaacacgatc tcgtgttcga ggtggtggta gaaccctagt ctacaccttc   1800

acaaactagt ctaacttcgg ttgaaacgtg ccaggttgag gtaacaacat gtctaaccca   1860

cgacaagtct tgctctagtg aaactgagtg ggttagtgat tcaagcaata ccgaacgtac   1920

agacgactga accttcaaca accaaggcct agaccaaggt acaggatgtg aacctgacca   1980

cgaaactagt gaggtacacg acgacttctt aggttcaacg gttagttggg taacaggttg   2040

agaaacaact ctgtggtgag gtaccaaatg aggtgatgaa ggtctaggcg aaggaactct   2100

gtcttcttcc aatgtaagct gtctaacgtc caaaacctgc tggtgatgtc tctacaaaac   2160

ttcctctact tccgattccg aaggtgacaa ttccgatcta acaacaggta actcctccga   2220
```

```
acattcaact gaggtggtgt gagacgattc aggttcaaac caatgccacg attcctacaa   2280
tctaggaaca ggaggtctcg acaattggtg tagtctaggc aaaccctcct aaacaacctc   2340
ctgtgactct gaggttagct gtgatgatag taccgattct tgctccaaaa gacacaagtt   2400
ggtctcttcc caccttcttt cggtcgatct aactagcaaa agggtctgaa cccacaatct   2460
caaacactct tctaccgaaa catgctgcaa caaaggtgaa acggtgtccg acaataccct   2520
ggtagaatgc caaaggttat gaggggtcct gtttctcaac tcaagaacca attgtgaacc   2580
ttcaggttct ttacaggtta ccctaagagg atgttgtgat ctacaaagct gaggtgacaa   2640
tgactcttgc tgtagtcttg tctcctcagg tagatggtca caacactgaa ccgaggtctt   2700
cgatctgttc gatagttcag gaactgactc tctaacatgt agccaccagg aaactgattg   2760
aggttccctg tcttgacacc aatgtcttct acatctcgaa ggccacaaaa ctgatgaagg   2820
acaccattgt gaaactgaac aatgaacttc cgatgacgac gaacatctcg acgatttaac   2880
gtcctgacat gatacaacca attgccattg ctgaaccaac aatagacact caggcgacca   2940
tgagttcttc tacgacgaag aaactctcaa aagtgtctcc gatactgatc tatgagacga   3000
ggtggaccac taggtggtgt tggtcttatg ctgaacctca actagtgaag gacaaggagg   3060
ttacaaccac aacgagtgct acgaaggcct ttctctcaaa tgatgaactg atctctgggt   3120
tgatgaggta accgatctcg acgaaccctt tgacaatctg tgtgaggtca attgaggacc   3180
aacccattgt agtagtacat gcgaggttga aacacccgat cttactagaa ctactgagtg   3240
aagaagaggt agaacaaccg agttctcgtt aacctttcc gaaacctgac agtctaaatg    3300
ccacgaacaa tgaggtaact cggtaacctg aacggtgtct agtaactctc taacgtgcca   3360
aacagacgaa agagaaacgt gagaatgagg ggaccacttt agttgtctca acgaaggaca   3420
aactctttca acccacaagg tggtaactct caaacctctg tgtctcgatc taggcaatct   3480
cgattcaaca acagggttcc accttctcga cgatgaacac cattcatgaa caagttgacc   3540
cgacaatctt gtttcaactt caactgagga taaggacgac gaagggttaa cctaaacagg   3600
ccaaccaaac aacgaccaat gttgccacca ctgtagatgg tgagaaacag gtctcgatct   3660
ggttctatta tctgatcacc tagg                                          3684
```

<210> SEQ ID NO 27
<211> LENGTH: 3765
<212> TYPE: DNA
<213> ORGANISM: artificial sequence
<220> FEATURE:
<223> OTHER INFORMATION: optimised sequence of NS4A-NS3-NS4B-NS5B in Pichia

<400> SEQUENCE: 27

```
atggggtccg ttgttatcgt tggtagaatc atcttgtctg gttctggttc cgctccaatt     60
actgcttact cccagcagac tagaggattg ttgggttgta tcatcacttc cttgactggt    120
agagacaaga accaagttga cggagaggtt caggttttgt ccactgctac tcagtctttc    180
ttggctactt gtgttaacgg tgtttgttgg actgtttacg ctggtgctgg ttctaaaact    240
ttggctggtc caaagggtcc aatcactcag atgtacacaa acgttgacca ggatttggtt    300
ggttggccag ctccaccagg tgctagatcc atgactccat gtacttgtgg ttcctccgac    360
ttgtacttgg ttactagaca cgctgacgtt atcccagtta gaagaagagg agactccaga    420
ggatctttgt tgtccccaag accagtttct tacttgaagg gatcttccgg tggtccattg    480
ttgtgtccat ccggtcacgt tgttggtatt ttcagagctg ctgtttgtac tagaggtgtt    540
```

-continued

```
gctaaggctg ttgacttcat cccagttgag tccatggaga ctactatgag atccccagtt    600
ttcactgaca actcttcccc acctgctgtt ccacaaactt tccaagttgc tcacttgcat    660
gctccaactg gttctggtaa gtccactaag gttccagctg cttacgctgc tcaaggttac    720
aaggttttgg ttttgaaccc atccgttgct gctactttgg gtttcggtgc ttacatgtct    780
aaggctcacg gtattgagcc aaacatcaga actggtgtta gaactatcac tactggtggt    840
cctattactt actccgctta cggaaagttt ttggctgacg gtggttgttc tggtggtgct    900
tacgacatca tcatctgtga cgagtgtcac tctactgact ggactactat cttgggtatc    960
ggtactgttt tggaccaagc tgaaactgct ggtgctagat tggttgtttt ggctactgct   1020
actccaccag gttccattac tgttccacac ccaaacatcg aggaagttgc tttgtctaac   1080
actggagaga tcccattcta cggaaaggct atcccaattg aggctatcaa gggtggtaga   1140
cacttgattt tctgtcactc caagaagaag tgtgacgagt tggctgctaa gttgactgga   1200
ttgggattga acgctgttgc ttactacaga ggattggacg tttccgttat cccaacttcc   1260
ggtgatgttg ttgttgttgc tactgacgct ttgatgactg gtttcactgg tgacttcgac   1320
tccgttatcg actgtaacac ttgtgttact cagactgttg acttctcctt ggacccaact   1380
ttcactatcg agactactac tgttcctcaa gacgctgttt ccagatccca aagaagaggt   1440
gctactggta gaggaagatc cggtatctac agattcgtta ctccaggtga aagaccatct   1500
ggaatgttcg actcctccgt tttgtgtgaa tgttacgacg ctggttgtgc ttggtacgaa   1560
ttgactccag ctgagactac tgttagattg agagcttact tgaacactcc aggattgcca   1620
gtttgtcaag accacttgga attctgggag tccgttttca ctggattgac tcacattgac   1680
gctcactttt tgtcccaaac taagcaggct ggtgacaact ttccatactt ggttgcttac   1740
caggctactg tttgtgctag agcacaagct ccaccaccat cttgggatca gatgtggaag   1800
tgtttgatca gattgaagcc aactttgcac ggtccaactc cattgttgta cagattgggt   1860
gctgttcaga acgagatcac tttgactcac ccaatcacta agttcgttat ggcttgcatg   1920
tctgctgact tggaagttgt ttccttgatg gctttcactg cttccattac ttccccattg   1980
actactcaga acactttgtt gttcaacatc ttgggaggat gggttgcagc tcaattgtcc   2040
atgtcctaca cttggactgg tgctttgatc actccatgtg ctgctgaaga atccaagttg   2100
ccaatcaacc cattgtccaa ctctttgttg agacaccact ccatggttta ctccactact   2160
tccagatccg cttccttgag acagaagaag gttacattcg acagattgca ggttttggac   2220
gaccactaca gagatgtttt gaaggagatg aaggctaagg cttccactgt taaggctaga   2280
ttgttgtcca ttgaggaggc ttgtaagttg actccaccac actctgctaa gtccaagttt   2340
ggttacggtg ctaaggatgt tagatccttg tcctccagag ctgttaacca catcaggtct   2400
gtttgggagg atttgttgga ggacactgag actccaatcg acactactat catggctaag   2460
aacgaggttt tctgtgttca accagagaag ggtggaagaa agccagctag attgatcgtt   2520
ttcccagact tgggtgttag agtttgtgag aagatggctt tgtacgacgt tgtttccact   2580
ttgccacagg ctgttatggg accatcttac ggtttccaat actccccagg acaaagagtt   2640
gagttcttgg ttaacacttg gaagtccaag aaatgtccaa tgggattctc ctacaacact   2700
agatgtttcg actccactgt tactgagaac gacatcagaa cagaggagtc catctaccag   2760
tgttgtgact tggctccaga agctagacaa gctatcaagt ccttgactga gagattgtac   2820
atcggtggtc ctttgactaa ctccaaggga cagaactgtg gttacagaag atgtagagct   2880
tccggtgttt tgactacttc ctgtggtaac actttgactt gttacttgaa ggctactgct   2940
```

```
gcttgtagag ctgctaaatt gcaggactgt actatgttgg ttaacggtaa cgacttggtt   3000

gttatctgtg agtccgctgg tactcaagaa gatgctgctt ctttgagagt tttcacagag   3060

gctatgacta gatactctgc tccacctggt gatccaccac aaccagaata cgacttggag   3120

ttgatcactt cctgttcctc caatgttggt gttgctcacg atgcttccgg aaagagagtt   3180

tactacttga ctagagaccc aactactcca ttggctagag ctgcttggga aactgttaga   3240

cacactccag ttaactcctg gttgggtaac atcatcatgt acgctccaac tttgtgggct   3300

agaatgatct tgatgactca cttcttctcc atcttgttgg ctcaagagca attggaaaag   3360

gctttggact gtcagattta cggtgcttgt tactccattg agccattgga cttgccacag   3420

atcattgaga gattgcacgg tttgtctgct ttctctttgc actcttactc ccctggtgaa   3480

atcaacagag ttgcttcctg tttgagaaag ttgggtgttc caccattgag agtttggaga   3540

cacagagcta gatccgttag agctaagttg ttgtcccaag gtggaagagc tgctacttgt   3600

ggtaagtact tgttcaactg ggctgttaga acaaagttga agttgactcc tattcctgct   3660

gcttcccaat tggatttgtc cggttggttt gttgctggtt acaacggtgg tgacatctac   3720

cactctttgt ccagagctag accaagataa tagactagtg gatcc                   3765
```

<210> SEQ ID NO 28
<211> LENGTH: 3765
<212> TYPE: DNA
<213> ORGANISM: artificial sequence
<220> FEATURE:
<223> OTHER INFORMATION: complementary strand of SEQ ID NO:27

<400> SEQUENCE: 28

```
taccccaggc aacaatagca accatcttag tagaacagac caagaccaag gcgaggttaa     60

tgacgaatga gggtcgtctg atctcctaac aacccaacat agtagtgaag gaactgacca    120

tctctgttct tggttcaact gcctctccaa gtccaaaaca ggtgacgatg agtcagaaag    180

aaccgatgaa cacaattgcc acaaacaacc tgacaaatgc gaccacgacc aagattttga    240

aaccgaccag gtttcccagg ttagtgagtc tacatgtgtt tgcaactggt cctaaaccaa    300

ccaaccggtc gaggtggtcc acgatctagg tactgaggta catgaacacc aaggaggctg    360

aacatgaacc aatgatctgt gcgactgcaa tagggtcaat cttcttctcc tctgaggtct    420

cctagaaaca acaggggttc tggtcaaaga atgaacttcc ctagaaggcc accaggtaac    480

aacacaggta ggccagtgca acaaccataa aagtctcgac gacaaacatg atctccacaa    540

cgattccgac aactgaagta gggtcaactc aggtacctct gatgatactc taggggtcaa    600

aagtgactgt tgagaagggg tggacgacaa ggtgtttgaa aggttcaacg agtgaacgta    660

cgaggttgac caagaccatt caggtgattc caaggtcgac gaatgcgacg agttccaatg    720

ttccaaaacc aaaacttggg taggcaacga cgatgaaacc caaagccacg aatgtacaga    780

ttccgagtgc cataactcgg tttgtagtct tgaccacaat cttgatagtg atgaccacca    840

ggataatgaa tgaggcgaat gcctttcaaa aaccgactgc caccaacaag accaccacga    900

atgctgtagt agtagacact gctcacagtg agatgactga cctgatgata gaacccatag    960

ccatgacaaa acctggttcg actttgacga ccacgatcta accaacaaaa ccgatgacga   1020

tgaggtggtc caaggtaatg acaaggtgtg ggtttgtagc tccttcaacg aaacagattg   1080

tgacctctct agggtaagat gcctttccga tagggttaac tccgatagtt cccaccatct   1140

gtgaactaaa agacagtgag gttcttcttc acactgctca accgacgatt caactgacct   1200

aaccctaact tgcgacaacg aatgatgtct cctaacctgc aaaggcaata gggttgaagg   1260
```

```
ccactacaac aacaacaacg atgactgcga aactactgac caaagtgacc actgaagctg   1320
aggcaatagc tgacattgtg aacacaatga gtctgacaac tgaagaggaa cctgggttga   1380
aagtgatagc tctgatgatg acaaggagtt ctgcgacaaa ggtctagggt ttcttctcca   1440
cgatgaccat ctccttctag gccatagatg tctaagcaat gaggtccact ttctggtaga   1500
ccttacaagc tgaggaggca aaacacactt acaatgctgc gaccaacacg aaccatgctt   1560
aactgaggtc gactctgatg acaatctaac tctcgaatga acttgtgagg tcctaacggt   1620
caaacagttc tggtgaacct taagaccctc aggcaaaagt gacctaactg agtgtaactg   1680
cgagtgaaaa acagggtttg attcgtccga ccactgttga aaggtatgaa ccaacgaatg   1740
gtccgatgac aaacacgatc tcgtgttcga ggtggtggta gaaccctagt ctacaccttc   1800
acaaactagt ctaacttcgg ttgaaacgtg ccaggttgag gtaacaacat gtctaaccca   1860
cgacaagtct tgctctagtg aaactgagtg ggttagtgat tcaagcaata ccgaacgtac   1920
agacgactga accttcaaca aaggaactac cgaaagtgac gaaggtaatg aaggggtaac   1980
tgatgagtct tgtgaaacaa caagttgtag aaccctccta cccaacgtcg agttaacagg   2040
tacaggatgt gaacctgacc acgaaactag tgaggtacac gacgacttct taggttcaac   2100
ggttagttgg gtaacaggtt gagaaacaac tctgtggtga ggtaccaaat gaggtgatga   2160
aggtctaggc gaaggaactc tgtcttcttc caatgtaagc tgtctaacgt ccaaaacctg   2220
ctggtgatgt ctctacaaaa cttcctctac ttccgattcc gaaggtgaca attccgatct   2280
aacaacaggt aactcctccg aacattcaac tgaggtggtg tgagacgatt caggttcaaa   2340
ccaatgccac gattcctaca atctaggaac aggaggtctc gacaattggt gtagtccaga   2400
caaaccctcc taaacaacct cctgtgactc tgaggttagc tgtgatgata gtaccgattc   2460
ttgctccaaa agacacaagt tggtctcttc ccaccttctt tcggtcgatc taactagcaa   2520
aagggtctga acccacaatc tcaaacactc ttctaccgaa acatgctgca acaaaggtga   2580
aacggtgtcc gacaataccc tggtagaatg ccaaaggtta tgaggggtcc tgtttctcaa   2640
ctcaagaacc aattgtgaac cttcaggttc tttacaggtt accctaagag gatgttgtga   2700
tctacaaagc tgaggtgaca atgactcttg ctgtagtctt gtctcctcag gtagatggtc   2760
acaacactga accgaggtct tcgatctgtt cgatagttca ggaactgact ctctaacatg   2820
tagccaccag gaaactgatt gaggttccct gtcttgacac caatgtcttc tacatctcga   2880
aggccacaaa actgatgaag gacaccattg tgaaactgaa caatgaactt ccgatgacga   2940
cgaacatctc gacgatttaa cgtcctgaca tgatacaacc aattgccatt gctgaaccaa   3000
caatagacac tcaggcgacc atgagttctt ctacgacgaa gaaactctca aaagtgtctc   3060
cgatactgat ctatgagacg aggtggacca ctaggtggtg ttggtcttat gctgaacctc   3120
aactagtgaa ggacaaggag gttacaacca caacgagtgc tacgaaggcc tttctctcaa   3180
atgatgaact gatctctggg ttgatgaggt aaccgatctc gacgaaccct ttgacaatct   3240
gtgtgaggtc aattgaggac caacccattg tagtagtaca tgcgaggttg aaacacccga   3300
tcttactaga actactgagt gaagaagagg tagaacaacc gagttctcgt taaccttttc   3360
cgaaacctga cagtctaaat gccacgaaca atgaggtaac tcggtaacct gaacggtgtc   3420
tagtaactct ctaacgtgcc aaacagacga aagagaaacg tgagaatgag gggaccactt   3480
tagttgtctc aacgaaggac aaactctttc aacccacaag gtggtaactc tcaaacctct   3540
gtgtctcgat ctaggcaatc tcgattcaac aacagggttc caccttctcg acgatgaaca   3600
ccattcatga acaagttgac ccgacaatct tgtttcaact tcaactgagg ataaggacga   3660
```

cgaagggtta acctaaacag gccaaccaaa caacgaccaa tgttgccacc actgtagatg 3720
gtgagaaaca ggtctcgatc tggttctatt atctgatcac ctagg 3765

<210> SEQ ID NO 29
<211> LENGTH: 3724
<212> TYPE: DNA
<213> ORGANISM: artificial sequence
<220> FEATURE:
<223> OTHER INFORMATION: optimised sequence of NS4A-NS3-NS5B in E.Coli

<400> SEQUENCE: 29
agggcgaatt gggtaccatg gggagcgttg ttattgttgg ccgcattatt ctgagcggta 60
gcggtagcgc cccgattacc gcctattctc agcaaacccg tggtctgctg ggttgtatta 120
ttaccagcct gaccggccgt gataaaaatc aggtggatgg cgaagttcag gttctgagca 180
ccgccaccca gagctttctg gcgacctgtg tgaatggtgt gtgctggacc gtttatgccg 240
gtgccggtag caaaaccctg gcgggtccga aaggtccgat tacccagatg tacaccaacg 300
tggatcagga tctggttggt tggccggcgc cgccgggtgc ccgtagcatg accccgtgta 360
cctgtggtag cagcgatctg tatctggtta cccgtcatgc cgatgttatt ccggttcgtc 420
gtcgtggtga tagccgtggt agcctgctgt ctccgcgtcc ggttagctat ctgaaaggta 480
gcagcggtgg tccgctgctg tgtccgagcg gtcatgtggt gggtattttt cgtgccgccg 540
tttgtacccg tggtgtggcg aaagcggtgg attttatccc ggttgaaagc atggaaacca 600
ccatgcgtag cccggtgttt accgataata gcagcccgcc ggcggttccg cagacctttc 660
aggttgccca tctgcatgcg ccgaccggta gcggtaaaag caccaaagtt ccggcggcgt 720
atgccgccca gggttataaa gtgctggtgc tgaatccgag cgtggcggcg accctgggtt 780
ttggtgccta tatgagcaaa gcccatggca ttgaaccgaa cattcgtacc ggcgttcgta 840
ccattaccac cggtggcccg attacctata gcgcctacgg caaatttctg gcggatggtg 900
gctgtagcgg tggcgcctat gatatcatca tctgtgatga atgccatagc accgattgga 960
ccaccattct gggtattggc accgttctgg atcaggcgga aaccgccggt gcccgtctgg 1020
ttgttctggc gaccgcaacg ccgccgggta gcattaccgt tccgcatccg aacattgaag 1080
aagtggccct gagcaatacc ggcgaaattc cgttttatgg caaagcgatt ccgatcgaag 1140
cgattaaagg cggccgtcat ctgatttttt gccacagcaa aaaaaaatgt gatgaactgg 1200
cggcgaaact gaccggtctg ggtctgaatg ccgtggcgta ttatcgtggt ctggatgtga 1260
gcgttattcc gaccagcggt gatgttgttg tggtggcgac cgatgccctg atgaccggtt 1320
ttaccggcga ttttgatagc gtgatcgatt gtaacacctg tgtgacccag accgttgatt 1380
ttagcctgga cccgaccttt accattgaaa ccaccaccgt tccgcaggat gccgttagcc 1440
gtagccagcg tcgtggtgcc accggtcgtg gtcgtagcgg catttatcgt tttgtgacgc 1500
cgggtgaacg tccgagcggt atgtttgata gcagcgtgct gtgtgaatgt tatgatgccg 1560
gctgtgcctg gtatgaactg accccggcgg aaaccaccgt tcgtctgcgc gcgtatctga 1620
atacgccggg tctgccggtt tgtcaggatc atctggaatt ctgggaaagc gtttttaccg 1680
gcctgaccca tattgatgcc cattttctga gccagaccaa acaggcgggt gataactttc 1740
cgtatctggt ggcgtatcag gcgaccgttt gtgcccgtgc ccaggcgccg ccgccgagct 1800
gggatcagat gtggaaatgc ctgattcgtc tgaaaccgac cctgcatggt ccgacccccgc 1860 tgctgtatcg tctgggtgcc gttcagaacg aaattaccct gacccatccg atcaccaaat 1920
ttgtgatggc gtgtatgagc gccgatctgg aagttgttgg tagcggtagc ggctctatga 1980

```
gctatacctg gaccggtgcc ctgattaccc cgtgtgccgc cgaagaaagc aaactgccga   2040

ttaacccgct gtctaatagc ctgctgcgtc atcatagcat ggtgtatagc accaccagcc   2100

gtagcgccag cctgcgtcag aaaaaagtga ccttcgatcg tctgcaggtg ctggatgatc   2160

attatcgtga tgtgctgaaa gaaatgaaag cgaaagcgag caccgttaaa gcccgtctgc   2220

tgtctattga agaagcgtgt aaactgaccc cgccgcatag cgccaaaagc aaatttggct   2280

atggcgccaa agatgttcgt agcctgagca gccgtgccgt taatcatatt cgtagcgtgt   2340

gggaagatct gctggaagat accgaaaccc cgattgatac caccatcatg gcgaaaaacg   2400

aagtgttttg tgttcagccg gaaaaaggtg gtcgtaaacc ggcccgtctg attgtttttc   2460

cggatctggg tgttcgtgtg tgtgaaaaaa tggcgctgta cgatgttgtt agcaccctgc   2520

cgcaggcggt tatgggtccg agctatggct ttcagtattc tccgggtcag cgtgttgaat   2580

ttctggtgaa cacctggaaa agcaaaaaat gcccgatggg cttcagctat aacacccgct   2640

gctttgatag caccgtgacc gaaaacgata tccgtaccga agaaagcatt taccagtgct   2700

gtgatctggc gccggaagcc cgtcaggcga ttaaaagcct gaccgaacgc ctgtatattg   2760

gcggtccgct gaccaatagc aaaggccaga actgtggtta tcgtcgttgt cgtgccagcg   2820

gtgttctgac caccagctgt ggtaataccc tgacctgcta cctgaaagcg accgccgcct   2880

gtcgtgccgc caaactgcag gattgtacca tgctggttaa cggcaatgat ctggtggtga   2940

tttgtgaaag cgccggcacc caggaagatg ccgccagcct gcgcgttttt accgaagcga   3000

tgacccgtta tagcgccccg ccgggtgatc cgccgcagcc ggaatatgat ctggaactga   3060

tcaccagctg tagcagcaat gttggtgttg cccatgatgc cagcggtaaa cgtgtgtatt   3120

acctgacccg tgatccgacc accccgctgg cccgtgccgc ctgggaaacc gttcgtcata   3180

ccccggttaa tagctggctg ggcaacatta ttatgtatgc cccgaccctg tgggcccgta   3240

tgattctgat gacccacttc tttagcattc tgctggccca ggaacagctg gaaaaagcgc   3300

tggattgcca gatttatggc gcctgctata gcattgaacc gctggatctg ccgcagatta   3360

ttgaacgtct gcatggcctg agcgccttta gcctgcatag ctactctccg ggtgaaatta   3420

atcgtgtggc gagctgtctg cgtaaactgg gtgttccgcc gctgcgtgtc tggcgtcatc   3480

gtgcccgtag cgttcgtgcc aaactgctgt ctcagggtgg ccgtgccgcc acctgtggta   3540

aatacctgtt taactgggcg gttcgtacca aactgaaact gaccccgatt ccggcggcga   3600

gccagctgga tctgagcggt tggtttgttg ccggttataa cggcggcgat atctatcata   3660

gcctgagccg tgcccgtccg cgttaataaa ctagtggatc cggagctcca gctttgttcc   3720

ctag                                                                 3724
```

<210> SEQ ID NO 30
<211> LENGTH: 3724
<212> TYPE: DNA
<213> ORGANISM: artificial sequence
<220> FEATURE:
<223> OTHER INFORMATION: complementary strand of SEQ ID NO29

<400> SEQUENCE: 30

```
tcccgcttaa cccatggtac ccctcgcaac aataacaacc ggcgtaataa gactcgccat     60

cgccatcgcg gggctaatgg cggataagag tcgtttgggc accagacgac ccaacataat    120

aatggtcgga ctggccggca ctattttag tccacctacc gcttcaagtc caagactcgt     180

ggcggtgggt ctcgaaagac cgctggacac acttaccaca cacgacctgg caaatacggc    240

cacggccatc gttttgggac cgcccaggct ttccaggcta atgggtctac atgtggttgc    300
```

-continued

```
acctagtcct agaccaacca accggccgcg gcggcccacg ggcatcgtac tggggcacat    360
ggacaccatc gtcgctagac atagaccaat gggcagtacg gctacaataa ggccaagcag    420
cagcaccact atcggcacca tcggacgaca gaggcgcagg ccaatcgata gactttccat    480
cgtcgccacc aggcgacgac acaggctcgc cagtacacca cccataaaaa gcacggcggc    540
aaacatgggc accacaccgc tttcgccacc taaaataggg ccaactttcg tacctttggt    600
ggtacgcatc gggccacaaa tggctattat cgtcgggcgg ccgccaaggc gtctggaaag    660
tccaacgggt agacgtacgc ggctggccat cgccattttc gtggtttcaa ggccgccgca    720
tacggcgggt cccaatattt cacgaccacg acttaggctc gcaccgccgc tgggacccaa    780
aaccacggat atactcgttt cgggtaccgt aacttggctt gtaagcatgg ccgcaagcat    840
ggtaatggtg gccaccgggc taatggatat cgcggatgcc gtttaaagac cgcctaccac    900
cgacatcgcc accgcggata ctatagtagt agacactact tacggtatcg tggctaacct    960
ggtggtaaga cccataaccg tggcaagacc tagtccgcct ttggcggcca cgggcagacc   1020
aacaagaccg ctggcgttgc ggcggcccat cgtaatggca aggcgtaggc ttgtaacttc   1080
ttcaccggga ctcgttatgg ccgctttaag gcaaaatacc gtttcgctaa ggctagcttc   1140
gctaatttcc gccggcagta gactaaaaaa cggtgtcgtt tttttttaca ctacttgacc   1200
gccgctttga ctggccagac ccagacttac ggcaccgcat aatagcacca gacctacact   1260
cgcaataagg ctggtcgcca ctacaacaac accaccgctg gctacgggac tactggccaa   1320
aatggccgct aaaactatcg cactagctaa cattgtggac acactgggtc tggcaactaa   1380
aatcggacct gggctggaaa tggtaacttt ggtggtggca aggcgtccta cggcaatcgg   1440
catcggtcgc agcaccacgg tggccagcac cagcatcgcc gtaaatagca aaacactgcg   1500
gcccacttgc aggctcgcca tacaaactat cgtcgcacga cacacttaca atactacggc   1560
cgacacggac catacttgac tggggccgcc tttggtggca agcagacgcg cgcatagact   1620
tatgcggccc agacggccaa acagtcctag tagaccttaa gaccctttcg caaaaatggc   1680
cggactgggt ataactacgg gtaaaagact cggtctggtt tgtccgccca ctattgaaag   1740
gcatagacca ccgcatagtc cgctggcaaa cacgggcacg ggtccgcggc ggcggctcga   1800
ccctagtcta cacctttacg gactaagcag actttggctg ggacgtacca ggctggggcg   1860
acgacatagc agacccacgg caagtcttgc tttaatggga ctgggtaggc tagtggttta   1920
aacactaccg cacatactcg cggctagacc ttcaacaacc atcgccatcg ccgagatact   1980
cgatatggac ctggccacgg gactaatggg gcacacggcg gcttctttcg tttgacggct   2040
aattgggcga cagattatcg gacgacgcag tagtatcgta ccacatatcg tggtggtcgg   2100
catcgcggtc ggacgcagtc ttttttcact ggaagctagc agacgtccac gacctactag   2160
taatagcact acacgacttt ctttactttc gctttcgctc gtggcaattt cgggcagacg   2220
acagataact tcttcgcaca tttgactggg gcggcgtatc gcggttttcg tttaaaccga   2280
taccgcggtt tctacaagca tcggactcgt cggcacggca attagtataa gcatcgcaca   2340
cccttctaga cgaccttcta tggctttggg gctaactatg gtggtagtac cgctttttgc   2400
ttcacaaaac acaagtcggc ctttttccac cagcatttgg ccgggcagac taacaaaaag   2460
gcctagaccc acaagcacac acactttttt accgcgacat gctacaacaa tcgtgggacg   2520
gcgtccgcca atacccaggc tcgataccga aagtcataag aggcccagtc gcacaactta   2580
aagaccactt gtggaccttt tcgtttttta cgggctaccc gaagtcgata ttgtgggcga   2640
cgaaactatc gtggcactgg cttttgctat aggcatggct tctttcgtaa atggtcacga   2700
```

-continued cactagaccg cggccttcgg gcagtccgct aattttcgga ctggcttgcg gacatataac 2760
cgccaggcga ctggttatcg tttccggtct tgacaccaat agcagcaaca gcacggtcgc 2820
cacaagactg gtggtcgaca ccattatggg actggacgat ggactttcgc tggcggcgga 2880
cagcacggcg gtttgacgtc ctaacatggt acgaccaatt gccgttacta gaccaccact 2940
aaacactttc gcggccgtgg gtccttctac ggcggtcgga cgcgcaaaaa tggcttcgct 3000
actgggcaat atcgcggggc ggcccactag gcggcgtcgg ccttatacta gaccttgact 3060
agtggtcgac atcgtcgtta caaccacaac gggtactacg gtcgccattt gcacacataa 3120
tggactgggc actaggctgg tggggcgacc gggcacggcg gaccctttgg caagcagtat 3180
ggggccaatt atcgaccgac ccgttgtaat aatacatacg gggctgggac acccgggcat 3240
actaagacta ctgggtgaag aaatcgtaag acgaccgggt ccttgtcgac ctttttcgcg 3300
acctaacggt ctaaataccg cggacgatat cgtaacttgg cgacctagac ggcgtctaat 3360
aacttgcaga cgtaccggac tcgcggaaat cggacgtatc gatgagaggc ccactttaat 3420
tagcacaccg ctcgacagac gcatttgacc cacaaggcgg cgacgcacag accgcagtag 3480
cacgggcatc gcaagcacgg tttgacgaca gagtcccacc ggcacggcgg tggacaccat 3540
ttatggacaa attgacccgc caagcatggt ttgactttga ctggggctaa ggccgccgct 3600
cggtcgacct agactcgcca accaaacaac ggccaatatt gccgccgcta tagatagtat 3660
cggactcggc acgggcaggc gcaattattt gatcacctag gcctcgaggt cgaaacaagg 3720
gatc 3724

<210> SEQ ID NO 31
<211> LENGTH: 3802
<212> TYPE: DNA
<213> ORGANISM: artificial sequence
<220> FEATURE:
<223> OTHER INFORMATION: optimised sequence of NS4A-NS3-NS4B-NS5B in E.Coli

<400> SEQUENCE: 31
gggcgaattg ggtaccatgg ggagcgttgt tattgttggc cgcattattc tgagcggtag 60
cggtagcgcc ccgattaccg cctattctca gcaaacccgt ggtctgctgg gttgtattat 120
taccagcctg accggccgtg ataaaaatca ggtggatggc gaagttcagg ttctgagcac 180
cgccacccag agctttctgg cgacctgtgt gaatggtgtg tgctggaccg tttatgccgg 240
tgccggtagc aaaaccctgg cgggtccgaa aggtccgatt acccagatgt acaccaacgt 300
ggatcaggat ctggttggtt ggccggcgcc gccgggtgcc cgtagcatga ccccgtgtac 360
ctgtggtagc agcgatctgt atctggttac ccgtcatgcc gatgttattc cggttcgtcg 420
tcgtggtgat agccgtggta gcctgctgtc tccgcgtccg gttagctatc tgaaaggtag 480
cagcggtggt ccgctgctgt gtccgagcgg tcatgtggtg ggtatttttc gtgccgccgt 540
ttgtacccgt ggtgtggcga aagcggtgga ttttatcccg gttgaaagca tggaaaccac 600
catgcgtagc ccggtgttta ccgataatag cagcccgccg gcggttccgc agacctttca 660
ggttgcccat ctgcatgcgc cgaccggtag cggtaaaagc accaaagttc cggcggcgta 720
tgccgcccag ggttataaag tgctggtgct gaatccgagc gtggcggcga ccctgggttt 780
tggtgcctat atgagcaaag cccatggcat tgaaccgaac attcgtaccg gcgttcgtac 840
cattaccacc ggtggcccga ttacctatag cgcctacggc aaatttctgg cggatggtgg 900
ctgtagcggt ggcgcctatg atatcatcat ctgtgatgaa tgccatagca ccgattggac 960
caccattctg ggtattggca ccgttctgga tcaggcggaa accgccggtg cccgtctggt 1020

```
tgttctggcg accgcaacgc cgccgggtag cattaccgtt ccgcatccga acattgaaga   1080
agtggccctg agcaataccg gcgaaattcc gttttatggc aaagcgattc cgatcgaagc   1140
gattaaaggc ggccgtcatc tgattttttg ccacagcaaa aaaaaatgtg atgaactggc   1200
ggcgaaactg accggtctgg gtctgaatgc cgtggcgtat tatcgtggtc tggatgtgag   1260
cgttattccg accagcggtg atgttgttgt ggtggcgacc gatgccctga tgaccggttt   1320
taccggcgat tttgatagcg tgatcgattg taacacctgt gtgacccaga ccgttgattt   1380
tagcctggac ccgaccttta ccattgaaac caccaccgtt ccgcaggatg ccgttagccg   1440
tagccagcgt cgtggtgcca ccggtcgtgg tcgtagcggc atttatcgtt ttgtgacgcc   1500
gggtgaacgt ccgagcggta tgtttgatag cagcgtgctg tgtgaatgtt atgatgccgg   1560
ctgtgcctgg tatgaactga ccccggcgga aaccaccgtt cgtctgcgcg cgtatctgaa   1620
tacgccgggt ctgccggttt gtcaggatca tctggaattc tgggaaagcg tttttaccgg   1680
cctgacccat attgatgccc attttctgag ccagaccaaa caggcgggtg ataactttcc   1740
gtatctggtg gcgtatcagg cgaccgtttg tgcccgtgcc caggcgccgc cgccgagctg   1800
ggatcagatg tggaaatgcc tgattcgtct gaaaccgacc ctgcatggtc cgaccccgct   1860
gctgtatcgt ctgggtgccg ttcagaacga aattaccctg acccatccga tcaccaaatt   1920
tgtgatggcg tgtatgagcg ccgatctgga agttgttagc ctgatggcgt ttaccgccag   1980
cattaccagc ccgctgacca cccagaatac cctgctgttt aacatcctgg gcggttgggt   2040
ggcggcccag ctgtctatga gctatacctg gaccggtgcc ctgattaccc cgtgtgccgc   2100
cgaagaaagc aaactgccga ttaacccgct gtctaatagc ctgctgcgtc atcatagcat   2160
ggtgtatagc accaccagcc gtagcgccag cctgcgtcag aaaaaagtga ccttcgatcg   2220
tctgcaggtg ctggatgatc attatcgtga tgtgctgaaa gaaatgaaag cgaaagcgag   2280
caccgttaaa gcccgtctgc tgtctattga agaagcgtgt aaactgaccc cgccgcatag   2340
cgccaaaagc aaatttggct atggcgccaa agatgttcgt agcctgagca gccgtgccgt   2400
taatcatatt cgtagcgtgt gggaagatct gctggaagat accgaaaccc cgattgatac   2460
caccatcatg gcgaaaaacg aagtgttttg tgttcagccg gaaaaaggtg gtcgtaaacc   2520
ggcccgtctg attgtttttc cggatctggg tgttcgtgtg tgtgaaaaaa tggcgctgta   2580
cgatgttgtt agcaccctgc cgcaggcggt tatgggtccg agctatggct ttcagtattc   2640
tccgggtcag cgtgttgaat ttctggtgaa cacctggaaa agcaaaaaat gcccgatggg   2700
cttcagctat aacacccgct gctttgatag caccgtgacc gaaaacgata tccgtaccga   2760
agaaagcatt taccagtgct gtgatctggc gccggaagcc cgtcaggcga ttaaaagcct   2820
gaccgaacgc ctgtatattg gcggtccgct gaccaatagc aaaggccaga actgtggtta   2880
tcgtcgttgt cgtgccagcg gtgttctgac caccagctgt ggtaataccc tgacctgcta   2940
cctgaaagcg accgccgcct gtcgtgccgc caaactgcag gattgtacca tgctggttaa   3000
cggcaatgat ctggtggtga tttgtgaaag cgccggcacc caggaagatg ccgccagcct   3060
gcgcgttttt accgaagcga tgacccgtta tagcgccccg ccgggtgatc cgccgcagcc   3120
ggaatatgat ctggaactga tcaccagctg tagcagcaat gttggtgttg cccatgatgc   3180
cagcggtaaa cgtgtgtatt acctgacccg tgatccgacc accccgctgg cccgtgccgc   3240
ctgggaaacc gttcgtcata ccccggttaa tagctggctg ggcaacatta ttatgtatgc   3300
cccgaccctg tgggcccgta tgattctgat gacccacttc tttagcattc tgctggccca   3360
ggaacagctg gaaaaagcgc tggattgcca gatttatggc gcctgctata gcattgaacc   3420
```

gctggatctg ccgcagatta ttgaacgtct gcatggcctg agcgccttta gcctgcatag 3480
ctactctccg ggtgaaatta atcgtgtggc gagctgtctg cgtaaactgg gtgttccgcc 3540
gctgcgtgtc tggcgtcatc gtgcccgtag cgttcgtgcc aaactgctgt ctcagggtgg 3600
ccgtgccgcc acctgtggta aatacctgtt taactgggcg gttcgtacca aactgaaact 3660
gaccccgatt ccggcggcga gccagctgga tctgagcggt tggtttgttg ccggttataa 3720
cggcggcgat atctatcata gcctgagccg tgcccgtccg cgttaataaa ctagtggatc 3780
cggagctcca gcttttgttc cc 3802

<210> SEQ ID NO 32
<211> LENGTH: 3802
<212> TYPE: DNA
<213> ORGANISM: artificial sequence
<220> FEATURE:
<223> OTHER INFORMATION: complementary strand of SEQ ID NO:31

<400> SEQUENCE: 32
cccgcttaac ccatggtacc cctcgcaaca ataacaaccg gcgtaataag actcgccatc 60
gccatcgcgg ggctaatggc ggataagagt cgtttgggca ccagacgacc caacataata 120
atggtcggac tggccggcac tatttttagt ccacctaccg cttcaagtcc aagactcgtg 180
gcggtgggtc tcgaaagacc gctggacaca cttaccacac acgacctggc aaatacggcc 240
acggccatcg ttttgggacc gcccaggctt tccaggctaa tgggtctaca tgtggttgca 300
cctagtccta gaccaaccaa ccggccgcgg cggcccacgg gcatcgtact ggggcacatg 360
gacaccatcg tcgctagaca tagaccaatg ggcagtacgg ctacaataag gccaagcagc 420
agcaccacta tcggcaccat cggacgacag aggcgcaggc caatcgatag actttccatc 480
gtcgccacca ggcgacgaca caggctcgcc agtacaccac ccataaaaag cacggcggca 540
aacatgggca ccacaccgct ttcgccacct aaaatagggc caactttcgt acctttggtg 600
gtacgcatcg ggccacaaat ggctattatc gtcgggcggc cgccaaggcg tctggaaagt 660
ccaacgggta gacgtacgcg gctggccatc gccattttcg tggtttcaag gccgccgcat 720
acggcgggtc ccaatatttc acgaccacga cttaggctcg caccgccgct gggacccaaa 780
accacggata tactcgtttc gggtaccgta acttggcttg taagcatggc cgcaagcatg 840
gtaatggtgg ccaccgggct aatggatatc gcggatgccg tttaaagacc gcctaccacc 900
gacatcgcca ccgcggatac tatagtagta gacactactt acggtatcgt ggctaacctg 960
gtggtaagac ccataaccgt ggcaagacct agtccgcctt tggcggccac gggcagacca 1020
acaagaccgc tggcgttgcg gcggcccatc gtaatggcaa ggcgtaggct tgtaacttct 1080
tcaccgggac tcgttatggc cgctttaagg caaaataccg tttcgctaag gctagcttcg 1140
ctaatttccg ccggcagtag actaaaaaac ggtgtcgttt ttttttacac tacttgaccg 1200
ccgctttgac tggccagacc cagacttacg gcaccgcata atagcaccag acctacactc 1260
gcaataaggc tggtcgccac tacaacaaca ccaccgctgg ctacgggact actggccaaa 1320
atggccgcta aaactatcgc actagctaac attgtggaca cactgggtct ggcaactaaa 1380
atcggacctg ggctggaaat ggtaactttg gtggtggcaa ggcgtcctac ggcaatcggc 1440
atcggtcgca gcaccacggt ggccagcacc agcatcgccg taaatagcaa aacactgcgg 1500
cccacttgca ggctcgccat acaaactatc gtcgcacgac acacttacaa tactacggcc 1560
gacacggacc atacttgact ggggccgcct ttggtggcaa gcagacgcgc gcatagactt 1620
atgcggccca gacggccaaa cagtcctagt agaccttaag accctttcgc aaaaatggcc 1680
ggactgggta taactacggg taaaagactc ggtctggttt gtccgcccac tattgaaagg 1740
catagaccac cgcatagtcc gctggcaaac acgggcacgg gtccgcggcg gcggctcgac 1800
cctagtctac acctttacgg actaagcaga ctttggctgg gacgtaccag gctggggcga 1860
cgacatagca gacccacggc aagtcttgct ttaatgggac tgggtaggct agtggtttaa 1920
acactaccgc acatactcgc ggctagacct tcaacaatcg gactaccgca aatggcggtc 1980
gtaatggtcg ggcgactggt gggtcttatg ggacgacaaa ttgtaggacc cgccaaccca 2040
ccgccgggtc gacagatact cgatatggac ctggccacgg gactaatggg gcacacggcg 2100
gcttctttcg tttgacggct aattgggcga cagattatcg gacgacgcag tagtatcgta 2160
ccacatatcg tggtggtcgg catcgcggtc ggacgcagtc ttttttcact ggaagctagc 2220
agacgtccac gacctactag taatagcact acacgacttt ctttactttc gctttcgctc 2280
gtggcaattt cgggcagacg acagataact tcttcgcaca tttgactggg gcggcgtatc 2340
gcggttttcg tttaaaccga taccgcggtt tctacaagca tcggactcgt cggcacggca 2400
attagtataa gcatcgcaca cccttctaga cgaccttcta tggctttggg gctaactatg 2460
gtggtagtac cgctttttgc ttcacaaaac acaagtcggc ctttttccac cagcatttgg 2520
ccgggcagac taacaaaaag gcctagaccc acaagcacac acactttttt accgcgacat 2580
gctacaacaa tcgtgggacg gcgtccgcca atacccaggc tcgataccga aagtcataag 2640
aggcccagtc gcacaactta aagaccactt gtggaccttt tcgtttttta cgggctaccc 2700
gaagtcgata ttgtgggcga cgaaactatc gtggcactgg cttttgctat aggcatggct 2760
tctttcgtaa atggtcacga cactagaccg cggccttcgg gcagtccgct aattttcgga 2820
ctggcttgcg gacatataac cgccaggcga ctggttatcg tttccggtct tgacaccaat 2880
agcagcaaca gcacggtcgc cacaagactg gtggtcgaca ccattatggg actggacgat 2940
ggactttcgc tggcggcgga cagcacggcg gtttgacgtc ctaacatggt acgaccaatt 3000
gccgttacta gaccaccact aaacactttc gcggccgtgg gtccttctac ggcggtcgga 3060
cgcgcaaaaa tggcttcgct actgggcaat atcgcggggc ggcccactag gcggcgtcgg 3120
ccttatacta gaccttgact agtggtcgac atcgtcgtta caaccacaac gggtactacg 3180
gtcgccattt gcacacataa tggactgggc actaggctgg tggggcgacc gggcacggcg 3240 gacccttttgg caagcagtat ggggccaatt atcgaccgac ccgttgtaat aatacatacg 3300
gggctgggac acccgggcat actaagacta ctgggtgaag aaatcgtaag acgaccgggt 3360
ccttgtcgac ctttttcgcg acctaacggt ctaaataccg cggacgatat cgtaacttgg 3420
cgacctagac ggcgtctaat aacttgcaga cgtaccggac tcgcggaaat cggacgtatc 3480
gatgagaggc ccactttaat tagcacaccg ctcgacagac gcatttgacc cacaaggcgg 3540
cgacgcacag accgcagtag cacgggcatc gcaagcacgg tttgacgaca gagtcccacc 3600
ggcacggcgg tggacaccat ttatggacaa attgacccgc caagcatggt ttgactttga 3660
ctggggctaa ggccgccgct cggtcgacct agactcgcca accaaacaac ggccaatatt 3720
gccgccgcta tagatagtat cggactcggc acgggcaggc gcaattattt gatcacctag 3780
gcctcgaggt cgaaaacaag gg 3802

<210> SEQ ID NO 33
<211> LENGTH: 3
<212> TYPE: PRT
<213> ORGANISM: Hepatitis C virus

<400> SEQUENCE: 33

-continued

```
Ser Gly Ser
1


<210> SEQ ID NO 34
<211> LENGTH: 5
<212> TYPE: PRT
<213> ORGANISM: Hepatitis C virus

<400> SEQUENCE: 34

Gly Ser Gly Ser Gly
1               5
```